US 7,495,077 B2

(12) United States Patent
Brady et al.

(10) Patent No.: US 7,495,077 B2
(45) Date of Patent: Feb. 24, 2009

(54) HOMOGENEOUS PREPARATIONS OF IL-28 AND IL-29

(75) Inventors: Lowell J. Brady, Tacoma, WA (US); Kevin M. Klucher, Bellevue, WA (US); Chung Chan, Issaquah, WA (US); Dennis L. Dong, Bellevue, WA (US); Hong Y. Liu, Seattle, WA (US); Paul O. Sheppard, Granite Falls, WA (US); Thomas R. Bukowski, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 84 days.

(21) Appl. No.: 11/549,490

(22) Filed: Oct. 13, 2006

(65) Prior Publication Data

US 2007/0048843 A1 Mar. 1, 2007

Related U.S. Application Data

(62) Division of application No. 10/914,772, filed on Aug. 9, 2004, now Pat. No. 7,157,559.

(60) Provisional application No. 60/559,142, filed on Apr. 2, 2004, provisional application No. 60/551,841, filed on Mar. 10, 2004, provisional application No. 60/493,194, filed on Aug. 7, 2003.

(51) Int. Cl.
C07K 14/47 (2006.01)
C12N 15/24 (2006.01)
C12N 15/64 (2006.01)
C12P 21/02 (2006.01)

(52) U.S. Cl. .................. 530/351; 424/85.2; 435/320.1; 435/471; 435/69.52; 435/810; 435/975; 536/23.5

(58) Field of Classification Search ........................ None
See application file for complete search history.

(56) References Cited

U.S. PATENT DOCUMENTS

| 4,766,106 | A | 8/1988 | Katre et al. |
|---|---|---|---|
| 4,853,332 | A | 8/1989 | Mark et al. |
| 5,206,344 | A | 4/1993 | Katre et al. |
| 6,822,082 | B2 | 11/2004 | Sheppard et al. |
| 6,927,040 | B2 | 8/2005 | Sheppard et al. |
| 7,038,032 | B2 | 5/2006 | Sheppard et al. |
| 7,135,170 | B2 | 11/2006 | Klucher et al. |
| 7,157,559 | B2 | 1/2007 | Brady et al. |
| 7,241,870 | B2 | 7/2007 | Sheppard et al. |
| 7,252,969 | B2 | 8/2007 | Sheppard et al. |
| 7,253,261 | B2 | 8/2007 | Sheppard et al. |
| 7,351,689 | B2 | 4/2008 | Doyle et al. |
| 2002/0055473 | A1 | 5/2002 | Ganguly et al. |
| 2004/0029228 | A1 | 2/2004 | Presnell et al. |
| 2007/0020227 | A1 | 1/2007 | Sheppard et al. |
| 2007/0041936 | A1 | 2/2007 | Brady et al. |
| 2007/0042468 | A1 | 2/2007 | Sheppard et al. |
| 2007/0042469 | A1 | 2/2007 | Brady et al. |
| 2007/0042470 | A1 | 2/2007 | Brady et al. |
| 2007/0042471 | A1 | 2/2007 | Brady et al. |
| 2007/0048274 | A1 | 3/2007 | Brady et al. |
| 2007/0048275 | A1 | 3/2007 | Brady et al. |
| 2007/0048276 | A1 | 3/2007 | Brady et al. |
| 2007/0048277 | A1 | 3/2007 | Brady et al. |
| 2007/0048841 | A1 | 3/2007 | Sheppard et al. |
| 2007/0048844 | A1 | 3/2007 | Brady et al. |
| 2007/0053875 | A1 | 3/2007 | Brady et al. |
| 2007/0053933 | A1 | 3/2007 | Sheppard et al. |
| 2007/0054374 | A1 | 3/2007 | Brady et al. |
| 2007/0054375 | A1 | 3/2007 | Brady et al. |
| 2007/0054376 | A1 | 3/2007 | Brady et al. |
| 2007/0054377 | A1 | 3/2007 | Brady et al. |
| 2007/0055051 | A1 | 3/2007 | Brady et al. |
| 2007/0059804 | A1 | 3/2007 | Brady et al. |
| 2007/0065406 | A1 | 3/2007 | Brady et al. |
| 2007/0128205 | A1 | 6/2007 | Sheppard et al. |
| 2007/0129538 | A1 | 6/2007 | Sheppard et al. |
| 2007/0154446 | A1 | 7/2007 | Brady et al. |
| 2007/0166282 | A1 | 7/2007 | Brady et al. |
| 2007/0172923 | A1 | 7/2007 | Brady et al. |
| 2007/0264684 | A1 | 11/2007 | Sheppard et al. |
| 2008/0032334 | A1 | 2/2008 | Sheppard et al. |

(Continued)

FOREIGN PATENT DOCUMENTS

CN 1 670 033 9/2005

(Continued)

OTHER PUBLICATIONS

Kotenko et al. Nature Immunology, vol. 4, pp. 69-77, (Published Dec. 16, 2002).*

(Continued)

*Primary Examiner*—Christine J Saoud
*Assistant Examiner*—Fozia M Hamud
(74) *Attorney, Agent, or Firm*—Brian J. Walsh

(57) ABSTRACT

Homogeneous preparations of IL-28A, IL-28B, and IL-29 have been produced by mutating one or more of the cysteine residues in the polynucleotide sequences encoding the mature proteins. The cysteine mutant proteins can be shown to either bind to their cognate receptor or exhibit biological activity. One type of biological activity that is shown is an antiviral activity.

14 Claims, No Drawings

U.S. PATENT DOCUMENTS

| | | | |
|---|---|---|---|
| 2008/0075693 A1 | 3/2008 | Klucher et al. |
| 2008/0081786 A1 | 4/2008 | Sheppard et al. |
| 2008/0096252 A1 | 4/2008 | Zamost et al. |
| 2008/0102490 A1 | 5/2008 | Sheppard et al. |

FOREIGN PATENT DOCUMENTS

| | | | |
|---|---|---|---|
| EP | 0 032 134 | | 7/1981 |
| WO | 00/55324 | | 9/2000 |
| WO | 02/02627 | | 1/2002 |
| WO | 02/20569 | | 3/2002 |
| WO | 02/086087 | | 10/2002 |
| WO | WO02092762 | * | 11/2002 |
| WO | 03/066002 | | 8/2003 |
| WO | 03/089603 | | 10/2003 |
| WO | 2004/037995 | | 5/2004 |
| WO | 2005/023862 | | 3/2005 |
| WO | 2005/097165 | | 10/2005 |
| WO | 2006/012644 | | 2/2006 |

OTHER PUBLICATIONS

Sheppard et al. Nature Immunology, vol. 4, pp. 63-68, (Published Dec. 2, 2002).*
Langer et al., "The Class II cytokine receptor (CRF2) family: overview and patterns of receptor-ligand interactions," *Cytokine and Growth Factor Reviews* 15:33-48, 2007.
Donnelly et al., "The expanded family of class II cytokines that share the IL-10 receptor-2 (IL-10R2) chain," *J. Leukocyte Biol.* 76:314-321, 2004.
Dumoutier et al., "Role of the Interleukin (IL)-28 Receptor Tyrosine Residues for Antiviral and Antiproliferative Activity of IL-29/Interferon-11," *J. Biochem.* 279(31):32269-32274, 2004.
University Calif. Santa Cruz Genome Browser - Chromosome 19, Apr. 20, 2001.
University Calif. Santa Cruz Genome Browser Database - Aug. 6, 2001, Accession No. C19001210.
University Calif. Santa Cruz Genome Browser Database - Aug. 6, 2001, Accession No. C19001212.
University Calif. Santa Cruz Genome Browser Database - Aug. 6, 2001, Accession No. C19001213.
University Calif. Santa Cruz Genome Browser Database - Dec. 22, 2001, Accession No. C19001260.
University Calif. Santa Cruz Genome Browser Database - Dec. 22, 2001, Accession No. C19001256.
University Calif. Santa Cruz Genome Browser Database - Dec. 22, 2001, Accession No. C19001257.
Ensembl Contig. View Sanger Institute - Apr. 19, 2001, Accession No. AC011445.
Ensembl Contig. View Sanger Institute - Apr. 18, 2001, Accession No. AC018477.
Adams et al., "3,400 expressed sequence tags identify diversity of transcripts from human brain," *Nat. Genet.* 4:256-267, 1993.
GenBank Submission XP-002202436, Oct. 12, 2000.
GenBank Submission XP-002202437, Dec. 12, 1999.
Kindsvogel et al., "Novel Interferon-Like Cytokines not Recognized by the Type I Interferon Receptor," *J. Interferon Cytokine Res.* 22(1):S-48, 2002.
Adams et al., Accession No. T07139, 1993.
DOE Joint Genome Institute Stanford Human Genome Center, Accession No. AC011445, 1999.
Muzney et al., Accession No. AC007458, 1999.
University of California Santa Cruz database using Softberry, Inc. gene prediction software, Accession No. C19001084, 2001.
Scott et al., "The Pendred syndrome gene encodes a chloride-iodide transport protein," *Nature Genetics*, 21:440-443, 1999.
Korba et al., "A cell culture assay for compounds which inhibit hepatitic B virus replication," *Antiviral Research* 15:217-228, 1991.
Brack et al., "Molecular analysis of the human interferon-a gene family," *Gene* 15:379-394, 1981.
Francis et al., "PEGylation of cytokines and other therapeutic proteins and peptides: the importance of biological optimization of coupling techniques," *International Journal of Hematology*, 68(1):1-18, 1998.
Rajarathnam et al., "Disulfide Bridges in Interleukin-8 Probed Using Non-Natural Disulfide Analogues: dissociation of Roles in Structure from Function," *Biochemistry* 38:7653-7658, 1999.
Luxon et al., "Pegylated Interferons for the Treatment of Chronic Hepatitis C Infection," *Clinical Therapeutics* 26(9):1363-1383, 2002.
Kozlowski et al., "Improvements in protein OEGylation: pegylated interferons for treatment of hepatitis C," *Journal of Controlled Release* 72:217-224, 2001.
Goodson et al., "Site-Directed Pegylation of Recombinant Interleukin-2 at its Glycosylation Site," *Bio/Technology* 8(4):343-346, 1990.
Pettit et al., "Structure-Function Studies of Interleukin 15 using Site-specific Mutagenesis, Polyethylene Glycol Conjugation, and Homology Modeling," *J. Biochem* 272(4):2312-2318, 1997.
Burge et al., "Prediction of Complete Gene Structures in Human Genomic DNA," *J. Mol. Biol.* 268:78-94, 1997.
Vilcek, "Novel interferons," Nature Immunology 4(1):8-9, 2003.
Kozlowski et al., Bio. Drug., 15(7): 419-429, 2001.
Wells, Biochemistry, 29(37): 8509-8517, 1990.
Brand et al., Gastroenterology, 128(4): A751, 2005.
Brand et al., Am. J. Physiol. Gastrointest. Liver Physiol., 289(5):G960-G968, 2005.
Meager et al., Cytokine, 31(2): 109-118, 2005.
Li et al., Journal of Biotechnology, 122(3): 334-340, 2006.
Xie et al., Journal of Biological Chemistry, 275(40): 31335-31339, 2000.
Sheppard et al., U.S. Appl. No. 11/539,043, filed Oct. 5, 2006.
Sheppard et al., U.S. Appl. No. 11/971,624, filed Jan. 9, 2008.
Sheppard et al., U.S. Appl. No. 11/873,272, filed Oct. 16, 2007.
Klucher et al., U.S. Appl. No. 11/929,063, filed Oct. 30, 2007.
Brady et al., U.S. Appl. No. 12/043,885, filed Mar. 6, 2008.
Doyle et al., U.S. Appl. No. 12/030,107, filed Feb. 12, 2008.

* cited by examiner

SEQUENCE LISTING

```
<160> NUMBER OF SEQ ID NOS: 161

<210> SEQ ID NO 1
<211> LENGTH: 734
<212> TYPE: DNA
<213> ORGANISM: Homo sapiens
<220> FEATURE:
<221> NAME/KEY: sig_peptide
<222> LOCATION: (53)...(127)
<220> FEATURE:
<221> NAME/KEY: mat_peptide
<222> LOCATION: (128)...(655)
<220> FEATURE:
<221> NAME/KEY: CDS
<222> LOCATION: (53)...(655)
```

<400> SEQUENCE: 1

```
tgggtgacag cctcagagtg tttcttctgc tgacaaagac cagagatcag ga atg aaa       58
                                                           Met Lys
                                                               -25 cta gac atg act ggg gac tgc acg cca gtg ctg gtg ctg atg gcc gca        106
Leu Asp Met Thr Gly Asp Cys Thr Pro Val Leu Val Leu Met Ala Ala
        -20                 -15                 -10 gtg ctg acc gtg act gga gca gtt cct gtc gcc agg ctc cac ggg gct        154
Val Leu Thr Val Thr Gly Ala Val Pro Val Ala Arg Leu His Gly Ala
    -5                   1               5 ctc ccg gat gca agg ggc tgc cac ata gcc cag ttc aag tcc ctg tct        202
Leu Pro Asp Ala Arg Gly Cys His Ile Ala Gln Phe Lys Ser Leu Ser
10                  15                  20                  25 cca cag gag ctg cag gcc ttt aag agg gcc aaa gat gcc tta gaa gag        250
Pro Gln Glu Leu Gln Ala Phe Lys Arg Ala Lys Asp Ala Leu Glu Glu
                30                  35                  40 tcg ctt ctg ctg aag gac tgc agg tgc cac tcc cgc ctc ttc ccc agg        298
Ser Leu Leu Leu Lys Asp Cys Arg Cys His Ser Arg Leu Phe Pro Arg
            45                  50                  55 acc tgg gac ctg agg cag ctg cag gtg agg gag cgc ccc atg gct ttg        346
Thr Trp Asp Leu Arg Gln Leu Gln Val Arg Glu Arg Pro Met Ala Leu
        60                  65                  70 gag gct gag ctg gcc ctg acg ctg aag gtt ctg gag gcc acc gct gac        394
Glu Ala Glu Leu Ala Leu Thr Leu Lys Val Leu Glu Ala Thr Ala Asp
    75                  80                  85 act gac cca gcc ctg gtg gac gtc ttg gac cag ccc ctt cac acc ctg        442
Thr Asp Pro Ala Leu Val Asp Val Leu Asp Gln Pro Leu His Thr Leu
90                  95                  100                 105 cac cat atc ctc tcc cag ttc cgg gcc tgt atc cag cct cag ccc acg        490
His His Ile Leu Ser Gln Phe Arg Ala Cys Ile Gln Pro Gln Pro Thr
            110                 115                 120 gca ggg ccc agg acc cgg ggc cgc ctc cac cat tgg ctg tac cgg ctc        538
Ala Gly Pro Arg Thr Arg Gly Arg Leu His His Trp Leu Tyr Arg Leu
        125                 130                 135 cag gag gcc cca aaa aag gag tcc cct ggc tgc ctc gag gcc tct gtc        586
Gln Glu Ala Pro Lys Lys Glu Ser Pro Gly Cys Leu Glu Ala Ser Val
    140                 145                 150 acc ttc aac ctc ttc cgc ctc ctc acg cga gac ctg aat tgt gtt gcc        634
Thr Phe Asn Leu Phe Arg Leu Leu Thr Arg Asp Leu Asn Cys Val Ala
155                 160                 165 agt ggg gac ctg tgt gtc tga ccctcccacc agtcatgcaa cctgagattt          685
Ser Gly Asp Leu Cys Val  *
170             175 tatttataaa ttagccactt gtcttaattt attgccaccc agtcgctat                 734
```

<210> SEQ ID NO 2
<211> LENGTH: 200
<212> TYPE: PRT
<213> ORGANISM: Homo sapiens
<220> FEATURE:
<221> NAME/KEY: SIGNAL
<222> LOCATION: (1)...(25)

<400> SEQUENCE: 2

```
Met Lys Leu Asp Met Thr Gly Asp Cys Thr Pro Val Leu Val Leu Met
-25                 -20                 -15                 -10

Ala Ala Val Leu Thr Val Thr Gly Ala Val Pro Val Ala Arg Leu His
            -5                   1               5

Gly Ala Leu Pro Asp Ala Arg Gly Cys His Ile Ala Gln Phe Lys Ser
```

-continued

```
                   10                  15                  20
Leu Ser Pro Gln Glu Leu Gln Ala Phe Lys Arg Ala Lys Asp Ala Leu
    25                  30                  35
Glu Glu Ser Leu Leu Leu Lys Asp Cys Arg Cys His Ser Arg Leu Phe
40                  45                  50                  55
Pro Arg Thr Trp Asp Leu Arg Gln Leu Gln Val Arg Glu Arg Pro Met
                60                  65                  70
Ala Leu Glu Ala Glu Leu Ala Leu Thr Leu Lys Val Leu Glu Ala Thr
            75                  80                  85
Ala Asp Thr Asp Pro Ala Leu Val Asp Val Leu Asp Gln Pro Leu His
        90                  95                  100
Thr Leu His His Ile Leu Ser Gln Phe Arg Ala Cys Ile Gln Pro Gln
    105                 110                 115
Pro Thr Ala Gly Pro Arg Thr Arg Gly Arg Leu His His Trp Leu Tyr
120                 125                 130                 135
Arg Leu Gln Glu Ala Pro Lys Lys Glu Ser Pro Gly Cys Leu Glu Ala
                140                 145                 150
Ser Val Thr Phe Asn Leu Phe Arg Leu Leu Thr Arg Asp Leu Asn Cys
            155                 160                 165
Val Ala Ser Gly Asp Leu Cys Val
        170                 175

<210> SEQ ID NO 3
<211> LENGTH: 856
<212> TYPE: DNA
<213> ORGANISM: Homo sapiens
<220> FEATURE:
<221> NAME/KEY: sig_peptide
<222> LOCATION: (98)...(154)
<220> FEATURE:
<221> NAME/KEY: mat_peptide
<222> LOCATION: (155)...(700)
<220> FEATURE:
<221> NAME/KEY: CDS
<222> LOCATION: (98)...(700)

<400> SEQUENCE: 3
aattaccttt tcactttaca cacatcatct tggattgccc attttgcgtg gctaaaaagc        60
agagccatgc cgctggggaa gcagttgcga tttagcc atg gct gca gct tgg acc       115
                                        Met Ala Ala Ala Trp Thr
                                                        -15 gtg gtg ctg gtg act ttg gtg cta ggc ttg gcc gtg gca ggc cct gtc       163
Val Val Leu Val Thr Leu Val Leu Gly Leu Ala Val Ala Gly Pro Val
            -10                  -5                   1 ccc act tcc aag ccc acc aca act ggg aag ggc tgc cac att ggc agg       211
Pro Thr Ser Lys Pro Thr Thr Thr Gly Lys Gly Cys His Ile Gly Arg
 5                  10                  15 ttc aaa tct ctg tca cca cag gag cta gcg agc ttc aag aag gcc agg       259
Phe Lys Ser Leu Ser Pro Gln Glu Leu Ala Ser Phe Lys Lys Ala Arg
     20                  25                  30                  35 gac gcc ttg gaa gag tca ctc aag ctg aaa aac tgg agt tgc agc tct       307
Asp Ala Leu Glu Glu Ser Leu Lys Leu Lys Asn Trp Ser Cys Ser Ser
                 40                  45                  50 cct gtc ttc ccc ggg aat tgg gac ctg agg ctt ctc cag gtg agg gag       355
Pro Val Phe Pro Gly Asn Trp Asp Leu Arg Leu Leu Gln Val Arg Glu
             55                  60                  65 cgc cct gtg gcc ttg gag gct gag ctg gcc ctg acg ctg aag gtc ctg       403
Arg Pro Val Ala Leu Glu Ala Glu Leu Ala Leu Thr Leu Lys Val Leu
         70                  75                  80
```

-continued

```
gag gcc gct gct ggc cca gcc ctg gag gac gtc cta gac cag ccc ctt    451
Glu Ala Ala Ala Gly Pro Ala Leu Glu Asp Val Leu Asp Gln Pro Leu
 85                  90                  95 cac acc ctg cac cac atc ctc tcc cag ctc cag gcc tgt atc cag cct    499
His Thr Leu His His Ile Leu Ser Gln Leu Gln Ala Cys Ile Gln Pro
100                 105                 110                 115 cag ccc aca gca ggg ccc agg ccc cgg ggc cgc ctc cac cac tgg ctg    547
Gln Pro Thr Ala Gly Pro Arg Pro Arg Gly Arg Leu His His Trp Leu
                120                 125                 130 cac cgg ctc cag gag gcc ccc aaa aag gag tcc gct ggc tgc ctg gag    595
His Arg Leu Gln Glu Ala Pro Lys Lys Glu Ser Ala Gly Cys Leu Glu
                135                 140                 145 gca tct gtc acc ttc aac ctc ttc cgc ctc ctc acg cga gac ctc aaa    643
Ala Ser Val Thr Phe Asn Leu Phe Arg Leu Leu Thr Arg Asp Leu Lys
150                 155                 160 tat gtg gcc gat ggg aac ctg tgt ctg aga acg tca acc cac cct gag    691
Tyr Val Ala Asp Gly Asn Leu Cys Leu Arg Thr Ser Thr His Pro Glu
165                 170                 175 tcc acc tga cacccccacac cttatttatg cgctgagccc tactccttcc           740
Ser Thr  *
180 ttaatttatt tcctctcacc ctttatttat gaagctgcag ccctgactga gacatagggc  800 tgagttatt gttttacttt tatacattat gcacaaataa acaacaagga attgga       856

<210> SEQ ID NO 4
<211> LENGTH: 200
<212> TYPE: PRT
<213> ORGANISM: Homo sapiens
<220> FEATURE:
<221> NAME/KEY: SIGNAL
<222> LOCATION: (1)...(19)

<400> SEQUENCE: 4

Met Ala Ala Ala Trp Thr Val Leu Val Thr Leu Val Leu Gly Leu
                -15                 -10                  -5

Ala Val Ala Gly Pro Val Pro Thr Ser Lys Pro Thr Thr Thr Gly Lys
                  1               5                  10

Gly Cys His Ile Gly Arg Phe Lys Ser Leu Ser Pro Gln Glu Leu Ala
         15                  20                  25

Ser Phe Lys Lys Ala Arg Asp Ala Leu Glu Glu Ser Leu Lys Leu Lys
 30                  35                  40                  45

Asn Trp Ser Cys Ser Ser Pro Val Phe Pro Gly Asn Trp Asp Leu Arg
                 50                  55                  60

Leu Leu Gln Val Arg Glu Arg Pro Val Ala Leu Glu Ala Glu Leu Ala
                 65                  70                  75

Leu Thr Leu Lys Val Leu Glu Ala Ala Ala Gly Pro Ala Leu Glu Asp
             80                  85                  90

Val Leu Asp Gln Pro Leu His Thr Leu His His Ile Leu Ser Gln Leu
             95                 100                 105

Gln Ala Cys Ile Gln Pro Gln Pro Thr Ala Gly Pro Arg Pro Arg Gly
110                 115                 120                 125

Arg Leu His His Trp Leu His Arg Leu Gln Glu Ala Pro Lys Lys Glu
                130                 135                 140

Ser Ala Gly Cys Leu Glu Ala Ser Val Thr Phe Asn Leu Phe Arg Leu
                145                 150                 155

Leu Thr Arg Asp Leu Lys Tyr Val Ala Asp Gly Asn Leu Cys Leu Arg
                160                 165                 170
```

```
Thr Ser Thr His Pro Glu Ser Thr
    175             180
```

<210> SEQ ID NO 5
<211> LENGTH: 734
<212> TYPE: DNA
<213> ORGANISM: Homo sapiens
<220> FEATURE:
<221> NAME/KEY: sig_peptide
<222> LOCATION: (53)...(127)
<220> FEATURE:
<221> NAME/KEY: mat_peptide
<222> LOCATION: (128)...(655)
<220> FEATURE:
<221> NAME/KEY: CDS
<222> LOCATION: (53)...(655)

<400> SEQUENCE: 5

```
tgggtgacag cctcagagtg tttcttctgc tgacaaagac cagagatcag ga atg aaa          58
                                                         Met Lys
                                                         -25 cta gac atg acc ggg gac tgc atg cca gtg ctg gtg ctg atg gcc gca          106
Leu Asp Met Thr Gly Asp Cys Met Pro Val Leu Val Leu Met Ala Ala
        -20             -15                 -10 gtg ctg acc gtg act gga gca gtt cct gtc gcc agg ctc cgc ggg gct          154
Val Leu Thr Val Thr Gly Ala Val Pro Val Ala Arg Leu Arg Gly Ala
    -5                   1               5 ctc ccg gat gca agg ggc tgc cac ata gcc cag ttc aag tcc ctg tct          202
Leu Pro Asp Ala Arg Gly Cys His Ile Ala Gln Phe Lys Ser Leu Ser
 10              15                  20                  25 cca cag gag ctg cag gcc ttt aag agg gcc aaa gat gcc tta gaa gag          250
Pro Gln Glu Leu Gln Ala Phe Lys Arg Ala Lys Asp Ala Leu Glu Glu
             30                  35                  40 tcg ctt ctg ctg aag gac tgc aag tgc cgc tcc cgc ctc ttc ccc agg          298
Ser Leu Leu Leu Lys Asp Cys Lys Cys Arg Ser Arg Leu Phe Pro Arg
                 45                  50                  55 acc tgg gac ctg agg cag ctg cag gtg agg gag cgc ccc gtg gct ttg          346
Thr Trp Asp Leu Arg Gln Leu Gln Val Arg Glu Arg Pro Val Ala Leu
             60                  65                  70 gag gct gag ctg gcc ctg acg ctg aag gtt ctg gag gcc acc gct gac          394
Glu Ala Glu Leu Ala Leu Thr Leu Lys Val Leu Glu Ala Thr Ala Asp
 75                  80                  85 act gac cca gcc ctg ggg gat gtc ttg gac cag ccc ctt cac acc ctg          442
Thr Asp Pro Ala Leu Gly Asp Val Leu Asp Gln Pro Leu His Thr Leu
 90                  95                 100                 105 cac cat atc ctc tcc cag ctc cgg gcc tgt atc cag cct cag ccc acg          490
His His Ile Leu Ser Gln Leu Arg Ala Cys Ile Gln Pro Gln Pro Thr
                 110                 115                 120 gca ggg ccc agg acc cgg ggc cgc ctc cac cat tgg ctg cac cgg ctc          538
Ala Gly Pro Arg Thr Arg Gly Arg Leu His His Trp Leu His Arg Leu
             125                 130                 135 cag gag gcc cca aaa aag gag tcc cct ggc tgc ctc gag gcc tct gtc          586
Gln Glu Ala Pro Lys Lys Glu Ser Pro Gly Cys Leu Glu Ala Ser Val
             140                 145                 150 acc ttc aac ctc ttc cgc ctc ctc acg cga gac ctg aat tgt gtt gcc          634
Thr Phe Asn Leu Phe Arg Leu Leu Thr Arg Asp Leu Asn Cys Val Ala
 155                 160                 165 agc ggg gac ctg tgt gtc tga cccttccgcc agtcatgcaa cctgagattt            685
Ser Gly Asp Leu Cys Val  *
 170             175 tatttataaa ttagccactt ggcttaattt attgccaccc agtcgctat                    734
```

<210> SEQ ID NO 6
<211> LENGTH: 200
<212> TYPE: PRT
<213> ORGANISM: Homo sapiens
<220> FEATURE:
<221> NAME/KEY: SIGNAL
<222> LOCATION: (1)...(25)

<400> SEQUENCE: 6

```
Met Lys Leu Asp Met Thr Gly Asp Cys Met Pro Val Leu Val Leu Met
-25                 -20                 -15                 -10

Ala Ala Val Leu Thr Val Thr Gly Ala Val Pro Val Ala Arg Leu Arg
            -5                   1               5

Gly Ala Leu Pro Asp Ala Arg Gly Cys His Ile Ala Gln Phe Lys Ser
        10                  15                  20

Leu Ser Pro Gln Glu Leu Gln Ala Phe Lys Arg Ala Lys Asp Ala Leu
        25                  30                  35

Glu Glu Ser Leu Leu Lys Asp Cys Lys Cys Arg Ser Arg Leu Phe
 40              45                  50                  55

Pro Arg Thr Trp Asp Leu Arg Gln Leu Gln Val Arg Glu Arg Pro Val
                60                  65                  70

Ala Leu Glu Ala Glu Leu Ala Leu Thr Leu Lys Val Leu Glu Ala Thr
            75                  80                  85

Ala Asp Thr Asp Pro Ala Leu Gly Asp Val Leu Asp Gln Pro Leu His
            90                  95                  100

Thr Leu His His Ile Leu Ser Gln Leu Arg Ala Cys Ile Gln Pro Gln
        105                 110                 115

Pro Thr Ala Gly Pro Arg Thr Arg Gly Arg Leu His His Trp Leu His
120                 125                 130                 135

Arg Leu Gln Glu Ala Pro Lys Lys Glu Ser Pro Gly Cys Leu Glu Ala
                140                 145                 150

Ser Val Thr Phe Asn Leu Phe Arg Leu Leu Thr Arg Asp Leu Asn Cys
            155                 160                 165

Val Ala Ser Gly Asp Leu Cys Val
        170                 175
```

<210> SEQ ID NO 7
<211> LENGTH: 633
<212> TYPE: DNA
<213> ORGANISM: Mus musculus
<220> FEATURE:
<221> NAME/KEY: sig_peptide
<222> LOCATION: (22)...(105)
<220> FEATURE:
<221> NAME/KEY: mat_peptide
<222> LOCATION: (106)...(630)
<220> FEATURE:
<221> NAME/KEY: CDS
<222> LOCATION: (22)...(630)

<400> SEQUENCE: 7

```
tcacagaccc cggagagcaa c atg aag cca gaa aca gct ggg ggc cac atg      51
                        Met Lys Pro Glu Thr Ala Gly Gly His Met
                            -25                 -20 ctc ctc ctg ctg ttg cct ctg ctg gcc gca gtg ctg aca aga acc         99
Leu Leu Leu Leu Leu Pro Leu Leu Ala Ala Val Leu Thr Arg Thr
            -15                 -10                  -5 caa gct gac cct gtc ccc agg gcc acc agg ctc cca gtg gaa gca aag    147
Gln Ala Asp Pro Val Pro Arg Ala Thr Arg Leu Pro Val Glu Ala Lys
     1               5                   10 gat tgc cac att gct cag ttc aag tct ctg tcc cca aaa gag ctg cag    195
```

```
Asp Cys His Ile Ala Gln Phe Lys Ser Leu Ser Pro Lys Glu Leu Gln
 15                  20                  25                  30 gcc ttc aaa aag gcc aag gat gcc atc gag aag agg ctg ctt gag aag       243
Ala Phe Lys Lys Ala Lys Asp Ala Ile Glu Lys Arg Leu Leu Glu Lys
             35                  40                  45 gac ctg agg tgc agt tcc cac ctc ttc ccc agg gcc tgg gac ctg aag       291
Asp Leu Arg Cys Ser Ser His Leu Phe Pro Arg Ala Trp Asp Leu Lys
                 50                  55                  60 cag ctg cag gtc caa gag cgc ccc aag gct ttg cag gct gag gtg gcc       339
Gln Leu Gln Val Gln Glu Arg Pro Lys Ala Leu Gln Ala Glu Val Ala
             65                  70                  75 ctg acc ctg aag gtc tgg gag aac atg act gac tca gcc ctg gcc acc       387
Leu Thr Leu Lys Val Trp Glu Asn Met Thr Asp Ser Ala Leu Ala Thr
         80                  85                  90 atc ctg ggc cag cct ctt cat aca ctg agc cac att cac tcc cag ctg       435
Ile Leu Gly Gln Pro Leu His Thr Leu Ser His Ile His Ser Gln Leu
 95                 100                 105                 110 cag acc tgt aca cag ctt cag gcc aca gca gag ccc agg tcc ccg agc       483
Gln Thr Cys Thr Gln Leu Gln Ala Thr Ala Glu Pro Arg Ser Pro Ser
                115                 120                 125 cgc cgc ctc tcc cgc tgg ctg cac agg ctc cag gag gcc cag agc aag       531
Arg Arg Leu Ser Arg Trp Leu His Arg Leu Gln Glu Ala Gln Ser Lys
            130                 135                 140 gag acc cct ggc tgc ctg gag gcc tct gtc acc tcc aac ctg ttt cgc       579
Glu Thr Pro Gly Cys Leu Glu Ala Ser Val Thr Ser Asn Leu Phe Arg
        145                 150                 155 ctg ctc acc cgg gac ctc aag tgt gtg gcc aat gga gac cag tgt gtc       627
Leu Leu Thr Arg Asp Leu Lys Cys Val Ala Asn Gly Asp Gln Cys Val
    160                 165                 170 tga cct                                                                633
 *

<210> SEQ ID NO 8
<211> LENGTH: 202
<212> TYPE: PRT
<213> ORGANISM: Mus musculus
<220> FEATURE:
<221> NAME/KEY: SIGNAL
<222> LOCATION: (1)...(28)

<400> SEQUENCE: 8

Met Lys Pro Glu Thr Ala Gly Gly His Met Leu Leu Leu Leu Pro
            -25                 -20                 -15

Leu Leu Leu Ala Ala Val Leu Thr Arg Thr Gln Ala Asp Pro Val Pro
        -10                  -5                   1

Arg Ala Thr Arg Leu Pro Val Glu Ala Lys Asp Cys His Ile Ala Gln
  5                  10                  15                  20

Phe Lys Ser Leu Ser Pro Lys Glu Leu Gln Ala Phe Lys Lys Ala Lys
                 25                  30                  35

Asp Ala Ile Glu Lys Arg Leu Leu Lys Asp Leu Arg Cys Ser Ser
             40                  45                  50

His Leu Phe Pro Arg Ala Trp Asp Leu Lys Gln Leu Gln Val Gln Glu
         55                  60                  65

Arg Pro Lys Ala Leu Gln Ala Glu Val Ala Leu Thr Leu Lys Val Trp
     70                  75                  80

Glu Asn Met Thr Asp Ser Ala Leu Ala Thr Ile Leu Gly Gln Pro Leu
 85                  90                  95                 100

His Thr Leu Ser His Ile His Ser Gln Leu Gln Thr Cys Thr Gln Leu
                105                 110                 115
```

```
Gln Ala Thr Ala Glu Pro Arg Ser Pro Ser Arg Arg Leu Ser Arg Trp
            120                 125                 130

Leu His Arg Leu Gln Glu Ala Gln Ser Lys Glu Thr Pro Gly Cys Leu
        135                 140                 145

Glu Ala Ser Val Thr Ser Asn Leu Phe Arg Leu Leu Thr Arg Asp Leu
    150                 155                 160

Lys Cys Val Ala Asn Gly Asp Gln Cys Val
165                 170

<210> SEQ ID NO 9
<211> LENGTH: 632
<212> TYPE: DNA
<213> ORGANISM: Mus musculus
<220> FEATURE:
<221> NAME/KEY: sig_peptide
<222> LOCATION: (22)...(105)
<220> FEATURE:
<221> NAME/KEY: mat_peptide
<222> LOCATION: (106)...(630)
<220> FEATURE:
<221> NAME/KEY: CDS
<222> LOCATION: (22)...(630)

<400> SEQUENCE: 9
tcacagaccc cggagagcaa c atg aag cca gaa aca gct ggg ggc cac atg        51
                        Met Lys Pro Glu Thr Ala Gly Gly His Met
                            -25                 -20 ctc ctc ctg ctg ttg cct ctg ctg ctg gcc gca gtg ctg aca aga acc        99
Leu Leu Leu Leu Leu Pro Leu Leu Leu Ala Ala Val Leu Thr Arg Thr
                -15                 -10                 -5 caa gct gac cct gtc ccc agg gcc acc agg ctc cca gtg gaa gca aag       147
Gln Ala Asp Pro Val Pro Arg Ala Thr Arg Leu Pro Val Glu Ala Lys
  1               5                  10 gat tgc cac att gct cag ttc aag tct ctg tcc cca aaa gag ctg cag       195
Asp Cys His Ile Ala Gln Phe Lys Ser Leu Ser Pro Lys Glu Leu Gln
 15                  20                  25                  30 gcc ttc aaa aag gcc aag ggt gcc atc gag aag agg ctg ctt gag aag       243
Ala Phe Lys Lys Ala Lys Gly Ala Ile Glu Lys Arg Leu Leu Glu Lys
                 35                  40                  45 gac atg agg tgc agt tcc cac ctc atc tcc agg gcc tgg gac ctg aag       291
Asp Met Arg Cys Ser Ser His Leu Ile Ser Arg Ala Trp Asp Leu Lys
             50                  55                  60 cag ctg cag gtc caa gag cgc ccc aag gcc ttg cag gct gag gtg gcc       339
Gln Leu Gln Val Gln Glu Arg Pro Lys Ala Leu Gln Ala Glu Val Ala
         65                  70                  75 ctg acc ctg aag gtc tgg gag aac ata aat gac tca gcc ctg acc acc       387
Leu Thr Leu Lys Val Trp Glu Asn Ile Asn Asp Ser Ala Leu Thr Thr
     80                  85                  90 atc ctg ggc cag cct ctt cat aca ctg agc cac att cac tcc cag ctg       435
Ile Leu Gly Gln Pro Leu His Thr Leu Ser His Ile His Ser Gln Leu
 95                 100                 105                 110 cag acc tgt aca cag ctt cag gcc aca gca gag ccc aag ccc ccg agt       483
Gln Thr Cys Thr Gln Leu Gln Ala Thr Ala Glu Pro Lys Pro Pro Ser
                115                 120                 125 cgc cgc ctc tcc cgc tgg ctg cac agg ctc cag gag gcc cag agc aag       531
Arg Arg Leu Ser Arg Trp Leu His Arg Leu Gln Glu Ala Gln Ser Lys
            130                 135                 140 gag act cct ggc tgc ctg gag gac tct gtc acc tcc aac ctg ttt caa       579
Glu Thr Pro Gly Cys Leu Glu Asp Ser Val Thr Ser Asn Leu Phe Gln
        145                 150                 155 ctg ctc ctc cgg gac ctc aag tgt gtg gcc agt gga gac cag tgt gtc       627
```

```
Leu Leu Leu Arg Asp Leu Lys Cys Val Ala Ser Gly Asp Gln Cys Val
        160             165             170 tga cc                                                                632
 *
```

```
<210> SEQ ID NO 10
<211> LENGTH: 202
<212> TYPE: PRT
<213> ORGANISM: Mus musculus
<220> FEATURE:
<221> NAME/KEY: SIGNAL
<222> LOCATION: (1)...(28)

<400> SEQUENCE: 10
```

```
Met Lys Pro Glu Thr Ala Gly Gly His Met Leu Leu Leu Leu Pro
        -25             -20             -15

Leu Leu Leu Ala Ala Val Leu Thr Arg Thr Gln Ala Asp Pro Val Pro
        -10             -5              1

Arg Ala Thr Arg Leu Pro Val Glu Ala Lys Asp Cys His Ile Ala Gln
 5               10              15              20

Phe Lys Ser Leu Ser Pro Lys Glu Leu Gln Ala Phe Lys Lys Ala Lys
                25              30              35

Gly Ala Ile Glu Lys Arg Leu Leu Glu Lys Asp Met Arg Cys Ser Ser
            40              45              50

His Leu Ile Ser Arg Ala Trp Asp Leu Lys Gln Leu Gln Val Gln Glu
        55              60              65

Arg Pro Lys Ala Leu Gln Ala Glu Val Ala Leu Thr Leu Lys Val Trp
 70              75              80

Glu Asn Ile Asn Asp Ser Ala Leu Thr Thr Ile Leu Gly Gln Pro Leu
85              90              95              100

His Thr Leu Ser His Ile His Ser Gln Leu Gln Thr Cys Thr Gln Leu
                105             110             115

Gln Ala Thr Ala Glu Pro Lys Pro Ser Arg Arg Leu Ser Arg Trp
            120             125             130

Leu His Arg Leu Gln Glu Ala Gln Ser Lys Glu Thr Pro Gly Cys Leu
        135             140             145

Glu Asp Ser Val Thr Ser Asn Leu Phe Gln Leu Leu Leu Arg Asp Leu
 150             155             160

Lys Cys Val Ala Ser Gly Asp Gln Cys Val
 165             170
```

```
<210> SEQ ID NO 11
<211> LENGTH: 520
<212> TYPE: PRT
<213> ORGANISM: Homo sapiens

<400> SEQUENCE: 11
```

```
Met Ala Gly Pro Glu Arg Trp Gly Pro Leu Leu Leu Cys Leu Leu Gln
 1               5               10              15

Ala Ala Pro Gly Arg Pro Arg Leu Ala Pro Pro Gln Asn Val Thr Leu
                20              25              30

Leu Ser Gln Asn Phe Ser Val Tyr Leu Thr Trp Leu Pro Gly Leu Gly
            35              40              45

Asn Pro Gln Asp Val Thr Tyr Phe Val Ala Tyr Gln Ser Ser Pro Thr
        50              55              60

Arg Arg Arg Trp Arg Glu Val Glu Glu Cys Ala Gly Thr Lys Glu Leu
65              70              75              80
```

-continued

```
Leu Cys Ser Met Met Cys Leu Lys Lys Gln Asp Leu Tyr Asn Lys Phe
                 85                  90                  95
Lys Gly Arg Val Arg Thr Val Ser Pro Ser Ser Lys Ser Pro Trp Val
            100                 105                 110
Glu Ser Glu Tyr Leu Asp Tyr Leu Phe Glu Val Glu Pro Ala Pro Pro
            115                 120                 125
Val Leu Val Leu Thr Gln Thr Glu Glu Ile Leu Ser Ala Asn Ala Thr
130                 135                 140
Tyr Gln Leu Pro Pro Cys Met Pro Pro Leu Asp Leu Lys Tyr Glu Val
145                 150                 155                 160
Ala Phe Trp Lys Glu Gly Ala Gly Asn Lys Thr Leu Phe Pro Val Thr
                165                 170                 175
Pro His Gly Gln Pro Val Gln Ile Thr Leu Gln Pro Ala Ala Ser Glu
                180                 185                 190
His His Cys Leu Ser Ala Arg Thr Ile Tyr Thr Phe Ser Val Pro Lys
            195                 200                 205
Tyr Ser Lys Phe Ser Lys Pro Thr Cys Phe Leu Leu Glu Val Pro Glu
210                 215                 220
Ala Asn Trp Ala Phe Leu Val Leu Pro Ser Leu Leu Ile Leu Leu Leu
225                 230                 235                 240
Val Ile Ala Ala Gly Gly Val Ile Trp Lys Thr Leu Met Gly Asn Pro
                245                 250                 255
Trp Phe Gln Arg Ala Lys Met Pro Arg Ala Leu Asp Phe Ser Gly His
                260                 265                 270
Thr His Pro Val Ala Thr Phe Gln Pro Ser Arg Pro Glu Ser Val Asn
            275                 280                 285
Asp Leu Phe Leu Cys Pro Gln Lys Glu Leu Thr Arg Gly Val Arg Pro
290                 295                 300
Thr Pro Arg Val Arg Ala Pro Ala Thr Gln Gln Thr Arg Trp Lys Lys
305                 310                 315                 320
Asp Leu Ala Glu Asp Glu Glu Glu Asp Glu Asp Thr Glu Asp
                325                 330                 335
Gly Val Ser Phe Gln Pro Tyr Ile Glu Pro Ser Phe Leu Gly Gln
                340                 345                 350
Glu His Gln Ala Pro Gly His Ser Glu Ala Gly Gly Val Asp Ser Gly
            355                 360                 365
Arg Pro Arg Ala Pro Leu Val Pro Ser Glu Gly Ser Ser Ala Trp Asp
370                 375                 380
Ser Ser Asp Arg Ser Trp Ala Ser Thr Val Asp Ser Ser Trp Asp Arg
385                 390                 395                 400
Ala Gly Ser Ser Gly Tyr Leu Ala Glu Lys Pro Gly Gln Gly Pro
                405                 410                 415
Gly Gly Asp Gly His Gln Glu Ser Leu Pro Pro Glu Phe Ser Lys
            420                 425                 430
Asp Ser Gly Phe Leu Glu Glu Leu Pro Glu Asp Asn Leu Ser Ser Trp
            435                 440                 445
Ala Thr Trp Gly Thr Leu Pro Pro Glu Pro Asn Leu Val Pro Gly Gly
            450                 455                 460
Pro Pro Val Ser Leu Gln Thr Leu Thr Phe Cys Trp Glu Ser Ser Pro
465                 470                 475                 480
Glu Glu Glu Glu Glu Ala Arg Glu Ser Glu Ile Glu Asp Ser Asp Ala
                485                 490                 495
Gly Ser Trp Gly Ala Glu Ser Thr Gln Arg Thr Glu Asp Arg Gly Arg
```

```
                    500             505             510
Thr Leu Gly His Tyr Met Ala Arg
        515             520

<210> SEQ ID NO 12
<211> LENGTH: 531
<212> TYPE: DNA
<213> ORGANISM: Artificial Sequence
<220> FEATURE:
<223> OTHER INFORMATION: mature protein of SEQ ID NO: 1, with 3' Met
      added
<220> FEATURE:
<221> NAME/KEY: CDS
<222> LOCATION: (1)...(531)

<400> SEQUENCE: 12 atg gtt cct gtc gcc agg ctc cac ggg gct ctc ccg gat gca agg ggc      48
Met Val Pro Val Ala Arg Leu His Gly Ala Leu Pro Asp Ala Arg Gly
 1               5                  10                  15 tgc cac ata gcc cag ttc aag tcc ctg tct cca cag gag ctg cag gcc      96
Cys His Ile Ala Gln Phe Lys Ser Leu Ser Pro Gln Glu Leu Gln Ala
             20                  25                  30 ttt aag agg gcc aaa gat gcc tta gaa gag tcg ctt ctg ctg aag gac     144
Phe Lys Arg Ala Lys Asp Ala Leu Glu Glu Ser Leu Leu Leu Lys Asp
         35                  40                  45 tgc agg tgc cac tcc cgc ctc ttc ccc agg acc tgg gac ctg agg cag     192
Cys Arg Cys His Ser Arg Leu Phe Pro Arg Thr Trp Asp Leu Arg Gln
     50                  55                  60 ctg cag gtg agg gag cgc ccc atg gct ttg gag gct gag ctg gcc ctg     240
Leu Gln Val Arg Glu Arg Pro Met Ala Leu Glu Ala Glu Leu Ala Leu
 65                  70                  75                  80 acg ctg aag gtt ctg gag gcc acc gct gac act gac cca gcc ctg gtg     288
Thr Leu Lys Val Leu Glu Ala Thr Ala Asp Thr Asp Pro Ala Leu Val
                 85                  90                  95 gac gtc ttg gac cag ccc ctt cac acc ctg cac cat atc ctc tcc cag     336
Asp Val Leu Asp Gln Pro Leu His Thr Leu His His Ile Leu Ser Gln
            100                 105                 110 ttc cgg gcc tgt atc cag cct cag ccc acg gca ggg ccc agg acc cgg     384
Phe Arg Ala Cys Ile Gln Pro Gln Pro Thr Ala Gly Pro Arg Thr Arg
        115                 120                 125 ggc cgc ctc cac cat tgg ctg tac cgg ctc cag gag gcc cca aaa aag     432
Gly Arg Leu His His Trp Leu Tyr Arg Leu Gln Glu Ala Pro Lys Lys
    130                 135                 140 gag tcc cct ggc tgc ctc gag gcc tct gtc acc ttc aac ctc ttc cgc     480
Glu Ser Pro Gly Cys Leu Glu Ala Ser Val Thr Phe Asn Leu Phe Arg
145                 150                 155                 160 ctc ctc acg cga gac ctg aat tgt gtt gcc agt ggg gac ctg tgt gtc     528
Leu Leu Thr Arg Asp Leu Asn Cys Val Ala Ser Gly Asp Leu Cys Val
                165                 170                 175 tga                                                                 531
 *

<210> SEQ ID NO 13
<211> LENGTH: 176
<212> TYPE: PRT
<213> ORGANISM: Artificial Sequence
<220> FEATURE:
<223> OTHER INFORMATION: mature protein of SEQ ID NO: 1, with 3' Met
      added

<400> SEQUENCE: 13

Met Val Pro Val Ala Arg Leu His Gly Ala Leu Pro Asp Ala Arg Gly
 1               5                  10                  15
```

```
Cys His Ile Ala Gln Phe Lys Ser Leu Ser Pro Gln Glu Leu Gln Ala
             20                  25                  30

Phe Lys Arg Ala Lys Asp Ala Leu Glu Glu Ser Leu Leu Leu Lys Asp
         35                  40                  45

Cys Arg Cys His Ser Arg Leu Phe Pro Arg Thr Trp Asp Leu Arg Gln
 50                  55                  60

Leu Gln Val Arg Glu Arg Pro Met Ala Leu Glu Ala Glu Leu Ala Leu
65                  70                  75                  80

Thr Leu Lys Val Leu Glu Ala Thr Ala Asp Thr Asp Pro Ala Leu Val
                 85                  90                  95

Asp Val Leu Asp Gln Pro Leu His Thr Leu His His Ile Leu Ser Gln
            100                 105                 110

Phe Arg Ala Cys Ile Gln Pro Gln Pro Thr Ala Gly Pro Arg Thr Arg
        115                 120                 125

Gly Arg Leu His His Trp Leu Tyr Arg Leu Gln Glu Ala Pro Lys Lys
130                 135                 140

Glu Ser Pro Gly Cys Leu Glu Ala Ser Val Thr Phe Asn Leu Phe Arg
145                 150                 155                 160

Leu Leu Thr Arg Asp Leu Asn Cys Val Ala Ser Gly Asp Leu Cys Val
                165                 170                 175

<210> SEQ ID NO 14
<211> LENGTH: 621
<212> TYPE: DNA
<213> ORGANISM: Artificial Sequence
<220> FEATURE:
<223> OTHER INFORMATION: mature protein of SEQ ID NO: 3, with 3' Met
      added
<220> FEATURE:
<221> NAME/KEY: CDS
<222> LOCATION: (1)...(549)

<400> SEQUENCE: 14 atg ggc cct gtc ccc act tcc aag ccc acc aca act ggg aag ggc tgc      48
Met Gly Pro Val Pro Thr Ser Lys Pro Thr Thr Thr Gly Lys Gly Cys
 1               5                  10                  15 cac att ggc agg ttc aaa tct ctg tca cca cag gag cta gcg agc ttc      96
His Ile Gly Arg Phe Lys Ser Leu Ser Pro Gln Glu Leu Ala Ser Phe
             20                  25                  30 aag aag gcc agg gac gcc ttg gaa gag tca ctc aag ctg aaa aac tgg     144
Lys Lys Ala Arg Asp Ala Leu Glu Glu Ser Leu Lys Leu Lys Asn Trp
         35                  40                  45 agt tgc agc tct cct gtc ttc ccc ggg aat tgg gac ctg agg ctt ctc     192
Ser Cys Ser Ser Pro Val Phe Pro Gly Asn Trp Asp Leu Arg Leu Leu
 50                  55                  60 cag gtg agg gag cgc cct gtg gcc ttg gag gct gag ctg gcc ctg acg     240
Gln Val Arg Glu Arg Pro Val Ala Leu Glu Ala Glu Leu Ala Leu Thr
65                  70                  75                  80 ctg aag gtc ctg gag gcc gct gct ggc cca gcc ctg gag gac gtc cta     288
Leu Lys Val Leu Glu Ala Ala Ala Gly Pro Ala Leu Glu Asp Val Leu
                 85                  90                  95 gac cag ccc ctt cac acc ctg cac cac atc ctc tcc cag ctc cag gcc     336
Asp Gln Pro Leu His Thr Leu His His Ile Leu Ser Gln Leu Gln Ala
            100                 105                 110 tgt atc cag cct cag ccc aca gca ggg cca agg ccc cgg ggc cgc ctc     384
Cys Ile Gln Pro Gln Pro Thr Ala Gly Pro Arg Pro Arg Gly Arg Leu
        115                 120                 125 cac cac tgg ctg cac cgg ctc cag gag gcc ccc aaa aag gag tcc gct     432
His His Trp Leu His Arg Leu Gln Glu Ala Pro Lys Lys Glu Ser Ala
```

```
                         130                 135                 140
ggc tgc ctg gag gca tct gtc acc ttc aac ctc ttc cgc ctc ctc acg           480
Gly Cys Leu Glu Ala Ser Val Thr Phe Asn Leu Phe Arg Leu Leu Thr
145                 150                 155                 160 cga gac ctc aaa tat gtg gcc gat ggg aac ctg tgt ctg aga acg tca           528
Arg Asp Leu Lys Tyr Val Ala Asp Gly Asn Leu Cys Leu Arg Thr Ser
                165                 170                 175 acc cac cct gag tcc acc tga cacccacac cttatttatg cgctgagccc              579
Thr His Pro Glu Ser Thr  *
            180 tactccttcc ttaatttatt tcctctcacc ctttatttat ga                           621

<210> SEQ ID NO 15
<211> LENGTH: 182
<212> TYPE: PRT
<213> ORGANISM: Artificial Sequence
<220> FEATURE:
<223> OTHER INFORMATION: mature protein of SEQ ID NO: 3, with 3' Met
      added

<400> SEQUENCE: 15

Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Cys Leu Arg Thr Ser
                165                 170                 175

Thr His Pro Glu Ser Thr
            180

<210> SEQ ID NO 16
<211> LENGTH: 531
<212> TYPE: DNA
<213> ORGANISM: Artificial Sequence
<220> FEATURE:
<223> OTHER INFORMATION: mature protein of SEQ ID NO: 5, with 3' Met
      added
<220> FEATURE:
<221> NAME/KEY: CDS
<222> LOCATION: (1)...(531)

<400> SEQUENCE: 16 atg gtt cct gtc gcc agg ctc cgc ggg gct ctc ccg gat gca agg ggc            48
Met Val Pro Val Ala Arg Leu Arg Gly Ala Leu Pro Asp Ala Arg Gly
```

```
                1               5              10              15 tgc cac ata gcc cag ttc aag tcc ctg tct cca cag gag ctg cag gcc      96
Cys His Ile Ala Gln Phe Lys Ser Leu Ser Pro Gln Glu Leu Gln Ala
            20                  25                  30 ttt aag agg gcc aaa gat gcc tta gaa gag tcg ctt ctg ctg aag gac     144
Phe Lys Arg Ala Lys Asp Ala Leu Glu Glu Ser Leu Leu Leu Lys Asp
        35                  40                  45 tgc aag tgc cgc tcc cgc ctc ttc ccc agg acc tgg gac ctg agg cag     192
Cys Lys Cys Arg Ser Arg Leu Phe Pro Arg Thr Trp Asp Leu Arg Gln
    50                  55                  60 ctg cag gtg agg gag cgc ccc gtg gct ttg gag gct gag ctg gcc ctg     240
Leu Gln Val Arg Glu Arg Pro Val Ala Leu Glu Ala Glu Leu Ala Leu
65                  70                  75                  80 acg ctg aag gtt ctg gag gcc acc gct gac act gac cca gcc ctg ggg     288
Thr Leu Lys Val Leu Glu Ala Thr Ala Asp Thr Asp Pro Ala Leu Gly
                85                  90                  95 gat gtc ttg gac cag ccc ctt cac acc ctg cac cat atc ctc tcc cag     336
Asp Val Leu Asp Gln Pro Leu His Thr Leu His His Ile Leu Ser Gln
            100                 105                 110 ctc cgg gcc tgt atc cag cct cag ccc acg gca ggg ccc agg acc cgg     384
Leu Arg Ala Cys Ile Gln Pro Gln Pro Thr Ala Gly Pro Arg Thr Arg
        115                 120                 125 ggc cgc ctc cac cat tgg ctg cac cgg ctc cag gag gcc cca aaa aag     432
Gly Arg Leu His His Trp Leu His Arg Leu Gln Glu Ala Pro Lys Lys
    130                 135                 140 gag tcc cct ggc tgc ctc gag gcc tct gtc acc ttc aac ctc ttc cgc     480
Glu Ser Pro Gly Cys Leu Glu Ala Ser Val Thr Phe Asn Leu Phe Arg
145                 150                 155                 160 ctc ctc acg cga gac ctg aat tgt gtt gcc agc ggg gac ctg tgt gtc     528
Leu Leu Thr Arg Asp Leu Asn Cys Val Ala Ser Gly Asp Leu Cys Val
                165                 170                 175 tga                                                                  531
 *
```

<210> SEQ ID NO 17
<211> LENGTH: 176
<212> TYPE: PRT
<213> ORGANISM: Artificial Sequence
<220> FEATURE:
<223> OTHER INFORMATION: mature protein of SEQ ID NO: 5, with 3' Met added

<400> SEQUENCE: 17

```
Met Val Pro Val Ala Arg Leu Arg Gly Ala Leu Pro Asp Ala Arg Gly
 1               5                  10                  15

Cys His Ile Ala Gln Phe Lys Ser Leu Ser Pro Gln Glu Leu Gln Ala
            20                  25                  30

Phe Lys Arg Ala Lys Asp Ala Leu Glu Glu Ser Leu Leu Leu Lys Asp
        35                  40                  45

Cys Lys Cys Arg Ser Arg Leu Phe Pro Arg Thr Trp Asp Leu Arg Gln
    50                  55                  60

Leu Gln Val Arg Glu Arg Pro Val Ala Leu Glu Ala Glu Leu Ala Leu
65                  70                  75                  80

Thr Leu Lys Val Leu Glu Ala Thr Ala Asp Thr Asp Pro Ala Leu Gly
                85                  90                  95

Asp Val Leu Asp Gln Pro Leu His Thr Leu His His Ile Leu Ser Gln
            100                 105                 110

Leu Arg Ala Cys Ile Gln Pro Gln Pro Thr Ala Gly Pro Arg Thr Arg
        115                 120                 125
```

```
Gly Arg Leu His His Trp Leu His Arg Leu Gln Glu Ala Pro Lys Lys
        130                 135                 140

Glu Ser Pro Gly Cys Leu Glu Ala Ser Val Thr Phe Asn Leu Phe Arg
145                 150                 155                 160

Leu Leu Thr Arg Asp Leu Asn Cys Val Ala Ser Gly Asp Leu Cys Val
                165                 170                 175

<210> SEQ ID NO 18
<211> LENGTH: 528
<212> TYPE: DNA
<213> ORGANISM: Artificial Sequence
<220> FEATURE:
<223> OTHER INFORMATION: IL-28A mutant C48S
<220> FEATURE:
<221> NAME/KEY: CDS
<222> LOCATION: (1)...(528)

<400> SEQUENCE: 18 gtt cct gtc gcc agg ctc cac ggg gct ctc ccg gat gca agg ggc tgc         48
Val Pro Val Ala Arg Leu His Gly Ala Leu Pro Asp Ala Arg Gly Cys
1               5                   10                  15 cac ata gcc cag ttc aag tcc ctg tct cca cag gag ctg cag gcc ttt         96
His Ile Ala Gln Phe Lys Ser Leu Ser Pro Gln Glu Leu Gln Ala Phe
                20                  25                  30 aag agg gcc aaa gat gcc tta gaa gag tcg ctt ctg ctg aag gac tcc        144
Lys Arg Ala Lys Asp Ala Leu Glu Glu Ser Leu Leu Leu Lys Asp Ser
        35                  40                  45 agg tgc cac tcc cgc ctc ttc ccc agg acc tgg gac ctg agg cag ctg        192
Arg Cys His Ser Arg Leu Phe Pro Arg Thr Trp Asp Leu Arg Gln Leu
    50                  55                  60 cag gtg agg gag cgc ccc atg gct ttg gag gct gag ctg gcc ctg acg        240
Gln Val Arg Glu Arg Pro Met Ala Leu Glu Ala Glu Leu Ala Leu Thr
65                  70                  75                  80 ctg aag gtt ctg gag gcc acc gct gac act gac cca gcc ctg gtg gac        288
Leu Lys Val Leu Glu Ala Thr Ala Asp Thr Asp Pro Ala Leu Val Asp
                85                  90                  95 gtc ttg gac cag ccc ctt cac acc ctg cac cat atc ctc tcc cag ttc        336
Val Leu Asp Gln Pro Leu His Thr Leu His His Ile Leu Ser Gln Phe
            100                 105                 110 cgg gcc tgt atc cag cct cag ccc acg gca ggg ccc agg acc cgg ggc        384
Arg Ala Cys Ile Gln Pro Gln Pro Thr Ala Gly Pro Arg Thr Arg Gly
        115                 120                 125 cgc ctc cac cat tgg ctg tac cgg ctc cag gag gcc cca aaa aag gag        432
Arg Leu His His Trp Leu Tyr Arg Leu Gln Glu Ala Pro Lys Lys Glu
    130                 135                 140 tcc cct ggc tgc ctc gag gcc tct gtc acc ttc aac ctc ttc cgc ctc        480
Ser Pro Gly Cys Leu Glu Ala Ser Val Thr Phe Asn Leu Phe Arg Leu
145                 150                 155                 160 ctc acg cga gac ctg aat tgt gtt gcc agt ggg gac ctg tgt gtc tga        528
Leu Thr Arg Asp Leu Asn Cys Val Ala Ser Gly Asp Leu Cys Val  *
                165                 170                 175

<210> SEQ ID NO 19
<211> LENGTH: 175
<212> TYPE: PRT
<213> ORGANISM: Artificial Sequence
<220> FEATURE:
<223> OTHER INFORMATION: IL-28A mutant C48S

<400> SEQUENCE: 19

Val Pro Val Ala Arg Leu His Gly Ala Leu Pro Asp Ala Arg Gly Cys
1               5                   10                  15
```

```
His Ile Ala Gln Phe Lys Ser Leu Ser Pro Gln Glu Leu Gln Ala Phe
             20                  25                  30

Lys Arg Ala Lys Asp Ala Leu Glu Glu Ser Leu Leu Leu Lys Asp Ser
         35                  40                  45

Arg Cys His Ser Arg Leu Phe Pro Arg Thr Trp Asp Leu Arg Gln Leu
     50                  55                  60

Gln Val Arg Glu Arg Pro Met Ala Leu Glu Ala Glu Leu Ala Leu Thr
 65                  70                  75                  80

Leu Lys Val Leu Glu Ala Thr Ala Asp Thr Asp Pro Ala Leu Val Asp
                 85                  90                  95

Val Leu Asp Gln Pro Leu His Thr Leu His Ile Leu Ser Gln Phe
            100                 105                 110

Arg Ala Cys Ile Gln Pro Gln Pro Thr Ala Gly Pro Arg Thr Arg Gly
            115                 120                 125

Arg Leu His His Trp Leu Tyr Arg Leu Gln Glu Ala Pro Lys Lys Glu
        130                 135                 140

Ser Pro Gly Cys Leu Glu Ala Ser Val Thr Phe Asn Leu Phe Arg Leu
145                 150                 155                 160

Leu Thr Arg Asp Leu Asn Cys Val Ala Ser Gly Asp Leu Cys Val
                165                 170                 175

<210> SEQ ID NO 20
<211> LENGTH: 531
<212> TYPE: DNA
<213> ORGANISM: Artificial Sequence
<220> FEATURE:
<223> OTHER INFORMATION: met IL-28A mutant C49S
<220> FEATURE:
<221> NAME/KEY: CDS
<222> LOCATION: (1)...(531)

<400> SEQUENCE: 20 atg gtt cct gtc gcc agg ctc cac ggg gct ctc ccg gat gca agg ggc      48
Met Val Pro Val Ala Arg Leu His Gly Ala Leu Pro Asp Ala Arg Gly
  1               5                  10                  15 tgc cac ata gcc cag ttc aag tcc ctg tct cca cag gag ctg cag gcc      96
Cys His Ile Ala Gln Phe Lys Ser Leu Ser Pro Gln Glu Leu Gln Ala
             20                  25                  30 ttt aag agg gcc aaa gat gcc tta gaa gag tcg ctt ctg ctg aag gac     144
Phe Lys Arg Ala Lys Asp Ala Leu Glu Glu Ser Leu Leu Leu Lys Asp
         35                  40                  45 tcc agg tgc cac tcc cgc ctc ttc ccc agg acc tgg gac ctg agg cag     192
Ser Arg Cys His Ser Arg Leu Phe Pro Arg Thr Trp Asp Leu Arg Gln
     50                  55                  60 ctg cag gtg agg gag cgc ccc atg gct ttg gag gct gag ctg gcc ctg     240
Leu Gln Val Arg Glu Arg Pro Met Ala Leu Glu Ala Glu Leu Ala Leu
 65                  70                  75                  80 acg ctg aag gtt ctg gag gcc acc gct gac act gac cca gcc ctg gtg     288
Thr Leu Lys Val Leu Glu Ala Thr Ala Asp Thr Asp Pro Ala Leu Val
                 85                  90                  95 gac gtc ttg gac cag ccc ctt cac acc ctg cac cat atc ctc tcc cag     336
Asp Val Leu Asp Gln Pro Leu His Thr Leu His His Ile Leu Ser Gln
            100                 105                 110 ttc cgg gcc tgt atc cag cct cag ccc acg gca ggg ccc agg acc cgg     384
Phe Arg Ala Cys Ile Gln Pro Gln Pro Thr Ala Gly Pro Arg Thr Arg
            115                 120                 125 ggc cgc ctc cac cat tgg ctg tac cgg ctc cag gag gcc cca aaa aag     432
Gly Arg Leu His His Trp Leu Tyr Arg Leu Gln Glu Ala Pro Lys Lys
        130                 135                 140
```

```
gag tcc cct ggc tgc ctc gag gcc tct gtc acc ttc aac ctc ttc cgc    480
Glu Ser Pro Gly Cys Leu Glu Ala Ser Val Thr Phe Asn Leu Phe Arg
145                 150                 155                 160 ctc ctc acg cga gac ctg aat tgt gtt gcc agt ggg gac ctg tgt gtc    528
Leu Leu Thr Arg Asp Leu Asn Cys Val Ala Ser Gly Asp Leu Cys Val
                165                 170                 175 tga                                                                531
*
```

<210> SEQ ID NO 21
<211> LENGTH: 176
<212> TYPE: PRT
<213> ORGANISM: Artificial Sequence
<220> FEATURE:
<223> OTHER INFORMATION: met IL-28A mutant C49S

<400> SEQUENCE: 21

```
Met Val Pro Val Ala Arg Leu His Gly Ala Leu Pro Asp Ala Arg Gly
 1               5                  10                  15

Cys His Ile Ala Gln Phe Lys Ser Leu Ser Pro Gln Glu Leu Gln Ala
             20                  25                  30

Phe Lys Arg Ala Lys Asp Ala Leu Glu Glu Ser Leu Leu Leu Lys Asp
         35                  40                  45

Ser Arg Cys His Ser Arg Leu Phe Pro Arg Thr Trp Asp Leu Arg Gln
 50                  55                  60

Leu Gln Val Arg Glu Arg Pro Met Ala Leu Glu Ala Glu Leu Ala Leu
 65                  70                  75                  80

Thr Leu Lys Val Leu Glu Ala Thr Ala Asp Thr Asp Pro Ala Leu Val
             85                  90                  95

Asp Val Leu Asp Gln Pro Leu His Thr Leu His His Ile Leu Ser Gln
            100                 105                 110

Phe Arg Ala Cys Ile Gln Pro Gln Pro Thr Ala Gly Pro Arg Thr Arg
        115                 120                 125

Gly Arg Leu His His Trp Leu Tyr Arg Leu Gln Glu Ala Pro Lys Lys
130                 135                 140

Glu Ser Pro Gly Cys Leu Glu Ala Ser Val Thr Phe Asn Leu Phe Arg
145                 150                 155                 160

Leu Leu Thr Arg Asp Leu Asn Cys Val Ala Ser Gly Asp Leu Cys Val
                165                 170                 175
```

<210> SEQ ID NO 22
<211> LENGTH: 528
<212> TYPE: DNA
<213> ORGANISM: Artificial Sequence
<220> FEATURE:
<223> OTHER INFORMATION: IL-28A mutant C50S
<220> FEATURE:
<221> NAME/KEY: CDS
<222> LOCATION: (1)...(528)

<400> SEQUENCE: 22

```
gtt cct gtc gcc agg ctc cac ggg gct ctc ccg gat gca agg ggc tgc    48
Val Pro Val Ala Arg Leu His Gly Ala Leu Pro Asp Ala Arg Gly Cys
 1               5                  10                  15 cac ata gcc cag ttc aag tcc ctg tct cca cag gag ctg cag gcc ttt    96
His Ile Ala Gln Phe Lys Ser Leu Ser Pro Gln Glu Leu Gln Ala Phe
             20                  25                  30 aag agg gcc aaa gat gcc tta gaa gag tcg ctt ctg ctg aag gac tgc   144
Lys Arg Ala Lys Asp Ala Leu Glu Glu Ser Leu Leu Leu Lys Asp Cys
         35                  40                  45
```

```
agg tcc cac tcc cgc ctc ttc ccc agg acc tgg gac ctg agg cag ctg      192
Arg Ser His Ser Arg Leu Phe Pro Arg Thr Trp Asp Leu Arg Gln Leu
    50                  55                  60 cag gtg agg gag cgc ccc atg gct ttg gag gct gag ctg gcc ctg acg      240
Gln Val Arg Glu Arg Pro Met Ala Leu Glu Ala Glu Leu Ala Leu Thr
65                  70                  75                  80 ctg aag gtt ctg gag gcc acc gct gac act gac cca gcc ctg gtg gac      288
Leu Lys Val Leu Glu Ala Thr Ala Asp Thr Asp Pro Ala Leu Val Asp
                85                  90                  95 gtc ttg gac cag ccc ctt cac acc ctg cac cat atc ctc tcc cag ttc      336
Val Leu Asp Gln Pro Leu His Thr Leu His His Ile Leu Ser Gln Phe
            100                 105                 110 cgg gcc tgt atc cag cct cag ccc acg gca ggg ccc agg acc cgg ggc      384
Arg Ala Cys Ile Gln Pro Gln Pro Thr Ala Gly Pro Arg Thr Arg Gly
        115                 120                 125 cgc ctc cac cat tgg ctg tac cgg ctc cag gag gcc cca aaa aag gag      432
Arg Leu His His Trp Leu Tyr Arg Leu Gln Glu Ala Pro Lys Lys Glu
    130                 135                 140 tcc cct ggc tgc ctc gag gcc tct gtc acc ttc aac ctc ttc cgc ctc      480
Ser Pro Gly Cys Leu Glu Ala Ser Val Thr Phe Asn Leu Phe Arg Leu
145                 150                 155                 160 ctc acg cga gac ctg aat tgt gtt gcc agt ggg gac ctg tgt gtc tga      528
Leu Thr Arg Asp Leu Asn Cys Val Ala Ser Gly Asp Leu Cys Val *
                165                 170                 175
```

<210> SEQ ID NO 23
<211> LENGTH: 175
<212> TYPE: PRT
<213> ORGANISM: Artificial Sequence
<220> FEATURE:
<223> OTHER INFORMATION: IL-28A mutant C50S

<400> SEQUENCE: 23

```
Val Pro Val Ala Arg Leu His Gly Ala Leu Pro Asp Ala Arg Gly Cys
1               5                   10                  15

His Ile Ala Gln Phe Lys Ser Leu Ser Pro Gln Glu Leu Gln Ala Phe
            20                  25                  30

Lys Arg Ala Lys Asp Ala Leu Glu Glu Ser Leu Leu Leu Lys Asp Cys
        35                  40                  45

Arg Ser His Ser Arg Leu Phe Pro Arg Thr Trp Asp Leu Arg Gln Leu
    50                  55                  60

Gln Val Arg Glu Arg Pro Met Ala Leu Glu Ala Glu Leu Ala Leu Thr
65                  70                  75                  80

Leu Lys Val Leu Glu Ala Thr Ala Asp Thr Asp Pro Ala Leu Val Asp
                85                  90                  95

Val Leu Asp Gln Pro Leu His Thr Leu His His Ile Leu Ser Gln Phe
            100                 105                 110

Arg Ala Cys Ile Gln Pro Gln Pro Thr Ala Gly Pro Arg Thr Arg Gly
        115                 120                 125

Arg Leu His His Trp Leu Tyr Arg Leu Gln Glu Ala Pro Lys Lys Glu
    130                 135                 140

Ser Pro Gly Cys Leu Glu Ala Ser Val Thr Phe Asn Leu Phe Arg Leu
145                 150                 155                 160

Leu Thr Arg Asp Leu Asn Cys Val Ala Ser Gly Asp Leu Cys Val
                165                 170                 175
```

<210> SEQ ID NO 24
<211> LENGTH: 531

```
<212> TYPE: DNA
<213> ORGANISM: Artificial Sequence
<220> FEATURE:
<223> OTHER INFORMATION: met IL-28A mutant C51S
<220> FEATURE:
<221> NAME/KEY: CDS
<222> LOCATION: (1)...(531)

<400> SEQUENCE: 24 atg gtt cct gtc gcc agg ctc cac ggg gct ctc ccg gat gca agg ggc      48
Met Val Pro Val Ala Arg Leu His Gly Ala Leu Pro Asp Ala Arg Gly
 1               5                  10                  15 tgc cac ata gcc cag ttc aag tcc ctg tct cca cag gag ctg cag gcc      96
Cys His Ile Ala Gln Phe Lys Ser Leu Ser Pro Gln Glu Leu Gln Ala
             20                  25                  30 ttt aag agg gcc aaa gat gcc tta gaa gag tcg ctt ctg ctg aag gac     144
Phe Lys Arg Ala Lys Asp Ala Leu Glu Glu Ser Leu Leu Leu Lys Asp
         35                  40                  45 tgc agg tcc cac tcc cgc ctc ttc ccc agg acc tgg gac ctg agg cag     192
Cys Arg Ser His Ser Arg Leu Phe Pro Arg Thr Trp Asp Leu Arg Gln
     50                  55                  60 ctg cag gtg agg gag cgc ccc atg gct ttg gag gct gag ctg gcc ctg     240
Leu Gln Val Arg Glu Arg Pro Met Ala Leu Glu Ala Glu Leu Ala Leu
 65                  70                  75                  80 acg ctg aag gtt ctg gag gcc acc gct gac act gac cca gcc ctg gtg     288
Thr Leu Lys Val Leu Glu Ala Thr Ala Asp Thr Asp Pro Ala Leu Val
                 85                  90                  95 gac gtc ttg gac cag ccc ctt cac acc ctg cac cat atc ctc tcc cag     336
Asp Val Leu Asp Gln Pro Leu His Thr Leu His His Ile Leu Ser Gln
            100                 105                 110 ttc cgg gcc tgt atc cag cct cag ccc acg gca ggg ccc agg acc cgg     384
Phe Arg Ala Cys Ile Gln Pro Gln Pro Thr Ala Gly Pro Arg Thr Arg
        115                 120                 125 ggc cgc ctc cac cat tgg ctg tac cgg ctc cag gag gcc cca aaa aag     432
Gly Arg Leu His His Trp Leu Tyr Arg Leu Gln Glu Ala Pro Lys Lys
    130                 135                 140 gag tcc cct ggc tgc ctc gag gcc tct gtc acc ttc aac ctc ttc cgc     480
Glu Ser Pro Gly Cys Leu Glu Ala Ser Val Thr Phe Asn Leu Phe Arg
145                 150                 155                 160 ctc ctc acg cga gac ctg aat tgt gtt gcc agt ggg gac ctg tgt gtc     528
Leu Leu Thr Arg Asp Leu Asn Cys Val Ala Ser Gly Asp Leu Cys Val
                165                 170                 175 tga                                                                  531
 *

<210> SEQ ID NO 25
<211> LENGTH: 176
<212> TYPE: PRT
<213> ORGANISM: Artificial Sequence
<220> FEATURE:
<223> OTHER INFORMATION: met IL-28A mutant C51S

<400> SEQUENCE: 25

Met Val Pro Val Ala Arg Leu His Gly Ala Leu Pro Asp Ala Arg Gly
 1               5                  10                  15

Cys His Ile Ala Gln Phe Lys Ser Leu Ser Pro Gln Glu Leu Gln Ala
             20                  25                  30

Phe Lys Arg Ala Lys Asp Ala Leu Glu Glu Ser Leu Leu Leu Lys Asp
         35                  40                  45

Cys Arg Ser His Ser Arg Leu Phe Pro Arg Thr Trp Asp Leu Arg Gln
     50                  55                  60
```

```
Leu Gln Val Arg Glu Arg Pro Met Ala Leu Glu Ala Glu Leu Ala Leu
 65                  70                  75                  80

Thr Leu Lys Val Leu Glu Ala Thr Ala Asp Thr Asp Pro Ala Leu Val
                 85                  90                  95

Asp Val Leu Asp Gln Pro Leu His Thr Leu His His Ile Leu Ser Gln
            100                 105                 110

Phe Arg Ala Cys Ile Gln Pro Gln Pro Thr Ala Gly Pro Arg Thr Arg
        115                 120                 125

Gly Arg Leu His His Trp Leu Tyr Arg Leu Gln Glu Ala Pro Lys Lys
    130                 135                 140

Glu Ser Pro Gly Cys Leu Glu Ala Ser Val Thr Phe Asn Leu Phe Arg
145                 150                 155                 160

Leu Leu Thr Arg Asp Leu Asn Cys Val Ala Ser Gly Asp Leu Cys Val
                165                 170                 175

<210> SEQ ID NO 26
<211> LENGTH: 546
<212> TYPE: DNA
<213> ORGANISM: Artificial Sequence
<220> FEATURE:
<223> OTHER INFORMATION: IL-29 mutant C171S
<220> FEATURE:
<221> NAME/KEY: CDS
<222> LOCATION: (1)...(546)

<400> SEQUENCE: 26 ggt ccg gtt ccg acc tct aaa cca acc acc act ggt aaa ggt tgc cac      48
Gly Pro Val Pro Thr Ser Lys Pro Thr Thr Thr Gly Lys Gly Cys His
  1               5                  10                  15 atc ggt cgt ttc aaa tct ctg tct ccg cag gaa ctg gct tct ttc aaa      96
Ile Gly Arg Phe Lys Ser Leu Ser Pro Gln Glu Leu Ala Ser Phe Lys
             20                  25                  30 aaa gct cgt gac gct ctg gaa gaa tct ctg aaa ctg aaa aac tgg tct     144
Lys Ala Arg Asp Ala Leu Glu Glu Ser Leu Lys Leu Lys Asn Trp Ser
         35                  40                  45 tgc tct tct ccg gtt ttc ccg ggt aac tgg gat ctg cgt ctg ctg cag     192
Cys Ser Ser Pro Val Phe Pro Gly Asn Trp Asp Leu Arg Leu Leu Gln
     50                  55                  60 gtt cgt gaa cgt ccg gtt gct ctg gaa gct gaa ctg gct ctg acc ctg     240
Val Arg Glu Arg Pro Val Ala Leu Glu Ala Glu Leu Ala Leu Thr Leu
 65                  70                  75                  80 aaa gtt ctg gaa gct gct gca ggt cct gct ctg gaa gat gtt ctg gat     288
Lys Val Leu Glu Ala Ala Ala Gly Pro Ala Leu Glu Asp Val Leu Asp
                 85                  90                  95 cag ccg ctg cac act ctg cac cac atc ctg tct cag ctg cag gct tgc     336
Gln Pro Leu His Thr Leu His His Ile Leu Ser Gln Leu Gln Ala Cys
            100                 105                 110 att caa ccg caa ccg acc gct ggt ccg cgt ccg cgt ggt cgt ctg cac     384
Ile Gln Pro Gln Pro Thr Ala Gly Pro Arg Pro Arg Gly Arg Leu His
        115                 120                 125 cac tgg ctg cat cgt ctg cag gaa gct ccg aaa aaa gaa tct gct ggt     432
His Trp Leu His Arg Leu Gln Glu Ala Pro Lys Lys Glu Ser Ala Gly
    130                 135                 140 tgc ctg gaa gct tct gtt acc ttc aac ctg ttc cgt ctg ctg acc cgt     480
Cys Leu Glu Ala Ser Val Thr Phe Asn Leu Phe Arg Leu Leu Thr Arg
145                 150                 155                 160 gat ctg aaa tac gtt gct gat ggt aac ctg tct ctg cgt acc tct acc     528
Asp Leu Lys Tyr Val Ala Asp Gly Asn Leu Ser Leu Arg Thr Ser Thr
                165                 170                 175 cat ccg gaa tct acc taa                                             546
```

His Pro Glu Ser Thr *
          180

<210> SEQ ID NO 27
<211> LENGTH: 181
<212> TYPE: PRT
<213> ORGANISM: Artificial Sequence
<220> FEATURE:
<223> OTHER INFORMATION: IL-29 mutant C171S

<400> SEQUENCE: 27

Gly Pro Val Pro Thr Ser Lys Pro Thr Thr Thr Gly Lys Gly Cys His
 1               5                  10                  15

Ile Gly Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
    50                  55                  60

Val Arg Glu Arg Pro Val Ala Leu Glu Ala Glu Leu Ala Leu Thr Leu
65                  70                  75                  80

Lys Val Leu Glu Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
    130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asn Leu Ser Leu Arg Thr Ser Thr
                165                 170                 175

His Pro Glu Ser Thr
          180

<210> SEQ ID NO 28
<211> LENGTH: 549
<212> TYPE: DNA
<213> ORGANISM: Artificial Sequence
<220> FEATURE:
<223> OTHER INFORMATION: met IL-29 mutant C172S
<220> FEATURE:
<221> NAME/KEY: CDS
<222> LOCATION: (1)...(549)

<400> SEQUENCE: 28 atg ggt ccg gtt ccg acc tct aaa cca acc acc act ggt aaa ggt tgc      48
Met Gly Pro Val Pro Thr Ser Lys Pro Thr Thr Thr Gly Lys Gly Cys
 1               5                  10                  15 cac atc ggt cgt ttc aaa tct ctg tct ccg cag gaa ctg gct tct ttc      96
His Ile Gly Arg Phe Lys Ser Leu Ser Pro Gln Glu Leu Ala Ser Phe
            20                  25                  30 aaa aaa gct cgt gac gct ctg gaa gaa tct ctg aaa ctg aaa aac tgg     144
Lys Lys Ala Arg Asp Ala Leu Glu Glu Ser Leu Lys Leu Lys Asn Trp
        35                  40                  45 tct tgc tct tct ccg gtt ttc ccg ggt aac tgg gat ctg cgt ctg ctg     192
Ser Cys Ser Ser Pro Val Phe Pro Gly Asn Trp Asp Leu Arg Leu Leu
    50                  55                  60 cag gtt cgt gaa cgt ccg gtt gct ctg gaa gct gaa ctg gct ctg acc     240

```
Gln Val Arg Glu Arg Pro Val Ala Leu Glu Ala Glu Leu Ala Leu Thr
 65                  70                  75                  80 ctg aaa gtt ctg gaa gct gct gca ggt cct gct ctg gaa gat gtt ctg      288
Leu Lys Val Leu Glu Ala Ala Ala Gly Pro Ala Leu Glu Asp Val Leu
                 85                  90                  95 gat cag ccg ctg cac act ctg cac cac atc ctg tct cag ctg cag gct      336
Asp Gln Pro Leu His Thr Leu His His Ile Leu Ser Gln Leu Gln Ala
            100                 105                 110 tgc att caa ccg caa ccg acc gct ggt ccg cgt ccg cgt ggt cgt ctg      384
Cys Ile Gln Pro Gln Pro Thr Ala Gly Pro Arg Pro Arg Gly Arg Leu
        115                 120                 125 cac cac tgg ctg cat cgt ctg cag gaa gct ccg aaa aaa gaa tct gct      432
His His Trp Leu His Arg Leu Gln Glu Ala Pro Lys Lys Glu Ser Ala
    130                 135                 140 ggt tgc ctg gaa gct tct gtt acc ttc aac ctg ttc cgt ctg ctg acc      480
Gly Cys Leu Glu Ala Ser Val Thr Phe Asn Leu Phe Arg Leu Leu Thr
145                 150                 155                 160 cgt gat ctg aaa tac gtt gct gat ggt aac ctg tct ctg cgt acc tct      528
Arg Asp Leu Lys Tyr Val Ala Asp Gly Asn Leu Ser Leu Arg Thr Ser
                165                 170                 175 acc cat ccg gaa tct acc taa                                           549
Thr His Pro Glu Ser Thr *
            180
```

<210> SEQ ID NO 29
<211> LENGTH: 182
<212> TYPE: PRT
<213> ORGANISM: Artificial Sequence
<220> FEATURE:
<223> OTHER INFORMATION: met IL-29 mutant C172S

<400> SEQUENCE: 29

```
Met Gly Pro Val Pro Thr Ser Lys Pro Thr Thr Thr Gly Lys Gly Cys
  1               5                  10                  15

His Ile Gly Arg Phe Lys Ser Leu Ser Pro Gln Glu Leu Ala Ser Phe
                 20                  25                  30

Lys Lys Ala Arg Asp Ala Leu Glu Glu Ser Leu Lys Leu Lys Asn Trp
             35                  40                  45

Ser Cys Ser Ser Pro Val Phe Pro Gly Asn Trp Asp Leu Arg Leu Leu
 50                  55                  60

Gln Val Arg Glu Arg Pro Val Ala Leu Glu Ala Glu Leu Ala Leu Thr
 65                  70                  75                  80

Leu Lys Val Leu Glu Ala Ala Ala Gly Pro Ala Leu Glu Asp Val Leu
                 85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Ser Leu Arg Thr Ser
                165                 170                 175

Thr His Pro Glu Ser Thr
            180
```

<210> SEQ ID NO 30

```
<211> LENGTH: 525
<212> TYPE: DNA
<213> ORGANISM: Artificial Sequence
<220> FEATURE:
<223> OTHER INFORMATION: degenerate sequence of SEQ ID NO: 18
<220> FEATURE:
<221> NAME/KEY: misc_feature
<222> LOCATION: (1)...(525)
<223> OTHER INFORMATION: n = A,T,C or G

<400> SEQUENCE: 30
gtnccngtng cnmgnytnca yggngcnytn ccngaygcnm gnggntgyca yathgcncar      60
ttyaarwsny tnwsnccnca rgarytncar gcnttyaarm gngcnaarga ygcnytngar    120
garwsnytny tnytnaarga ywsnmgntgy caywsnmgny tnttyccnmg nacntgggay    180
ytnmgncary tncargtnmg ngarmgnccn atggcnytng argcngaryt ngcnytnacn    240
ytnaargtny tngargcnac ncngayacn gayccngcny tgtngaygt nytngaycar     300 ccnytncaya cnytncayca yathytnwsn carttymgng cntgyathca rccncarccn    360 acngcggnc cnmgnacnmg nggnmgnytn caycaytggy tntaymgnyt ncargargcn     420
ccnaaraarg arwsnccngg ntgyytngar gcnwsngtna cnttyaayyt nttymgnytn    480
ytnacnmgng ayytnaaytg ygtngcnwsn ggngayytnt gygtn                    525

<210> SEQ ID NO 31
<211> LENGTH: 525
<212> TYPE: DNA
<213> ORGANISM: Artificial Sequence
<220> FEATURE:
<223> OTHER INFORMATION: degenerate sequence of SEQ ID NO: 20
<220> FEATURE:
<221> NAME/KEY: misc_feature
<222> LOCATION: (1)...(525)
<223> OTHER INFORMATION: n = A,T,C or G

<400> SEQUENCE: 31
gtnccngtng cnmgnytnca yggngcnytn ccngaygcnm gnggntgyca yathgcncar      60
ttyaarwsny tnwsnccnca rgarytncar gcnttyaarm gngcnaarga ygcnytngar    120
garwsnytny tnytnaarga ywsnmgntgy caywsnmgny tnttyccnmg nacntgggay    180
ytnmgncary tncargtnmg ngarmgnccn atggcnytng argcngaryt ngcnytnacn    240
ytnaargtny tngargcnac ncngayacn gayccngcny tgtngaygt nytngaycar     300 ccnytncaya cnytncayca yathytnwsn carttymgng cntgyathca rccncarccn    360 acngcggnc cnmgnacnmg nggnmgnytn caycaytggy tntaymgnyt ncargargcn     420
ccnaaraarg arwsnccngg ntgyytngar gcnwsngtna cnttyaayyt nttymgnytn    480
ytnacnmgng ayytnaaytg ygtngcnwsn ggngayytnt gygtn                    525

<210> SEQ ID NO 32
<211> LENGTH: 525
<212> TYPE: DNA
<213> ORGANISM: Artificial Sequence
<220> FEATURE:
<223> OTHER INFORMATION: degenerate sequence of SEQ ID NO: 22
<220> FEATURE:
<221> NAME/KEY: misc_feature
<222> LOCATION: (1)...(525)
<223> OTHER INFORMATION: n = A,T,C or G

<400> SEQUENCE: 32
gtnccngtng cnmgnytnca yggngcnytn ccngaygcnm gnggntgyca yathgcncar      60
ttyaarwsny tnwsnccnca rgarytncar gcnttyaarm gngcnaarga ygcnytngar    120
```

```
garwsnytny tnytnaarga ywsnmgntgy caywsnmgny tnttyccnmg nacntgggay    180
ytnmgncary tncargtnmg ngarmgnccn atggcnytng argcngaryt ngcnytnacn    240
ytnaargtny tngargcnac ngcngayacn gayccngcny tngtngaygt nyt

<210> SEQ ID NO 35
<211> LENGTH: 525
<212> TYPE: DNA
<213> ORGANISM: Artificial Sequence
<220> FEATURE:
<223> OTHER INFORMATION: degenerate sequence of SEQ ID NO: 28
<220> FEATURE:
<221> NAME/KEY: misc_feature
<222> LOCATION: (1)...(525)
<223> OTHER INFORMATION: n = A,T,C or G

<400> SEQUENCE: 35

```
gtnccngtng cnmgnytnca yggngcnytn ccngaygcnm gnggntgyca yathgcncar      60
ttyaarwsny tnwsnccnca rgarytncar gcnttyaarm gngcnaarga ygcnytngar     120
garwsnytny tnytnaarga ywsnmgntgy caywsnmgny tnttyccnmg nacntgggay     180
ytnmgncary tncargtnmg ngarmgnccn atggcnytng argcngaryt ngcnytnacn     240
ytnaargtny tngargcnac ngcngayacn gayccngcny tngtngaygt nytngaycar     300
ccnytncaya cnytncayca yathytnwsn carttymgng cntgyathca rccncarccn     360
acngcnggnc cnmgnacnmg nggnmgnytn caycaytggy tntaymgnyt ncargargcn     420
ccnaaraarg arwsnccngg ntgyytngar gcnwsngtna cnttyaayyt nttymgnytn     480
ytnacnmgng ayytnaaytg ygtngcnwsn ggngayytnt gygtn                    525
```

<210> SEQ ID NO 36
<211> LENGTH: 175
<212> TYPE: PRT
<213> ORGANISM: Artificial Sequence
<220> FEATURE:
<223> OTHER INFORMATION: IL-28A mutant C48X
<220> FEATURE:
<221> NAME/KEY: VARIANT
<222> LOCATION: (48)...(48)
<223> OTHER INFORMATION: Xaa = Ser, Ala, Thr, Val or Asn

<400> SEQUENCE: 36

```
Val Pro Val Ala Arg Leu His Gly Ala Leu Pro Asp Ala Arg Gly Cys
 1               5                  10                  15

His Ile Ala Gln Phe Lys Ser Leu Ser Pro Gln Glu Leu Gln Ala Phe
            20                  25                  30

Lys Arg Ala Lys Asp Ala Leu Glu Glu Ser Leu Leu Leu Lys Asp Xaa
        35                  40                  45

Arg Cys His Ser Arg Leu Phe Pro Arg Thr Trp Asp Leu Arg Gln Leu
    50                  55                  60

Gln Val Arg Glu Arg Pro Met Ala Leu Glu Ala Glu Leu Ala Leu Thr
65                  70                  75                  80

Leu Lys Val Leu Glu Ala Thr Ala Asp Thr Asp Pro Ala Leu Val Asp
                85                  90                  95

Val Leu Asp Gln Pro Leu His Thr Leu His His Ile Leu Ser Gln Phe
            100                 105                 110

Arg Ala Cys Ile Gln Pro Gln Pro Thr Ala Gly Pro Arg Thr Arg Gly
        115                 120                 125

Arg Leu His His Trp Leu Tyr Arg Leu Gln Glu Ala Pro Lys Lys Glu
    130                 135                 140

Ser Pro Gly Cys Leu Glu Ala Ser Val Thr Phe Asn Leu Phe Arg Leu
145                 150                 155                 160

Leu Thr Arg Asp Leu Asn Cys Val Ala Ser Gly Asp Leu Cys Val
                165                 170                 175
```

```
<210> SEQ ID NO 37
<211> LENGTH: 176
<212> TYPE: PRT
<213> ORGANISM: Artificial Sequence
<220> FEATURE:
<223> OTHER INFORMATION: met IL-28A mutant C49X
<220> FEATURE:
<221> NAME/KEY: VARIANT
<222> LOCATION: (49)...(49)
<223> OTHER INFORMATION: Xaa = Ser, Ala, Thr, Val or Asn

<400> SEQUENCE: 37

Met Val Pro Val Ala Arg Leu His Gly Ala Leu Pro Asp Ala Arg Gly
  1               5                  10                  15

Cys His Ile Ala Gln Phe Lys Ser Leu Ser Pro Gln Glu Leu Gln Ala
             20                  25                  30

Phe Lys Arg Ala Lys Asp Ala Leu Glu Glu Ser Leu Leu Leu Lys Asp
         35                  40                  45

Xaa Arg Cys His Ser Arg Leu Phe Pro Arg Thr Trp Asp Leu Arg Gln
 50                  55                  60

Leu Gln Val Arg Glu Arg Pro Met Ala Leu Glu Ala Glu Leu Ala Leu
 65                  70                  75                  80

Thr Leu Lys Val Leu Glu Ala Thr Ala Asp Thr Asp Pro Ala Leu Val
                 85                  90                  95

Asp Val Leu Asp Gln Pro Leu His Thr Leu His His Ile Leu Ser Gln
                100                 105                 110

Phe Arg Ala Cys Ile Gln Pro Gln Pro Thr Ala Gly Pro Arg Thr Arg
            115                 120                 125

Gly Arg Leu His His Trp Leu Tyr Arg Leu Gln Glu Ala Pro Lys Lys
        130                 135                 140

Glu Ser Pro Gly Cys Leu Glu Ala Ser Val Thr Phe Asn Leu Phe Arg
145                 150                 155                 160

Leu Leu Thr Arg Asp Leu Asn Cys Val Ala Ser Gly Asp Leu Cys Val
                165                 170                 175

<210> SEQ ID NO 38
<211> LENGTH: 175
<212> TYPE: PRT
<213> ORGANISM: Artificial Sequence
<220> FEATURE:
<223> OTHER INFORMATION: IL-28A mutant C50X
<220> FEATURE:
<221> NAME/KEY: VARIANT
<222> LOCATION: (50)...(50)
<223> OTHER INFORMATION: Xaa = Ser, Ala, Thr, Val or Asn

<400> SEQUENCE: 38

Val Pro Val Ala Arg Leu His Gly Ala Leu Pro Asp Ala Arg Gly Cys
  1               5                  10                  15

His Ile Ala Gln Phe Lys Ser Leu Ser Pro Gln Glu Leu Gln Ala Phe
             20                  25                  30

Lys Arg Ala Lys Asp Ala Leu Glu Glu Ser Leu Leu Leu Lys Asp Cys
         35                  40                  45

Arg Xaa His Ser Arg Leu Phe Pro Arg Thr Trp Asp Leu Arg Gln Leu
 50                  55                  60

Gln Val Arg Glu Arg Pro Met Ala Leu Glu Ala Glu Leu Ala Leu Thr
 65                  70                  75                  80

Leu Lys Val Leu Glu Ala Thr Ala Asp Thr Asp Pro Ala Leu Val Asp
                 85                  90                  95
```

```
Val Leu Asp Gln Pro Leu His Thr Leu His His Ile Leu Ser Gln Phe
            100                 105                 110

Arg Ala Cys Ile Gln Pro Gln Pro Thr Ala Gly Pro Arg Thr Arg Gly
            115                 120                 125

Arg Leu His His Trp Leu Tyr Arg Leu Gln Glu Ala Pro Lys Lys Glu
            130                 135                 140

Ser Pro Gly Cys Leu Glu Ala Ser Val Thr Phe Asn Leu Phe Arg Leu
145                 150                 155                 160

Leu Thr Arg Asp Leu Asn Cys Val Ala Ser Gly Asp Leu Cys Val
                165                 170                 175

<210> SEQ ID NO 39
<211> LENGTH: 176
<212> TYPE: PRT
<213> ORGANISM: Artificial Sequence
<220> FEATURE:
<223> OTHER INFORMATION: met IL-28A mutant C51X
<220> FEATURE:
<221> NAME/KEY: VARIANT
<222> LOCATION: (51)...(51)
<223> OTHER INFORMATION: Xaa = Ser, Ala, Thr, Val or Asn

<400> SEQUENCE: 39

Met Val Pro Val Ala Arg Leu His Gly Ala Leu Pro Asp Ala Arg Gly
1               5                   10                  15

Cys His Ile Ala Gln Phe Lys Ser Leu Ser Pro Gln Glu Leu Gln Ala
                20                  25                  30

Phe Lys Arg Ala Lys Asp Ala Leu Glu Glu Ser Leu Leu Leu Lys Asp
            35                  40                  45

Cys Arg Xaa His Ser Arg Leu Phe Pro Arg Thr Trp Asp Leu Arg Gln
50                  55                  60

Leu Gln Val Arg Glu Arg Pro Met Ala Leu Glu Ala Glu Leu Ala Leu
65                  70                  75                  80

Thr Leu Lys Val Leu Glu Ala Thr Ala Asp Thr Asp Pro Ala Leu Val
                85                  90                  95

Asp Val Leu Asp Gln Pro Leu His Thr Leu His His Ile Leu Ser Gln
            100                 105                 110

Phe Arg Ala Cys Ile Gln Pro Gln Pro Thr Ala Gly Pro Arg Thr Arg
            115                 120                 125

Gly Arg Leu His His Trp Leu Tyr Arg Leu Gln Glu Ala Pro Lys Lys
        130                 135                 140

Glu Ser Pro Gly Cys Leu Glu Ala Ser Val Thr Phe Asn Leu Phe Arg
145                 150                 155                 160

Leu Leu Thr Arg Asp Leu Asn Cys Val Ala Ser Gly Asp Leu Cys Val
                165                 170                 175

<210> SEQ ID NO 40
<211> LENGTH: 181
<212> TYPE: PRT
<213> ORGANISM: Artificial Sequence
<220> FEATURE:
<223> OTHER INFORMATION: IL-29 mutant C171X
<220> FEATURE:
<221> NAME/KEY: VARIANT
<222> LOCATION: (171)...(171)
<223> OTHER INFORMATION: Xaa = Ser, Ala, Thr, Val or Asn

<400> SEQUENCE: 40

Gly Pro Val Pro Thr Ser Lys Pro Thr Thr Thr Gly Lys Gly Cys His
1               5                   10                  15
```

```
Ile Gly Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
 50                  55                  60

Val Arg Glu Arg Pro Val Ala Leu Glu Ala Glu Leu Ala Leu Thr Leu
 65                  70                  75                  80

Lys Val Leu Glu Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asn Leu Xaa Leu Arg Thr Ser Thr
                165                 170                 175

His Pro Glu Ser Thr
            180

<210> SEQ ID NO 41
<211> LENGTH: 182
<212> TYPE: PRT
<213> ORGANISM: Artificial Sequence
<220> FEATURE:
<223> OTHER INFORMATION: met IL-29 mutant C172X
<220> FEATURE:
<221> NAME/KEY: VARIANT
<222> LOCATION: (172)...(172)
<223> OTHER INFORMATION: Xaa = Ser, Ala, Thr, Val or Asn

<400> SEQUENCE: 41

Met Gly Pro Val Pro Thr Ser Lys Pro Thr Thr Thr Gly Lys Gly Cys
 1               5                  10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
 50                  55                  60

Gln Val Arg Glu Arg Pro Val Ala Leu Glu Ala Glu Leu Ala Leu Thr
 65                  70                  75                  80

Leu Lys Val Leu Glu Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Xaa Leu Arg Thr Ser
                165                 170                 175
```

Thr His Pro Glu Ser Thr
            180

<210> SEQ ID NO 42
<211> LENGTH: 49
<212> TYPE: DNA
<213> ORGANISM: Artificial Sequence
<220> FEATURE:
<223> OTHER INFORMATION: oligonucleotide primer ZC40923

<400> SEQUENCE: 42
tccagggaat tcatataggc cggccaccat gaaactagac atgactggg         49

<210> SEQ ID NO 43
<211> LENGTH: 74
<212> TYPE: DNA
<213> ORGANISM: Artificial Sequence
<220> FEATURE:
<223> OTHER INFORMATION: oligonucleotide primer ZC43152

<400> SEQUENCE: 43
ggggtgggta caccccaga gctgttttaa ggcgcgcctc tagactattt ttagacacac    60
aggtccccac tggc                                                    74

<210> SEQ ID NO 44
<211> LENGTH: 50
<212> TYPE: DNA
<213> ORGANISM: Artificial Sequence
<220> FEATURE:
<223> OTHER INFORMATION: oligonucleotide primer ZC29740

<400> SEQUENCE: 44
ttgacaatta atcatcggct cgtataatgt gtggaattgt gagcggataa             50

<210> SEQ ID NO 45
<211> LENGTH: 42
<212> TYPE: DNA
<213> ORGANISM: Artificial Sequence
<220> FEATURE:
<223> OTHER INFORMATION: oligonucleotide primer ZC29741

<400> SEQUENCE: 45
tctgatttaa tctgtatcag gctgaaaatc ttatctcatc cg                    42

<210> SEQ ID NO 46
<211> LENGTH: 62
<212> TYPE: DNA
<213> ORGANISM: Artificial Sequence
<220> FEATURE:
<223> OTHER INFORMATION: oligonucleotide primer ZC29736

<400> SEQUENCE: 46
gtggaattgt gagcggataa caatttcaca cagaattcat taaagaggag aaattaactc   60
cc                                                                 62

<210> SEQ ID NO 47
<211> LENGTH: 63
<212> TYPE: DNA
<213> ORGANISM: Artificial Sequence
<220> FEATURE:
<223> OTHER INFORMATION: oligonucleotide primer ZC29738

<400> SEQUENCE: 47
gctgaaaatc ttatctcatc cgccaaaaca cccgggagtt aatttctcct ctttaatgaa   60
ttc                                                              63

<210> SEQ ID NO 48
<211> LENGTH: 78
<212> TYPE: DNA
<213> ORGANISM: Artificial Sequence
<220> FEATURE:
<223> OTHER INFORMATION: oligonucleotide primer ZC44566

<400> SEQUENCE: 48
tcttccagag cgtcacgagc tttttgaaa gaagccagtt cctgcggaga cagagatttg    60
aaacgaccga tgtggcaa                                                78

<210> SEQ ID NO 49
<211> LENGTH: 84
<212> TYPE: DNA
<213> ORGANISM: Artificial Sequence
<220> FEATURE:
<223> OTHER INFORMATION: oligonucleotide primer ZC44565

<400> SEQUENCE: 49
tcgtgacgct ctggaagaat ctctgaaact gaaaaactgg tcttgctctt ctccggtttt    60
cccgggtaac tgggatctgc gtct                                         84

<210> SEQ ID NO 50
<211> LENGTH: 71
<212> TYPE: DNA
<213> ORGANISM: Artificial Sequence
<220> FEATURE:
<223> OTHER INFORMATION: oligonucleotide primer ZC44564

<400> SEQUENCE: 50
aacagaagct tccaggcaac cagcagattc ttttttcgga gcttcctgca gacgatgcag    60
ccagtggtgc a                                                       71

<210> SEQ ID NO 51
<211> LENGTH: 73
<212> TYPE: DNA
<213> ORGANISM: Artificial Sequence
<220> FEATURE:
<223> OTHER INFORMATION: oligonucleotide primer ZC44563

<400> SEQUENCE: 51
aactggctct gaccctgaaa gttctggaag ctgctgcagg tcctgctctg aagatgttc     60 tggatcagcc gct                                                     73

<210> SEQ ID NO 52
<211> LENGTH: 74
<212> TYPE: DNA
<213> ORGANISM: Artificial Sequence
<220> FEATURE:
<223> OTHER INFORMATION: oligonucleotide primer ZC44562

<400> SEQUENCE: 52
tcagggtcag agccagttca gcttccagag caaccggacg ttcacgaacc tgcagcagac    60
gcagatccca gtta                                                    74

<210> SEQ ID NO 53
<211> LENGTH: 76
<212> TYPE: DNA
<213> ORGANISM: Artificial Sequence
<220> FEATURE:

-continued

<223> OTHER INFORMATION: oligonucleotide primer ZC44561

<400> SEQUENCE: 53
tcagctgcag gcttgcattc aaccgcaacc gaccgctggt ccgcgtccgc gtggtcgtct    60
gcaccactgg ctgcat    76

<210> SEQ ID NO 54
<211> LENGTH: 60
<212> TYPE: DNA
<213> ORGANISM: Artificial Sequence
<220> FEATURE:
<223> OTHER INFORMATION: oligonucleotide primer ZC44560

<400> SEQUENCE: 54
atgcaagcct gcagctgaga caggatgtgg tgcagagtgt gcagcggctg atccagaaca    60

<210> SEQ ID NO 55
<211> LENGTH: 62
<212> TYPE: DNA
<213> ORGANISM: Artificial Sequence
<220> FEATURE:
<223> OTHER INFORMATION: oligonucleotide primer ZC44559

<400> SEQUENCE: 55
atgggtccgg ttccgacctc taaaccaacc accactggta aaggttgcca catcggtcgt    60
tt    62

<210> SEQ ID NO 56
<211> LENGTH: 65
<212> TYPE: DNA
<213> ORGANISM: Artificial Sequence
<220> FEATURE:
<223> OTHER INFORMATION: oligonucleotide primer ZC44558

<400> SEQUENCE: 56
ttaggtagat tccggatggg tagaggtacg caggcacagg ttaccatcag caacgtattt    60
cagat    65

<210> SEQ ID NO 57
<211> LENGTH: 69
<212> TYPE: DNA
<213> ORGANISM: Artificial Sequence
<220> FEATURE:
<223> OTHER INFORMATION: oligonucleotide primer ZC44557

<400> SEQUENCE: 57
tgcctggaag cttctgttac cttcaacctg ttccgtctgc tgacccgtga tctgaaatac    60
gttgctgat    69

<210> SEQ ID NO 58
<211> LENGTH: 41
<212> TYPE: DNA
<213> ORGANISM: Artificial Sequence
<220> FEATURE:
<223> OTHER INFORMATION: oligonucleotide primer ZC44340

<400> SEQUENCE: 58
cgttgctgat ggtaacctgt ctctgcgtac ctctacccat c    41

<210> SEQ ID NO 59
<211> LENGTH: 41
<212> TYPE: DNA
<213> ORGANISM: Artificial Sequence
<220> FEATURE:
<223> OTHER INFORMATION: oligonucleotide primer ZC44341

<400> SEQUENCE: 59
gatgggtaga ggtacgcaga gacaggttac catcagcaac g                41

<210> SEQ ID NO 60
<211> LENGTH: 68
<212> TYPE: DNA
<213> ORGANISM: Artificial Sequence
<220> FEATURE:
<223> OTHER INFORMATION: oligonucleotide primer ZC41212

<400> SEQUENCE: 60
ctagaaataa ttttgtttaa ctttaagaag gagatatata tatgggccct gtccccactt    60
ccaagccc                                                             68

<210> SEQ ID NO 61
<211> LENGTH: 67
<212> TYPE: DNA
<213> ORGANISM: Artificial Sequence
<220> FEATURE:
<223> OTHER INFORMATION: oligonucleotide primer ZC41041

<400> SEQUENCE: 61
tctgtatcag gctgaaaatc ttatctcatc cgccaaaaca ttaggtggac tcagggtggg    60
ttgacgt                                                              67

<210> SEQ ID NO 62
<211> LENGTH: 65
<212> TYPE: DNA
<213> ORGANISM: Artificial Sequence
<220> FEATURE:
<223> OTHER INFORMATION: oligonucleotide primer ZC43431

<400> SEQUENCE: 62
ctagaaataa ttttgtttaa ctttaagaag gagatatata tatggttcct gtcgccaggc    60
tccac                                                                65

<210> SEQ ID NO 63
<211> LENGTH: 67
<212> TYPE: DNA
<213> ORGANISM: Artificial Sequence
<220> FEATURE:
<223> OTHER INFORMATION: oligonucleotide primer ZC43437

<400> SEQUENCE: 63
taatctgtat caggctgaaa atcttatctc atccgccaaa acatcagaca cacaggtccc    60
cactggc                                                              67

<210> SEQ ID NO 64
<211> LENGTH: 39
<212> TYPE: DNA
<213> ORGANISM: Artificial Sequence
<220> FEATURE:
<223> OTHER INFORMATION: oligonucleotide primer ZC44327

<400> SEQUENCE: 64
gtggccgatg ggaacctgtc cctgagaacg tcaacccac                           39

<210> SEQ ID NO 65
<211> LENGTH: 39
<212> TYPE: DNA

<210> SEQ ID NO 65
<211> LENGTH: 39
<212> TYPE: DNA
<213> ORGANISM: Artificial Sequence
<220> FEATURE:
<223> OTHER INFORMATION: oligonucleotide primer ZC44328

<400> SEQUENCE: 65
gtgggttgac gttctcaggg acaggttccc atcggccac                              39

<210> SEQ ID NO 66
<211> LENGTH: 83
<212> TYPE: DNA
<213> ORGANISM: Artificial Sequence
<220> FEATURE:
<223> OTHER INFORMATION: oligonucleotide primer ZC45399

<400> SEQUENCE: 66
tcaggtccca ggtcctgggg aagaggcggg agtggcacct ggagtccttc agcagaagcg      60
actcttctaa ggcatctttg gcc                                              83

<210> SEQ ID NO 67
<211> LENGTH: 531
<212> TYPE: DNA
<213> ORGANISM: Artificial Sequence
<220> FEATURE:
<223> OTHER INFORMATION: zcyto20 mature start from pYEL7b
<220> FEATURE:
<221> NAME/KEY: CDS
<222> LOCATION: (1)...(531)

<400> SEQUENCE: 67

```
atg gtt cct gtc gcc agg ctc cac ggg gct ctc ccg gat gca agg ggc        48
Met Val Pro Val Ala Arg Leu His Gly Ala Leu Pro Asp Ala Arg Gly
 1               5                  10                  15 tgc cac ata gcc cag ttc aag tcc ctg tct cca cag gag ctg cag gcc        96
Cys His Ile Ala Gln Phe Lys Ser Leu Ser Pro Gln Glu Leu Gln Ala
                20                  25                  30 ttt aag agg gcc aaa gat gcc tta gaa gag tcg ctt ctg ctg aag gac       144
Phe Lys Arg Ala Lys Asp Ala Leu Glu Glu Ser Leu Leu Leu Lys Asp
            35                  40                  45 tgc agg tgc cac tcc cgc ctc ttc ccc agg acc tgg gac ctg agg cag       192
Cys Arg Cys His Ser Arg Leu Phe Pro Arg Thr Trp Asp Leu Arg Gln
        50                  55                  60 ctg cag gtg agg gag cgc ccc atg gct ttg gag gct gag ctg gcc ctg       240
Leu Gln Val Arg Glu Arg Pro Met Ala Leu Glu Ala Glu Leu Ala Leu
 65                  70                  75                  80 acg ctg aag gtt ctg gag gcc acc gct gac act gac cca gcc ctg gtg       288
Thr Leu Lys Val Leu Glu Ala Thr Ala Asp Thr Asp Pro Ala Leu Val
                 85                  90                  95 gac gtc ttg gac cag ccc ctt cac acc ctg cac cat atc ctc tcc cag       336
Asp Val Leu Asp Gln Pro Leu His Thr Leu His His Ile Leu Ser Gln
            100                 105                 110 ttc cgg gcc tgt atc cag cct cag ccc acg gca ggg ccc agg acc cgg       384
Phe Arg Ala Cys Ile Gln Pro Gln Pro Thr Ala Gly Pro Arg Thr Arg
        115                 120                 125 ggc cgc ctc cac cat tgg ctg tac cgg ctc cag gag gcc cca aaa aag       432
Gly Arg Leu His His Trp Leu Tyr Arg Leu Gln Glu Ala Pro Lys Lys
    130                 135                 140 gag tcc cct ggc tgc ctc gag gcc tct gtc acc ttc aac ctc ttc cgc       480
Glu Ser Pro Gly Cys Leu Glu Ala Ser Val Thr Phe Asn Leu Phe Arg
145                 150                 155                 160 ctc ctc acg cga gac ctg aat tgt gtt gcc agt ggg gac ctg tgt gtc       528
Leu Leu Thr Arg Asp Leu Asn Cys Val Ala Ser Gly Asp Leu Cys Val
                165                 170                 175
```

```
tga                                                                  531
*

<210> SEQ ID NO 68
<211> LENGTH: 83
<212> TYPE: DNA
<213> ORGANISM: Artificial Sequence
<220> FEATURE:
<223> OTHER INFORMATION: oligonucleotide primer ZC45398

<400> SEQUENCE: 68
ggccaaagat gccttagaag agtcgcttct gctgaaggac tccaggtgcc actcccgcct    60
cttccccagg acctgggacc tga                                            83

<210> SEQ ID NO 69
<211> LENGTH: 83
<212> TYPE: DNA
<213> ORGANISM: Artificial Sequence
<220> FEATURE:
<223> OTHER INFORMATION: oligonucleotide primer ZC45397

<400> SEQUENCE: 69
gctgcctcag gtcccaggtc ctggggaaga ggcgggagtg ggacctgcag tccttcagca    60
gaagcgactc ttctaaggca tct                                            83

<210> SEQ ID NO 70
<211> LENGTH: 83
<212> TYPE: DNA
<213> ORGANISM: Artificial Sequence
<220> FEATURE:
<223> OTHER INFORMATION: oligonucleotide primer ZC45396

<400> SEQUENCE: 70
agatgcctta gaagagtcgc ttctgctgaa ggactgcagg tcccactccc gcctcttccc    60
caggacctgg gacctgaggc agc                                            83

<210> SEQ ID NO 71
<211> LENGTH: 1013
<212> TYPE: DNA
<213> ORGANISM: Homo sapiens
<220> FEATURE:
<221> NAME/KEY: CDS
<222> LOCATION: (14)...(991)

<400> SEQUENCE: 71
ccagcgtccg tcc atg gcg tgg agc ctt ggg agc tgg ctg ggt ggc tgc       49
              Met Ala Trp Ser Leu Gly Ser Trp Leu Gly Gly Cys
                1               5                   10 ctg ctg gtg tca gca ttg gga atg gta cca cct ccc gaa aat gtc aga      97
Leu Leu Val Ser Ala Leu Gly Met Val Pro Pro Pro Glu Asn Val Arg
         15                  20                  25 atg aat tct gtt aat ttc aag aac att cta cag tgg gag tca cct gct     145
Met Asn Ser Val Asn Phe Lys Asn Ile Leu Gln Trp Glu Ser Pro Ala
 30                  35                  40 ttt gcc aaa ggg aac ctg act ttc aca gct cag tac cta agt tat agg     193
Phe Ala Lys Gly Asn Leu Thr Phe Thr Ala Gln Tyr Leu Ser Tyr Arg
 45                  50                  55                  60 ata ttc caa gat aaa tgc atg aat act acc ttg acg gaa tgt gat ttc     241
Ile Phe Gln Asp Lys Cys Met Asn Thr Thr Leu Thr Glu Cys Asp Phe
                 65                  70                  75 tca agt ctt tcc aag tat ggt gac cac acc ttg aga gtc agg gct gaa     289
Ser Ser Leu Ser Lys Tyr Gly Asp His Thr Leu Arg Val Arg Ala Glu
             80                  85                  90
```

```
ttt gca gat gag cat tca gac tgg gta aac atc acc ttc tgt cct gtg      337
Phe Ala Asp Glu His Ser Asp Trp Val Asn Ile Thr Phe Cys Pro Val
         95                 100                 105 gat gac acc att att gga ccc cct gga atg caa gta gaa gta ctt gct      385
Asp Asp Thr Ile Ile Gly Pro Pro Gly Met Gln Val Glu Val Leu Ala
    110                 115                 120 gat tct tta cat atg cgt ttc tta gcc cct aaa att gag aat gaa tac      433
Asp Ser Leu His Met Arg Phe Leu Ala Pro Lys Ile Glu Asn Glu Tyr
125                 130                 135                 140 gaa act tgg act atg aag aat gtg tat aac tca tgg act tat aat gtg      481
Glu Thr Trp Thr Met Lys Asn Val Tyr Asn Ser Trp Thr Tyr Asn Val
                145                 150                 155 caa tac tgg aaa aac ggt act gat gaa aag ttt caa att act ccc cag      529
Gln Tyr Trp Lys Asn Gly Thr Asp Glu Lys Phe Gln Ile Thr Pro Gln
            160                 165                 170 tat gac ttt gag gtc ctc aga aac ctg gag cca tgg aca act tat tgt      577
Tyr Asp Phe Glu Val Leu Arg Asn Leu Glu Pro Trp Thr Thr Tyr Cys
        175                 180                 185 gtt caa gtt cga ggg ttt ctt cct gat cgg aac aaa gct ggg gaa tgg      625
Val Gln Val Arg Gly Phe Leu Pro Asp Arg Asn Lys Ala Gly Glu Trp
    190                 195                 200 agt gag cct gtc tgt gag caa aca acc cat gac gaa acg gtc ccc tcc      673
Ser Glu Pro Val Cys Glu Gln Thr Thr His Asp Glu Thr Val Pro Ser
205                 210                 215                 220 tgg atg gtg gcc gtc atc ctc atg gcc tcg gtc ttc atg gtc tgc ctg      721
Trp Met Val Ala Val Ile Leu Met Ala Ser Val Phe Met Val Cys Leu
                225                 230                 235 gca ctc ctc ggc tgc ttc tcc ttg ctg tgg tgc gtt tac aag aag aca      769
Ala Leu Leu Gly Cys Phe Ser Leu Leu Trp Cys Val Tyr Lys Lys Thr
            240                 245                 250 aag tac gcc ttc tcc cct agg aat tct ctt cca cag cac ctg aaa gag      817
Lys Tyr Ala Phe Ser Pro Arg Asn Ser Leu Pro Gln His Leu Lys Glu
        255                 260                 265 ttt ttg ggc cat cct cat cat aac aca ctt ctg ttt ttc tcc ttt cca      865
Phe Leu Gly His Pro His His Asn Thr Leu Leu Phe Phe Ser Phe Pro
    270                 275                 280 ttg tcg gat gag aat gat gtt ttt gac aag cta agt gtc att gca gaa      913
Leu Ser Asp Glu Asn Asp Val Phe Asp Lys Leu Ser Val Ile Ala Glu
285                 290                 295                 300 gac tct gag agc ggc aag cag aat cct ggt gac agc tgc agc ctc ggg      961
Asp Ser Glu Ser Gly Lys Gln Asn Pro Gly Asp Ser Cys Ser Leu Gly
                305                 310                 315 acc ccg cct ggg cag ggg ccc caa agc tag gctctgagaa ggaaacacac       1011
Thr Pro Pro Gly Gln Gly Pro Gln Ser *
            320                 325 tc                                                                  1013

<210> SEQ ID NO 72
<211> LENGTH: 49
<212> TYPE: DNA
<213> ORGANISM: Artificial Sequence
<220> FEATURE:
<223> OTHER INFORMATION: oligonucleotide primer ZC40922

<400> SEQUENCE: 72
tccagggaat tcatataggc cggccaccat ggctgcagct tggaccgtg                49

<210> SEQ ID NO 73
<211> LENGTH: 71
<212> TYPE: DNA
```

<213> ORGANISM: Artificial Sequence
<220> FEATURE:
<223> OTHER INFORMATION: oligonucleotide primer ZC43153

<400> SEQUENCE: 73

```
ggggtgggta caaccccaga gctgttttaa ggcgcgcctc tagactattt ttaggtggac    60
tcagggtggg t                                                          71
```

<210> SEQ ID NO 74
<211> LENGTH: 546
<212> TYPE: DNA
<213> ORGANISM: Artificial Sequence
<220> FEATURE:
<223> OTHER INFORMATION: IL29 mutant C15X, Asn169
<220> FEATURE:
<221> NAME/KEY: CDS
<222> LOCATION: (1)...(546)
<220> FEATURE:
<221> NAME/KEY: variation
<222> LOCATION: (44)...(45)
<223> OTHER INFORMATION: n = A, G, T, or C

<400> SEQUENCE: 74

```
ggc cct gtc ccc act tcc aag ccc acc aca act ggg aag ggc dnn cac      48
Gly Pro Val Pro Thr Ser Lys Pro Thr Thr Thr Gly Lys Gly Xaa His
 1               5                  10                  15 att ggc agg ttc aaa tct ctg tca cca cag gag cta gcg agc ttc aag      96
Ile Gly Arg Phe Lys Ser Leu Ser Pro Gln Glu Leu Ala Ser Phe Lys
             20                  25                  30 aag gcc agg gac gcc ttg gaa gag tca ctc aag ctg aaa aac tgg agt     144
Lys Ala Arg Asp Ala Leu Glu Glu Ser Leu Lys Leu Lys Asn Trp Ser
         35                  40                  45 tgc agc tct cct gtc ttc ccc ggg aat tgg gac ctg agg ctt ctc cag     192
Cys Ser Ser Pro Val Phe Pro Gly Asn Trp Asp Leu Arg Leu Leu Gln
     50                  55                  60 gtg agg gag cgc cct gtg gcc ttg gag gct gag ctg gcc ctg acg ctg     240
Val Arg Glu Arg Pro Val Ala Leu Glu Ala Glu Leu Ala Leu Thr Leu
 65                  70                  75                  80 aag gtc ctg gag gcc gct gct ggc cca gcc ctg gag gac gtc cta gac     288
Lys Val Leu Glu Ala Ala Ala Gly Pro Ala Leu Glu Asp Val Leu Asp
                 85                  90                  95 cag ccc ctt cac acc ctg cac cac atc ctc tcc cag ctc cag gcc tgt     336
Gln Pro Leu His Thr Leu His His Ile Leu Ser Gln Leu Gln Ala Cys
            100                 105                 110 atc cag cct cag ccc aca gca ggg ccc agg ccc cgg ggc cgc ctc cac     384
Ile Gln Pro Gln Pro Thr Ala Gly Pro Arg Pro Arg Gly Arg Leu His
        115                 120                 125 cac tgg ctg cac cgg ctc cag gag gcc ccc aaa aag gag tcc gct ggc     432
His Trp Leu His Arg Leu Gln Glu Ala Pro Lys Lys Glu Ser Ala Gly
    130                 135                 140 tgc ctg gag gca tct gtc acc ttc aac ctc ttc cgc ctc ctc acg cga     480
Cys Leu Glu Ala Ser Val Thr Phe Asn Leu Phe Arg Leu Leu Thr Arg
145                 150                 155                 160 gac ctc aaa tat gtg gcc gat ggg aay ctg tgt ctg aga acg tca acc     528
Asp Leu Lys Tyr Val Ala Asp Gly Asn Leu Cys Leu Arg Thr Ser Thr
                165                 170                 175 cac cct gag tcc acc tga                                             546
His Pro Glu Ser Thr *
            180
```

<210> SEQ ID NO 75
<211> LENGTH: 181
<212> TYPE: PRT

<213> ORGANISM: Artificial Sequence
<220> FEATURE:
<221> NAME/KEY: VARIANT
<222> LOCATION: (15)...(15)
<223> OTHER INFORMATION: Xaa = Ser, Ala, Thr, Val, or Asn
<220> FEATURE:
<223> OTHER INFORMATION: IL29 mutant C15X, Asn169

<400> SEQUENCE: 75

Gly Pro Val Pro Thr Ser Lys Pro Thr Thr Thr Gly Lys Gly Xaa His
1               5                   10                  15

Ile Gly Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
    50                  55                  60

Val Arg Glu Arg Pro Val Ala Leu Glu Ala Glu Leu Ala Leu Thr Leu
65                  70                  75                  80

Lys Val Leu Glu Ala Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
    130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asn Leu Cys Leu Arg Thr Ser Thr
                165                 170                 175

His Pro Glu Ser Thr
            180

<210> SEQ ID NO 76
<211> LENGTH: 549
<212> TYPE: DNA
<213> ORGANISM: Artificial Sequence
<220> FEATURE:
<223> OTHER INFORMATION: Met IL29 mutant C16X, Asn170
<220> FEATURE:
<221> NAME/KEY: CDS
<222> LOCATION: (1)...(549)
<220> FEATURE:
<221> NAME/KEY: variation
<222> LOCATION: (47)...(48)
<223> OTHER INFORMATION: n = A, T, G, or C

<400> SEQUENCE: 76 atg ggc cct gtc ccc act tcc aag ccc acc aca act ggg aag ggc dnn    48
Met Gly Pro Val Pro Thr Ser Lys Pro Thr Thr Thr Gly Lys Gly Xaa
1               5                   10                  15 cac att ggc agg ttc aaa tct ctg tca cca cag gag cta gcg agc ttc    96
His Ile Gly Arg Phe Lys Ser Leu Ser Pro Gln Glu Leu Ala Ser Phe
            20                  25                  30 aag aag gcc agg gac gcc ttg gaa gag tca ctc aag ctg aaa aac tgg    144
Lys Lys Ala Arg Asp Ala Leu Glu Glu Ser Leu Lys Leu Lys Asn Trp
        35                  40                  45 agt tgc agc tct cct gtc ttc ccc ggg aat tgg gac ctg agg ctt ctc    192
Ser Cys Ser Ser Pro Val Phe Pro Gly Asn Trp Asp Leu Arg Leu Leu
    50                  55                  60

-continued

```
cag gtg agg gag cgc cct gtg gcc ttg gag gct gag ctg gcc ctg acg      240
Gln Val Arg Glu Arg Pro Val Ala Leu Glu Ala Glu Leu Ala Leu Thr
 65                  70                  75                  80 ctg aag gtc ctg gag gcc gct gct ggc cca gcc ctg gag gac gtc cta      288
Leu Lys Val Leu Glu Ala Ala Ala Gly Pro Ala Leu Glu Asp Val Leu
                 85                  90                  95 gac cag ccc ctt cac acc ctg cac cac atc ctc tcc cag ctc cag gcc      336
Asp Gln Pro Leu His Thr Leu His His Ile Leu Ser Gln Leu Gln Ala
            100                 105                 110 tgt atc cag cct cag ccc aca gca ggg ccc agg ccc cgg ggc cgc ctc      384
Cys Ile Gln Pro Gln Pro Thr Ala Gly Pro Arg Pro Arg Gly Arg Leu
        115                 120                 125 cac cac tgg ctg cac cgg ctc cag gag gcc ccc aaa aag gag tcc gct      432
His His Trp Leu His Arg Leu Gln Glu Ala Pro Lys Lys Glu Ser Ala
    130                 135                 140 ggc tgc ctg gag gca tct gtc acc ttc aac ctc ttc cgc ctc ctc acg      480
Gly Cys Leu Glu Ala Ser Val Thr Phe Asn Leu Phe Arg Leu Leu Thr
145                 150                 155                 160 cga gac ctc aaa tat gtg gcc gat ggg aay ctg tgt ctg aga acg tca      528
Arg Asp Leu Lys Tyr Val Ala Asp Gly Asn Leu Cys Leu Arg Thr Ser
                165                 170                 175 acc cac cct gag tcc acc tga                                          549
Thr His Pro Glu Ser Thr *
            180
```

<210> SEQ ID NO 77
<211> LENGTH: 182
<212> TYPE: PRT
<213> ORGANISM: Artificial Sequence
<220> FEATURE:
<221> NAME/KEY: VARIANT
<222> LOCATION: (16)...(16)
<223> OTHER INFORMATION: Xaa = Ser, Ala, Thr, Val, or Asn
<220> FEATURE:
<223> OTHER INFORMATION: Met IL29 mutant C16X, Asn170

<400> SEQUENCE: 77

```
Met Gly Pro Val Pro Thr Ser Lys Pro Thr Thr Thr Gly Lys Gly Xaa
 1               5                   10                  15

His Ile Gly Arg Phe Lys Ser Leu Ser Pro Gln Glu Leu Ala Ser Phe
                20                  25                  30

Lys Lys Ala Arg Asp Ala Leu Glu Glu Ser Leu Lys Leu Lys Asn Trp
            35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
 65                  70                  75                  80

Leu Lys Val Leu Glu Ala Ala Ala Gly Pro Ala Leu Glu Asp Val Leu
                 85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Cys Leu Arg Thr Ser
                165                 170                 175
```

```
Thr His Pro Glu Ser Thr
            180

<210> SEQ ID NO 78
<211> LENGTH: 546
<212> TYPE: DNA
<213> ORGANISM: Artificial Sequence
<220> FEATURE:
<223> OTHER INFORMATION: IL29 mutant C15X, Asp169
<220> FEATURE:
<221> NAME/KEY: CDS
<222> LOCATION: (1)...(546)
<220> FEATURE:
<221> NAME/KEY: variation
<222> LOCATION: (44)...(45)
<223> OTHER INFORMATION: n = A, T, G, or C

<400> SEQUENCE: 78 ggc cct gtc ccc act tcc aag ccc acc aca act ggg aag ggc dnn cac      48
Gly Pro Val Pro Thr Ser Lys Pro Thr Thr Thr Gly Lys Gly Xaa His
1               5                   10                  15 att ggc agg ttc aaa tct ctg tca cca cag gag cta gcg agc ttc aag      96
Ile Gly Arg Phe Lys Ser Leu Ser Pro Gln Glu Leu Ala Ser Phe Lys
                20                  25                  30 aag gcc agg gac gcc ttg gaa gag tca ctc aag ctg aaa aac tgg agt     144
Lys Ala Arg Asp Ala Leu Glu Glu Ser Leu Lys Leu Lys Asn Trp Ser
        35                  40                  45 tgc agc tct cct gtc ttc ccc ggg aat tgg gac ctg agg ctt ctc cag     192
Cys Ser Ser Pro Val Phe Pro Gly Asn Trp Asp Leu Arg Leu Leu Gln
    50                  55                  60 gtg agg gag cgc cct gtg gcc ttg gag gct gag ctg gcc ctg acg ctg     240
Val Arg Glu Arg Pro Val Ala Leu Glu Ala Glu Leu Ala Leu Thr Leu
65                  70                  75                  80 aag gtc ctg gag gcc gct gct ggc cca gcc ctg gag gac gtc cta gac     288
Lys Val Leu Glu Ala Ala Ala Gly Pro Ala Leu Glu Asp Val Leu Asp
                85                  90                  95 cag ccc ctt cac acc ctg cac cac atc ctc tcc cag ctc cag gcc tgt     336
Gln Pro Leu His Thr Leu His His Ile Leu Ser Gln Leu Gln Ala Cys
            100                 105                 110 atc cag cct cag ccc aca gca ggg ccc agg ccc cgg ggc cgc ctc cac     384
Ile Gln Pro Gln Pro Thr Ala Gly Pro Arg Pro Arg Gly Arg Leu His
        115                 120                 125 cac tgg ctg cac cgg ctc cag gag gcc ccc aaa aag gag tcc gct ggc     432
His Trp Leu His Arg Leu Gln Glu Ala Pro Lys Lys Glu Ser Ala Gly
    130                 135                 140 tgc ctg gag gca tct gtc acc ttc aac ctc ttc cgc ctc ctc acg cga     480
Cys Leu Glu Ala Ser Val Thr Phe Asn Leu Phe Arg Leu Leu Thr Arg
145                 150                 155                 160 gac ctc aaa tat gtg gcc gat ggg gay ctg tgt ctg aga acg tca acc     528
Asp Leu Lys Tyr Val Ala Asp Gly Asp Leu Cys Leu Arg Thr Ser Thr
                165                 170                 175 cac cct gag tcc acc tga                                             546
His Pro Glu Ser Thr *
            180

<210> SEQ ID NO 79
<211> LENGTH: 181
<212> TYPE: PRT
<213> ORGANISM: Artificial Sequence
<220> FEATURE:
<223> OTHER INFORMATION: IL29 mutant C15X, Asp169
<220> FEATURE:
<221> NAME/KEY: VARIANT
<222> LOCATION: (15)...(15)
<223> OTHER INFORMATION: Xaa = Ser, Ala, Thr, Val, or Asn
```

<400> SEQUENCE: 79

Gly Pro Val Pro Thr Ser Lys Pro Thr Thr Thr Gly Lys Gly Xaa His
1               5                   10                  15

Ile Gly Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
50                  55                  60

Val Arg Glu Arg Pro Val Ala Leu Glu Ala Glu Leu Ala Leu Thr Leu
65                  70                  75                  80

Lys Val Leu Glu Ala Ala Gly Pro Ala Leu Glu Asp Val Leu Asp
            85                  90                  95

Gln Pro Leu His Thr Leu His His Ile Leu Ser Gln Leu Gln Ala Cys
        100                 105                 110

Ile Gln Pro Gln Pro Thr Ala Gly Pro Arg Pro Arg Gly Arg Leu His
            115                 120                 125

His Trp Leu His Arg Leu Gln Glu Ala Pro Lys Lys Glu Ser Ala Gly
    130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asp Leu Cys Leu Arg Thr Ser Thr
                165                 170                 175

His Pro Glu Ser Thr
            180

<210> SEQ ID NO 80
<211> LENGTH: 549
<212> TYPE: DNA
<213> ORGANISM: Artificial Sequence
<220> FEATURE:
<223> OTHER INFORMATION: Met IL29 mutant C16X, Asp170
<220> FEATURE:
<221> NAME/KEY: CDS
<222> LOCATION: (1)...(549)
<220> FEATURE:
<221> NAME/KEY: variation
<222> LOCATION: (47)...(48)
<223> OTHER INFORMATION: n = A, T, G, or C

<400> SEQUENCE: 80 atg ggc cct gtc ccc act tcc aag ccc acc aca act ggg aag ggc dnn     48
Met Gly Pro Val Pro Thr Ser Lys Pro Thr Thr Thr Gly Lys Gly Xaa
1               5                   10                  15 cac att ggc agg ttc aaa tct ctg tca cca cag gag cta gcg agc ttc     96
His Ile Gly Arg Phe Lys Ser Leu Ser Pro Gln Glu Leu Ala Ser Phe
            20                  25                  30 aag aag gcc agg gac gcc ttg gaa gag tca ctc aag ctg aaa aac tgg    144
Lys Lys Ala Arg Asp Ala Leu Glu Glu Ser Leu Lys Leu Lys Asn Trp
        35                  40                  45 agt tgc agc tct cct gtc ttc ccc ggg aat tgg gac ctg agg ctt ctc    192
Ser Cys Ser Ser Pro Val Phe Pro Gly Asn Trp Asp Leu Arg Leu Leu
    50                  55                  60 cag gtg agg gag cgc cct gtg gcc ttg gag gct gag ctg gcc ctg acg    240
Gln Val Arg Glu Arg Pro Val Ala Leu Glu Ala Glu Leu Ala Leu Thr
65                  70                  75                  80 ctg aag gtc ctg gag gcc gct gct ggc cca gcc ctg gag gac gtc cta    288
Leu Lys Val Leu Glu Ala Ala Ala Gly Pro Ala Leu Glu Asp Val Leu
            85                  90                  95

```
gac cag ccc ctt cac acc ctg cac cac atc ctc tcc cag ctc cag gcc    336
Asp Gln Pro Leu His Thr Leu His His Ile Leu Ser Gln Leu Gln Ala
            100                 105                 110 tgt atc cag cct cag ccc aca gca ggg ccc agg ccc cgg ggc cgc ctc    384
Cys Ile Gln Pro Gln Pro Thr Ala Gly Pro Arg Pro Arg Gly Arg Leu
        115                 120                 125 cac cac tgg ctg cac cgg ctc cag gag gcc ccc aaa aag gag tcc gct    432
His His Trp Leu His Arg Leu Gln Glu Ala Pro Lys Lys Glu Ser Ala
130                 135                 140 ggc tgc ctg gag gca tct gtc acc ttc aac ctc ttc cgc ctc ctc acg    480
Gly Cys Leu Glu Ala Ser Val Thr Phe Asn Leu Phe Arg Leu Leu Thr
145                 150                 155                 160 cga gac ctc aaa tat gtg gcc gat ggg gay ctg tgt ctg aga acg tca    528
Arg Asp Leu Lys Tyr Val Ala Asp Gly Asp Leu Cys Leu Arg Thr Ser
                165                 170                 175 acc cac cct gag tcc acc tga                                        549
Thr His Pro Glu Ser Thr *
            180
```

<210> SEQ ID NO 81
<211> LENGTH: 182
<212> TYPE: PRT
<213> ORGANISM: Artificial Sequence
<220> FEATURE:
<223> OTHER INFORMATION: Met IL29 mutant C16X, Asp170
<220> FEATURE:
<221> NAME/KEY: VARIANT
<222> LOCATION: (16)...(16)
<223> OTHER INFORMATION: Xaa = Ser, Ala, Thr, Val, or Asn

<400> SEQUENCE: 81

```
Met Gly Pro Val Pro Thr Ser Lys Pro Thr Thr Thr Gly Lys Gly Xaa
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
50                  55                  60

Gln Val Arg Glu Arg Pro Val Ala Leu Glu Ala Glu Leu Ala Leu Thr
65                  70                  75                  80

Leu Lys Val Leu Glu Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asp Leu Cys Leu Arg Thr Ser
                165                 170                 175

Thr His Pro Glu Ser Thr
            180
```

<210> SEQ ID NO 82
<211> LENGTH: 546
<212> TYPE: DNA

<213> ORGANISM: Artificial Sequence
<220> FEATURE:
<223> OTHER INFORMATION: IL29 mutant Asp169, C171X
<220> FEATURE:
<221> NAME/KEY: CDS
<222> LOCATION: (1)...(546)
<220> FEATURE:
<221> NAME/KEY: variation
<222> LOCATION: (512)...(513)
<223> OTHER INFORMATION: n = A, T, G, or C

<400> SEQUENCE: 82

```
ggc cct gtc ccc act tcc aag ccc acc aca act ggg aag ggc tgc cac      48
Gly Pro Val Pro Thr Ser Lys Pro Thr Thr Thr Gly Lys Gly Cys His
1               5                   10                  15 att ggc agg ttc aaa tct ctg tca cca cag gag cta gcg agc ttc aag      96
Ile Gly Arg Phe Lys Ser Leu Ser Pro Gln Glu Leu Ala Ser Phe Lys
            20                  25                  30 aag gcc agg gac gcc ttg gaa gag tca ctc aag ctg aaa aac tgg agt     144
Lys Ala Arg Asp Ala Leu Glu Glu Ser Leu Lys Leu Lys Asn Trp Ser
        35                  40                  45 tgc agc tct cct gtc ttc ccc ggg aat tgg gac ctg agg ctt ctc cag     192
Cys Ser Ser Pro Val Phe Pro Gly Asn Trp Asp Leu Arg Leu Leu Gln
50                  55                  60 gtg agg gag cgc cct gtg gcc ttg gag gct gag ctg gcc ctg acg ctg     240
Val Arg Glu Arg Pro Val Ala Leu Glu Ala Glu Leu Ala Leu Thr Leu
65                  70                  75                  80 aag gtc ctg gag gcc gct gct ggc cca gcc ctg gag gac gtc cta gac     288
Lys Val Leu Glu Ala Ala Ala Gly Pro Ala Leu Glu Asp Val Leu Asp
                85                  90                  95 cag ccc ctt cac acc ctg cac cac atc ctc tcc cag ctc cag gcc tgt     336
Gln Pro Leu His Thr Leu His His Ile Leu Ser Gln Leu Gln Ala Cys
            100                 105                 110 atc cag cct cag ccc aca gca ggg ccc agg ccc cgg ggc cgc ctc cac     384
Ile Gln Pro Gln Pro Thr Ala Gly Pro Arg Pro Arg Gly Arg Leu His
        115                 120                 125 cac tgg ctg cac cgg ctc cag gag gcc ccc aaa aag gag tcc gct ggc     432
His Trp Leu His Arg Leu Gln Glu Ala Pro Lys Lys Glu Ser Ala Gly
    130                 135                 140 tgc ctg gag gca tct gtc acc ttc aac ctc ttc cgc ctc ctc acg cga     480
Cys Leu Glu Ala Ser Val Thr Phe Asn Leu Phe Arg Leu Leu Thr Arg
145                 150                 155                 160 gac ctc aaa tat gtg gcc gat ggg gay ctg dnn ctg aga acg tca acc     528
Asp Leu Lys Tyr Val Ala Asp Gly Asp Leu Xaa Leu Arg Thr Ser Thr
                165                 170                 175 cac cct gag tcc acc tga                                             546
His Pro Glu Ser Thr *
            180
```

<210> SEQ ID NO 83
<211> LENGTH: 181
<212> TYPE: PRT
<213> ORGANISM: Artificial Sequence
<220> FEATURE:
<223> OTHER INFORMATION: IL29 mutant Asp169, C171X
<220> FEATURE:
<221> NAME/KEY: VARIANT
<222> LOCATION: (171)...(171)
<223> OTHER INFORMATION: Xaa = Ser, Ala, Thr, Val, or Asn

<400> SEQUENCE: 83

```
Gly Pro Val Pro Thr Ser Lys Pro Thr Thr Thr Gly Lys Gly Cys His
1               5                   10                  15

Ile Gly Arg Phe Lys Ser Leu Ser Pro Gln Glu Leu Ala Ser Phe Lys
```

-continued

```
                    20                  25                  30
Lys Ala Arg Asp Ala Leu Glu Glu Ser Leu Lys Leu Lys Asn Trp Ser
             35                  40                  45

Cys Ser Ser Pro Val Phe Pro Gly Asn Trp Asp Leu Arg Leu Leu Gln
         50                  55                  60

Val Arg Glu Arg Pro Val Ala Leu Glu Ala Glu Leu Ala Leu Thr Leu
 65                  70                  75                  80

Lys Val Leu Glu Ala Ala Ala Gly Pro Ala Leu Glu Asp Val Leu Asp
                 85                  90                  95

Gln Pro Leu His Thr Leu His His Ile Leu Ser Gln Leu Gln Ala Cys
             100                 105                 110

Ile Gln Pro Gln Pro Thr Ala Gly Pro Arg Pro Arg Gly Arg Leu His
         115                 120                 125

His Trp Leu His Arg Leu Gln Glu Ala Pro Lys Lys Glu Ser Ala Gly
130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asp Leu Xaa Leu Arg Thr Ser Thr
                165                 170                 175

His Pro Glu Ser Thr
            180

<210> SEQ ID NO 84
<211> LENGTH: 549
<212> TYPE: DNA
<213> ORGANISM: Artificial Sequence
<220> FEATURE:
<223> OTHER INFORMATION: Met IL29 mutant Asp170, C172X
<220> FEATURE:
<221> NAME/KEY: CDS
<222> LOCATION: (1)...(549)
<220> FEATURE:
<221> NAME/KEY: variation
<222> LOCATION: (515)...(516)
<223> OTHER INFORMATION: n = A, T, G, or C

<400> SEQUENCE: 84 atg ggc cct gtc ccc act tcc aag ccc acc aca act ggg aag ggc tgc      48
Met Gly Pro Val Pro Thr Ser Lys Pro Thr Thr Thr Gly Lys Gly Cys
 1               5                  10                  15 cac att ggc agg ttc aaa tct ctg tca cca cag gag cta gcg agc ttc      96
His Ile Gly Arg Phe Lys Ser Leu Ser Pro Gln Glu Leu Ala Ser Phe
             20                  25                  30 aag aag gcc agg gac gcc ttg gaa gag tca ctc aag ctg aaa aac tgg     144
Lys Lys Ala Arg Asp Ala Leu Glu Glu Ser Leu Lys Leu Lys Asn Trp
         35                  40                  45 agt tgc agc tct cct gtc ttc ccc ggg aat tgg gac ctg agg ctt ctc     192
Ser Cys Ser Ser Pro Val Phe Pro Gly Asn Trp Asp Leu Arg Leu Leu
     50                  55                  60 cag gtg agg gag cgc cct gtg gcc ttg gag gct gag ctg gcc ctg acg     240
Gln Val Arg Glu Arg Pro Val Ala Leu Glu Ala Glu Leu Ala Leu Thr
 65                  70                  75                  80 ctg aag gtc ctg gag gcc gct gct ggc cca gcc ctg gag gac gtc cta     288
Leu Lys Val Leu Glu Ala Ala Ala Gly Pro Ala Leu Glu Asp Val Leu
                 85                  90                  95 gac cag ccc ctt cac acc ctg cac cac atc ctc tcc cag ctc cag gcc     336
Asp Gln Pro Leu His Thr Leu His His Ile Leu Ser Gln Leu Gln Ala
             100                 105                 110 tgt atc cag cct cag ccc aca gca ggg ccc agg ccc cgg ggc cgc ctc     384
Cys Ile Gln Pro Gln Pro Thr Ala Gly Pro Arg Pro Arg Gly Arg Leu
```

-continued

```
              115                 120                 125
cac cac tgg ctg cac cgg ctc cag gag gcc ccc aaa aag gag tcc gct    432
His His Trp Leu His Arg Leu Gln Glu Ala Pro Lys Lys Glu Ser Ala
        130                 135                 140 ggc tgc ctg gag gca tct gtc acc ttc aac ctc ttc cgc ctc ctc acg    480
Gly Cys Leu Glu Ala Ser Val Thr Phe Asn Leu Phe Arg Leu Leu Thr
145                 150                 155                 160 cga gac ctc aaa tat gtg gcc gat ggg gay ctg dnn ctg aga acg tca    528
Arg Asp Leu Lys Tyr Val Ala Asp Gly Asp Leu Xaa Leu Arg Thr Ser
                165                 170                 175 acc cac cct gag tcc acc tga                                        549
Thr His Pro Glu Ser Thr  *
            180
```

```
<210> SEQ ID NO 85
<211> LENGTH: 182
<212> TYPE: PRT
<213> ORGANISM: Artificial Sequence
<220> FEATURE:
<223> OTHER INFORMATION: Met IL29 mutant Asp170, C172X
<220> FEATURE:
<221> NAME/KEY: VARIANT
<222> LOCATION: (172)...(172)
<223> OTHER INFORMATION: Xaa = Ser, Ala, Thr, Val, or Asn

<400> SEQUENCE: 85

Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asp Leu Xaa Leu Arg Thr Ser
                165                 170                 175

Thr His Pro Glu Ser Thr
            180
```

```
<210> SEQ ID NO 86
<211> LENGTH: 546
<212> TYPE: DNA
<213> ORGANISM: Artificial Sequence
<220> FEATURE:
<223> OTHER INFORMATION: IL29 mutant T10P, Asn169, C171X
<220> FEATURE:
<221> NAME/KEY: CDS
<222> LOCATION: (1)...(546)
<220> FEATURE:
```

-continued

```
<221> NAME/KEY: variation
<222> LOCATION: (512)...(513)
<223> OTHER INFORMATION: n = A, T, G, or C

<400> SEQUENCE: 86 ggc cct gtc ccc act tcc aag ccc acc ccn act ggg aag ggc tgc cac      48
Gly Pro Val Pro Thr Ser Lys Pro Thr Pro Thr Gly Lys Gly Cys His
 1               5                  10                  15 att ggc agg ttc aaa tct ctg tca cca cag gag cta gcg agc ttc aag      96
Ile Gly Arg Phe Lys Ser Leu Ser Pro Gln Glu Leu Ala Ser Phe Lys
                20                  25                  30 aag gcc agg gac gcc ttg gaa gag tca ctc aag ctg aaa aac tgg agt     144
Lys Ala Arg Asp Ala Leu Glu Glu Ser Leu Lys Leu Lys Asn Trp Ser
            35                  40                  45 tgc agc tct cct gtc ttc ccc ggg aat tgg gac ctg agg ctt ctc cag     192
Cys Ser Ser Pro Val Phe Pro Gly Asn Trp Asp Leu Arg Leu Leu Gln
        50                  55                  60 gtg agg gag cgc cct gtg gcc ttg gag gct gag ctg gcc ctg acg ctg     240
Val Arg Glu Arg Pro Val Ala Leu Glu Ala Glu Leu Ala Leu Thr Leu
 65                  70                  75                  80 aag gtc ctg gag gcc gct gct ggc cca gcc ctg gag gac gtc cta gac     288
Lys Val Leu Glu Ala Ala Ala Gly Pro Ala Leu Glu Asp Val Leu Asp
                 85                  90                  95 cag ccc ctt cac acc ctg cac cac atc ctc tcc cag ctc cag gcc tgt     336
Gln Pro Leu His Thr Leu His His Ile Leu Ser Gln Leu Gln Ala Cys
            100                 105                 110 atc cag cct cag ccc aca gca ggg cca agg ccc cgg ggc cgc ctc cac     384
Ile Gln Pro Gln Pro Thr Ala Gly Pro Arg Pro Arg Gly Arg Leu His
        115                 120                 125 cac tgg ctg cac cgg ctc cag gag gcc ccc aaa aag gag tcc gct ggc     432
His Trp Leu His Arg Leu Gln Glu Ala Pro Lys Lys Glu Ser Ala Gly
    130                 135                 140 tgc ctg gag gca tct gtc acc ttc aac ctc ttc cgc ctc ctc acg cga     480
Cys Leu Glu Ala Ser Val Thr Phe Asn Leu Phe Arg Leu Leu Thr Arg
145                 150                 155                 160 gac ctc aaa tat gtg gcc gat ggg aac ctg dnn ctg aga acg tca acc     528
Asp Leu Lys Tyr Val Ala Asp Gly Asn Leu Xaa Leu Arg Thr Ser Thr
                165                 170                 175 cac cct gag tcc acc tga                                             546
His Pro Glu Ser Thr *
            180

<210> SEQ ID NO 87
<211> LENGTH: 181
<212> TYPE: PRT
<213> ORGANISM: Artificial Sequence
<220> FEATURE:
<223> OTHER INFORMATION: IL29 mutant T10P, Asn169, C171X
<220> FEATURE:
<221> NAME/KEY: VARIANT
<222> LOCATION: (171)...(171)
<223> OTHER INFORMATION: Xaa = Ser, Ala, Thr, Val, or Asn

<400> SEQUENCE: 87

Gly Pro Val Pro Thr Ser Lys Pro Thr Pro Thr Gly Lys Gly Cys His
 1               5                  10                  15

Ile Gly Arg Phe Lys Ser Leu Ser Pro Gln Glu Leu Ala Ser Phe Lys
                20                  25                  30

Lys Ala Arg Asp Ala Leu Glu Glu Ser Leu Lys Leu Lys Asn Trp Ser
            35                  40                  45

Cys Ser Ser Pro Val Phe Pro Gly Asn Trp Asp Leu Arg Leu Leu Gln
        50                  55                  60
```

```
Val Arg Glu Arg Pro Val Ala Leu Glu Ala Glu Leu Ala Leu Thr Leu
 65                  70                  75                  80

Lys Val Leu Glu Ala Ala Ala Gly Pro Ala Leu Glu Asp Val Leu Asp
                 85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
    130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asn Leu Xaa Leu Arg Thr Ser Thr
                165                 170                 175

His Pro Glu Ser Thr
            180

<210> SEQ ID NO 88
<211> LENGTH: 549
<212> TYPE: DNA
<213> ORGANISM: Artificial Sequence
<220> FEATURE:
<223> OTHER INFORMATION: Met IL29 mutant T11P, Asn170, C172X
<220> FEATURE:
<221> NAME/KEY: CDS
<222> LOCATION: (1)...(549)
<220> FEATURE:
<221> NAME/KEY: variation
<222> LOCATION: (515)...(516)
<223> OTHER INFORMATION: n = A, T, G, or C

<400> SEQUENCE: 88 atg ggc cct gtc ccc act tcc aag ccc acc ccn act ggg aag ggc tgc     48
Met Gly Pro Val Pro Thr Ser Lys Pro Thr Pro Thr Gly Lys Gly Cys
  1               5                  10                  15 cac att ggc agg ttc aaa tct ctg tca cca cag gag cta gcg agc ttc     96
His Ile Gly Arg Phe Lys Ser Leu Ser Pro Gln Glu Leu Ala Ser Phe
             20                  25                  30 aag aag gcc agg gac gcc ttg gaa gag tca ctc aag ctg aaa aac tgg    144
Lys Lys Ala Arg Asp Ala Leu Glu Glu Ser Leu Lys Leu Lys Asn Trp
         35                  40                  45 agt tgc agc tct cct gtc ttc ccc ggg aat tgg gac ctg agg ctt ctc    192
Ser Cys Ser Ser Pro Val Phe Pro Gly Asn Trp Asp Leu Arg Leu Leu
     50                  55                  60 cag gtg agg gag cgc cct gtg gcc ttg gag gct gag ctg gcc ctg acg    240
Gln Val Arg Glu Arg Pro Val Ala Leu Glu Ala Glu Leu Ala Leu Thr
 65                  70                  75                  80 ctg aag gtc ctg gag gcc gct gct ggc cca gcc ctg gag gac gtc cta    288
Leu Lys Val Leu Glu Ala Ala Ala Gly Pro Ala Leu Glu Asp Val Leu
                 85                  90                  95 gac cag ccc ctt cac acc ctg cac cac atc ctc tcc cag ctc cag gcc    336
Asp Gln Pro Leu His Thr Leu His His Ile Leu Ser Gln Leu Gln Ala
            100                 105                 110 tgt atc cag cct cag ccc aca gca ggg ccc agg ccc cgg ggc cgc ctc    384
Cys Ile Gln Pro Gln Pro Thr Ala Gly Pro Arg Pro Arg Gly Arg Leu
        115                 120                 125 cac cac tgg ctg cac cgg ctc cag gag gcc ccc aaa aag gag tcc gct    432
His His Trp Leu His Arg Leu Gln Glu Ala Pro Lys Lys Glu Ser Ala
    130                 135                 140 ggc tgc ctg gag gca tct gtc acc ttc aac ctc ttc cgc ctc ctc acg    480
Gly Cys Leu Glu Ala Ser Val Thr Phe Asn Leu Phe Arg Leu Leu Thr
```

```
Gly Cys Leu Glu Ala Ser Val Thr Phe Asn Leu Phe Arg Leu Leu Thr
145                 150                 155                 160 cga gac ctc aaa tat gtg gcc gat ggg aac ctg dnn ctg aga acg tca        528
Arg Asp Leu Lys Tyr Val Ala Asp Gly Asn Leu Xaa Leu Arg Thr Ser
                165                 170                 175 acc cac cct gag tcc acc tga                                             549
Thr His Pro Glu Ser Thr *
            180

<210> SEQ ID NO 89
<211> LENGTH: 182
<212> TYPE: PRT
<213> ORGANISM: Artificial Sequence
<220> FEATURE:
<223> OTHER INFORMATION: Met IL29 mutant T11P, Asn170, C172X
<220> FEATURE:
<221> NAME/KEY: VARIANT
<222> LOCATION: (172)...(172)
<223> OTHER INFORMATION: Xaa = Ser, Ala, Thr, Val, or Asn

<400> SEQUENCE: 89

Met Gly Pro Val Pro Thr Ser Lys Pro Thr Pro Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Xaa Leu Arg Thr Ser
                165                 170                 175

Thr His Pro Glu Ser Thr
            180

<210> SEQ ID NO 90
<211> LENGTH: 546
<212> TYPE: DNA
<213> ORGANISM: Artificial Sequence
<220> FEATURE:
<223> OTHER INFORMATION: IL29 mutant T10P, C15X, Asn169
<220> FEATURE:
<221> NAME/KEY: CDS
<222> LOCATION: (1)...(546)
<220> FEATURE:
<221> NAME/KEY: variation
<222> LOCATION: 30, 44, 45
<223> OTHER INFORMATION: n = A, T, G, or C

<400> SEQUENCE: 90 ggc cct gtc ccc act tcc aag ccc acc ccn act ggg aag ggc dnn cac        48
```

```
Gly Pro Val Pro Thr Ser Lys Pro Thr Pro Thr Gly Lys Gly Xaa His
1               5                   10                  15 att ggc agg ttc aaa tct ctg tca cca cag gag cta gcg agc ttc aag     96
Ile Gly Arg Phe Lys Ser Leu Ser Pro Gln Glu Leu Ala Ser Phe Lys
                20                  25                  30 aag gcc agg gac gcc ttg gaa gag tca ctc aag ctg aaa aac tgg agt    144
Lys Ala Arg Asp Ala Leu Glu Glu Ser Leu Lys Leu Lys Asn Trp Ser
            35                  40                  45 tgc agc tct cct gtc ttc ccc ggg aat tgg gac ctg agg ctt ctc cag    192
Cys Ser Ser Pro Val Phe Pro Gly Asn Trp Asp Leu Arg Leu Leu Gln
        50                  55                  60 gtg agg gag cgc cct gtg gcc ttg gag gct gag ctg gcc ctg acg ctg    240
Val Arg Glu Arg Pro Val Ala Leu Glu Ala Glu Leu Ala Leu Thr Leu
65                  70                  75                  80 aag gtc ctg gag gcc gct gct ggc cca gcc ctg gag gac gtc cta gac    288
Lys Val Leu Glu Ala Ala Ala Gly Pro Ala Leu Glu Asp Val Leu Asp
                85                  90                  95 cag ccc ctt cac acc ctg cac cac atc ctc tcc cag ctc cag gcc tgt    336
Gln Pro Leu His Thr Leu His His Ile Leu Ser Gln Leu Gln Ala Cys
            100                 105                 110 atc cag cct cag ccc aca gca ggg ccc agg ccc cgg ggc cgc ctc cac    384
Ile Gln Pro Gln Pro Thr Ala Gly Pro Arg Pro Arg Gly Arg Leu His
        115                 120                 125 cac tgg ctg cac cgg ctc cag gag gcc ccc aaa aag gag tcc gct ggc    432
His Trp Leu His Arg Leu Gln Glu Ala Pro Lys Lys Glu Ser Ala Gly
    130                 135                 140 tgc ctg gag gca tct gtc acc ttc aac ctc ttc cgc ctc ctc acg cga    480
Cys Leu Glu Ala Ser Val Thr Phe Asn Leu Phe Arg Leu Leu Thr Arg
145                 150                 155                 160 gac ctc aaa tat gtg gcc gat ggg aay ctg tgt ctg aga acg tca acc    528
Asp Leu Lys Tyr Val Ala Asp Gly Asn Leu Cys Leu Arg Thr Ser Thr
                165                 170                 175 cac cct gag tcc acc tga                                            546
His Pro Glu Ser Thr *
            180

<210> SEQ ID NO 91
<211> LENGTH: 181
<212> TYPE: PRT
<213> ORGANISM: Artificial Sequence
<220> FEATURE:
<223> OTHER INFORMATION: IL29 mutant T10P, C15X, Asn169
<220> FEATURE:
<221> NAME/KEY: VARIANT
<222> LOCATION: (15)...(15)
<223> OTHER INFORMATION: Xaa = Ser, Ala, Thr, Val, or Asn

<400> SEQUENCE: 91

Gly Pro Val Pro Thr Ser Lys Pro Thr Pro Thr Gly Lys Gly Xaa His
1               5                   10                  15

Ile Gly Arg Phe Lys Ser Leu Ser Pro Gln Glu Leu Ala Ser Phe Lys
                20                  25                  30

Lys Ala Arg Asp Ala Leu Glu Glu Ser Leu Lys Leu Lys Asn Trp Ser
            35                  40                  45

Cys Ser Ser Pro Val Phe Pro Gly Asn Trp Asp Leu Arg Leu Leu Gln
        50                  55                  60

Val Arg Glu Arg Pro Val Ala Leu Glu Ala Glu Leu Ala Leu Thr Leu
65                  70                  75                  80

Lys Val Leu Glu Ala Ala Ala Gly Pro Ala Leu Glu Asp Val Leu Asp
                85                  90                  95
```

```
Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
            115                 120                 125

His Trp Leu His Arg Leu Gln Glu Ala Pro Lys Lys Glu Ser Ala Gly
    130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asn Leu Cys Leu Arg Thr Ser Thr
                165                 170                 175

His Pro Glu Ser Thr
            180

<210> SEQ ID NO 92
<211> LENGTH: 549
<212> TYPE: DNA
<213> ORGANISM: Artificial Sequence
<220> FEATURE:
<223> OTHER INFORMATION: Met IL29 mutant T11P, C16X, Asn170
<220> FEATURE:
<221> NAME/KEY: CDS
<222> LOCATION: (1)...(549)
<220> FEATURE:
<221> NAME/KEY: variation
<222> LOCATION: 33, 47, 48
<223> OTHER INFORMATION: n = A, T, G, or C

<400> SEQUENCE: 92 atg ggc cct gtc ccc act tcc aag ccc acc ccn act ggg aag ggc dnn     48
Met Gly Pro Val Pro Thr Ser Lys Pro Thr Pro Thr Gly Lys Gly Xaa
 1               5                  10                  15 cac att ggc agg ttc aaa tct ctg tca cca cag gag cta gcg agc ttc     96
His Ile Gly Arg Phe Lys Ser Leu Ser Pro Gln Glu Leu Ala Ser Phe
                20                  25                  30 aag aag gcc agg gac gcc ttg gaa gag tca ctc aag ctg aaa aac tgg    144
Lys Lys Ala Arg Asp Ala Leu Glu Glu Ser Leu Lys Leu Lys Asn Trp
            35                  40                  45 agt tgc agc tct cct gtc ttc ccc ggg aat tgg gac ctg agg ctt ctc    192
Ser Cys Ser Ser Pro Val Phe Pro Gly Asn Trp Asp Leu Arg Leu Leu
    50                  55                  60 cag gtg agg gag cgc cct gtg gcc ttg gag gct gag ctg gcc ctg acg    240
Gln Val Arg Glu Arg Pro Val Ala Leu Glu Ala Glu Leu Ala Leu Thr
65                  70                  75                  80 ctg aag gtc ctg gag gcc gct gct ggc cca gcc ctg gag gac gtc cta    288
Leu Lys Val Leu Glu Ala Ala Ala Gly Pro Ala Leu Glu Asp Val Leu
                85                  90                  95 gac cag ccc ctt cac acc ctg cac cac atc ctc tcc cag ctc cag gcc    336
Asp Gln Pro Leu His Thr Leu His His Ile Leu Ser Gln Leu Gln Ala
            100                 105                 110 tgt atc cag cct cag ccc aca gca ggg ccc agg ccc cgg ggc cgc ctc    384
Cys Ile Gln Pro Gln Pro Thr Ala Gly Pro Arg Pro Arg Gly Arg Leu
        115                 120                 125 cac cac tgg ctg cac cgg ctc cag gag gcc ccc aaa aag gag tcc gct    432
His His Trp Leu His Arg Leu Gln Glu Ala Pro Lys Lys Glu Ser Ala
    130                 135                 140 ggc tgc ctg gag gca tct gtc acc ttc aac ctc ttc cgc ctc ctc acg    480
Gly Cys Leu Glu Ala Ser Val Thr Phe Asn Leu Phe Arg Leu Leu Thr
145                 150                 155                 160 cga gac ctc aaa tat gtg gcc gat ggg aay ctg tgt ctg aga acg tca    528
Arg Asp Leu Lys Tyr Val Ala Asp Gly Asn Leu Cys Leu Arg Thr Ser
                165                 170                 175
```

```
acc cac cct gag tcc acc tga                                              549
Thr His Pro Glu Ser Thr *
            180
```

<210> SEQ ID NO 93
<211> LENGTH: 182
<212> TYPE: PRT
<213> ORGANISM: Artificial Sequence
<220> FEATURE:
<223> OTHER INFORMATION: Met IL29 mutant T11P, C16X, Asn170
<220> FEATURE:
<221> NAME/KEY: VARIANT
<222> LOCATION: (16)...(16)
<223> OTHER INFORMATION: Xaa = Ser, Ala, Thr, Val, or Asn

<400> SEQUENCE: 93

```
Met Gly Pro Val Pro Thr Ser Lys Pro Thr Pro Thr Gly Lys Gly Xaa
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Cys Leu Arg Thr Ser
                165                 170                 175

Thr His Pro Glu Ser Thr
            180
```

<210> SEQ ID NO 94
<211> LENGTH: 546
<212> TYPE: DNA
<213> ORGANISM: Artificial Sequence
<220> FEATURE:
<223> OTHER INFORMATION: IL29 mutant T10P, Asp169, C171X
<220> FEATURE:
<221> NAME/KEY: CDS
<222> LOCATION: (1)...(546)
<220> FEATURE:
<221> NAME/KEY: variation
<222> LOCATION: 30, 512, 513
<223> OTHER INFORMATION: n = A, T, G, or C

<400> SEQUENCE: 94

```
ggc cct gtc ccc act tcc aag ccc acc ccn act ggg aag ggc tgc cac        48
Gly Pro Val Pro Thr Ser Lys Pro Thr Pro Thr Gly Lys Gly Cys His
1               5                   10                  15 att ggc agg ttc aaa tct ctg tca cca cag gag cta gcg agc ttc aag        96
Ile Gly Arg Phe Lys Ser Leu Ser Pro Gln Glu Leu Ala Ser Phe Lys
            20                  25                  30
```

-continued

```
aag gcc agg gac gcc ttg gaa gag tca ctc aag ctg aaa aac tgg agt       144
Lys Ala Arg Asp Ala Leu Glu Glu Ser Leu Lys Leu Lys Asn Trp Ser
        35                  40                  45 tgc agc tct cct gtc ttc ccc ggg aat tgg gac ctg agg ctt ctc cag       192
Cys Ser Ser Pro Val Phe Pro Gly Asn Trp Asp Leu Arg Leu Leu Gln
 50                  55                  60 gtg agg gag cgc cct gtg gcc ttg gag gct gag ctg gcc ctg acg ctg       240
Val Arg Glu Arg Pro Val Ala Leu Glu Ala Glu Leu Ala Leu Thr Leu
 65                  70                  75                  80 aag gtc ctg gag gcc gct gct ggc cca gcc ctg gag gac gtc cta gac       288
Lys Val Leu Glu Ala Ala Ala Gly Pro Ala Leu Glu Asp Val Leu Asp
                 85                  90                  95 cag ccc ctt cac acc ctg cac cac atc ctc tcc cag ctc cag gcc tgt       336
Gln Pro Leu His Thr Leu His His Ile Leu Ser Gln Leu Gln Ala Cys
            100                 105                 110 atc cag cct cag ccc aca gca ggg ccc agg ccc cgg ggc cgc ctc cac       384
Ile Gln Pro Gln Pro Thr Ala Gly Pro Arg Pro Arg Gly Arg Leu His
        115                 120                 125 cac tgg ctg cac cgg ctc cag gag gcc ccc aaa aag gag tcc gct ggc       432
His Trp Leu His Arg Leu Gln Glu Ala Pro Lys Lys Glu Ser Ala Gly
130                 135                 140 tgc ctg gag gca tct gtc acc ttc aac ctc ttc cgc ctc ctc acg cga       480
Cys Leu Glu Ala Ser Val Thr Phe Asn Leu Phe Arg Leu Leu Thr Arg
145                 150                 155                 160 gac ctc aaa tat gtg gcc gat ggg gay ctg dnn ctg aga acg tca acc       528
Asp Leu Lys Tyr Val Ala Asp Gly Asp Leu Xaa Leu Arg Thr Ser Thr
                165                 170                 175 cac cct gag tcc acc tga                                               546
His Pro Glu Ser Thr *
            180
```

<210> SEQ ID NO 95
<211> LENGTH: 181
<212> TYPE: PRT
<213> ORGANISM: Artificial Sequence
<220> FEATURE:
<223> OTHER INFORMATION: IL29 mutant T10P, Asp169, C171X
<220> FEATURE:
<221> NAME/KEY: VARIANT
<222> LOCATION: (171)...(171)
<223> OTHER INFORMATION: Xaa = Ser, Ala, Thr, Val, or Asn

<400> SEQUENCE: 95

```
Gly Pro Val Pro Thr Ser Lys Pro Thr Pro Thr Gly Lys Gly Cys His
 1               5                  10                  15

Ile Gly Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
 50                  55                  60

Val Arg Glu Arg Pro Val Ala Leu Glu Ala Glu Leu Ala Leu Thr Leu
 65                  70                  75                  80

Lys Val Leu Glu Ala Ala Ala Gly Pro Ala Leu Glu Asp Val Leu Asp
                 85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
```

```
                 130                 135                 140
Cys Leu Glu Ala Ser Val Thr Phe Asn Leu Phe Arg Leu Leu Thr Arg
145                 150                 155                 160

Asp Leu Lys Tyr Val Ala Asp Gly Asp Leu Xaa Leu Arg Thr Ser Thr
                165                 170                 175

His Pro Glu Ser Thr
            180

<210> SEQ ID NO 96
<211> LENGTH: 549
<212> TYPE: DNA
<213> ORGANISM: Artificial Sequence
<220> FEATURE:
<223> OTHER INFORMATION: Met IL29 mutant T11P, Asp170, C172X
<220> FEATURE:
<221> NAME/KEY: CDS
<222> LOCATION: (1)...(549)
<220> FEATURE:
<221> NAME/KEY: variation
<222> LOCATION: 33, 515, 516
<223> OTHER INFORMATION: n = A, T, G, or C

<400> SEQUENCE: 96 atg ggc cct gtc ccc act tcc aag ccc acc ccn act ggg aag ggc tgc        48
Met Gly Pro Val Pro Thr Ser Lys Pro Thr Pro Thr Gly Lys Gly Cys
  1               5                  10                  15 cac att ggc agg ttc aaa tct ctg tca cca cag gag cta gcg agc ttc        96
His Ile Gly Arg Phe Lys Ser Leu Ser Pro Gln Glu Leu Ala Ser Phe
                 20                  25                  30 aag aag gcc agg gac gcc ttg gaa gag tca ctc aag ctg aaa aac tgg       144
Lys Lys Ala Arg Asp Ala Leu Glu Glu Ser Leu Lys Leu Lys Asn Trp
             35                  40                  45 agt tgc agc tct cct gtc ttc ccc ggg aat tgg gac ctg agg ctt ctc       192
Ser Cys Ser Ser Pro Val Phe Pro Gly Asn Trp Asp Leu Arg Leu Leu
         50                  55                  60 cag gtg agg gag cgc cct gtg gcc ttg gag gct gag ctg gcc ctg acg       240
Gln Val Arg Glu Arg Pro Val Ala Leu Glu Ala Glu Leu Ala Leu Thr
 65                  70                  75                  80 ctg aag gtc ctg gag gcc gct gct ggc cca gcc ctg gag gac gtc cta       288
Leu Lys Val Leu Glu Ala Ala Ala Gly Pro Ala Leu Glu Asp Val Leu
                 85                  90                  95 gac cag ccc ctt cac acc ctg cac cac atc ctc tcc cag ctc cag gcc       336
Asp Gln Pro Leu His Thr Leu His His Ile Leu Ser Gln Leu Gln Ala
            100                 105                 110 tgt atc cag cct cag ccc aca gca ggg ccc agg ccc cgg ggc cgc ctc       384
Cys Ile Gln Pro Gln Pro Thr Ala Gly Pro Arg Pro Arg Gly Arg Leu
        115                 120                 125 cac cac tgg ctg cac cgg ctc cag gag gcc ccc aaa aag gag tcc gct       432
His His Trp Leu His Arg Leu Gln Glu Ala Pro Lys Lys Glu Ser Ala
    130                 135                 140 ggc tgc ctg gag gca tct gtc acc ttc aac ctc ttc cgc ctc ctc acg       480
Gly Cys Leu Glu Ala Ser Val Thr Phe Asn Leu Phe Arg Leu Leu Thr
145                 150                 155                 160 cga gac ctc aaa tat gtg gcc gat ggg gay ctg dnn ctg aga acg tca       528
Arg Asp Leu Lys Tyr Val Ala Asp Gly Asp Leu Xaa Leu Arg Thr Ser
                165                 170                 175 acc cac cct gag tcc acc tga                                           549
Thr His Pro Glu Ser Thr *
            180

<210> SEQ ID NO 97
<211> LENGTH: 182
```

```
<212> TYPE: PRT
<213> ORGANISM: Artificial Sequence
<220> FEATURE:
<223> OTHER INFORMATION: Met IL29 mutant T11P, Asp170, C172X
<220> FEATURE:
<221> NAME/KEY: VARIANT
<222> LOCATION: (172)...(172)
<223> OTHER INFORMATION: Xaa = Ser, Ala, Thr, Val, or Asn

<400> SEQUENCE: 97
```

Met Gly Pro Val Pro Thr Ser Lys Pro Thr Pro Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asp Leu Xaa Leu Arg Thr Ser
                165                 170                 175

Thr His Pro Glu Ser Thr
            180

```
<210> SEQ ID NO 98
<211> LENGTH: 546
<212> TYPE: DNA
<213> ORGANISM: Artificial Sequence
<220> FEATURE:
<223> OTHER INFORMATION: IL29 mutant T10P, C15X, Asp169
<220> FEATURE:
<221> NAME/KEY: CDS
<222> LOCATION: (1)...(546)
<220> FEATURE:
<221> NAME/KEY: variation
<222> LOCATION: 30, 44, 45
<223> OTHER INFORMATION: n = A, T, G, or C

<400> SEQUENCE: 98
``` ggc cct gtc ccc act tcc aag ccc acc ccn act ggg aag ggc dnn cac      48
Gly Pro Val Pro Thr Ser Lys Pro Thr Pro Thr Gly Lys Gly Xaa His
1               5                   10                  15 att ggc agg ttc aaa tct ctg tca cca cag gag cta gcg agc ttc aag      96
Ile Gly Arg Phe Lys Ser Leu Ser Pro Gln Glu Leu Ala Ser Phe Lys
            20                  25                  30 aag gcc agg gac gcc ttg gaa gag tca ctc aag ctg aaa aac tgg agt     144
Lys Ala Arg Asp Ala Leu Glu Glu Ser Leu Lys Leu Lys Asn Trp Ser
        35                  40                  45 tgc agc tct cct gtc ttc ccc ggg aat tgg gac ctg agg ctt ctc cag     192
Cys Ser Ser Pro Val Phe Pro Gly Asn Trp Asp Leu Arg Leu Leu Gln
    50                  55                  60

```
gtg agg gag cgc cct gtg gcc ttg gag gct gag ctg gcc ctg acg ctg      240
Val Arg Glu Arg Pro Val Ala Leu Glu Ala Glu Leu Ala Leu Thr Leu
 65                  70                  75                  80 aag gtc ctg gag gcc gct gct ggc cca gcc ctg gag gac gtc cta gac      288
Lys Val Leu Glu Ala Ala Ala Gly Pro Ala Leu Glu Asp Val Leu Asp
                 85                  90                  95 cag ccc ctt cac acc ctg cac cac atc ctc tcc cag ctc cag gcc tgt      336
Gln Pro Leu His Thr Leu His His Ile Leu Ser Gln Leu Gln Ala Cys
            100                 105                 110 atc cag cct cag ccc aca gca ggg ccc agg ccc cgg ggc cgc ctc cac      384
Ile Gln Pro Gln Pro Thr Ala Gly Pro Arg Pro Arg Gly Arg Leu His
        115                 120                 125 cac tgg ctg cac cgg ctc cag gag gcc ccc aaa aag gag tcc gct ggc      432
His Trp Leu His Arg Leu Gln Glu Ala Pro Lys Lys Glu Ser Ala Gly
130                 135                 140 tgc ctg gag gca tct gtc acc ttc aac ctc ttc cgc ctc ctc acg cga      480
Cys Leu Glu Ala Ser Val Thr Phe Asn Leu Phe Arg Leu Leu Thr Arg
145                 150                 155                 160 gac ctc aaa tat gtg gcc gat ggg gay ctg tgt ctg aga acg tca acc      528
Asp Leu Lys Tyr Val Ala Asp Gly Asp Leu Cys Leu Arg Thr Ser Thr
                165                 170                 175 cac cct gag tcc acc tga                                              546
His Pro Glu Ser Thr *
180
```

<210> SEQ ID NO 99
<211> LENGTH: 181
<212> TYPE: PRT
<213> ORGANISM: Artificial Sequence
<220> FEATURE:
<223> OTHER INFORMATION: IL29 mutant T10P, C15X, Asp169
<220> FEATURE:
<221> NAME/KEY: VARIANT
<222> LOCATION: (15)...(15)
<223> OTHER INFORMATION: Xaa = Ser, Ala, Thr, Val, or Asn

<400> SEQUENCE: 99

```
Gly Pro Val Pro Thr Ser Lys Pro Thr Pro Thr Gly Lys Gly Xaa His
 1               5                  10                  15

Ile Gly Arg Phe Lys Ser Leu Ser Pro Gln Glu Leu Ala Ser Phe Lys
                20                  25                  30

Lys Ala Arg Asp Ala Leu Glu Glu Ser Leu Lys Leu Lys Asn Trp Ser
            35                  40                  45

Cys Ser Ser Pro Val Phe Pro Gly Asn Trp Asp Leu Arg Leu Leu Gln
 50                  55                  60

Val Arg Glu Arg Pro Val Ala Leu Glu Ala Glu Leu Ala Leu Thr Leu
 65                  70                  75                  80

Lys Val Leu Glu Ala Ala Ala Gly Pro Ala Leu Glu Asp Val Leu Asp
                 85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asp Leu Cys Leu Arg Thr Ser Thr
                165                 170                 175
```

His Pro Glu Ser Thr
            180

<210> SEQ ID NO 100
<211> LENGTH: 549
<212> TYPE: DNA
<213> ORGANISM: Artificial Sequence
<220> FEATURE:
<223> OTHER INFORMATION: Met IL29 mutant T11P, C16X, Asp170
<220> FEATURE:
<221> NAME/KEY: CDS
<222> LOCATION: (1)...(549)
<220> FEATURE:
<221> NAME/KEY: variation
<222> LOCATION: 33, 47, 48
<223> OTHER INFORMATION: n = A, T, G, or C

<400> SEQUENCE: 100

```
atg ggc cct gtc ccc act tcc aag ccc acc ccn act ggg aag ggc dnn        48
Met Gly Pro Val Pro Thr Ser Lys Pro Thr Pro Thr Gly Lys Gly Xaa
  1               5                  10                  15 cac att ggc agg ttc aaa tct ctg tca cca cag gag cta gcg agc ttc        96
His Ile Gly Arg Phe Lys Ser Leu Ser Pro Gln Glu Leu Ala Ser Phe
             20                  25                  30 aag aag gcc agg gac gcc ttg gaa gag tca ctc aag ctg aaa aac tgg       144
Lys Lys Ala Arg Asp Ala Leu Glu Glu Ser Leu Lys Leu Lys Asn Trp
         35                  40                  45 agt tgc agc tct cct gtc ttc ccc ggg aat tgg gac ctg agg ctt ctc       192
Ser Cys Ser Ser Pro Val Phe Pro Gly Asn Trp Asp Leu Arg Leu Leu
     50                  55                  60 cag gtg agg gag cgc cct gtg gcc ttg gag gct gag ctg gcc ctg acg       240
Gln Val Arg Glu Arg Pro Val Ala Leu Glu Ala Glu Leu Ala Leu Thr
 65                  70                  75                  80 ctg aag gtc ctg gag gcc gct gct ggc cca gcc ctg gag gac gtc cta       288
Leu Lys Val Leu Glu Ala Ala Ala Gly Pro Ala Leu Glu Asp Val Leu
                 85                  90                  95 gac cag ccc ctt cac acc ctg cac cac atc ctc tcc cag ctc cag gcc       336
Asp Gln Pro Leu His Thr Leu His His Ile Leu Ser Gln Leu Gln Ala
            100                 105                 110 tgt atc cag cct cag ccc aca gca ggg ccc agg ccc cgg ggc cgc ctc       384
Cys Ile Gln Pro Gln Pro Thr Ala Gly Pro Arg Pro Arg Gly Arg Leu
        115                 120                 125 cac cac tgg ctg cac cgg ctc cag gag gcc ccc aaa aag gag tcc gct       432
His His Trp Leu His Arg Leu Gln Glu Ala Pro Lys Lys Glu Ser Ala
    130                 135                 140 ggc tgc ctg gag gca tct gtc acc ttc aac ctc ttc cgc ctc ctc acg       480
Gly Cys Leu Glu Ala Ser Val Thr Phe Asn Leu Phe Arg Leu Leu Thr
145                 150                 155                 160 cga gac ctc aaa tat gtg gcc gat ggg gay ctg tgt ctg aga acg tca       528
Arg Asp Leu Lys Tyr Val Ala Asp Gly Asp Leu Cys Leu Arg Thr Ser
                165                 170                 175 acc cac cct gag tcc acc tga                                           549
Thr His Pro Glu Ser Thr *
            180
```

<210> SEQ ID NO 101
<211> LENGTH: 182
<212> TYPE: PRT
<213> ORGANISM: Artificial Sequence
<220> FEATURE:
<223> OTHER INFORMATION: Met IL29 mutant T11P, C16X, Asp170
<220> FEATURE:
<221> NAME/KEY: VARIANT
<222> LOCATION: (16)...(16)

```
<223> OTHER INFORMATION: Xaa = Ser, Ala, Thr, Val, or Asn

<400> SEQUENCE: 101

Met Gly Pro Val Pro Thr Ser Lys Pro Thr Pro Thr Gly Lys Gly Xaa
 1               5                  10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asp Leu Cys Leu Arg Thr Ser
                165                 170                 175

Thr His Pro Glu Ser Thr
            180

<210> SEQ ID NO 102
<211> LENGTH: 546
<212> TYPE: DNA
<213> ORGANISM: Artificial Sequence
<220> FEATURE:
<223> OTHER INFORMATION: IL29 mutant G18D, Asn169, C171X
<220> FEATURE:
<221> NAME/KEY: CDS
<222> LOCATION: (1)...(546)
<220> FEATURE:
<221> NAME/KEY: variation
<222> LOCATION: (512)...(513)
<223> OTHER INFORMATION: n = A, T, G, or C

<400> SEQUENCE: 102 ggc cct gtc ccc act tcc aag ccc acc aca act ggg aag ggc tgc cac      48
Gly Pro Val Pro Thr Ser Lys Pro Thr Thr Thr Gly Lys Gly Cys His
 1               5                  10                  15 att gay agg ttc aaa tct ctg tca cca cag gag cta gcg agc ttc aag      96
Ile Asp Arg Phe Lys Ser Leu Ser Pro Gln Glu Leu Ala Ser Phe Lys
            20                  25                  30 aag gcc agg gac gcc ttg gaa gag tca ctc aag ctg aaa aac tgg agt     144
Lys Ala Arg Asp Ala Leu Glu Glu Ser Leu Lys Leu Lys Asn Trp Ser
        35                  40                  45 tgc agc tct cct gtc ttc ccc ggg aat tgg gac ctg agg ctt ctc cag     192
Cys Ser Ser Pro Val Phe Pro Gly Asn Trp Asp Leu Arg Leu Leu Gln
50                  55                  60 gtg agg gag cgc cct gtg gcc ttg gag gct gag ctg gcc ctg acg ctg     240
Val Arg Glu Arg Pro Val Ala Leu Glu Ala Glu Leu Ala Leu Thr Leu
65                  70                  75                  80 aag gtc ctg gag gcc gct gct ggc cca gcc ctg gag gac gtc cta gac     288
Lys Val Leu Glu Ala Ala Ala Gly Pro Ala Leu Glu Asp Val Leu Asp
```

```
                85                    90                    95
cag ccc ctt cac acc ctg cac cac atc ctc tcc cag ctc cag gcc tgt        336
Gln Pro Leu His Thr Leu His His Ile Leu Ser Gln Leu Gln Ala Cys
            100                   105                   110 atc cag cct cag ccc aca gca ggg ccc agg ccc cgg ggc cgc ctc cac        384
Ile Gln Pro Gln Pro Thr Ala Gly Pro Arg Pro Arg Gly Arg Leu His
            115                   120                   125 cac tgg ctg cac cgg ctc cag gag gcc ccc aaa aag gag tcc gct ggc        432
His Trp Leu His Arg Leu Gln Glu Ala Pro Lys Lys Glu Ser Ala Gly
130                   135                   140 tgc ctg gag gca tct gtc acc ttc aac ctc ttc cgc ctc ctc acg cga        480
Cys Leu Glu Ala Ser Val Thr Phe Asn Leu Phe Arg Leu Leu Thr Arg
145                   150                   155                   160 gac ctc aaa tat gtg gcc gat ggg aac ctg dnn ctg aga acg tca acc        528
Asp Leu Lys Tyr Val Ala Asp Gly Asn Leu Xaa Leu Arg Thr Ser Thr
                165                   170                   175 cac cct gag tcc acc tga                                                546
His Pro Glu Ser Thr *
            180

<210> SEQ ID NO 103
<211> LENGTH: 181
<212> TYPE: PRT
<213> ORGANISM: Artificial Sequence
<220> FEATURE:
<223> OTHER INFORMATION: IL29 mutant G18D, Asn169, C171X
<220> FEATURE:
<221> NAME/KEY: VARIANT
<222> LOCATION: (171)...(171)
<223> OTHER INFORMATION: Xaa = Ser, Ala, Thr, Val, or Asn

<400> SEQUENCE: 103

Gly Pro Val Pro Thr Ser Lys Pro Thr Thr Thr Gly Lys Gly Cys His
1               5                   10                  15

Ile Asp Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
    50                  55                  60

Val Arg Glu Arg Pro Val Ala Leu Glu Ala Glu Leu Ala Leu Thr Leu
65                  70                  75                  80

Lys Val Leu Glu Ala Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
    130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asn Leu Xaa Leu Arg Thr Ser Thr
                165                 170                 175

His Pro Glu Ser Thr
            180

<210> SEQ ID NO 104
<211> LENGTH: 549
```

```
<212> TYPE: DNA
<213> ORGANISM: Artificial Sequence
<220> FEATURE:
<223> OTHER INFORMATION: Met IL29 mutant G19D, Asn170, C172X
<220> FEATURE:
<221> NAME/KEY: CDS
<222> LOCATION: (1)...(549)
<220> FEATURE:
<221> NAME/KEY: variation
<222> LOCATION: (515)...(516)
<223> OTHER INFORMATION: n = A, T, G, or C

<400> SEQUENCE: 104 atg ggc cct gtc ccc act tcc aag ccc acc aca act ggg aag ggc tgc      48
Met Gly Pro Val Pro Thr Ser Lys Pro Thr Thr Thr Gly Lys Gly Cys
 1               5                  10                  15 cac att gay agg ttc aaa tct ctg tca cca cag gag cta gcg agc ttc      96
His Ile Asp Arg Phe Lys Ser Leu Ser Pro Gln Glu Leu Ala Ser Phe
                20                  25                  30 aag aag gcc agg gac gcc ttg gaa gag tca ctc aag ctg aaa aac tgg     144
Lys Lys Ala Arg Asp Ala Leu Glu Glu Ser Leu Lys Leu Lys Asn Trp
            35                  40                  45 agt tgc agc tct cct gtc ttc ccc ggg aat tgg gac ctg agg ctt ctc     192
Ser Cys Ser Ser Pro Val Phe Pro Gly Asn Trp Asp Leu Arg Leu Leu
 50                  55                  60 cag gtg agg gag cgc cct gtg gcc ttg gag gct gag ctg gcc ctg acg     240
Gln Val Arg Glu Arg Pro Val Ala Leu Glu Ala Glu Leu Ala Leu Thr
 65                  70                  75                  80 ctg aag gtc ctg gag gcc gct gct ggc cca gcc ctg gag gac gtc cta     288
Leu Lys Val Leu Glu Ala Ala Ala Gly Pro Ala Leu Glu Asp Val Leu
                85                  90                  95 gac cag ccc ctt cac acc ctg cac cac atc ctc tcc cag ctc cag gcc     336
Asp Gln Pro Leu His Thr Leu His His Ile Leu Ser Gln Leu Gln Ala
            100                 105                 110 tgt atc cag cct cag ccc aca gca ggg ccc agg ccc cgg ggc cgc ctc     384
Cys Ile Gln Pro Gln Pro Thr Ala Gly Pro Arg Pro Arg Gly Arg Leu
        115                 120                 125 cac cac tgg ctg cac cgg ctc cag gag gcc ccc aaa aag gag tcc gct     432
His His Trp Leu His Arg Leu Gln Glu Ala Pro Lys Lys Glu Ser Ala
    130                 135                 140 ggc tgc ctg gag gca tct gtc acc ttc aac ctc ttc cgc ctc ctc acg     480
Gly Cys Leu Glu Ala Ser Val Thr Phe Asn Leu Phe Arg Leu Leu Thr
145                 150                 155                 160 cga gac ctc aaa tat gtg gcc gat ggg aac ctg dnn ctg aga acg tca     528
Arg Asp Leu Lys Tyr Val Ala Asp Gly Asn Leu Xaa Leu Arg Thr Ser
                165                 170                 175 acc cac cct gag tcc acc tga                                         549
Thr His Pro Glu Ser Thr *
            180

<210> SEQ ID NO 105
<211> LENGTH: 182
<212> TYPE: PRT
<213> ORGANISM: Artificial Sequence
<220> FEATURE:
<223> OTHER INFORMATION: Met IL29 mutant G19D, Asn170, C172X
<220> FEATURE:
<221> NAME/KEY: VARIANT
<222> LOCATION: (172)...(172)
<223> OTHER INFORMATION: Xaa = Ser, Ala, Thr, Val, or Asn

<400> SEQUENCE: 105

Met Gly Pro Val Pro Thr Ser Lys Pro Thr Thr Thr Gly Lys Gly Cys
 1               5                  10                  15
```

```
His Ile Asp Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Xaa Leu Arg Thr Ser
                165                 170                 175

Thr His Pro Glu Ser Thr
            180

<210> SEQ ID NO 106
<211> LENGTH: 546
<212> TYPE: DNA
<213> ORGANISM: Artificial Sequence
<220> FEATURE:
<223> OTHER INFORMATION: IL29 mutant C15X, G18D, Asn169
<220> FEATURE:
<221> NAME/KEY: CDS
<222> LOCATION: (1)...(546)
<220> FEATURE:
<221> NAME/KEY: variation
<222> LOCATION: (44)...(45)
<223> OTHER INFORMATION: n = A, T, G, or C

<400> SEQUENCE: 106 ggc cct gtc ccc act tcc aag ccc acc aca act ggg aag ggc dnn cac      48
Gly Pro Val Pro Thr Ser Lys Pro Thr Thr Thr Gly Lys Gly Xaa His
1               5                   10                  15 att gay agg ttc aaa tct ctg tca cca cag gag cta gcg agc ttc aag      96
Ile Asp Arg Phe Lys Ser Leu Ser Pro Gln Glu Leu Ala Ser Phe Lys
            20                  25                  30 aag gcc agg gac gcc ttg gaa gag tca ctc aag ctg aaa aac tgg agt     144
Lys Ala Arg Asp Ala Leu Glu Glu Ser Leu Lys Leu Lys Asn Trp Ser
        35                  40                  45 tgc agc tct cct gtc ttc ccc ggg aat tgg gac ctg agg ctt ctc cag     192
Cys Ser Ser Pro Val Phe Pro Gly Asn Trp Asp Leu Arg Leu Leu Gln
    50                  55                  60 gtg agg gag cgc cct gtg gcc ttg gag gct gag ctg gcc ctg acg ctg     240
Val Arg Glu Arg Pro Val Ala Leu Glu Ala Glu Leu Ala Leu Thr Leu
65                  70                  75                  80 aag gtc ctg gag gcc gct gct ggc cca gcc ctg gag gac gtc cta gac     288
Lys Val Leu Glu Ala Ala Ala Gly Pro Ala Leu Glu Asp Val Leu Asp
                85                  90                  95 cag ccc ctt cac acc ctg cac cac atc ctc tcc cag ctc cag gcc tgt     336
Gln Pro Leu His Thr Leu His His Ile Leu Ser Gln Leu Gln Ala Cys
            100                 105                 110 atc cag cct cag ccc aca gca ggg ccc agg ccc cgg ggc cgc ctc cac     384
```

```
Ile Gln Pro Gln Pro Thr Ala Gly Pro Arg Pro Arg Gly Arg Leu His
            115                 120                 125 cac tgg ctg cac cgg ctc cag gag gcc ccc aaa aag gag tcc gct ggc      432
His Trp Leu His Arg Leu Gln Glu Ala Pro Lys Lys Glu Ser Ala Gly
130                 135                 140 tgc ctg gag gca tct gtc acc ttc aac ctc ttc cgc ctc ctc acg cga      480
Cys Leu Glu Ala Ser Val Thr Phe Asn Leu Phe Arg Leu Leu Thr Arg
145                 150                 155                 160 gac ctc aaa tat gtg gcc gat ggg aay ctg tgt ctg aga acg tca acc      528
Asp Leu Lys Tyr Val Ala Asp Gly Asn Leu Cys Leu Arg Thr Ser Thr
                165                 170                 175 cac cct gag tcc acc tga                                              546
His Pro Glu Ser Thr *
            180

<210> SEQ ID NO 107
<211> LENGTH: 181
<212> TYPE: PRT
<213> ORGANISM: Artificial Sequence
<220> FEATURE:
<223> OTHER INFORMATION: IL29 mutant C15X, G18D, Asn169
<220> FEATURE:
<221> NAME/KEY: VARIANT
<222> LOCATION: (15)...(15)
<223> OTHER INFORMATION: Xaa = Ser, Ala, Thr, Val, or Asn

<400> SEQUENCE: 107

Gly Pro Val Pro Thr Ser Lys Pro Thr Thr Thr Gly Lys Gly Xaa His
1               5                   10                  15

Ile Asp Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
    50                  55                  60

Val Arg Glu Arg Pro Val Ala Leu Glu Ala Glu Leu Ala Leu Thr Leu
65                  70                  75                  80

Lys Val Leu Glu Ala Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asn Leu Cys Leu Arg Thr Ser Thr
                165                 170                 175

His Pro Glu Ser Thr
            180

<210> SEQ ID NO 108
<211> LENGTH: 549
<212> TYPE: DNA
<213> ORGANISM: Artificial Sequence
<220> FEATURE:
<223> OTHER INFORMATION: Met IL29 mutant C16X, G19D, Asn170
<220> FEATURE:
<221> NAME/KEY: CDS
<222> LOCATION: (1)...(549)
```

<220> FEATURE:
<221> NAME/KEY: variation
<222> LOCATION: (47)...(48)
<223> OTHER INFORMATION: n = A, T, G, or C

<400> SEQUENCE: 108

| | | | | | | | | | | | | | | | | |
|---|---|---|---|---|---|---|---|---|---|---|---|---|---|---|---|---|
| atg | ggc | cct | gtc | ccc | act | tcc | aag | ccc | acc | aca | act | ggg | aag | ggc | dnn | 48 |
| Met | Gly | Pro | Val | Pro | Thr | Ser | Lys | Pro | Thr | Thr | Thr | Gly | Lys | Gly | Xaa | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cac | att | gay | agg | ttc | aaa | tct | ctg | tca | cca | cag | gag | cta | gcg | agc | ttc | 96 |
| His | Ile | Asp | Arg | Phe | Lys | Ser | Leu | Ser | Pro | Gln | Glu | Leu | Ala | Ser | Phe | |
| | | | 20 | | | | | 25 | | | | | 30 | | | |

| | | | | | | | | | | | | | | | | |
|---|---|---|---|---|---|---|---|---|---|---|---|---|---|---|---|---|
| aag | aag | gcc | agg | gac | gcc | ttg | gaa | gag | tca | ctc | aag | ctg | aaa | aac | tgg | 144 |
| Lys | Lys | Ala | Arg | Asp | Ala | Leu | Glu | Glu | Ser | Leu | Lys | Leu | Lys | Asn | Trp | |
| | | 35 | | | | | 40 | | | | | 45 | | | | |

| | | | | | | | | | | | | | | | | |
|---|---|---|---|---|---|---|---|---|---|---|---|---|---|---|---|---|
| agt | tgc | agc | tct | cct | gtc | ttc | ccc | ggg | aat | tgg | gac | ctg | agg | ctt | ctc | 192 |
| Ser | Cys | Ser | Ser | Pro | Val | Phe | Pro | Gly | Asn | Trp | Asp | Leu | Arg | Leu | Leu | |
| | 50 | | | | | 55 | | | | | 60 | | | | | |

| | | | | | | | | | | | | | | | | |
|---|---|---|---|---|---|---|---|---|---|---|---|---|---|---|---|---|
| cag | gtg | agg | gag | cgc | cct | gtg | gcc | ttg | gag | gct | gag | ctg | gcc | ctg | acg | 240 |
| Gln | Val | Arg | Glu | Arg | Pro | Val | Ala | Leu | Glu | Ala | Glu | Leu | Ala | Leu | Thr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctg | aag | gtc | ctg | gag | gcc | gct | gct | ggc | cca | gcc | ctg | gag | gac | gtc | cta | 288 |
| Leu | Lys | Val | Leu | Glu | Ala | Ala | Ala | Gly | Pro | Ala | Leu | Glu | Asp | Val | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| gac | cag | ccc | ctt | cac | acc | ctg | cac | cac | atc | ctc | tcc | cag | ctc | cag | gcc | 336 |
| Asp | Gln | Pro | Leu | His | Thr | Leu | His | His | Ile | Leu | Ser | Gln | Leu | Gln | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| tgt | atc | cag | cct | cag | ccc | aca | gca | ggg | ccc | agg | ccc | cgg | ggc | cgc | ctc | 384 |
| Cys | Ile | Gln | Pro | Gln | Pro | Thr | Ala | Gly | Pro | Arg | Pro | Arg | Gly | Arg | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| cac | cac | tgg | ctg | cac | cgg | ctc | cag | gag | gcc | ccc | aaa | aag | gag | tcc | gct | 432 |
| His | His | Trp | Leu | His | Arg | Leu | Gln | Glu | Ala | Pro | Lys | Lys | Glu | Ser | Ala | |
| | 130 | | | | | 135 | | | | | 140 | | | | | |

| | | | | | | | | | | | | | | | | |
|---|---|---|---|---|---|---|---|---|---|---|---|---|---|---|---|---|
| ggc | tgc | ctg | gag | gca | tct | gtc | acc | ttc | aac | ctc | ttc | cgc | ctc | ctc | acg | 480 |
| Gly | Cys | Leu | Glu | Ala | Ser | Val | Thr | Phe | Asn | Leu | Phe | Arg | Leu | Leu | Thr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cga | gac | ctc | aaa | tat | gtg | gcc | gat | ggg | aay | ctg | tgt | ctg | aga | acg | tca | 528 |
| Arg | Asp | Leu | Lys | Tyr | Val | Ala | Asp | Gly | Asn | Leu | Cys | Leu | Arg | Thr | Ser | |
| | | | | 165 | | | | | 170 | | | | | 175 | | |

| | | | | | | |
|---|---|---|---|---|---|---|
| acc | cac | cct | gag | tcc | acc | tga | 549 |
| Thr | His | Pro | Glu | Ser | Thr | * | |
| | | | 180 | | | | |

<210> SEQ ID NO 109
<211> LENGTH: 182
<212> TYPE: PRT
<213> ORGANISM: Artificial Sequence
<220> FEATURE:
<223> OTHER INFORMATION: Met IL29 mutant C16X, G19D, Asn170
<220> FEATURE:
<221> NAME/KEY: VARIANT
<222> LOCATION: (16)...(16)
<223> OTHER INFORMATION: Xaa = Ser, Ala, Thr, Val, or Asn

<400> SEQUENCE: 109

| | | | | | | | | | | | | | | | |
|---|---|---|---|---|---|---|---|---|---|---|---|---|---|---|---|
| Met | Gly | Pro | Val | Pro | Thr | Ser | Lys | Pro | Thr | Thr | Thr | Gly | Lys | Gly | Xaa |
| 1 | | | | 5 | | | | | 10 | | | | | 15 | |

| | | | | | | | | | | | | | | | |
|---|---|---|---|---|---|---|---|---|---|---|---|---|---|---|---|
| His | Ile | Asp | Arg | Phe | Lys | Ser | Leu | Ser | Pro | Gln | Glu | Leu | Ala | Ser | Phe |
| | | | 20 | | | | | 25 | | | | | 30 | | |

| | | | | | | | | | | | | | | | |
|---|---|---|---|---|---|---|---|---|---|---|---|---|---|---|---|
| Lys | Lys | Ala | Arg | Asp | Ala | Leu | Glu | Glu | Ser | Leu | Lys | Leu | Lys | Asn | Trp |
| | | 35 | | | | | 40 | | | | | 45 | | | |

| | | | | | | | | | | | | | | | |
|---|---|---|---|---|---|---|---|---|---|---|---|---|---|---|---|
| Ser | Cys | Ser | Ser | Pro | Val | Phe | Pro | Gly | Asn | Trp | Asp | Leu | Arg | Leu | Leu |

```
                    50                  55                  60
Gln Val Arg Glu Arg Pro Val Ala Leu Glu Ala Glu Leu Ala Leu Thr
 65                  70                  75                  80

Leu Lys Val Leu Glu Ala Ala Ala Gly Pro Ala Leu Glu Asp Val Leu
                 85                  90                  95

Asp Gln Pro Leu His Thr Leu His His Ile Leu Ser Gln Leu Gln Ala
                100                 105                 110

Cys Ile Gln Pro Gln Pro Thr Ala Gly Pro Arg Pro Arg Gly Arg Leu
                115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Cys Leu Arg Thr Ser
                165                 170                 175

Thr His Pro Glu Ser Thr
            180

<210> SEQ ID NO 110
<211> LENGTH: 546
<212> TYPE: DNA
<213> ORGANISM: Artificial Sequence
<220> FEATURE:
<223> OTHER INFORMATION: IL29 mutant G18D, Asp169, C171X
<220> FEATURE:
<221> NAME/KEY: CDS
<222> LOCATION: (1)...(546)
<220> FEATURE:
<221> NAME/KEY: variation
<222> LOCATION: (512)...(513)
<223> OTHER INFORMATION: n = A, T, G, or C

<400> SEQUENCE: 110 ggc cct gtc ccc act tcc aag ccc acc aca act ggg aag ggc tgc cac        48
Gly Pro Val Pro Thr Ser Lys Pro Thr Thr Thr Gly Lys Gly Cys His
  1               5                  10                  15 att gay agg ttc aaa tct ctg tca cca cag gag cta gcg agc ttc aag        96
Ile Asp Arg Phe Lys Ser Leu Ser Pro Gln Glu Leu Ala Ser Phe Lys
                 20                  25                  30 aag gcc agg gac gcc ttg gaa gag tca ctc aag ctg aaa aac tgg agt       144
Lys Ala Arg Asp Ala Leu Glu Glu Ser Leu Lys Leu Lys Asn Trp Ser
             35                  40                  45 tgc agc tct cct gtc ttc ccc ggg aat tgg gac ctg agg ctt ctc cag       192
Cys Ser Ser Pro Val Phe Pro Gly Asn Trp Asp Leu Arg Leu Leu Gln
         50                  55                  60 gtg agg gag cgc cct gtg gcc ttg gag gct gag ctg gcc ctg acg ctg       240
Val Arg Glu Arg Pro Val Ala Leu Glu Ala Glu Leu Ala Leu Thr Leu
 65                  70                  75                  80 aag gtc ctg gag gcc gct gct ggc cca gcc ctg gag gac gtc cta gac       288
Lys Val Leu Glu Ala Ala Ala Gly Pro Ala Leu Glu Asp Val Leu Asp
                 85                  90                  95 cag ccc ctt cac acc ctg cac cac atc ctc tcc cag ctc cag gcc tgt       336
Gln Pro Leu His Thr Leu His His Ile Leu Ser Gln Leu Gln Ala Cys
                100                 105                 110 atc cag cct cag ccc aca gca ggg ccc agg ccc cgg ggc cgc ctc cac       384
Ile Gln Pro Gln Pro Thr Ala Gly Pro Arg Pro Arg Gly Arg Leu His
            115                 120                 125 cac tgg ctg cac cgg ctc cag gag gcc ccc aaa aag gag tcc gct ggc       432
His Trp Leu His Arg Leu Gln Glu Ala Pro Lys Lys Glu Ser Ala Gly
        130                 135                 140
```

```
tgc ctg gag gca tct gtc acc ttc aac ctc ttc cgc ctc ctc acg cga    480
Cys Leu Glu Ala Ser Val Thr Phe Asn Leu Phe Arg Leu Leu Thr Arg
145             150                 155                 160 gac ctc aaa tat gtg gcc gat ggg gay ctg dnn ctg aga acg tca acc    528
Asp Leu Lys Tyr Val Ala Asp Gly Asp Leu Xaa Leu Arg Thr Ser Thr
            165                 170                 175 cac cct gag tcc acc tga                                             546
His Pro Glu Ser Thr *
        180
```

<210> SEQ ID NO 111
<211> LENGTH: 181
<212> TYPE: PRT
<213> ORGANISM: Artificial Sequence
<220> FEATURE:
<223> OTHER INFORMATION: IL29 mutant G18D, Asp169, C171X
<220> FEATURE:
<221> NAME/KEY: VARIANT
<222> LOCATION: (171)...(171)
<223> OTHER INFORMATION: Xaa = Ser, Ala, Thr, Val, or Asn

<400> SEQUENCE: 111

```
Gly Pro Val Pro Thr Ser Lys Pro Thr Thr Thr Gly Lys Gly Cys His
 1               5                  10                  15

Ile Asp Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
 50                  55                  60

Val Arg Glu Arg Pro Val Ala Leu Glu Ala Glu Leu Ala Leu Thr Leu
 65                  70                  75                  80

Lys Val Leu Glu Ala Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asp Leu Xaa Leu Arg Thr Ser Thr
            165                 170                 175

His Pro Glu Ser Thr
        180
```

<210> SEQ ID NO 112
<211> LENGTH: 549
<212> TYPE: DNA
<213> ORGANISM: Artificial Sequence
<220> FEATURE:
<223> OTHER INFORMATION: Met IL29 mutant G19D, Asp170, C172X
<220> FEATURE:
<221> NAME/KEY: CDS
<222> LOCATION: (1)...(549)
<220> FEATURE:
<221> NAME/KEY: variation
<222> LOCATION: (515)...(516)
<223> OTHER INFORMATION: n = A, T, G, or C

<400> SEQUENCE: 112

```
atg ggc cct gtc ccc act tcc aag ccc acc aca act ggg aag ggc tgc         48
Met Gly Pro Val Pro Thr Ser Lys Pro Thr Thr Thr Gly Lys Gly Cys
 1               5                  10                  15 cac att gay agg ttc aaa tct ctg tca cca cag gag cta gcg agc ttc         96
His Ile Asp Arg Phe Lys Ser Leu Ser Pro Gln Glu Leu Ala Ser Phe
                 20                  25                  30 aag aag gcc agg gac gcc ttg gaa gag tca ctc aag ctg aaa aac tgg        144
Lys Lys Ala Arg Asp Ala Leu Glu Glu Ser Leu Lys Leu Lys Asn Trp
             35                  40                  45 agt tgc agc tct cct gtc ttc ccc ggg aat tgg gac ctg agg ctt ctc        192
Ser Cys Ser Ser Pro Val Phe Pro Gly Asn Trp Asp Leu Arg Leu Leu
 50                  55                  60 cag gtg agg gag cgc cct gtg gcc ttg gag gct gag ctg gcc ctg acg        240
Gln Val Arg Glu Arg Pro Val Ala Leu Glu Ala Glu Leu Ala Leu Thr
 65                  70                  75                  80 ctg aag gtc ctg gag gcc gct gct ggc cca gcc ctg gag gac gtc cta        288
Leu Lys Val Leu Glu Ala Ala Ala Gly Pro Ala Leu Glu Asp Val Leu
                 85                  90                  95 gac cag ccc ctt cac acc ctg cac cac atc ctc tcc cag ctc cag gcc        336
Asp Gln Pro Leu His Thr Leu His His Ile Leu Ser Gln Leu Gln Ala
            100                 105                 110 tgt atc cag cct cag ccc aca gca ggg ccc agg ccc cgg ggc cgc ctc        384
Cys Ile Gln Pro Gln Pro Thr Ala Gly Pro Arg Pro Arg Gly Arg Leu
            115                 120                 125 cac cac tgg ctg cac cgg ctc cag gag gcc ccc aaa aag gag tcc gct        432
His His Trp Leu His Arg Leu Gln Glu Ala Pro Lys Lys Glu Ser Ala
    130                 135                 140 ggc tgc ctg gag gca tct gtc acc ttc aac ctc ttc cgc ctc ctc acg        480
Gly Cys Leu Glu Ala Ser Val Thr Phe Asn Leu Phe Arg Leu Leu Thr
145                 150                 155                 160 cga gac ctc aaa tat gtg gcc gat ggg gay ctg dnn ctg aga acg tca        528
Arg Asp Leu Lys Tyr Val Ala Asp Gly Asp Leu Xaa Leu Arg Thr Ser
                165                 170                 175 acc cac cct gag tcc acc tga                                            549
Thr His Pro Glu Ser Thr  *
            180
```

<210> SEQ ID NO 113
<211> LENGTH: 182
<212> TYPE: PRT
<213> ORGANISM: Artificial Sequence
<220> FEATURE:
<223> OTHER INFORMATION: Met IL29 mutant G19D, Asp170, C172X
<220> FEATURE:
<221> NAME/KEY: VARIANT
<222> LOCATION: (172)...(172)
<223> OTHER INFORMATION: Xaa = Ser, Ala, Thr, Val, or Asn

<400> SEQUENCE: 113

```
Met Gly Pro Val Pro Thr Ser Lys Pro Thr Thr Thr Gly Lys Gly Cys
 1               5                  10                  15

His Ile Asp Arg Phe Lys Ser Leu Ser Pro Gln Glu Leu Ala Ser Phe
                 20                  25                  30

Lys Lys Ala Arg Asp Ala Leu Glu Glu Ser Leu Lys Leu Lys Asn Trp
             35                  40                  45

Ser Cys Ser Ser Pro Val Phe Pro Gly Asn Trp Asp Leu Arg Leu Leu
 50                  55                  60

Gln Val Arg Glu Arg Pro Val Ala Leu Glu Ala Glu Leu Ala Leu Thr
 65                  70                  75                  80

Leu Lys Val Leu Glu Ala Ala Ala Gly Pro Ala Leu Glu Asp Val Leu
                 85                  90                  95
```

```
Asp Gln Pro Leu His Thr Leu His His Ile Leu Ser Gln Leu Gln Ala
                100                 105                 110

Cys Ile Gln Pro Gln Pro Thr Ala Gly Pro Arg Pro Arg Gly Arg Leu
            115                 120                 125

His His Trp Leu His Arg Leu Gln Glu Ala Pro Lys Lys Glu Ser Ala
        130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asp Leu Xaa Leu Arg Thr Ser
                165                 170                 175

Thr His Pro Glu Ser Thr
            180

<210> SEQ ID NO 114
<211> LENGTH: 546
<212> TYPE: DNA
<213> ORGANISM: Artificial Sequence
<220> FEATURE:
<223> OTHER INFORMATION: IL29 mutant C15X, G18D, Asp169
<220> FEATURE:
<221> NAME/KEY: CDS
<222> LOCATION: (1)...(546)
<220> FEATURE:
<221> NAME/KEY: variation
<222> LOCATION: (44)...(45)
<223> OTHER INFORMATION: n = A, T, G, or C

<400> SEQUENCE: 114 ggc cct gtc ccc act tcc aag ccc acc aca act ggg aag ggc dnn cac      48
Gly Pro Val Pro Thr Ser Lys Pro Thr Thr Thr Gly Lys Gly Xaa His
1               5                   10                  15 att gay agg ttc aaa tct ctg tca cca cag gag cta gcg agc ttc aag      96
Ile Asp Arg Phe Lys Ser Leu Ser Pro Gln Glu Leu Ala Ser Phe Lys
                20                  25                  30 aag gcc agg gac gcc ttg gaa gag tca ctc aag ctg aaa aac tgg agt     144
Lys Ala Arg Asp Ala Leu Glu Glu Ser Leu Lys Leu Lys Asn Trp Ser
            35                  40                  45 tgc agc tct cct gtc ttc ccc ggg aat tgg gac ctg agg ctt ctc cag     192
Cys Ser Ser Pro Val Phe Pro Gly Asn Trp Asp Leu Arg Leu Leu Gln
        50                  55                  60 gtg agg gag cgc cct gtg gcc ttg gag gct gag ctg gcc ctg acg ctg     240
Val Arg Glu Arg Pro Val Ala Leu Glu Ala Glu Leu Ala Leu Thr Leu
65                  70                  75                  80 aag gtc ctg gag gcc gct gct ggc cca gcc ctg gag gac gtc cta gac     288
Lys Val Leu Glu Ala Ala Ala Gly Pro Ala Leu Glu Asp Val Leu Asp
                85                  90                  95 cag ccc ctt cac acc ctg cac cac atc ctc tcc cag ctc cag gcc tgt     336
Gln Pro Leu His Thr Leu His His Ile Leu Ser Gln Leu Gln Ala Cys
                100                 105                 110 atc cag cct cag ccc aca gca ggg ccc agg ccc cgg ggc cgc ctc cac     384
Ile Gln Pro Gln Pro Thr Ala Gly Pro Arg Pro Arg Gly Arg Leu His
            115                 120                 125 cac tgg ctg cac cgg ctc cag gag gcc ccc aaa aag gag tcc gct ggc     432
His Trp Leu His Arg Leu Gln Glu Ala Pro Lys Lys Glu Ser Ala Gly
        130                 135                 140 tgc ctg gag gca tct gtc acc ttc aac ctc ttc cgc ctc ctc acg cga     480
Cys Leu Glu Ala Ser Val Thr Phe Asn Leu Phe Arg Leu Leu Thr Arg
145                 150                 155                 160 gac ctc aaa tat gtg gcc gat ggg gay ctg tgt ctg aga acg tca acc     528
Asp Leu Lys Tyr Val Ala Asp Gly Asp Leu Cys Leu Arg Thr Ser Thr
                165                 170                 175
```

```
cac cct gag tcc acc tga                                              546
His Pro Glu Ser Thr *
            180
```

<210> SEQ ID NO 115
<211> LENGTH: 181
<212> TYPE: PRT
<213> ORGANISM: Artificial Sequence
<220> FEATURE:
<223> OTHER INFORMATION: IL29 mutant C15X, G18D, Asp169
<220> FEATURE:
<221> NAME/KEY: VARIANT
<222> LOCATION: (15)...(15)
<223> OTHER INFORMATION: Xaa = Ser, Ala, Thr, Val, or Asn

<400> SEQUENCE: 115

```
Gly Pro Val Pro Thr Ser Lys Pro Thr Thr Thr Gly Lys Gly Xaa His
 1               5                  10                  15

Ile Asp Arg Phe Lys Ser Leu Ser Pro Gln Glu Leu Ala Ser Phe Lys
                20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
50                  55                  60

Val Arg Glu Arg Pro Val Ala Leu Glu Ala Glu Leu Ala Leu Thr Leu
65                  70                  75                  80

Lys Val Leu Glu Ala Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asp Leu Cys Leu Arg Thr Ser Thr
                165                 170                 175

His Pro Glu Ser Thr
            180
```

<210> SEQ ID NO 116
<211> LENGTH: 549
<212> TYPE: DNA
<213> ORGANISM: Artificial Sequence
<220> FEATURE:
<223> OTHER INFORMATION: Met IL29 mutant C16X, G19D, Asp170
<220> FEATURE:
<221> NAME/KEY: CDS
<222> LOCATION: (1)...(549)
<220> FEATURE:
<221> NAME/KEY: variation
<222> LOCATION: (47)...(48)
<223> OTHER INFORMATION: n = A, T, G, or C

<400> SEQUENCE: 116

```
atg ggc cct gtc ccc act tcc aag ccc acc aca act ggg aag ggc dnn   48
Met Gly Pro Val Pro Thr Ser Lys Pro Thr Thr Thr Gly Lys Gly Xaa
 1               5                  10                  15 cac att gay agg ttc aaa tct ctg tca cca cag gag cta gcg agc ttc   96
His Ile Asp Arg Phe Lys Ser Leu Ser Pro Gln Glu Leu Ala Ser Phe
                20                  25                  30
```

```
aag aag gcc agg gac gcc ttg gaa gag tca ctc aag ctg aaa aac tgg      144
Lys Lys Ala Arg Asp Ala Leu Glu Glu Ser Leu Lys Leu Lys Asn Trp
         35                  40                  45 agt tgc agc tct cct gtc ttc ccc ggg aat tgg gac ctg agg ctt ctc      192
Ser Cys Ser Ser Pro Val Phe Pro Gly Asn Trp Asp Leu Arg Leu Leu
 50                  55                  60 cag gtg agg gag cgc cct gtg gcc ttg gag gct gag ctg gcc ctg acg      240
Gln Val Arg Glu Arg Pro Val Ala Leu Glu Ala Glu Leu Ala Leu Thr
 65                  70                  75                  80 ctg aag gtc ctg gag gcc gct gct ggc cca gcc ctg gag gac gtc cta      288
Leu Lys Val Leu Glu Ala Ala Ala Gly Pro Ala Leu Glu Asp Val Leu
             85                  90                  95 gac cag ccc ctt cac acc ctg cac cac atc ctc tcc cag ctc cag gcc      336
Asp Gln Pro Leu His Thr Leu His His Ile Leu Ser Gln Leu Gln Ala
            100                 105                 110 tgt atc cag cct cag ccc aca gca ggg ccc agg ccc cgg ggc cgc ctc      384
Cys Ile Gln Pro Gln Pro Thr Ala Gly Pro Arg Pro Arg Gly Arg Leu
        115                 120                 125 cac cac tgg ctg cac cgg ctc cag gag gcc ccc aaa aag gag tcc gct      432
His His Trp Leu His Arg Leu Gln Glu Ala Pro Lys Lys Glu Ser Ala
130                 135                 140 ggc tgc ctg gag gca tct gtc acc ttc aac ctc ttc cgc ctc ctc acg      480
Gly Cys Leu Glu Ala Ser Val Thr Phe Asn Leu Phe Arg Leu Leu Thr
145                 150                 155                 160 cga gac ctc aaa tat gtg gcc gat ggg gay ctg tgt ctg aga acg tca      528
Arg Asp Leu Lys Tyr Val Ala Asp Gly Asp Leu Cys Leu Arg Thr Ser
                165                 170                 175 acc cac cct gag tcc acc tga                                          549
Thr His Pro Glu Ser Thr  *
180

<210> SEQ ID NO 117
<211> LENGTH: 182
<212> TYPE: PRT
<213> ORGANISM: Artificial Sequence
<220> FEATURE:
<223> OTHER INFORMATION: Met IL29 mutant C16X, G19D, Asp170
<220> FEATURE:
<221> NAME/KEY: VARIANT
<222> LOCATION: (16)...(16)
<223> OTHER INFORMATION: Xaa = Ser, Ala, Thr, Val, or Asn

<400> SEQUENCE: 117

Met Gly Pro Val Pro Thr Ser Lys Pro Thr Thr Thr Gly Lys Gly Xaa
 1               5                  10                  15

His Ile Asp Arg Phe Lys Ser Leu Ser Pro Gln Glu Leu Ala Ser Phe
             20                  25                  30

Lys Lys Ala Arg Asp Ala Leu Glu Glu Ser Leu Lys Leu Lys Asn Trp
         35                  40                  45

Ser Cys Ser Ser Pro Val Phe Pro Gly Asn Trp Asp Leu Arg Leu Leu
 50                  55                  60

Gln Val Arg Glu Arg Pro Val Ala Leu Glu Ala Glu Leu Ala Leu Thr
 65                  70                  75                  80

Leu Lys Val Leu Glu Ala Ala Ala Gly Pro Ala Leu Glu Asp Val Leu
             85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125
```

```
His His Trp Leu His Arg Leu Gln Glu Ala Pro Lys Lys Glu Ser Ala
        130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asp Leu Cys Leu Arg Thr Ser
                165                 170                 175

Thr His Pro Glu Ser Thr
            180

<210> SEQ ID NO 118
<211> LENGTH: 57
<212> TYPE: DNA
<213> ORGANISM: Artificial Sequence
<220> FEATURE:
<223> OTHER INFORMATION: Signal sequence
<220> FEATURE:
<221> NAME/KEY: CDS
<222> LOCATION: (1)...(57)

<400> SEQUENCE: 118 atg gct gca gct tgg acc gtg gtg ctg gtg act ttg gtg cta ggc ttg      48
Met Ala Ala Ala Trp Thr Val Val Leu Val Thr Leu Val Leu Gly Leu
 1               5                  10                  15 gcc gtg gca                                                          57
Ala Val Ala <210> SEQ ID NO 119
<211> LENGTH: 19
<212> TYPE: PRT
<213> ORGANISM: Artificial Sequence
<220> FEATURE:
<223> OTHER INFORMATION: Signal sequence

<400> SEQUENCE: 119

Met Ala Ala Ala Trp Thr Val Val Leu Val Thr Leu Val Leu Gly Leu
 1               5                  10                  15

Ala Val Ala

<210> SEQ ID NO 120
<211> LENGTH: 66
<212> TYPE: DNA
<213> ORGANISM: Artificial Sequence
<220> FEATURE:
<223> OTHER INFORMATION: Signal sequence
<220> FEATURE:
<221> NAME/KEY: CDS
<222> LOCATION: (1)...(66)

<400> SEQUENCE: 120 atg gtg ccc acc aca ttg gct tgg acc gtg gtg ctg gtg act ttg gtg      48
Met Val Pro Thr Thr Leu Ala Trp Thr Val Val Leu Val Thr Leu Val
 1               5                  10                  15 cta ggc ttg gcc gtg gca                                              66
Leu Gly Leu Ala Val Ala
            20

<210> SEQ ID NO 121
<211> LENGTH: 22
<212> TYPE: PRT
<213> ORGANISM: Artificial Sequence
<220> FEATURE:
<223> OTHER INFORMATION: Signal sequence

<400> SEQUENCE: 121

Met Val Pro Thr Thr Leu Ala Trp Thr Val Val Leu Val Thr Leu Val
```

```
                1               5              10              15
Leu Gly Leu Ala Val Ala
            20

<210> SEQ ID NO 122
<211> LENGTH: 528
<212> TYPE: DNA
<213> ORGANISM: Artificial Sequence
<220> FEATURE:
<223> OTHER INFORMATION: IL-28B C48S
<220> FEATURE:
<221> NAME/KEY: CDS
<222> LOCATION: (1)...(528)
<220> FEATURE:
<221> NAME/KEY: variation
<222> LOCATION: (143)...(144)
<223> OTHER INFORMATION: n = A, T, G, or C

<400> SEQUENCE: 122 gtt cct gtc gcc agg ctc cgc ggg gct ctc ccg gat gca agg ggc tgc      48
Val Pro Val Ala Arg Leu Arg Gly Ala Leu Pro Asp Ala Arg Gly Cys
 1               5                  10                  15 cac ata gcc cag ttc aag tcc ctg tct cca cag gag ctg cag gcc ttt      96
His Ile Ala Gln Phe Lys Ser Leu Ser Pro Gln Glu Leu Gln Ala Phe
             20                  25                  30 aag agg gcc aaa gat gcc tta gaa gag tcg ctt ctg ctg aag gac dnn     144
Lys Arg Ala Lys Asp Ala Leu Glu Glu Ser Leu Leu Leu Lys Asp Xaa
         35                  40                  45 aag tgc cgc tcc cgc ctc ttc ccc agg acc tgg gac ctg agg cag ctg     192
Lys Cys Arg Ser Arg Leu Phe Pro Arg Thr Trp Asp Leu Arg Gln Leu
     50                  55                  60 cag gtg agg gag cgc ccc gtg gct ttg gag gct gag ctg gcc ctg acg     240
Gln Val Arg Glu Arg Pro Val Ala Leu Glu Ala Glu Leu Ala Leu Thr
 65                  70                  75                  80 ctg aag gtt ctg gag gcc acc gct gac act gac cca gcc ctg ggg gat     288
Leu Lys Val Leu Glu Ala Thr Ala Asp Thr Asp Pro Ala Leu Gly Asp
                 85                  90                  95 gtc ttg gac cag ccc ctt cac acc ctg cac cat atc ctc tcc cag ctc     336
Val Leu Asp Gln Pro Leu His Thr Leu His His Ile Leu Ser Gln Leu
            100                 105                 110 cgg gcc tgt atc cag cct cag ccc acg gca ggg ccc agg acc cgg ggc     384
Arg Ala Cys Ile Gln Pro Gln Pro Thr Ala Gly Pro Arg Thr Arg Gly
        115                 120                 125 cgc ctc cac cat tgg ctg cac cgg ctc cag gag gcc cca aaa aag gag     432
Arg Leu His His Trp Leu His Arg Leu Gln Glu Ala Pro Lys Lys Glu
    130                 135                 140 tcc cct ggc tgc ctc gag gcc tct gtc acc ttc aac ctc ttc cgc ctc     480
Ser Pro Gly Cys Leu Glu Ala Ser Val Thr Phe Asn Leu Phe Arg Leu
145                 150                 155                 160 ctc acg cga gac ctg aat tgt gtt gcc agc ggg gac ctg tgt gtc tga     528
Leu Thr Arg Asp Leu Asn Cys Val Ala Ser Gly Asp Leu Cys Val *
                165                 170                 175

<210> SEQ ID NO 123
<211> LENGTH: 175
<212> TYPE: PRT
<213> ORGANISM: Artificial Sequence
<220> FEATURE:
<221> NAME/KEY: VARIANT
<222> LOCATION: (48)...(48)
<223> OTHER INFORMATION: Xaa = Ser, Ala, Thr, Val, or Asn
<220> FEATURE:
<223> OTHER INFORMATION: IL-28B C48S

<400> SEQUENCE: 123
```

```
Val Pro Val Ala Arg Leu Arg Gly Ala Leu Pro Asp Ala Arg Gly Cys
 1               5                  10                  15

His Ile Ala Gln Phe Lys Ser Leu Ser Pro Gln Glu Leu Gln Ala Phe
            20                  25                  30

Lys Arg Ala Lys Asp Ala Leu Glu Glu Ser Leu Leu Leu Lys Asp Xaa
        35                  40                  45

Lys Cys Arg Ser Arg Leu Phe Pro Arg Thr Trp Asp Leu Arg Gln Leu
 50                  55                  60

Gln Val Arg Glu Arg Pro Val Ala Leu Glu Ala Glu Leu Ala Leu Thr
65                  70                  75                  80

Leu Lys Val Leu Glu Ala Thr Ala Asp Thr Asp Pro Ala Leu Gly Asp
                85                  90                  95

Val Leu Asp Gln Pro Leu His Thr Leu His His Ile Leu Ser Gln Leu
            100                 105                 110

Arg Ala Cys Ile Gln Pro Gln Pro Thr Ala Gly Pro Arg Thr Arg Gly
        115                 120                 125

Arg Leu His His Trp Leu His Arg Leu Gln Glu Ala Pro Lys Lys Glu
    130                 135                 140

Ser Pro Gly Cys Leu Glu Ala Ser Val Thr Phe Asn Leu Phe Arg Leu
145                 150                 155                 160

Leu Thr Arg Asp Leu Asn Cys Val Ala Ser Gly Asp Leu Cys Val
                165                 170                 175

<210> SEQ ID NO 124
<211> LENGTH: 531
<212> TYPE: DNA
<213> ORGANISM: Artificial Sequence
<220> FEATURE:
<223> OTHER INFORMATION: Met IL-28B C49S
<220> FEATURE:
<221> NAME/KEY: CDS
<222> LOCATION: (1)...(531)
<220> FEATURE:
<221> NAME/KEY: variation
<222> LOCATION: (146)...(147)
<223> OTHER INFORMATION: n = A, T, G, or C

<400> SEQUENCE: 124 atg gtt cct gtc gcc agg ctc cgc ggg gct ctc ccg gat gca agg ggc      48
Met Val Pro Val Ala Arg Leu Arg Gly Ala Leu Pro Asp Ala Arg Gly
 1               5                  10                  15 tgc cac ata gcc cag ttc aag tcc ctg tct cca cag gag ctg cag gcc      96
Cys His Ile Ala Gln Phe Lys Ser Leu Ser Pro Gln Glu Leu Gln Ala
            20                  25                  30 ttt aag agg gcc aaa gat gcc tta gaa gag tcg ctt ctg ctg aag gac     144
Phe Lys Arg Ala Lys Asp Ala Leu Glu Glu Ser Leu Leu Leu Lys Asp
        35                  40                  45 dnn aag tgc cgc tcc cgc ctc ttc ccc agg acc tgg gac ctg agg cag     192
Xaa Lys Cys Arg Ser Arg Leu Phe Pro Arg Thr Trp Asp Leu Arg Gln
 50                  55                  60 ctg cag gtg agg gag cgc ccc gtg gct ttg gag gct gag ctg gcc ctg     240
Leu Gln Val Arg Glu Arg Pro Val Ala Leu Glu Ala Glu Leu Ala Leu
65                  70                  75                  80 acg ctg aag gtt ctg gag gcc acc gct gac act gac cca gcc ctg ggg     288
Thr Leu Lys Val Leu Glu Ala Thr Ala Asp Thr Asp Pro Ala Leu Gly
                85                  90                  95 gat gtc ttg gac cag ccc ctt cac acc ctg cac cat atc ctc tcc cag     336
Asp Val Leu Asp Gln Pro Leu His Thr Leu His His Ile Leu Ser Gln
            100                 105                 110
```

```
ctc cgg gcc tgt atc cag cct cag ccc acg gca ggg ccc agg acc cgg    384
Leu Arg Ala Cys Ile Gln Pro Gln Pro Thr Ala Gly Pro Arg Thr Arg
        115                 120                 125 ggc cgc ctc cac cat tgg ctg cac cgg ctc cag gag gcc cca aaa aag    432
Gly Arg Leu His His Trp Leu His Arg Leu Gln Glu Ala Pro Lys Lys
    130                 135                 140 gag tcc cct ggc tgc ctc gag gcc tct gtc acc ttc aac ctc ttc cgc    480
Glu Ser Pro Gly Cys Leu Glu Ala Ser Val Thr Phe Asn Leu Phe Arg
145                 150                 155                 160 ctc ctc acg cga gac ctg aat tgt gtt gcc agc ggg gac ctg tgt gtc    528
Leu Leu Thr Arg Asp Leu Asn Cys Val Ala Ser Gly Asp Leu Cys Val
            165                 170                 175 tga                                                                531
*
```

```
<210> SEQ ID NO 125
<211> LENGTH: 176
<212> TYPE: PRT
<213> ORGANISM: Artificial Sequence
<220> FEATURE:
<221> NAME/KEY: VARIANT
<222> LOCATION: (49)...(49)
<223> OTHER INFORMATION: Xaa = Ser, Ala, Thr, Val, or Asn
<220> FEATURE:
<223> OTHER INFORMATION: Met IL-28B C49S

<400> SEQUENCE: 125
```

```
Met Val Pro Val Ala Arg Leu Arg Gly Ala Leu Pro Asp Ala Arg Gly
  1               5                  10                  15

Cys His Ile Ala Gln Phe Lys Ser Leu Ser Pro Gln Glu Leu Gln Ala
             20                  25                  30

Phe Lys Arg Ala Lys Asp Ala Leu Glu Glu Ser Leu Leu Leu Lys Asp
         35                  40                  45

Xaa Lys Cys Arg Ser Arg Leu Phe Pro Arg Thr Trp Asp Leu Arg Gln
 50                  55                  60

Leu Gln Val Arg Glu Arg Pro Val Ala Leu Glu Ala Glu Leu Ala Leu
 65                  70                  75                  80

Thr Leu Lys Val Leu Glu Ala Thr Ala Asp Thr Asp Pro Ala Leu Gly
                 85                  90                  95

Asp Val Leu Asp Gln Pro Leu His Thr Leu His His Ile Leu Ser Gln
            100                 105                 110

Leu Arg Ala Cys Ile Gln Pro Gln Pro Thr Ala Gly Pro Arg Thr Arg
        115                 120                 125

Gly Arg Leu His His Trp Leu His Arg Leu Gln Glu Ala Pro Lys Lys
    130                 135                 140

Glu Ser Pro Gly Cys Leu Glu Ala Ser Val Thr Phe Asn Leu Phe Arg
145                 150                 155                 160

Leu Leu Thr Arg Asp Leu Asn Cys Val Ala Ser Gly Asp Leu Cys Val
            165                 170                 175
```

```
<210> SEQ ID NO 126
<211> LENGTH: 528
<212> TYPE: DNA
<213> ORGANISM: Artificial Sequence
<220> FEATURE:
<223> OTHER INFORMATION: IL-28B C50S
<220> FEATURE:
<221> NAME/KEY: CDS
<222> LOCATION: (1)...(528)
<220> FEATURE:
<221> NAME/KEY: variation
<222> LOCATION: (149)...(150)
```

<223> OTHER INFORMATION: n = A, T, G, or C

<400> SEQUENCE: 126

```
gtt cct gtc gcc agg ctc cgc ggg gct ctc ccg gat gca agg ggc tgc      48
Val Pro Val Ala Arg Leu Arg Gly Ala Leu Pro Asp Ala Arg Gly Cys
 1               5                  10                  15 cac ata gcc cag ttc aag tcc ctg tct cca cag gag ctg cag gcc ttt      96
His Ile Ala Gln Phe Lys Ser Leu Ser Pro Gln Glu Leu Gln Ala Phe
             20                  25                  30 aag agg gcc aaa gat gcc tta gaa gag tcg ctt ctg ctg aag gac tgc     144
Lys Arg Ala Lys Asp Ala Leu Glu Glu Ser Leu Leu Leu Lys Asp Cys
         35                  40                  45 aag dnn cgc tcc cgc ctc ttc ccc agg acc tgg gac ctg agg cag ctg     192
Lys Xaa Arg Ser Arg Leu Phe Pro Arg Thr Trp Asp Leu Arg Gln Leu
     50                  55                  60 cag gtg agg gag cgc ccc gtg gct ttg gag gct gag ctg gcc ctg acg     240
Gln Val Arg Glu Arg Pro Val Ala Leu Glu Ala Glu Leu Ala Leu Thr
 65                  70                  75                  80 ctg aag gtt ctg gag gcc acc gct gac act gac cca gcc ctg ggg gat     288
Leu Lys Val Leu Glu Ala Thr Ala Asp Thr Asp Pro Ala Leu Gly Asp
                 85                  90                  95 gtc ttg gac cag ccc ctt cac acc ctg cac cat atc ctc tcc cag ctc     336
Val Leu Asp Gln Pro Leu His Thr Leu His His Ile Leu Ser Gln Leu
            100                 105                 110 cgg gcc tgt atc cag cct cag ccc acg gca ggg ccc agg acc cgg ggc     384
Arg Ala Cys Ile Gln Pro Gln Pro Thr Ala Gly Pro Arg Thr Arg Gly
        115                 120                 125 cgc ctc cac cat tgg ctg cac cgg ctc cag gag gcc cca aaa aag gag     432
Arg Leu His His Trp Leu His Arg Leu Gln Glu Ala Pro Lys Lys Glu
    130                 135                 140 tcc cct ggc tgc ctc gag gcc tct gtc acc ttc aac ctc ttc cgc ctc     480
Ser Pro Gly Cys Leu Glu Ala Ser Val Thr Phe Asn Leu Phe Arg Leu
145                 150                 155                 160 ctc acg cga gac ctg aat tgt gtt gcc agc ggg gac ctg tgt gtc tga     528
Leu Thr Arg Asp Leu Asn Cys Val Ala Ser Gly Asp Leu Cys Val *
                165                 170                 175
```

<210> SEQ ID NO 127
<211> LENGTH: 175
<212> TYPE: PRT
<213> ORGANISM: Artificial Sequence
<220> FEATURE:
<221> NAME/KEY: VARIANT
<222> LOCATION: (50)...(50)
<223> OTHER INFORMATION: Xaa = Ser, Ala, Thr, Val, or Asn
<220> FEATURE:
<223> OTHER INFORMATION: IL-28B C50S

<400> SEQUENCE: 127

```
Val Pro Val Ala Arg Leu Arg Gly Ala Leu Pro Asp Ala Arg Gly Cys
 1               5                  10                  15

His Ile Ala Gln Phe Lys Ser Leu Ser Pro Gln Glu Leu Gln Ala Phe
             20                  25                  30

Lys Arg Ala Lys Asp Ala Leu Glu Glu Ser Leu Leu Leu Lys Asp Cys
         35                  40                  45

Lys Xaa Arg Ser Arg Leu Phe Pro Arg Thr Trp Asp Leu Arg Gln Leu
     50                  55                  60

Gln Val Arg Glu Arg Pro Val Ala Leu Glu Ala Glu Leu Ala Leu Thr
 65                  70                  75                  80

Leu Lys Val Leu Glu Ala Thr Ala Asp Thr Asp Pro Ala Leu Gly Asp
                 85                  90                  95
```

```
Val Leu Asp Gln Pro Leu His Thr Leu His His Ile Leu Ser Gln Leu
            100                 105                 110

Arg Ala Cys Ile Gln Pro Gln Pro Thr Ala Gly Pro Arg Thr Arg Gly
        115                 120                 125

Arg Leu His His Trp Leu His Arg Leu Gln Glu Ala Pro Lys Lys Glu
    130                 135                 140

Ser Pro Gly Cys Leu Glu Ala Ser Val Thr Phe Asn Leu Phe Arg Leu
145                 150                 155                 160

Leu Thr Arg Asp Leu Asn Cys Val Ala Ser Gly Asp Leu Cys Val
                165                 170                 175

<210> SEQ ID NO 128
<211> LENGTH: 531
<212> TYPE: DNA
<213> ORGANISM: Artificial Sequence
<220> FEATURE:
<223> OTHER INFORMATION: Met IL-28B C51S
<220> FEATURE:
<221> NAME/KEY: CDS
<222> LOCATION: (1)...(531)
<220> FEATURE:
<221> NAME/KEY: variation
<222> LOCATION: (152)...(153)
<223> OTHER INFORMATION: n = A, T, G, or C

<400> SEQUENCE: 128 atg gtt cct gtc gcc agg ctc cgc ggg gct ctc ccg gat gca agg ggc     48
Met Val Pro Val Ala Arg Leu Arg Gly Ala Leu Pro Asp Ala Arg Gly
  1               5                  10                  15 tgc cac ata gcc cag ttc aag tcc ctg tct cca cag gag ctg cag gcc     96
Cys His Ile Ala Gln Phe Lys Ser Leu Ser Pro Gln Glu Leu Gln Ala
             20                  25                  30 ttt aag agg gcc aaa gat gcc tta gaa gag tcg ctt ctg ctg aag gac    144
Phe Lys Arg Ala Lys Asp Ala Leu Glu Glu Ser Leu Leu Leu Lys Asp
         35                  40                  45 tgc aag dnn cgc tcc cgc ctc ttc ccc agg acc tgg gac ctg agg cag    192
Cys Lys Xaa Arg Ser Arg Leu Phe Pro Arg Thr Trp Asp Leu Arg Gln
     50                  55                  60 ctg cag gtg agg gag cgc ccc gtg gct ttg gag gct gag ctg gcc ctg    240
Leu Gln Val Arg Glu Arg Pro Val Ala Leu Glu Ala Glu Leu Ala Leu
 65                  70                  75                  80 acg ctg aag gtt ctg gag gcc acc gct gac act gac cca gcc ctg ggg    288
Thr Leu Lys Val Leu Glu Ala Thr Ala Asp Thr Asp Pro Ala Leu Gly
                 85                  90                  95 gat gtc ttg gac cag ccc ctt cac acc ctg cac cat atc ctc tcc cag    336
Asp Val Leu Asp Gln Pro Leu His Thr Leu His His Ile Leu Ser Gln
            100                 105                 110 ctc cgg gcc tgt atc cag cct cag ccc acg gca ggg ccc agg acc cgg    384
Leu Arg Ala Cys Ile Gln Pro Gln Pro Thr Ala Gly Pro Arg Thr Arg
        115                 120                 125 ggc cgc ctc cac cat tgg ctg cac cgg ctc cag gag gcc cca aaa aag    432
Gly Arg Leu His His Trp Leu His Arg Leu Gln Glu Ala Pro Lys Lys
    130                 135                 140 gag tcc cct ggc tgc ctc gag gcc tct gtc acc ttc aac ctc ttc cgc    480
Glu Ser Pro Gly Cys Leu Glu Ala Ser Val Thr Phe Asn Leu Phe Arg
145                 150                 155                 160 ctc ctc acg cga gac ctg aat tgt gtt gcc agc ggg gac ctg tgt gtc    528
Leu Leu Thr Arg Asp Leu Asn Cys Val Ala Ser Gly Asp Leu Cys Val
                165                 170                 175 tga                                                                531
 *
```

<210> SEQ ID NO 129
<211> LENGTH: 176
<212> TYPE: PRT
<213> ORGANISM: Artificial Sequence
<220> FEATURE:
<221> NAME/KEY: VARIANT
<222> LOCATION: (51)...(51)
<223> OTHER INFORMATION: Xaa = Ser, Ala, Thr, Val, or Asn
<220> FEATURE:
<223> OTHER INFORMATION: Met IL-28B C51S

<400> SEQUENCE: 129

Met Val Pro Val Ala Arg Leu Arg Gly Ala Leu Pro Asp Ala Arg Gly
 1               5                  10                  15

Cys His Ile Ala Gln Phe Lys Ser Leu Ser Pro Gln Glu Leu Gln Ala
            20                  25                  30

Phe Lys Arg Ala Lys Asp Ala Leu Glu Glu Ser Leu Leu Leu Lys Asp
        35                  40                  45

Cys Lys Xaa Arg Ser Arg Leu Phe Pro Arg Thr Trp Asp Leu Arg Gln
    50                  55                  60

Leu Gln Val Arg Glu Arg Pro Val Ala Leu Glu Ala Glu Leu Ala Leu
65                  70                  75                  80

Thr Leu Lys Val Leu Glu Ala Thr Ala Asp Thr Asp Pro Ala Leu Gly
                85                  90                  95

Asp Val Leu Asp Gln Pro Leu His Thr Leu His His Ile Leu Ser Gln
            100                 105                 110

Leu Arg Ala Cys Ile Gln Pro Gln Pro Thr Ala Gly Pro Arg Thr Arg
        115                 120                 125

Gly Arg Leu His His Trp Leu His Arg Leu Gln Glu Ala Pro Lys Lys
    130                 135                 140

Glu Ser Pro Gly Cys Leu Glu Ala Ser Val Thr Phe Asn Leu Phe Arg
145                 150                 155                 160

Leu Leu Thr Arg Asp Leu Asn Cys Val Ala Ser Gly Asp Leu Cys Val
                165                 170                 175

<210> SEQ ID NO 130
<211> LENGTH: 528
<212> TYPE: DNA
<213> ORGANISM: Artificial Sequence
<220> FEATURE:
<223> OTHER INFORMATION: IL-28B C48S T87S H135Y
<220> FEATURE:
<221> NAME/KEY: CDS
<222> LOCATION: (1)...(528)
<220> FEATURE:
<221> NAME/KEY: variation
<222> LOCATION: 143, 144, 261
<223> OTHER INFORMATION: n = A, T, G, or C

<400> SEQUENCE: 130 gtt cct gtc gcc agg ctc cgc ggg gct ctc ccg gat gca agg ggc tgc     48
Val Pro Val Ala Arg Leu Arg Gly Ala Leu Pro Asp Ala Arg Gly Cys
 1               5                  10                  15 cac ata gcc cag ttc aag tcc ctg tct cca cag gag ctg cag gcc ttt     96
His Ile Ala Gln Phe Lys Ser Leu Ser Pro Gln Glu Leu Gln Ala Phe
            20                  25                  30 aag agg gcc aaa gat gcc tta gaa gag tcg ctt ctg ctg aag gac dnn    144
Lys Arg Ala Lys Asp Ala Leu Glu Glu Ser Leu Leu Leu Lys Asp Xaa
        35                  40                  45 aag tgc cgc tcc cgc ctc ttc ccc agg acc tgg gac ctg agg cag ctg    192
Lys Cys Arg Ser Arg Leu Phe Pro Arg Thr Trp Asp Leu Arg Gln Leu

```
                50                    55                   60
cag gtg agg gag cgc ccc gtg gct ttg gag gct gag ctg gcc ctg acg        240
Gln Val Arg Glu Arg Pro Val Ala Leu Glu Ala Glu Leu Ala Leu Thr
 65                  70                  75                  80 ctg aag gtt ctg gag gcc wsn gct gac act gac cca gcc ctg ggg gat        288
Leu Lys Val Leu Glu Ala Xaa Ala Asp Thr Asp Pro Ala Leu Gly Asp
                     85                  90                  95 gtc ttg gac cag ccc ctt cac acc ctg cac cat atc ctc tcc cag ctc        336
Val Leu Asp Gln Pro Leu His Thr Leu His His Ile Leu Ser Gln Leu
                100                 105                 110 cgg gcc tgt atc cag cct cag ccc acg gca ggg ccc agg acc cgg ggc        384
Arg Ala Cys Ile Gln Pro Gln Pro Thr Ala Gly Pro Arg Thr Arg Gly
            115                 120                 125 cgc ctc cac cat tgg ctg tay cgg ctc cag gag gcc cca aaa aag gag        432
Arg Leu His His Trp Leu Tyr Arg Leu Gln Glu Ala Pro Lys Lys Glu
        130                 135                 140 tcc cct ggc tgc ctc gag gcc tct gtc acc ttc aac ctc ttc cgc ctc        480
Ser Pro Gly Cys Leu Glu Ala Ser Val Thr Phe Asn Leu Phe Arg Leu
145                 150                 155                 160 ctc acg cga gac ctg aat tgt gtt gcc agc ggg gac ctg tgt gtc tga        528
Leu Thr Arg Asp Leu Asn Cys Val Ala Ser Gly Asp Leu Cys Val  *
                165                 170                 175

<210> SEQ ID NO 131
<211> LENGTH: 175
<212> TYPE: PRT
<213> ORGANISM: Artificial Sequence
<220> FEATURE:
<221> NAME/KEY: VARIANT
<222> LOCATION: (48)...(48)
<223> OTHER INFORMATION: Xaa = Ser, Ala, Thr, Val, or Asn
<220> FEATURE:
<221> NAME/KEY: VARIANT
<222> LOCATION: (87)...(87)
<223> OTHER INFORMATION: Xaa = Ser
<220> FEATURE:
<223> OTHER INFORMATION: IL-28B C48S T87S H135Y

<400> SEQUENCE: 131

Val Pro Val Ala Arg Leu Arg Gly Ala Leu Pro Asp Ala Arg Gly Cys
 1               5                  10                  15

His Ile Ala Gln Phe Lys Ser Leu Ser Pro Gln Glu Leu Gln Ala Phe
            20                  25                  30

Lys Arg Ala Lys Asp Ala Leu Glu Glu Ser Leu Leu Leu Lys Asp Xaa
        35                  40                  45

Lys Cys Arg Ser Arg Leu Phe Pro Arg Thr Trp Asp Leu Arg Gln Leu
 50                  55                  60

Gln Val Arg Glu Arg Pro Val Ala Leu Glu Ala Glu Leu Ala Leu Thr
 65                  70                  75                  80

Leu Lys Val Leu Glu Ala Xaa Ala Asp Thr Asp Pro Ala Leu Gly Asp
                     85                  90                  95

Val Leu Asp Gln Pro Leu His Thr Leu His His Ile Leu Ser Gln Leu
                100                 105                 110

Arg Ala Cys Ile Gln Pro Gln Pro Thr Ala Gly Pro Arg Thr Arg Gly
            115                 120                 125

Arg Leu His His Trp Leu Tyr Arg Leu Gln Glu Ala Pro Lys Lys Glu
        130                 135                 140

Ser Pro Gly Cys Leu Glu Ala Ser Val Thr Phe Asn Leu Phe Arg Leu
145                 150                 155                 160

Leu Thr Arg Asp Leu Asn Cys Val Ala Ser Gly Asp Leu Cys Val
```

```
                               165              170              175

<210> SEQ ID NO 132
<211> LENGTH: 531
<212> TYPE: DNA
<213> ORGANISM: Artificial Sequence
<220> FEATURE:
<223> OTHER INFORMATION: Met IL-28B C49S T88S H136Y
<220> FEATURE:
<221> NAME/KEY: CDS
<222> LOCATION: (1)...(531)
<220> FEATURE:
<221> NAME/KEY: variation
<222> LOCATION: 146, 147, 264
<223> OTHER INFORMATION: n = A, T, G, or C

<400> SEQUENCE: 132 atg gtt cct gtc gcc agg ctc cgc ggg gct ctc ccg gat gca agg ggc      48
Met Val Pro Val Ala Arg Leu Arg Gly Ala Leu Pro Asp Ala Arg Gly
 1               5                  10                  15 tgc cac ata gcc cag ttc aag tcc ctg tct cca cag gag ctg cag gcc      96
Cys His Ile Ala Gln Phe Lys Ser Leu Ser Pro Gln Glu Leu Gln Ala
             20                  25                  30 ttt aag agg gcc aaa gat gcc tta gaa gag tcg ctt ctg ctg aag gac     144
Phe Lys Arg Ala Lys Asp Ala Leu Glu Glu Ser Leu Leu Leu Lys Asp
         35                  40                  45 dnn aag tgc cgc tcc cgc ctc ttc ccc agg acc tgg gac ctg agg cag     192
Xaa Lys Cys Arg Ser Arg Leu Phe Pro Arg Thr Trp Asp Leu Arg Gln
     50                  55                  60 ctg cag gtg agg gag cgc ccc gtg gct ttg gag gct gag ctg gcc ctg     240
Leu Gln Val Arg Glu Arg Pro Val Ala Leu Glu Ala Glu Leu Ala Leu
 65                  70                  75                  80 acg ctg aag gtt ctg gag gcc wsn gct gac act gac cca gcc ctg ggg     288
Thr Leu Lys Val Leu Glu Ala Xaa Ala Asp Thr Asp Pro Ala Leu Gly
                 85                  90                  95 gat gtc ttg gac cag ccc ctt cac acc ctg cac cat atc ctc tcc cag     336
Asp Val Leu Asp Gln Pro Leu His Thr Leu His His Ile Leu Ser Gln
            100                 105                 110 ctc cgg gcc tgt atc cag cct cag ccc acg gca ggg ccc agg acc cgg     384
Leu Arg Ala Cys Ile Gln Pro Gln Pro Thr Ala Gly Pro Arg Thr Arg
        115                 120                 125 ggc cgc ctc cac cat tgg ctg tay cgg ctc cag gag gcc cca aaa aag     432
Gly Arg Leu His His Trp Leu Tyr Arg Leu Gln Glu Ala Pro Lys Lys
    130                 135                 140 gag tcc cct ggc tgc ctc gag gcc tct gtc acc ttc aac ctc ttc cgc     480
Glu Ser Pro Gly Cys Leu Glu Ala Ser Val Thr Phe Asn Leu Phe Arg
145                 150                 155                 160 ctc ctc acg cga gac ctg aat tgt gtt gcc agc ggg gac ctg tgt gtc     528
Leu Leu Thr Arg Asp Leu Asn Cys Val Ala Ser Gly Asp Leu Cys Val
                165                 170                 175 tga                                                                  531
 *

<210> SEQ ID NO 133
<211> LENGTH: 176
<212> TYPE: PRT
<213> ORGANISM: Artificial Sequence
<220> FEATURE:
<221> NAME/KEY: VARIANT
<222> LOCATION: (49)...(49)
<223> OTHER INFORMATION: Xaa = Ser, Ala, Thr, Val, or Asn
<220> FEATURE:
<221> NAME/KEY: VARIANT
<222> LOCATION: (88)...(88)
<223> OTHER INFORMATION: Xaa = Ser
```

<220> FEATURE:
<223> OTHER INFORMATION: Met IL-28B C49S T88S H136Y

<400> SEQUENCE: 133

| | | | | | | | | | | | | | | |
|---|---|---|---|---|---|---|---|---|---|---|---|---|---|---|
| Met | Val | Pro | Val | Ala | Arg | Leu | Arg | Gly | Ala | Leu | Pro | Asp | Ala | Arg | Gly |
| 1 | | | | 5 | | | | | 10 | | | | | 15 | |

Cys His Ile Ala Gln Phe Lys Ser Leu Ser Pro Gln Glu Leu Gln Ala
              20                  25                  30

Phe Lys Arg Ala Lys Asp Ala Leu Glu Glu Ser Leu Leu Leu Lys Asp
            35                  40                  45

Xaa Lys Cys Arg Ser Arg Leu Phe Pro Arg Thr Trp Asp Leu Arg Gln
 50                  55                  60

Leu Gln Val Arg Glu Arg Pro Val Ala Leu Glu Ala Glu Leu Ala Leu
 65                  70                  75                  80

Thr Leu Lys Val Leu Glu Ala Xaa Ala Asp Thr Asp Pro Ala Leu Gly
                85                  90                  95

Asp Val Leu Asp Gln Pro Leu His Thr Leu His Ile Leu Ser Gln
            100                 105                 110

Leu Arg Ala Cys Ile Gln Pro Gln Pro Thr Ala Gly Pro Arg Thr Arg
            115                 120                 125

Gly Arg Leu His His Trp Leu Tyr Arg Leu Gln Glu Ala Pro Lys Lys
130                 135                 140

Glu Ser Pro Gly Cys Leu Glu Ala Ser Val Thr Phe Asn Leu Phe Arg
145                 150                 155                 160

Leu Leu Thr Arg Asp Leu Asn Cys Val Ala Ser Gly Asp Leu Cys Val
                165                 170                 175

<210> SEQ ID NO 134
<211> LENGTH: 528
<212> TYPE: DNA
<213> ORGANISM: Artificial Sequence
<220> FEATURE:
<223> OTHER INFORMATION: IL-28B C50S T87S H135Y
<220> FEATURE:
<221> NAME/KEY: CDS
<222> LOCATION: (1)...(528)
<220> FEATURE:
<221> NAME/KEY: variation
<222> LOCATION: 149, 150, 261
<223> OTHER INFORMATION: n = A, T, G, or C

<400> SEQUENCE: 134

```
gtt cct gtc gcc agg ctc cgc ggg gct ctc ccg gat gca agg ggc tgc      48
Val Pro Val Ala Arg Leu Arg Gly Ala Leu Pro Asp Ala Arg Gly Cys
 1               5                  10                  15 cac ata gcc cag ttc aag tcc ctg tct cca cag gag ctg cag gcc ttt      96
His Ile Ala Gln Phe Lys Ser Leu Ser Pro Gln Glu Leu Gln Ala Phe
            20                  25                  30 aag agg gcc aaa gat gcc tta gaa gag tcg ctt ctg ctg aag gac tgc     144
Lys Arg Ala Lys Asp Ala Leu Glu Glu Ser Leu Leu Leu Lys Asp Cys
        35                  40                  45 aag dnn cgc tcc cgc ctc ttc ccc agg acc tgg gac ctg agg cag ctg     192
Lys Xaa Arg Ser Arg Leu Phe Pro Arg Thr Trp Asp Leu Arg Gln Leu
 50                  55                  60 cag gtg agg gag cgc ccc gtg gct ttg gag gct gag ctg gcc ctg acg     240
Gln Val Arg Glu Arg Pro Val Ala Leu Glu Ala Glu Leu Ala Leu Thr
 65                  70                  75                  80 ctg aag gtt ctg gag gcc wsn gct gac act gac cca gcc ctg ggg gat     288
Leu Lys Val Leu Glu Ala Xaa Ala Asp Thr Asp Pro Ala Leu Gly Asp
                85                  90                  95
```

-continued

```
gtc ttg gac cag ccc ctt cac acc ctg cac cat atc ctc tcc cag ctc      336
Val Leu Asp Gln Pro Leu His Thr Leu His His Ile Leu Ser Gln Leu
            100                 105                 110 cgg gcc tgt atc cag cct cag ccc acg gca ggg ccc agg acc cgg ggc      384
Arg Ala Cys Ile Gln Pro Gln Pro Thr Ala Gly Pro Arg Thr Arg Gly
        115                 120                 125 cgc ctc cac cat tgg ctg tay cgg ctc cag gag gcc cca aaa aag gag      432
Arg Leu His His Trp Leu Tyr Arg Leu Gln Glu Ala Pro Lys Lys Glu
    130                 135                 140 tcc cct ggc tgc ctc gag gcc tct gtc acc ttc aac ctc ttc cgc ctc      480
Ser Pro Gly Cys Leu Glu Ala Ser Val Thr Phe Asn Leu Phe Arg Leu
145                 150                 155                 160 ctc acg cga gac ctg aat tgt gtt gcc agc ggg gac ctg tgt gtc tga      528
Leu Thr Arg Asp Leu Asn Cys Val Ala Ser Gly Asp Leu Cys Val *
                165                 170                 175
```

<210> SEQ ID NO 135
<211> LENGTH: 175
<212> TYPE: PRT
<213> ORGANISM: Artificial Sequence
<220> FEATURE:
<221> NAME/KEY: VARIANT
<222> LOCATION: (50)...(50)
<223> OTHER INFORMATION: Xaa = Ser, Ala, Thr, Val, or Asn
<220> FEATURE:
<221> NAME/KEY: VARIANT
<222> LOCATION: (87)...(87)
<223> OTHER INFORMATION: Xaa = Ser
<220> FEATURE:
<223> OTHER INFORMATION: IL-28B C50S T87S H135Y

<400> SEQUENCE: 135

```
Val Pro Val Ala Arg Leu Arg Gly Ala Leu Pro Asp Ala Arg Gly Cys
1               5                   10                  15

His Ile Ala Gln Phe Lys Ser Leu Ser Pro Gln Glu Leu Gln Ala Phe
            20                  25                  30

Lys Arg Ala Lys Asp Ala Leu Glu Glu Ser Leu Leu Leu Lys Asp Cys
        35                  40                  45

Lys Xaa Arg Ser Arg Leu Phe Pro Arg Thr Trp Asp Leu Arg Gln Leu
    50                  55                  60

Gln Val Arg Glu Arg Pro Val Ala Leu Glu Ala Glu Leu Ala Leu Thr
65                  70                  75                  80

Leu Lys Val Leu Glu Ala Xaa Ala Asp Thr Asp Pro Ala Leu Gly Asp
                85                  90                  95

Val Leu Asp Gln Pro Leu His Thr Leu His His Ile Leu Ser Gln Leu
            100                 105                 110

Arg Ala Cys Ile Gln Pro Gln Pro Thr Ala Gly Pro Arg Thr Arg Gly
        115                 120                 125

Arg Leu His His Trp Leu Tyr Arg Leu Gln Glu Ala Pro Lys Lys Glu
    130                 135                 140

Ser Pro Gly Cys Leu Glu Ala Ser Val Thr Phe Asn Leu Phe Arg Leu
145                 150                 155                 160

Leu Thr Arg Asp Leu Asn Cys Val Ala Ser Gly Asp Leu Cys Val
                165                 170                 175
```

<210> SEQ ID NO 136
<211> LENGTH: 531
<212> TYPE: DNA
<213> ORGANISM: Artificial Sequence
<220> FEATURE:
<223> OTHER INFORMATION: Met IL-28B C51S T88S H136Y
<220> FEATURE:

```
<221> NAME/KEY: CDS
<222> LOCATION: (1)...(531)
<220> FEATURE:
<221> NAME/KEY: variation
<222> LOCATION: 152, 153, 264
<223> OTHER INFORMATION: n = A, T, G, or C

<400> SEQUENCE: 136 atg gtt cct gtc gcc agg ctc cgc ggg gct ctc ccg gat gca agg ggc       48
Met Val Pro Val Ala Arg Leu Arg Gly Ala Leu Pro Asp Ala Arg Gly
1               5                   10                  15 tgc cac ata gcc cag ttc aag tcc ctg tct cca cag gag ctg cag gcc       96
Cys His Ile Ala Gln Phe Lys Ser Leu Ser Pro Gln Glu Leu Gln Ala
            20                  25                  30 ttt aag agg gcc aaa gat gcc tta gaa gag tcg ctt ctg ctg aag gac      144
Phe Lys Arg Ala Lys Asp Ala Leu Glu Glu Ser Leu Leu Leu Lys Asp
        35                  40                  45 tgc aag dnn cgc tcc cgc ctc ttc ccc agg acc tgg gac ctg agg cag      192
Cys Lys Xaa Arg Ser Arg Leu Phe Pro Arg Thr Trp Asp Leu Arg Gln
    50                  55                  60 ctg cag gtg agg gag cgc ccc gtg gct ttg gag gct gag ctg gcc ctg      240
Leu Gln Val Arg Glu Arg Pro Val Ala Leu Glu Ala Glu Leu Ala Leu
65                  70                  75                  80 acg ctg aag gtt ctg gag gcc wsn gct gac act gac cca gcc ctg ggg      288
Thr Leu Lys Val Leu Glu Ala Xaa Ala Asp Thr Asp Pro Ala Leu Gly
                85                  90                  95 gat gtc ttg gac cag ccc ctt cac acc ctg cac cat atc ctc tcc cag      336
Asp Val Leu Asp Gln Pro Leu His Thr Leu His His Ile Leu Ser Gln
            100                 105                 110 ctc cgg gcc tgt atc cag cct cag ccc acg gca ggg ccc agg acc cgg      384
Leu Arg Ala Cys Ile Gln Pro Gln Pro Thr Ala Gly Pro Arg Thr Arg
        115                 120                 125 ggc cgc ctc cac cat tgg ctg tay cgg ctc cag gag gcc cca aaa aag      432
Gly Arg Leu His His Trp Leu Tyr Arg Leu Gln Glu Ala Pro Lys Lys
    130                 135                 140 gag tcc cct ggc tgc ctc gag gcc tct gtc acc ttc aac ctc ttc cgc      480
Glu Ser Pro Gly Cys Leu Glu Ala Ser Val Thr Phe Asn Leu Phe Arg
145                 150                 155                 160 ctc ctc acg cga gac ctg aat tgt gtt gcc agc ggg gac ctg tgt gtc      528
Leu Leu Thr Arg Asp Leu Asn Cys Val Ala Ser Gly Asp Leu Cys Val
                165                 170                 175 tga                                                                  531
*

<210> SEQ ID NO 137
<211> LENGTH: 176
<212> TYPE: PRT
<213> ORGANISM: Artificial Sequence
<220> FEATURE:
<221> NAME/KEY: VARIANT
<222> LOCATION: (51)...(51)
<223> OTHER INFORMATION: Xaa = Ser, Ala, Thr, Val, or Asn
<220> FEATURE:
<221> NAME/KEY: VARIANT
<222> LOCATION: (88)...(88)
<223> OTHER INFORMATION: Xaa = Ser
<220> FEATURE:
<223> OTHER INFORMATION: Met IL-28B C51S T88S H136Y

<400> SEQUENCE: 137

Met Val Pro Val Ala Arg Leu Arg Gly Ala Leu Pro Asp Ala Arg Gly
1               5                   10                  15

Cys His Ile Ala Gln Phe Lys Ser Leu Ser Pro Gln Glu Leu Gln Ala
            20                  25                  30
```

```
Phe Lys Arg Ala Lys Asp Ala Leu Glu Glu Ser Leu Leu Lys Asp
            35                  40                  45

Cys Lys Xaa Arg Ser Arg Leu Phe Pro Arg Thr Trp Asp Leu Arg Gln
 50                  55                  60

Leu Gln Val Arg Glu Arg Pro Val Ala Leu Glu Ala Glu Leu Ala Leu
 65                  70                  75                  80

Thr Leu Lys Val Leu Glu Ala Xaa Ala Asp Thr Asp Pro Ala Leu Gly
                 85                  90                  95

Asp Val Leu Asp Gln Pro Leu His Thr Leu His His Ile Leu Ser Gln
            100                 105                 110

Leu Arg Ala Cys Ile Gln Pro Gln Pro Thr Ala Gly Pro Arg Thr Arg
        115                 120                 125

Gly Arg Leu His His Trp Leu Tyr Arg Leu Gln Glu Ala Pro Lys Lys
    130                 135                 140

Glu Ser Pro Gly Cys Leu Glu Ala Ser Val Thr Phe Asn Leu Phe Arg
145                 150                 155                 160

Leu Leu Thr Arg Asp Leu Asn Cys Val Ala Ser Gly Asp Leu Cys Val
                165                 170                 175

<210> SEQ ID NO 138
<211> LENGTH: 543
<212> TYPE: DNA
<213> ORGANISM: Artificial Sequence
<220> FEATURE:
<223> OTHER INFORMATION: IL-29 C170X, truncated after N-terminal
      Methionine and Glycine
<220> FEATURE:
<221> NAME/KEY: variation
<222> LOCATION: (509)...(510)
<223> OTHER INFORMATION: n = A, T, G, or C
<220> FEATURE:
<221> NAME/KEY: CDS
<222> LOCATION: (1)...(543)

<400> SEQUENCE: 138 cct gtc ccc act tcc aag ccc acc aca act ggg aag ggc tgc cac att     48
Pro Val Pro Thr Ser Lys Pro Thr Thr Thr Gly Lys Gly Cys His Ile
  1               5                  10                  15 ggc agg ttc aaa tct ctg tca cca cag gag cta gcg agc ttc aag aag     96
Gly Arg Phe Lys Ser Leu Ser Pro Gln Glu Leu Ala Ser Phe Lys Lys
             20                  25                  30 gcc agg gac gcc ttg gaa gag tca ctc aag ctg aaa aac tgg agt tgc    144
Ala Arg Asp Ala Leu Glu Glu Ser Leu Lys Leu Lys Asn Trp Ser Cys
         35                  40                  45 agc tct cct gtc ttc ccc ggg aat tgg gac ctg agg ctt ctc cag gtg    192
Ser Ser Pro Val Phe Pro Gly Asn Trp Asp Leu Arg Leu Leu Gln Val
     50                  55                  60 agg gag cgc cct gtg gcc ttg gag gct gag ctg gcc ctg acg ctg aag    240
Arg Glu Arg Pro Val Ala Leu Glu Ala Glu Leu Ala Leu Thr Leu Lys
 65                  70                  75                  80 gtc ctg gag gcc gct gct ggc cca gcc ctg gag gac gtc cta gac cag    288
Val Leu Glu Ala Ala Ala Gly Pro Ala Leu Glu Asp Val Leu Asp Gln
                 85                  90                  95 ccc ctt cac acc ctg cac cac atc ctc tcc cag ctc cag gcc tgt atc    336
Pro Leu His Thr Leu His His Ile Leu Ser Gln Leu Gln Ala Cys Ile
            100                 105                 110 cag cct cag ccc aca gca ggg ccc agg ccc ggg cgc ctc cac cac        384
Gln Pro Gln Pro Thr Ala Gly Pro Arg Pro Gly Arg Leu His His
        115                 120                 125 tgg ctg cac cgg ctc cag gag gcc ccc aaa aag gag tcc gct ggc tgc    432
```

```
                Trp Leu His Arg Leu Gln Glu Ala Pro Lys Lys Glu Ser Ala Gly Cys
                130                 135                 140 ctg gag gca tct gtc acc ttc aac ctc ttc cgc ctc ctc acg cga gac         480
Leu Glu Ala Ser Val Thr Phe Asn Leu Phe Arg Leu Leu Thr Arg Asp
145                 150                 155                 160 ctc aaa tat gtg gcc gat ggg aac ctg dnn ctg aga acg tca acc cac         528
Leu Lys Tyr Val Ala Asp Gly Asn Leu Xaa Leu Arg Thr Ser Thr His
                165                 170                 175 cct gag tcc acc tga                                                     543
Pro Glu Ser Thr  *
        180
```

<210> SEQ ID NO 139
<211> LENGTH: 180
<212> TYPE: PRT
<213> ORGANISM: Artificial Sequence
<220> FEATURE:
<221> NAME/KEY: VARIANT
<222> LOCATION: (170)...(170)
<223> OTHER INFORMATION: Xaa = Ser, Ala, Thr, Val, or Asn
<220> FEATURE:
<223> OTHER INFORMATION: IL-29 C170X, truncated after N-terminal
      Methionine and Glycine

<400> SEQUENCE: 139

```
Pro Val Pro Thr Ser Lys Pro Thr Thr Thr Gly Lys Gly Cys His Ile
1               5                   10                  15

Gly Arg Phe Lys Ser Leu Ser Pro Gln Glu Leu Ala Ser Phe Lys Lys
                20                  25                  30

Ala Arg Asp Ala Leu Glu Glu Ser Leu Lys Leu Lys Asn Trp Ser Cys
            35                  40                  45

Ser Ser Pro Val Phe Pro Gly Asn Trp Asp Leu Arg Leu Leu Gln Val
50                  55                  60

Arg Glu Arg Pro Val Ala Leu Glu Ala Glu Leu Ala Leu Thr Leu Lys
65                  70                  75                  80

Val Leu Glu Ala Ala Ala Gly Pro Ala Leu Glu Asp Val Leu Asp Gln
                85                  90                  95

Pro Leu His Thr Leu His His Ile Leu Ser Gln Leu Gln Ala Cys Ile
            100                 105                 110

Gln Pro Gln Pro Thr Ala Gly Pro Arg Pro Arg Gly Arg Leu His His
        115                 120                 125

Trp Leu His Arg Leu Gln Glu Ala Pro Lys Lys Glu Ser Ala Gly Cys
130                 135                 140

Leu Glu Ala Ser Val Thr Phe Asn Leu Phe Arg Leu Leu Thr Arg Asp
145                 150                 155                 160

Leu Lys Tyr Val Ala Asp Gly Asn Leu Xaa Leu Arg Thr Ser Thr His
                165                 170                 175

Pro Glu Ser Thr
        180
```

<210> SEQ ID NO 140
<211> LENGTH: 540
<212> TYPE: DNA
<213> ORGANISM: Artificial Sequence
<220> FEATURE:
<223> OTHER INFORMATION: IL-29 C169X, truncated after N-terminal
      Methionine, Glycine, and Proline
<220> FEATURE:
<221> NAME/KEY: variation
<222> LOCATION: (506)...(507)
<223> OTHER INFORMATION: n = A, T, G, or C
<220> FEATURE:

<221> NAME/KEY: CDS
<222> LOCATION: (1)...(540)

<400> SEQUENCE: 140

| | | | | | | | | | | | | | | | | |
|---|---|---|---|---|---|---|---|---|---|---|---|---|---|---|---|---|
| gtc | ccc | act | tcc | aag | ccc | acc | aca | act | ggg | aag | ggc | tgc | cac | att | ggc | 48 |
| Val | Pro | Thr | Ser | Lys | Pro | Thr | Thr | Thr | Gly | Lys | Gly | Cys | His | Ile | Gly | |
| 1 | | | | 5 | | | | | 10 | | | | | 15 | | |

```
agg ttc aaa tct ctg tca cca cag gag cta gcg agc ttc aag aag gcc      96
Arg Phe Lys Ser Leu Ser Pro Gln Glu Leu Ala Ser Phe Lys Lys Ala
             20                  25                  30 agg gac gcc ttg gaa gag tca ctc aag ctg aaa aac tgg agt tgc agc     144
Arg Asp Ala Leu Glu Glu Ser Leu Lys Leu Lys Asn Trp Ser Cys Ser
         35                  40                  45 tct cct gtc ttc ccc ggg aat tgg gac ctg agg ctt ctc cag gtg agg     192
Ser Pro Val Phe Pro Gly Asn Trp Asp Leu Arg Leu Leu Gln Val Arg
     50                  55                  60 gag cgc cct gtg gcc ttg gag gct gag ctg gcc ctg acg ctg aag gtc     240
Glu Arg Pro Val Ala Leu Glu Ala Glu Leu Ala Leu Thr Leu Lys Val
 65                  70                  75                  80 ctg gag gcc gct gct ggc cca gcc ctg gag gac gtc cta gac cag ccc     288
Leu Glu Ala Ala Ala Gly Pro Ala Leu Glu Asp Val Leu Asp Gln Pro
                 85                  90                  95 ctt cac acc ctg cac cac atc ctc tcc cag ctc cag gcc tgt atc cag     336
Leu His Thr Leu His His Ile Leu Ser Gln Leu Gln Ala Cys Ile Gln
            100                 105                 110 cct cag ccc aca gca ggg ccc agg ccc cgg ggc cgc ctc cac cac tgg     384
Pro Gln Pro Thr Ala Gly Pro Arg Pro Arg Gly Arg Leu His His Trp
        115                 120                 125 ctg cac cgg ctc cag gag gcc ccc aaa aag gag tcc gct ggc tgc ctg     432
Leu His Arg Leu Gln Glu Ala Pro Lys Lys Glu Ser Ala Gly Cys Leu
    130                 135                 140 gag gca tct gtc acc ttc aac ctc ttc cgc ctc ctc acg cga gac ctc     480
Glu Ala Ser Val Thr Phe Asn Leu Phe Arg Leu Leu Thr Arg Asp Leu
145                 150                 155                 160 aaa tat gtg gcc gat ggg aac ctg dnn ctg aga acg tca acc cac cct     528
Lys Tyr Val Ala Asp Gly Asn Leu Xaa Leu Arg Thr Ser Thr His Pro
                165                 170                 175 gag tcc acc tga                                                     540
Glu Ser Thr *
```

<210> SEQ ID NO 141
<211> LENGTH: 179
<212> TYPE: PRT
<213> ORGANISM: Artificial Sequence
<220> FEATURE:
<221> NAME/KEY: VARIANT
<222> LOCATION: (169)...(169)
<223> OTHER INFORMATION: Xaa = Ser, Ala, Thr, Val, or Asn
<220> FEATURE:
<223> OTHER INFORMATION: L-29 C169X, truncated after N-terminal
      Methionine, Glycine, and Proline

<400> SEQUENCE: 141

```
Val Pro Thr Ser Lys Pro Thr Thr Thr Gly Lys Gly Cys His Ile Gly
 1               5                  10                  15

Arg Phe Lys Ser Leu Ser Pro Gln Glu Leu Ala Ser Phe Lys Lys Ala
             20                  25                  30

Arg Asp Ala Leu Glu Glu Ser Leu Lys Leu Lys Asn Trp Ser Cys Ser
         35                  40                  45

Ser Pro Val Phe Pro Gly Asn Trp Asp Leu Arg Leu Leu Gln Val Arg
     50                  55                  60
```

```
Glu Arg Pro Val Ala Leu Glu Ala Glu Leu Ala Leu Thr Leu Lys Val
 65                  70                  75                  80

Leu Glu Ala Ala Ala Gly Pro Ala Leu Glu Asp Val Leu Asp Gln Pro
                 85                  90                  95

Leu His Thr Leu His His Ile Leu Ser Gln Leu Gln Ala Cys Ile Gln
            100                 105                 110

Pro Gln Pro Thr Ala Gly Pro Arg Pro Arg Gly Arg Leu His His Trp
        115                 120                 125

Leu His Arg Leu Gln Glu Ala Pro Lys Lys Glu Ser Ala Gly Cys Leu
    130                 135                 140

Glu Ala Ser Val Thr Phe Asn Leu Phe Arg Leu Leu Thr Arg Asp Leu
145                 150                 155                 160

Lys Tyr Val Ala Asp Gly Asn Leu Xaa Leu Arg Thr Ser Thr His Pro
                165                 170                 175

Glu Ser Thr

<210> SEQ ID NO 142
<211> LENGTH: 537
<212> TYPE: DNA
<213> ORGANISM: Artificial Sequence
<220> FEATURE:
<223> OTHER INFORMATION: IL-29 C168X, truncated after N-terminal
      Methionine, Glycine, Proline, and Valine
<220> FEATURE:
<221> NAME/KEY: variation
<222> LOCATION: (503)...(504)
<223> OTHER INFORMATION: n = A, T, G, or C
<220> FEATURE:
<221> NAME/KEY: CDS
<222> LOCATION: (1)...(537)

<400> SEQUENCE: 142 ccc act tcc aag ccc acc aca act ggg aag ggc tgc cac att ggc agg        48
Pro Thr Ser Lys Pro Thr Thr Thr Gly Lys Gly Cys His Ile Gly Arg
  1               5                  10                  15 ttc aaa tct ctg tca cca cag gag cta gcg agc ttc aag aag gcc agg        96
Phe Lys Ser Leu Ser Pro Gln Glu Leu Ala Ser Phe Lys Lys Ala Arg
                 20                  25                  30 gac gcc ttg gaa gag tca ctc aag ctg aaa aac tgg agt tgc agc tct       144
Asp Ala Leu Glu Glu Ser Leu Lys Leu Lys Asn Trp Ser Cys Ser Ser
            35                  40                  45 cct gtc ttc ccc ggg aat tgg gac ctg agg ctt ctc cag gtg agg gag       192
Pro Val Phe Pro Gly Asn Trp Asp Leu Arg Leu Leu Gln Val Arg Glu
        50                  55                  60 cgc cct gtg gcc ttg gag gct gag ctg gcc ctg acg ctg aag gtc ctg       240
Arg Pro Val Ala Leu Glu Ala Glu Leu Ala Leu Thr Leu Lys Val Leu
 65                  70                  75                  80 gag gcc gct gct ggc cca gcc ctg gag gac gtc cta gac cag ccc ctt       288
Glu Ala Ala Ala Gly Pro Ala Leu Glu Asp Val Leu Asp Gln Pro Leu
                 85                  90                  95 cac acc ctg cac cac atc ctc tcc cag ctc cag gcc tgt atc cag cct       336
His Thr Leu His His Ile Leu Ser Gln Leu Gln Ala Cys Ile Gln Pro
            100                 105                 110 cag ccc aca gca ggg ccc agg ccc cgg ggc cgc ctc cac cac tgg ctg       384
Gln Pro Thr Ala Gly Pro Arg Pro Arg Gly Arg Leu His His Trp Leu
        115                 120                 125 cac cgg ctc cag gag gcc ccc aaa aag gag tcc gct ggc tgc ctg gag       432
His Arg Leu Gln Glu Ala Pro Lys Lys Glu Ser Ala Gly Cys Leu Glu
    130                 135                 140 gca tct gtc acc ttc aac ctc ttc cgc ctc ctc acg cga gac ctc aaa       480
Ala Ser Val Thr Phe Asn Leu Phe Arg Leu Leu Thr Arg Asp Leu Lys
```

```
                         145                 150                 155                 160
tat gtg gcc gat ggg aac ctg dnn ctg aga acg tca acc cac cct gag         528
Tyr Val Ala Asp Gly Asn Leu Xaa Leu Arg Thr Ser Thr His Pro Glu
                    165                 170                 175 tcc acc tga                                                              537
Ser Thr *
```

<210> SEQ ID NO 143
<211> LENGTH: 178
<212> TYPE: PRT
<213> ORGANISM: Artificial Sequence
<220> FEATURE:
<223> OTHER INFORMATION: IL-29 C168X, truncated after N-terminal
      Methionine, Glycine, Proline, and Valine
<220> FEATURE:
<221> NAME/KEY: VARIANT
<222> LOCATION: (168)...(168)
<223> OTHER INFORMATION: Xaa = Ser, Ala, Thr, Val, or Asn

<400> SEQUENCE: 143

```
Pro Thr Ser Lys Pro Thr Thr Thr Gly Lys Gly Cys His Ile Gly Arg
 1               5                  10                  15

Phe Lys Ser Leu Ser Pro Gln Glu Leu Ala Ser Phe Lys Lys Ala Arg
            20                  25                  30

Asp Ala Leu Glu Glu Ser Leu Lys Leu Lys Asn Trp Ser Cys Ser Ser
        35                  40                  45

Pro Val Phe Pro Gly Asn Trp Asp Leu Arg Leu Leu Gln Val Arg Glu
    50                  55                  60

Arg Pro Val Ala Leu Glu Ala Glu Leu Ala Leu Thr Leu Lys Val Leu
65                  70                  75                  80

Glu Ala Ala Ala Gly Pro Ala Leu Glu Asp Val Leu Asp Gln Pro Leu
                85                  90                  95

His Thr Leu His His Ile Leu Ser Gln Leu Gln Ala Cys Ile Gln Pro
            100                 105                 110

Gln Pro Thr Ala Gly Pro Arg Pro Arg Gly Arg Leu His His Trp Leu
        115                 120                 125

His Arg Leu Gln Glu Ala Pro Lys Lys Glu Ser Ala Gly Cys Leu Glu
    130                 135                 140

Ala Ser Val Thr Phe Asn Leu Phe Arg Leu Leu Thr Arg Asp Leu Lys
145                 150                 155                 160

Tyr Val Ala Asp Gly Asn Leu Xaa Leu Arg Thr Ser Thr His Pro Glu
                165                 170                 175

Ser Thr
```

<210> SEQ ID NO 144
<211> LENGTH: 534
<212> TYPE: DNA
<213> ORGANISM: Artificial Sequence
<220> FEATURE:
<223> OTHER INFORMATION: IL-29 C167X, truncated after N-terminal
      Methionine, Glycine, Proline, Valine, and Proline
<220> FEATURE:
<221> NAME/KEY: variation
<222> LOCATION: (500)...(501)
<223> OTHER INFORMATION: n = A, T, G, or C
<220> FEATURE:
<221> NAME/KEY: CDS
<222> LOCATION: (1)...(534)

<400> SEQUENCE: 144

```
act tcc aag ccc acc aca act ggg aag ggc tgc cac att ggc agg ttc          48
Thr Ser Lys Pro Thr Thr Thr Gly Lys Gly Cys His Ile Gly Arg Phe
```

-continued

```
               1               5              10              15 aaa tct ctg tca cca cag gag cta gcg agc ttc aag aag gcc agg gac    96
Lys Ser Leu Ser Pro Gln Glu Leu Ala Ser Phe Lys Lys Ala Arg Asp
                 20              25              30 gcc ttg gaa gag tca ctc aag ctg aaa aac tgg agt tgc agc tct cct   144
Ala Leu Glu Glu Ser Leu Lys Leu Lys Asn Trp Ser Cys Ser Ser Pro
             35              40              45 gtc ttc ccc ggg aat tgg gac ctg agg ctt ctc cag gtg agg gag cgc   192
Val Phe Pro Gly Asn Trp Asp Leu Arg Leu Leu Gln Val Arg Glu Arg
         50              55              60 cct gtg gcc ttg gag gct gag ctg gcc ctg acg ctg aag gtc ctg gag   240
Pro Val Ala Leu Glu Ala Glu Leu Ala Leu Thr Leu Lys Val Leu Glu
 65              70              75              80 gcc gct gct ggc cca gcc ctg gag gac gtc cta gac cag ccc ctt cac   288
Ala Ala Ala Gly Pro Ala Leu Glu Asp Val Leu Asp Gln Pro Leu His
                 85              90              95 acc ctg cac cac atc ctc tcc cag ctc cag gcc tgt atc cag cct cag   336
Thr Leu His His Ile Leu Ser Gln Leu Gln Ala Cys Ile Gln Pro Gln
             100             105             110 ccc aca gca ggg ccc agg ccc cgg ggc cgc ctc cac cac tgg ctg cac   384
Pro Thr Ala Gly Pro Arg Pro Arg Gly Arg Leu His His Trp Leu His
         115             120             125 cgg ctc cag gag gcc ccc aaa aag gag tcc gct ggc tgc ctg gag gca   432
Arg Leu Gln Glu Ala Pro Lys Lys Glu Ser Ala Gly Cys Leu Glu Ala
 130             135             140 tct gtc acc ttc aac ctc ttc cgc ctc ctc acg cga gac ctc aaa tat   480
Ser Val Thr Phe Asn Leu Phe Arg Leu Leu Thr Arg Asp Leu Lys Tyr
145             150             155             160 gtg gcc gat ggg aac ctg dnn ctg aga acg tca acc cac cct gag tcc   528
Val Ala Asp Gly Asn Leu Xaa Leu Arg Thr Ser Thr His Pro Glu Ser
                 165             170             175 acc tga                                                           534
Thr *
```

<210> SEQ ID NO 145
<211> LENGTH: 177
<212> TYPE: PRT
<213> ORGANISM: Artificial Sequence
<220> FEATURE:
<223> OTHER INFORMATION: IL-29 C167X, truncated after N-terminal
      Methionine, Glycine, Proline, Valine, and Proline
<220> FEATURE:
<221> NAME/KEY: VARIANT
<222> LOCATION: (167)...(167)
<223> OTHER INFORMATION: Xaa = Ser, Ala, Thr, Val, or Asn

<400> SEQUENCE: 145

```
Thr Ser Lys Pro Thr Thr Thr Gly Lys Gly Cys His Ile Gly Arg Phe
 1               5                  10                  15

Lys Ser Leu Ser Pro Gln Glu Leu Ala Ser Phe Lys Lys Ala Arg Asp
                 20                  25                  30

Ala Leu Glu Glu Ser Leu Lys Leu Lys Asn Trp Ser Cys Ser Ser Pro
             35                  40                  45

Val Phe Pro Gly Asn Trp Asp Leu Arg Leu Leu Gln Val Arg Glu Arg
         50                  55                  60

Pro Val Ala Leu Glu Ala Glu Leu Ala Leu Thr Leu Lys Val Leu Glu
 65                  70                  75                  80

Ala Ala Ala Gly Pro Ala Leu Glu Asp Val Leu Asp Gln Pro Leu His
                 85                  90                  95

Thr Leu His His Ile Leu Ser Gln Leu Gln Ala Cys Ile Gln Pro Gln
```

```
                        100                 105                 110
Pro Thr Ala Gly Pro Arg Pro Arg Gly Arg Leu His His Trp Leu His
            115                 120                 125

Arg Leu Gln Glu Ala Pro Lys Lys Glu Ser Ala Gly Cys Leu Glu Ala
        130                 135                 140

Ser Val Thr Phe Asn Leu Phe Arg Leu Leu Thr Arg Asp Leu Lys Tyr
145                 150                 155                 160

Val Ala Asp Gly Asn Leu Xaa Leu Arg Thr Ser Thr His Pro Glu Ser
                    165                 170                 175

Thr

<210> SEQ ID NO 146
<211> LENGTH: 531
<212> TYPE: DNA
<213> ORGANISM: Artificial Sequence
<220> FEATURE:
<223> OTHER INFORMATION: IL-29 C166X, truncated after N-terminal
      Methionine, Glycine, Proline, Valine, Proline, and
      Threonine
<220> FEATURE:
<221> NAME/KEY: variation
<222> LOCATION: (497)...(498)
<223> OTHER INFORMATION: n = A, T, G, or C
<220> FEATURE:
<221> NAME/KEY: CDS
<222> LOCATION: (1)...(531)

<400> SEQUENCE: 146 tcc aag ccc acc aca act ggg aag ggc tgc cac att ggc agg ttc aaa     48
Ser Lys Pro Thr Thr Thr Gly Lys Gly Cys His Ile Gly Arg Phe Lys
  1               5                  10                  15 tct ctg tca cca cag gag cta gcg agc ttc aag aag gcc agg gac gcc     96
Ser Leu Ser Pro Gln Glu Leu Ala Ser Phe Lys Lys Ala Arg Asp Ala
             20                  25                  30 ttg gaa gag tca ctc aag ctg aaa aac tgg agt tgc agc tct cct gtc    144
Leu Glu Glu Ser Leu Lys Leu Lys Asn Trp Ser Cys Ser Ser Pro Val
         35                  40                  45 ttc ccc ggg aat tgg gac ctg agg ctt ctc cag gtg agg gag cgc cct    192
Phe Pro Gly Asn Trp Asp Leu Arg Leu Leu Gln Val Arg Glu Arg Pro
     50                  55                  60 gtg gcc ttg gag gct gag ctg gcc ctg acg ctg aag gtc ctg gag gcc    240
Val Ala Leu Glu Ala Glu Leu Ala Leu Thr Leu Lys Val Leu Glu Ala
 65                  70                  75                  80 gct gct ggc cca gcc ctg gag gac gtc cta gac cag ccc ctt cac acc    288
Ala Ala Gly Pro Ala Leu Glu Asp Val Leu Asp Gln Pro Leu His Thr
                 85                  90                  95 ctg cac cac atc ctc tcc cag ctc cag gcc tgt atc cag cct cag ccc    336
Leu His His Ile Leu Ser Gln Leu Gln Ala Cys Ile Gln Pro Gln Pro
            100                 105                 110 aca gca ggg ccc agg ccc cgg ggc cgc ctc cac cac tgg ctg cac cgg    384
Thr Ala Gly Pro Arg Pro Arg Gly Arg Leu His His Trp Leu His Arg
        115                 120                 125 ctc cag gag gcc ccc aaa aag gag tcc gct ggc tgc ctg gag gca tct    432
Leu Gln Glu Ala Pro Lys Lys Glu Ser Ala Gly Cys Leu Glu Ala Ser
    130                 135                 140 gtc acc ttc aac ctc ttc cgc ctc ctc acg cga gac ctc aaa tat gtg    480
Val Thr Phe Asn Leu Phe Arg Leu Leu Thr Arg Asp Leu Lys Tyr Val
145                 150                 155                 160 gcc gat ggg aac ctg dnn ctg aga acg tca acc cac cct gag tcc acc    528
Ala Asp Gly Asn Leu Xaa Leu Arg Thr Ser Thr His Pro Glu Ser Thr
                165                 170                 175
```

```
tga                                                                    531
 *
```

<210> SEQ ID NO 147
<211> LENGTH: 176
<212> TYPE: PRT
<213> ORGANISM: Artificial Sequence
<220> FEATURE:
<223> OTHER INFORMATION: IL-29 C166X, truncated after N-terminal
      Methionine, Glycine, Proline, Valine, Proline, and
      Threonine
<220> FEATURE:
<221> NAME/KEY: VARIANT
<222> LOCATION: (166)...(166)
<223> OTHER INFORMATION: Xaa = Ser, Ala, Thr, Val, or Asn

<400> SEQUENCE: 147

```
Ser Lys Pro Thr Thr Thr Gly Lys Gly Cys His Ile Gly Arg Phe Lys
 1               5                  10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Lys Tyr Val
145                 150                 155                 160

Ala Asp Gly Asn Leu Xaa Leu Arg Thr Ser Thr His Pro Glu Ser Thr
                165                 170                 175
```

<210> SEQ ID NO 148
<211> LENGTH: 528
<212> TYPE: DNA
<213> ORGANISM: Artificial Sequence
<220> FEATURE:
<223> OTHER INFORMATION: IL-29 C165X, truncated after N-terminal
      Methionine, Glycine, Proline, Valine, Proline,
      Threonine, and Serine
<220> FEATURE:
<221> NAME/KEY: variation
<222> LOCATION: (494)...(495)
<223> OTHER INFORMATION: n = A, T, G, or C
<220> FEATURE:
<221> NAME/KEY: CDS
<222> LOCATION: (1)...(528)

<400> SEQUENCE: 148

```
aag ccc acc aca act ggg aag ggc tgc cac att ggc agg ttc aaa tct    48
Lys Pro Thr Thr Thr Gly Lys Gly Cys His Ile Gly Arg Phe Lys Ser
 1               5                  10                  15 ctg tca cca cag gag cta gcg agc ttc aag aag gcc agg gac gcc ttg    96
Leu Ser Pro Gln Glu Leu Ala Ser Phe Lys Lys Ala Arg Asp Ala Leu
            20                  25                  30
```

```
gaa gag tca ctc aag ctg aaa aac tgg agt tgc agc tct cct gtc ttc      144
Glu Glu Ser Leu Lys Leu Lys Asn Trp Ser Cys Ser Ser Pro Val Phe
        35                  40                  45 ccc ggg aat tgg gac ctg agg ctt ctc cag gtg agg gag cgc cct gtg      192
Pro Gly Asn Trp Asp Leu Arg Leu Leu Gln Val Arg Glu Arg Pro Val
    50                  55                  60 gcc ttg gag gct gag ctg gcc ctg acg ctg aag gtc ctg gag gcc gct      240
Ala Leu Glu Ala Glu Leu Ala Leu Thr Leu Lys Val Leu Glu Ala Ala
65                  70                  75                  80 gct ggc cca gcc ctg gag gac gtc cta gac cag ccc ctt cac acc ctg      288
Ala Gly Pro Ala Leu Glu Asp Val Leu Asp Gln Pro Leu His Thr Leu
                85                  90                  95 cac cac atc ctc tcc cag ctc cag gcc tgt atc cag cct cag ccc aca      336
His His Ile Leu Ser Gln Leu Gln Ala Cys Ile Gln Pro Gln Pro Thr
            100                 105                 110 gca ggg ccc agg ccc cgg ggc cgc ctc cac cac tgg ctg cac cgg ctc      384
Ala Gly Pro Arg Pro Arg Gly Arg Leu His His Trp Leu His Arg Leu
        115                 120                 125 cag gag gcc ccc aaa aag gag tcc gct ggc tgc ctg gag gca tct gtc      432
Gln Glu Ala Pro Lys Lys Glu Ser Ala Gly Cys Leu Glu Ala Ser Val
130                 135                 140 acc ttc aac ctc ttc cgc ctc ctc acg cga gac ctc aaa tat gtg gcc      480
Thr Phe Asn Leu Phe Arg Leu Leu Thr Arg Asp Leu Lys Tyr Val Ala
145                 150                 155                 160 gat ggg aac ctg dnn ctg aga acg tca acc cac cct gag tcc acc tga      528
Asp Gly Asn Leu Xaa Leu Arg Thr Ser Thr His Pro Glu Ser Thr  *
                165                 170                 175

<210> SEQ ID NO 149
<211> LENGTH: 175
<212> TYPE: PRT
<213> ORGANISM: Artificial Sequence
<220> FEATURE:
<223> OTHER INFORMATION: IL-29 C165X, truncated after N-terminal
      Methionine, Glycine, Proline, Valine, Proline,
      Threonine, and Serine
<220> FEATURE:
<221> NAME/KEY: VARIANT
<222> LOCATION: (165)...(165)
<223> OTHER INFORMATION: Xaa = Ser, Ala, Thr, Val, or Asn

<400> SEQUENCE: 149

Lys Pro Thr Thr Thr Gly Lys Gly Cys His Ile Gly Arg Phe Lys Ser
1               5                   10                  15

Leu Ser Pro Gln Glu Leu Ala Ser Phe Lys Lys Ala Arg Asp Ala Leu
            20                  25                  30

Glu Glu Ser Leu Lys Leu Lys Asn Trp Ser Cys Ser Ser Pro Val Phe
        35                  40                  45

Pro Gly Asn Trp Asp Leu Arg Leu Leu Gln Val Arg Glu Arg Pro Val
    50                  55                  60

Ala Leu Glu Ala Glu Leu Ala Leu Thr Leu Lys Val Leu Glu Ala Ala
65                  70                  75                  80

Ala Gly Pro Ala Leu Glu Asp Val Leu Asp Gln Pro Leu His Thr Leu
                85                  90                  95

His His Ile Leu Ser Gln Leu Gln Ala Cys Ile Gln Pro Gln Pro Thr
            100                 105                 110

Ala Gly Pro Arg Pro Arg Gly Arg Leu His His Trp Leu His Arg Leu
        115                 120                 125

Gln Glu Ala Pro Lys Lys Glu Ser Ala Gly Cys Leu Glu Ala Ser Val
130                 135                 140
```

```
Thr Phe Asn Leu Phe Arg Leu Leu Thr Arg Asp Leu Lys Tyr Val Ala
145                 150                 155                 160

Asp Gly Asn Leu Xaa Leu Arg Thr Ser Thr His Pro Glu Ser Thr
                165                 170                 175

<210> SEQ ID NO 150
<211> LENGTH: 552
<212> TYPE: DNA
<213> ORGANISM: Artificial Sequence
<220> FEATURE:
<223> OTHER INFORMATION: IL-29 Leu insert after N-terminal Met, C173X
<220> FEATURE:
<221> NAME/KEY: variation
<222> LOCATION: (518)...(519)
<223> OTHER INFORMATION: n = A, T, G, or C
<220> FEATURE:
<221> NAME/KEY: CDS
<222> LOCATION: (1)...(552)

<400> SEQUENCE: 150
```

| | | | | | | | | | | | | | | | | |
|---|---|---|---|---|---|---|---|---|---|---|---|---|---|---|---|---|
| atg | ytn | ggc | cct | gtc | ccc | act | tcc | aag | ccc | acc | aca | act | ggg | aag | ggc | 48 |
| Met | Leu | Gly | Pro | Val | Pro | Thr | Ser | Lys | Pro | Thr | Thr | Thr | Gly | Lys | Gly | |
| 1 | | | | 5 | | | | | 10 | | | | | 15 | | |

```
tgc cac att ggc agg ttc aaa tct ctg tca cca cag gag cta gcg agc       96
Cys His Ile Gly Arg Phe Lys Ser Leu Ser Pro Gln Glu Leu Ala Ser
             20                  25                  30 ttc aag aag gcc agg gac gcc ttg gaa gag tca ctc aag ctg aaa aac      144
Phe Lys Lys Ala Arg Asp Ala Leu Glu Glu Ser Leu Lys Leu Lys Asn
         35                  40                  45 tgg agt tgc agc tct cct gtc ttc ccc ggg aat tgg gac ctg agg ctt      192
Trp Ser Cys Ser Ser Pro Val Phe Pro Gly Asn Trp Asp Leu Arg Leu
 50                  55                  60 ctc cag gtg agg gag cgc cct gtg gcc ttg gag gct gag ctg gcc ctg      240
Leu Gln Val Arg Glu Arg Pro Val Ala Leu Glu Ala Glu Leu Ala Leu
 65                  70                  75                  80 acg ctg aag gtc ctg gag gcc gct gct ggc cca gcc ctg gag gac gtc      288
Thr Leu Lys Val Leu Glu Ala Ala Ala Gly Pro Ala Leu Glu Asp Val
                 85                  90                  95 cta gac cag ccc ctt cac acc ctg cac cac atc ctc tcc cag ctc cag      336
Leu Asp Gln Pro Leu His Thr Leu His His Ile Leu Ser Gln Leu Gln
            100                 105                 110 gcc tgt atc cag cct cag ccc aca gca ggg ccc agg ccc cgg ggc cgc      384
Ala Cys Ile Gln Pro Gln Pro Thr Ala Gly Pro Arg Pro Arg Gly Arg
        115                 120                 125 ctc cac cac tgg ctg cac cgg ctc cag gag gcc ccc aaa aag gag tcc      432
Leu His His Trp Leu His Arg Leu Gln Glu Ala Pro Lys Lys Glu Ser
    130                 135                 140 gct ggc tgc ctg gag gca tct gtc acc ttc aac ctc ttc cgc ctc ctc      480
Ala Gly Cys Leu Glu Ala Ser Val Thr Phe Asn Leu Phe Arg Leu Leu
145                 150                 155                 160 acg cga gac ctc aaa tat gtg gcc gat ggg aac ctg dnn ctg aga acg      528
Thr Arg Asp Leu Lys Tyr Val Ala Asp Gly Asn Leu Xaa Leu Arg Thr
                165                 170                 175 tca acc cac cct gag tcc acc tga                                      552
Ser Thr His Pro Glu Ser Thr *
            180

<210> SEQ ID NO 151
<211> LENGTH: 183
<212> TYPE: PRT
<213> ORGANISM: Artificial Sequence
<220> FEATURE:
<223> OTHER INFORMATION: IL-29 Leu insert after N-terminal Met, C173X
<220> FEATURE:
```

<221> NAME/KEY: VARIANT
<222> LOCATION: (173)...(173)
<223> OTHER INFORMATION: Xaa = Ser, Ala, Thr, Val, or Asn

<400> SEQUENCE: 151

Met Leu Gly Pro Val Pro Thr Ser Lys Pro Thr Thr Thr Gly Lys Gly
1               5                   10                  15

Cys His Ile Gly Arg Phe Lys Ser Leu Ser Pro Gln Glu Leu Ala Ser
            20                  25                  30

Phe Lys Lys Ala Arg Asp Ala Leu Glu Glu Ser Leu Lys Leu Lys Asn
        35                  40                  45

Trp Ser Cys Ser Ser Pro Val Phe Pro Gly Asn Trp Asp Leu Arg Leu
50                  55                  60

Leu Gln Val Arg Glu Arg Pro Val Ala Leu Glu Ala Glu Leu Ala Leu
65                  70                  75                  80

Thr Leu Lys Val Leu Glu Ala Ala Gly Pro Ala Leu Glu Asp Val
                85                  90                  95

Leu Asp Gln Pro Leu His Thr Leu His His Ile Leu Ser Gln Leu Gln
            100                 105                 110

Ala Cys Ile Gln Pro Gln Pro Thr Ala Gly Pro Arg Pro Arg Gly Arg
        115                 120                 125

Leu His His Trp Leu His Arg Leu Gln Glu Ala Pro Lys Lys Glu Ser
130                 135                 140

Ala Gly Cys Leu Glu Ala Ser Val Thr Phe Asn Leu Phe Arg Leu Leu
145                 150                 155                 160

Thr Arg Asp Leu Lys Tyr Val Ala Asp Gly Asn Leu Xaa Leu Arg Thr
                165                 170                 175

Ser Thr His Pro Glu Ser Thr
            180

<210> SEQ ID NO 152
<211> LENGTH: 549
<212> TYPE: DNA
<213> ORGANISM: Artificial Sequence
<220> FEATURE:
<223> OTHER INFORMATION: IL-29 G2L C172X
<220> FEATURE:
<221> NAME/KEY: variation
<222> LOCATION: (515)...(516)
<223> OTHER INFORMATION: n = A, T, G, or C
<220> FEATURE:
<221> NAME/KEY: CDS
<222> LOCATION: (1)...(549)

<400> SEQUENCE: 152 atg ytn cct gtc ccc act tcc aag ccc acc aca act ggg aag ggc tgc      48
Met Leu Pro Val Pro Thr Ser Lys Pro Thr Thr Thr Gly Lys Gly Cys
1               5                   10                  15 cac att ggc agg ttc aaa tct ctg tca cca cag gag cta gcg agc ttc      96
His Ile Gly Arg Phe Lys Ser Leu Ser Pro Gln Glu Leu Ala Ser Phe
            20                  25                  30 aag aag gcc agg gac gcc ttg gaa gag tca ctc aag ctg aaa aac tgg     144
Lys Lys Ala Arg Asp Ala Leu Glu Glu Ser Leu Lys Leu Lys Asn Trp
        35                  40                  45 agt tgc agc tct cct gtc ttc ccc ggg aat tgg gac ctg agg ctt ctc     192
Ser Cys Ser Ser Pro Val Phe Pro Gly Asn Trp Asp Leu Arg Leu Leu
50                  55                  60 cag gtg agg gag cgc cct gtg gcc ttg gag gct gag ctg gcc ctg acg     240
Gln Val Arg Glu Arg Pro Val Ala Leu Glu Ala Glu Leu Ala Leu Thr
65                  70                  75                  80

```
ctg aag gtc ctg gag gcc gct gct ggc cca gcc ctg gag gac gtc cta        288
Leu Lys Val Leu Glu Ala Ala Ala Gly Pro Ala Leu Glu Asp Val Leu
            85                  90                  95 gac cag ccc ctt cac acc ctg cac cac atc ctc tcc cag ctc cag gcc        336
Asp Gln Pro Leu His Thr Leu His His Ile Leu Ser Gln Leu Gln Ala
        100                 105                 110 tgt atc cag cct cag ccc aca gca ggg ccc agg ccc cgg ggc cgc ctc        384
Cys Ile Gln Pro Gln Pro Thr Ala Gly Pro Arg Pro Arg Gly Arg Leu
    115                 120                 125 cac cac tgg ctg cac cgg ctc cag gag gcc ccc aaa aag gag tcc gct        432
His His Trp Leu His Arg Leu Gln Glu Ala Pro Lys Lys Glu Ser Ala
130                 135                 140 ggc tgc ctg gag gca tct gtc acc ttc aac ctc ttc cgc ctc ctc acg        480
Gly Cys Leu Glu Ala Ser Val Thr Phe Asn Leu Phe Arg Leu Leu Thr
145                 150                 155                 160 cga gac ctc aaa tat gtg gcc gat ggg aac ctg dnn ctg aga acg tca        528
Arg Asp Leu Lys Tyr Val Ala Asp Gly Asn Leu Xaa Leu Arg Thr Ser
                165                 170                 175 acc cac cct gag tcc acc tga                                            549
Thr His Pro Glu Ser Thr *
            180

<210> SEQ ID NO 153
<211> LENGTH: 182
<212> TYPE: PRT
<213> ORGANISM: Artificial Sequence
<220> FEATURE:
<223> OTHER INFORMATION: IL-29 G2L C172X
<220> FEATURE:
<221> NAME/KEY: VARIANT
<222> LOCATION: (172)...(172)
<223> OTHER INFORMATION: Xaa = Ser, Ala, Thr, Val, or Asn

<400> SEQUENCE: 153

Met Leu Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
            85                  90                  95

Asp Gln Pro Leu His Thr Leu His His Ile Leu Ser Gln Leu Gln Ala
        100                 105                 110

Cys Ile Gln Pro Gln Pro Thr Ala Gly Pro Arg Pro Arg Gly Arg Leu
    115                 120                 125

His His Trp Leu His Arg Leu Gln Glu Ala Pro Lys Lys Glu Ser Ala
130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Xaa Leu Arg Thr Ser
                165                 170                 175

Thr His Pro Glu Ser Thr
            180
```

<210> SEQ ID NO 154
<211> LENGTH: 552
<212> TYPE: DNA
<213> ORGANISM: Artificial Sequence
<220> FEATURE:
<223> OTHER INFORMATION: IL-29 Ile insert after N-terminal Met, C173X
<220> FEATURE:
<221> NAME/KEY: variation
<222> LOCATION: (518)...(519)
<223> OTHER INFORMATION: n = A, T, G, or C
<220> FEATURE:
<221> NAME/KEY: CDS
<222> LOCATION: (1)...(552)

<400> SEQUENCE: 154

```
atg ath ggc cct gtc ccc act tcc aag ccc acc aca act ggg aag ggc      48
Met Ile Gly Pro Val Pro Thr Ser Lys Pro Thr Thr Thr Gly Lys Gly
  1               5                  10                  15 tgc cac att ggc agg ttc aaa tct ctg tca cca cag gag cta gcg agc      96
Cys His Ile Gly Arg Phe Lys Ser Leu Ser Pro Gln Glu Leu Ala Ser
             20                  25                  30 ttc aag aag gcc agg gac gcc ttg gaa gag tca ctc aag ctg aaa aac     144
Phe Lys Lys Ala Arg Asp Ala Leu Glu Glu Ser Leu Lys Leu Lys Asn
         35                  40                  45 tgg agt tgc agc tct cct gtc ttc ccc ggg aat tgg gac ctg agg ctt     192
Trp Ser Cys Ser Ser Pro Val Phe Pro Gly Asn Trp Asp Leu Arg Leu
     50                  55                  60 ctc cag gtg agg gag cgc cct gtg gcc ttg gag gct gag ctg gcc ctg     240
Leu Gln Val Arg Glu Arg Pro Val Ala Leu Glu Ala Glu Leu Ala Leu
 65                  70                  75                  80 acg ctg aag gtc ctg gag gcc gct gct ggc cca gcc ctg gag gac gtc     288
Thr Leu Lys Val Leu Glu Ala Ala Ala Gly Pro Ala Leu Glu Asp Val
                 85                  90                  95 cta gac cag ccc ctt cac acc ctg cac cac atc ctc tcc cag ctc cag     336
Leu Asp Gln Pro Leu His Thr Leu His His Ile Leu Ser Gln Leu Gln
            100                 105                 110 gcc tgt atc cag cct cag ccc aca gca ggg ccc agg ccc cgg ggc cgc     384
Ala Cys Ile Gln Pro Gln Pro Thr Ala Gly Pro Arg Pro Arg Gly Arg
        115                 120                 125 ctc cac cac tgg ctg cac cgg ctc cag gag gcc ccc aaa aag gag tcc     432
Leu His His Trp Leu His Arg Leu Gln Glu Ala Pro Lys Lys Glu Ser
    130                 135                 140 gct ggc tgc ctg gag gca tct gtc acc ttc aac ctc ttc cgc ctc ctc     480
Ala Gly Cys Leu Glu Ala Ser Val Thr Phe Asn Leu Phe Arg Leu Leu
145                 150                 155                 160 acg cga gac ctc aaa tat gtg gcc gat ggg aac ctg dnn ctg aga acg     528
Thr Arg Asp Leu Lys Tyr Val Ala Asp Gly Asn Leu Xaa Leu Arg Thr
                165                 170                 175 tca acc cac cct gag tcc acc tga                                     552
Ser Thr His Pro Glu Ser Thr *
            180
```

<210> SEQ ID NO 155
<211> LENGTH: 183
<212> TYPE: PRT
<213> ORGANISM: Artificial Sequence
<220> FEATURE:
<223> OTHER INFORMATION: IL-29 Ile insert after N-terminal Met, C173X
<220> FEATURE:
<221> NAME/KEY: VARIANT
<222> LOCATION: (173)...(173)
<223> OTHER INFORMATION: Xaa = Ser, Ala, Thr, Val, or Asn

<400> SEQUENCE: 155

Met Ile Gly Pro Val Pro Thr Ser Lys Pro Thr Thr Thr Gly Lys Gly

```
                1               5                   10                  15
Cys His Ile Gly Arg Phe Lys Ser Leu Ser Pro Gln Glu Leu Ala Ser
                    20                  25                  30

Phe Lys Lys Ala Arg Asp Ala Leu Glu Glu Ser Leu Lys Leu Lys Asn
                    35                  40                  45

Trp Ser Cys Ser Ser Pro Val Phe Pro Gly Asn Trp Asp Leu Arg Leu
                50                  55                  60

Leu Gln Val Arg Glu Arg Pro Val Ala Leu Glu Ala Glu Leu Ala Leu
 65                  70                  75                  80

Thr Leu Lys Val Leu Glu Ala Ala Gly Pro Ala Leu Glu Asp Val
                    85                  90                  95

Leu Asp Gln Pro Leu His Thr Leu His His Ile Leu Ser Gln Leu Gln
                    100                 105                 110

Ala Cys Ile Gln Pro Gln Pro Thr Ala Gly Pro Arg Pro Arg Gly Arg
                    115                 120                 125

Leu His His Trp Leu His Arg Leu Gln Glu Ala Pro Lys Lys Glu Ser
                    130                 135                 140

Ala Gly Cys Leu Glu Ala Ser Val Thr Phe Asn Leu Phe Arg Leu Leu
145                 150                 155                 160

Thr Arg Asp Leu Lys Tyr Val Ala Asp Gly Asn Leu Xaa Leu Arg Thr
                    165                 170                 175

Ser Thr His Pro Glu Ser Thr
                180

<210> SEQ ID NO 156
<211> LENGTH: 549
<212> TYPE: DNA
<213> ORGANISM: Artificial Sequence
<220> FEATURE:
<223> OTHER INFORMATION: IL-29 G2I C172X
<220> FEATURE:
<221> NAME/KEY: variation
<222> LOCATION: (515)...(516)
<223> OTHER INFORMATION: n = A, T, G, or C
<220> FEATURE:
<221> NAME/KEY: CDS
<222> LOCATION: (1)...(549)

<400> SEQUENCE: 156 atg ath cct gtc ccc act tcc aag ccc acc aca act ggg aag ggc tgc       48
Met Ile Pro Val Pro Thr Ser Lys Pro Thr Thr Thr Gly Lys Gly Cys
 1               5                   10                  15 cac att ggc agg ttc aaa tct ctg tca cca cag gag cta gcg agc ttc       96
His Ile Gly Arg Phe Lys Ser Leu Ser Pro Gln Glu Leu Ala Ser Phe
                20                  25                  30 aag aag gcc agg gac gcc ttg gaa gag tca ctc aag ctg aaa aac tgg      144
Lys Lys Ala Arg Asp Ala Leu Glu Glu Ser Leu Lys Leu Lys Asn Trp
            35                  40                  45 agt tgc agc tct cct gtc ttc ccc ggg aat tgg gac ctg agg ctt ctc      192
Ser Cys Ser Ser Pro Val Phe Pro Gly Asn Trp Asp Leu Arg Leu Leu
        50                  55                  60 cag gtg agg gag cgc cct gtg gcc ttg gag gct gag ctg gcc ctg acg      240
Gln Val Arg Glu Arg Pro Val Ala Leu Glu Ala Glu Leu Ala Leu Thr
 65                  70                  75                  80 ctg aag gtc ctg gag gcc gct gct ggc cca gcc ctg gag gac gtc cta      288
Leu Lys Val Leu Glu Ala Ala Ala Gly Pro Ala Leu Glu Asp Val Leu
                85                  90                  95 gac cag ccc ctt cac acc ctg cac cac atc ctc tcc cag ctc cag gcc      336
Asp Gln Pro Leu His Thr Leu His His Ile Leu Ser Gln Leu Gln Ala
            100                 105                 110
```

```
tgt atc cag cct cag ccc aca gca ggg ccc agg ccc cgg ggc cgc ctc      384
Cys Ile Gln Pro Gln Pro Thr Ala Gly Pro Arg Pro Arg Gly Arg Leu
        115                 120                 125 cac cac tgg ctg cac cgg ctc cag gag gcc ccc aaa aag gag tcc gct      432
His His Trp Leu His Arg Leu Gln Glu Ala Pro Lys Lys Glu Ser Ala
    130                 135                 140 ggc tgc ctg gag gca tct gtc acc ttc aac ctc ttc cgc ctc ctc acg      480
Gly Cys Leu Glu Ala Ser Val Thr Phe Asn Leu Phe Arg Leu Leu Thr
145                 150                 155                 160 cga gac ctc aaa tat gtg gcc gat ggg aac ctg dnn ctg aga acg tca      528
Arg Asp Leu Lys Tyr Val Ala Asp Gly Asn Leu Xaa Leu Arg Thr Ser
                165                 170                 175 acc cac cct gag tcc acc tga                                          549
Thr His Pro Glu Ser Thr  *
            180
```

<210> SEQ ID NO 157
<211> LENGTH: 182
<212> TYPE: PRT
<213> ORGANISM: Artificial Sequence
<220> FEATURE:
<223> OTHER INFORMATION: IL-29 G2I C172X
<220> FEATURE:
<221> NAME/KEY: VARIANT
<222> LOCATION: (172)...(172)
<223> OTHER INFORMATION: Xaa = Ser, Ala, Thr, Val, or Asn

<400> SEQUENCE: 157

```
Met Ile Pro Val Pro Thr Ser Lys Pro Thr Thr Thr Gly Lys Gly Cys
 1               5                  10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Xaa Leu Arg Thr Ser
                165                 170                 175

Thr His Pro Glu Ser Thr
            180
```

<210> SEQ ID NO 158
<211> LENGTH: 531
<212> TYPE: DNA
<213> ORGANISM: Artificial Sequence
<220> FEATURE:
<223> OTHER INFORMATION: IL-29 after N-terminal Met amino acid residues
      2-7 deleted, C166X

```
<220> FEATURE:
<221> NAME/KEY: variation
<222> LOCATION: (497)...(498)
<223> OTHER INFORMATION: n = A, T, G, or C
<220> FEATURE:
<221> NAME/KEY: CDS
<222> LOCATION: (1)...(531)

<400> SEQUENCE: 158 atg aag ccc acc aca act ggg aag ggc tgc cac att ggc agg ttc aaa        48
Met Lys Pro Thr Thr Thr Gly Lys Gly Cys His Ile Gly Arg Phe Lys
 1               5                  10                  15 tct ctg tca cca cag gag cta gcg agc ttc aag aag gcc agg gac gcc        96
Ser Leu Ser Pro Gln Glu Leu Ala Ser Phe Lys Lys Ala Arg Asp Ala
             20                  25                  30 ttg gaa gag tca ctc aag ctg aaa aac tgg agt tgc agc tct cct gtc       144
Leu Glu Glu Ser Leu Lys Leu Lys Asn Trp Ser Cys Ser Ser Pro Val
         35                  40                  45 ttc ccc ggg aat tgg gac ctg agg ctt ctc cag gtg agg gag cgc cct       192
Phe Pro Gly Asn Trp Asp Leu Arg Leu Leu Gln Val Arg Glu Arg Pro
     50                  55                  60 gtg gcc ttg gag gct gag ctg gcc ctg acg ctg aag gtc ctg gag gcc       240
Val Ala Leu Glu Ala Glu Leu Ala Leu Thr Leu Lys Val Leu Glu Ala
 65                  70                  75                  80 gct gct ggc cca gcc ctg gag gac gtc cta gac cag ccc ctt cac acc       288
Ala Ala Gly Pro Ala Leu Glu Asp Val Leu Asp Gln Pro Leu His Thr
                 85                  90                  95 ctg cac cac atc ctc tcc cag ctc cag gcc tgt atc cag cct cag ccc       336
Leu His His Ile Leu Ser Gln Leu Gln Ala Cys Ile Gln Pro Gln Pro
            100                 105                 110 aca gca ggg ccc agg ccc cgg ggc cgc ctc cac cac tgg ctg cac cgg       384
Thr Ala Gly Pro Arg Pro Arg Gly Arg Leu His His Trp Leu His Arg
        115                 120                 125 ctc cag gag gcc ccc aaa aag gag tcc gct ggc tgc ctg gag gca tct       432
Leu Gln Glu Ala Pro Lys Lys Glu Ser Ala Gly Cys Leu Glu Ala Ser
    130                 135                 140 gtc acc ttc aac ctc ttc cgc ctc ctc acg cga gac ctc aaa tat gtg       480
Val Thr Phe Asn Leu Phe Arg Leu Leu Thr Arg Asp Leu Lys Tyr Val
145                 150                 155                 160 gcc gat ggg aac ctg dnn ctg aga acg tca acc cac cct gag tcc acc       528
Ala Asp Gly Asn Leu Xaa Leu Arg Thr Ser Thr His Pro Glu Ser Thr
                165                 170                 175 tga                                                                   531
 *

<210> SEQ ID NO 159
<211> LENGTH: 176
<212> TYPE: PRT
<213> ORGANISM: Artificial Sequence
<220> FEATURE:
<223> OTHER INFORMATION: IL-29 after N-terminal Met amino acid residues
      2-7 deleted, C166X
<220> FEATURE:
<221> NAME/KEY: VARIANT
<222> LOCATION: (166)...(166)
<223> OTHER INFORMATION: Xaa = Ser, Ala, Thr, Val, or Asn

<400> SEQUENCE: 159

Met Lys Pro Thr Thr Thr Gly Lys Gly Cys His Ile Gly Arg Phe Lys
 1               5                  10                  15

Ser Leu Ser Pro Gln Glu Leu Ala Ser Phe Lys Lys Ala Arg Asp Ala
             20                  25                  30

Leu Glu Glu Ser Leu Lys Leu Lys Asn Trp Ser Cys Ser Ser Pro Val
```

-continued

```
                35                  40                  45
Phe Pro Gly Asn Trp Asp Leu Arg Leu Leu Gln Val Arg Glu Arg Pro
     50                  55                  60

Val Ala Leu Glu Ala Glu Leu Ala Leu Thr Leu Lys Val Leu Glu Ala
 65                  70                  75                  80

Ala Ala Gly Pro Ala Leu Glu Asp Val Leu Asp Gln Pro Leu His Thr
                 85                  90                  95

Leu His His Ile Leu Ser Gln Leu Gln Ala Cys Ile Gln Pro Gln Pro
                100                 105                 110

Thr Ala Gly Pro Arg Pro Arg Gly Arg Leu His His Trp Leu His Arg
            115                 120                 125

Leu Gln Glu Ala Pro Lys Lys Glu Ser Ala Gly Cys Leu Glu Ala Ser
        130                 135                 140

Val Thr Phe Asn Leu Phe Arg Leu Leu Thr Arg Asp Leu Lys Tyr Val
145                 150                 155                 160

Ala Asp Gly Asn Leu Xaa Leu Arg Thr Ser Thr His Pro Glu Ser Thr
                165                 170                 175

<210> SEQ ID NO 160
<211> LENGTH: 558
<212> TYPE: DNA
<213> ORGANISM: Artificial Sequence
<220> FEATURE:
<223> OTHER INFORMATION: IL-29 Glu, Ala, and Glu inserted after
      N-terminal Met, C175X
<220> FEATURE:
<221> NAME/KEY: variation
<222> LOCATION: (524)...(525)
<223> OTHER INFORMATION: n = A, T, G, or C
<220> FEATURE:
<221> NAME/KEY: CDS
<222> LOCATION: (1)...(558)

<400> SEQUENCE: 160 atg gar gcn gar ggc cct gtc ccc act tcc aag ccc acc aca act ggg      48
Met Glu Ala Glu Gly Pro Val Pro Thr Ser Lys Pro Thr Thr Thr Gly
 1               5                  10                  15 aag ggc tgc cac att ggc agg ttc aaa tct ctg tca cca cag gag cta      96
Lys Gly Cys His Ile Gly Arg Phe Lys Ser Leu Ser Pro Gln Glu Leu
                 20                  25                  30 gcg agc ttc aag aag gcc agg gac gcc ttg gaa gag tca ctc aag ctg     144
Ala Ser Phe Lys Lys Ala Arg Asp Ala Leu Glu Glu Ser Leu Lys Leu
             35                  40                  45 aaa aac tgg agt tgc agc tct cct gtc ttc ccc ggg aat tgg gac ctg     192
Lys Asn Trp Ser Cys Ser Ser Pro Val Phe Pro Gly Asn Trp Asp Leu
     50                  55                  60 agg ctt ctc cag gtg agg gag cgc cct gtg gcc ttg gag gct gag ctg     240
Arg Leu Leu Gln Val Arg Glu Arg Pro Val Ala Leu Glu Ala Glu Leu
 65                  70                  75                  80 gcc ctg acg ctg aag gtc ctg gag gcc gct gct ggc cca gcc ctg gag     288
Ala Leu Thr Leu Lys Val Leu Glu Ala Ala Ala Gly Pro Ala Leu Glu
                 85                  90                  95 gac gtc cta gac cag ccc ctt cac acc ctg cac cac atc ctc tcc cag     336
Asp Val Leu Asp Gln Pro Leu His Thr Leu His His Ile Leu Ser Gln
                100                 105                 110 ctc cag gcc tgt atc cag cct cag ccc aca gca ggg ccc agg ccc cgg     384
Leu Gln Ala Cys Ile Gln Pro Gln Pro Thr Ala Gly Pro Arg Pro Arg
            115                 120                 125 ggc cgc ctc cac cac tgg ctg cac cgg ctc cag gag gcc ccc aaa aag     432
Gly Arg Leu His His Trp Leu His Arg Leu Gln Glu Ala Pro Lys Lys
        130                 135                 140
```

```
gag tcc gct ggc tgc ctg gag gca tct gtc acc ttc aac ctc ttc cgc    480
Glu Ser Ala Gly Cys Leu Glu Ala Ser Val Thr Phe Asn Leu Phe Arg
145             150                 155                 160 ctc ctc acg cga gac ctc aaa tat gtg gcc gat ggg aac ctg dnn ctg    528
Leu Leu Thr Arg Asp Leu Lys Tyr Val Ala Asp Gly Asn Leu Xaa Leu
            165                 170                 175 aga acg tca acc cac cct gag tcc acc tga                            558
Arg Thr Ser Thr His Pro Glu Ser Thr *
                180                 185

<210> SEQ ID NO 161
<211> LENGTH: 185
<212> TYPE: PRT
<213> ORGANISM: Artificial Sequence
<220> FEATURE:
<223> OTHER INFORMATION: IL-29 Glu, Ala, and Glu inserted after
      N-terminal Met, C175X
<220> FEATURE:
<221> NAME/KEY: VARIANT
<222> LOCATION: (175)...(175)
<223> OTHER INFORMATION: Xaa = Ser, Ala, Thr, Val, or Asn

<400> SEQUENCE: 161

Met Glu Ala Glu Gly Pro Val Pro Thr Ser Lys Pro Thr Thr Thr Gly
 1               5                  10                  15

Lys Gly Cys His Ile Gly Arg Phe Lys Ser Leu Ser Pro Gln Glu Leu
             20                  25                  30

Ala Ser Phe Lys Lys Ala Arg Asp Ala Leu Glu Glu Ser Leu Lys Leu
         35                  40                  45

Lys Asn Trp Ser Cys Ser Ser Pro Val Phe Pro Gly Asn Trp Asp Leu
     50                  55                  60

Arg Leu Leu Gln Val Arg Glu Arg Pro Val Ala Leu Glu Ala Glu Leu
 65                  70                  75                  80

Ala Leu Thr Leu Lys Val Leu Glu Ala Ala Ala Gly Pro Ala Leu Glu
                 85                  90                  95

Asp Val Leu Asp Gln Pro Leu His Thr Leu His His Ile Leu Ser Gln
            100                 105                 110

Leu Gln Ala Cys Ile Gln Pro Gln Pro Thr Ala Gly Pro Arg Pro Arg
        115                 120                 125

Gly Arg Leu His His Trp Leu His Arg Leu Gln Glu Ala Pro Lys Lys
    130                 135                 140

Glu Ser Ala Gly Cys Leu Glu Ala Ser Val Thr Phe Asn Leu Phe Arg
145                 150                 155                 160

Leu Leu Thr Arg Asp Leu Lys Tyr Val Ala Asp Gly Asn Leu Xaa Leu
                165                 170                 175

Arg Thr Ser Thr His Pro Glu Ser Thr
                180                 185
```

HOMOGENEOUS PREPARATIONS OF IL-28 AND IL-29

The present application is a divisional of U.S. patent application Ser. No. 10/914,772, filed Aug. 9, 2004, now U.S. Pat. No. 7,157,559 which claims the benefit of U.S. patent application Ser. Nos. 60/493,194, filed Aug. 7, 2003, 60/551,841, filed Mar. 10, 2004, and 60/559,142, filed Apr. 2, 2004, all of which are herein incorporated by reference.

BACKGROUND OF THE INVENTION

Cytokines play important roles in the regulation of hematopoiesis and immune responses, and can influence lymphocyte development. The human class II cytokine family includes interferon-α (IFN-α) subtypes, interferon-β (IFN-β), interferon-γ (IFN-γ), IL-10, IL-19 (U.S. Pat. No. 5,985,614), MDA-7 (Jiang et al., *Oncogene* 11, 2477-2486, (1995)), IL-20 (Jiang et al., *Oncogene* 11, 2477-2486, (1995)), IL-22 (Xie et al., *J. Biol. Chem.* 275, 31335-31339, (2000)), and AK-155 (Knappe et al., *J. Virol.* 74, 3881-3887, (2000)). Most cytokines bind and transduce signals through either Class I or Class II cytokine receptors. Members of human class II cytokine receptor family include interferon-αR1 (IFN-αR1), interferon-γ-R2 (IFN-γ-R2), interferon-γ R1 (IFN-γ R1), interferon-γR2 (IFN-γR2), IL-10R (Liu et al., *J. Immunol.* 152, 1821-1829, (1994)), CRF2-4 (Lutfalla et al. *Genomics* 16, 366-373, (1993)), IL-20Rβ (Blumberg et al., *Cell* 104, 9-19, (2001)) (also known as zcytor7 (U.S. Pat. No. 5,945,511) and CRF2-8 (Kotenko et al., *Oncogene* 19, 2557-2565, (2000)), IL-20Rβ (Blumberg et al., *ibid*, (2001)) (also known as DIRS1 (PCT WO 99/46379)), IL-22RA1 (IL-22 receptor-α1, submitted to HUGO for approval) (also known as IL-22R (Xie et al., *J. Biol. Chem.* 275, 31335-31339, (2000)), zcytor11 (U.S. Pat. No. 5,965,704) and CRF2-9 (Kotenko et al., *Oncogene* 19, 2557-2565, (2000)), and tissue factor.

Class II cytokine receptors are typically heterodimers composed of two distinct receptor chains, the α and β receptor subunits (Stahl et al., *Cell* 74, 587-590, (1993)). In general, the α subunits are the primary cytokine binding proteins, and the β subunits are required for formation of high affinity binding sites, as well as for signal transduction. An exception is the IL-20 receptor in which both subunits are required for IL-20 binding (Blumberg et al., *ibid*, (2001)).

The class II cytokine receptors are identified by a conserved cytokine-binding domain of about 200 amino acids (D200) in the extracellular portion of the receptor. This cytokine-binding domain is comprised of two fibronectin type III (FnIII) domains of approximately 100 amino acids each (Bazan J. F. *Proc. Natl. Acad. Sci. USA* 87, 6934-6938, (1990); Thoreau et al., *FEBS Lett.* 282, 16-31, (1991)). Each FnIII domain contains conserved Cys, Pro, and Trp residues that determine a characteristic folding pattern of seven β-strands similar to the constant domain of immunoglobulins (Uze et al., *J. Interferon Cytokine Res.* 15, 3-26, (1995)). The conserved structural elements of the class II cytokine receptor family make it possible to identify new members of this family on the basis of primary amino acid sequence homology.

The interleukins are a family of cytokines that mediate immunological responses, including inflammation. Central to an immune response is the T cell, which produce many cytokines and adaptive immunity to antigens. Cytokines produced by the T cell have been classified as type 1 and type 2 (Kelso, A. *Immun. Cell Biol.* 76:300-317, 1998). Type 1 cytokines include IL-2, interferon-gamma (IFN-γ), LT-α, and are involved in inflammatory responses, viral immunity, intracellular parasite immunity and allograft rejection. Type 2 cytokines include IL-4, IL-5, IL-6, IL-10 and IL-13, and are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

Of particular interest, from a therapeutic standpoint, are the interferons (reviews on interferons are provided by De Maeyer and De Maeyer-Guignard, "Interferons," in *The Cytokine Handbook*, 3$^{rd}$ *Edition*, Thompson (ed.), pages 491-516 (Academic Press Ltd. 1998), and by Walsh, *Biopharmaceuticals: Biochemistry and Biotechnology*, pages 158-188 (John Wiley & Sons 1998)). Interferons exhibit a variety of biological activities, and are useful for the treatment of certain autoimmune diseases, particular cancers, and the enhancement of the immune response against infectious agents, including viruses, bacteria, fungi, and protozoa. To date, six forms of interferon have been identified, which have been classified into two major groups. The so-called "type I" IFNs include IFN-α, IFN-β, IFN-ω, IFN-δ, and interferon-τ. Currently, IFN-γ and one subclass of IFN-α are the only type II IFNs.

Type I IFNs, which are thought to be derived from the same ancestral gene, have retained sufficient similar structure to act by the same cell surface receptor. The α-chain of the human IFN-α/β receptor comprises an extracellular N-terminal domain, which has the characteristics of a class II cytokine receptor. IFN-γ does not share significant homology with the type I IFN or with the type II IFN-α subtype, but shares a number of biological activities with the type I IFN.

Clinicians are taking advantage of the multiple activities of interferons by using the proteins to treat a wide range of conditions. For example, one form of IFN-α has been approved for use in more than 50 countries for the treatment of medical conditions such as hairy cell leukemia, renal cell carcinoma, basal cell carcinoma, malignant melanoma, AIDS-related Kaposi's sarcoma, multiple myeloma, chronic myelogenous leukemia, non-Hodgkin's lymphoma, laryngeal papillomatosis, mycosis fungoides, condyloma acuminata, chronic hepatitis B, hepatitis C, chronic hepatitis D, and chronic non-A, non-B/C hepatitis. The U.S. Food and Drug Administration has approved the use of IFN-β to treat multiple sclerosis, a chronic disease of the nervous system. IFN-γ is used to treat chronic granulomatous diseases, in which the interferon enhances the patient's immune response to destroy infectious bacterial, fungal, and protozoal pathogens. Clinical studies also indicate that IFN-γ may be useful in the treatment of AIDS, leishmaniasis, and lepromatous leprosy.

IL-28A, IL-28B, and IL-29 comprise a recently discovered new family of proteins that have sequence homology to type I interferons and genomic homology to IL-10. This new family is fully described in co-owned PCT application WO 02/086087 and Sheppard et al., *Nature Immunol.* 4:63-68, 2003; both incorporated by reference herein. Functionally, IL-28 and IL-29 resemble type I INFs in their ability to induce an antiviral state in cells but, unlike type I IFNs, they do not display antiproliferative activity against certain B cell lines.

IL-28 and IL-29 are known to have an odd number of cysteines (PCT application WO 02/086087 and Sheppard et al., supra.) Expression of recombinant IL-28 and IL-29 can result in a heterogeneous mixture of proteins composed of intramolecular disulfide bonding in multiple conformations.

The separation of these forms can be difficult and laborious. It is therefore desirable to provide IL-28 and IL-29 molecules having a single intramolecular disulfide bonding pattern upon expression and methods for refolding and purifying these preparations to maintain homogeneity. Thus, the present invention provides for compositions and methods to produce homogeneous preparations of IL-28 and IL-29.

DETAILED DESCRIPTION OF THE INVENTION

DEFINITIONS

In the description that follows, a number of terms are used extensively. The following definitions are provided to facilitate understanding of the invention.

Unless otherwise specified, "a," "an," "the," and "at least one" are used interchangeably and mean one or more than one.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "level" when referring to immune cells, such as NK cells, T cells, in particular cytotoxic T cells, B cells and the like, an increased level is either increased number of cells or enhanced activity of cell function.

The term "level" when referring to viral infections refers to a change in the level of viral infection and includes, but is not limited to, a change in the level of CTLs or NK cells (as described above), a decrease in viral load, an increase antiviral antibody titer, decrease in serological levels of alanine aminotransferase, or improvement as determined by histological examination of a target tissue or organ. Determination of whether these changes in level are significant differences or changes is well within the skill of one in the art.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

"zcyto20", "zcyto21", "zcyto22" are the previous designations for human IL-28A, human IL-29, and human IL-28B, respectively. The nucleotide and amino acid sequence for IL-28A are shown in SEQ ID NO:1 and SEQ ID NO:2, respectively. The nucleotide and amino acid sequences for IL-29 are shown in SEQ ID NO:3 and SEQ ID NO:4, respectively. The nucleotide and amino acid sequence for IL-28B are shown in SEQ ID NO:5 and SEQ ID NO:6, respectively. These sequences are fully described in PCT application WO 02/086087 commonly assigned to ZymoGenetics, Inc., incorporated herein by reference.

"zcyto24" and "zcyto25" are the previous designations for mouse IL-28, and are shown in SEQ ID NOs: 7, 8, 9, 10, respectively. The polynucleotide and polypeptides are fully described in PCT application WO 02/086087 commonly assigned to ZymoGenetics, Inc., incorporated herein by reference.

"zcytor19" is the previous designation for IL-28 receptor α-subunit, and is shown in SEQ ID NO:11. The polynucleotides and polypeptides are described in PCT application WO 02/20569 on behalf of Schering, Inc., and WO 02/44209 assigned to ZymoGenetics, Inc and incorporated herein by reference. "IL-28 receptor" denotes the IL-28 a.-subunit and CRF2-4 subunit forming a heterodimeric receptor.

The present invention provides polynucleotide molecules, including DNA and RNA molecules, that encode Cysteine mutants of IL-28 and IL-29 that result in expression of a recombinant IL-28 or IL-29 preparation that is a homogeneous preparation. For the purposes of this invention, a homogeneous preparation of IL-28 and IL-29 is a preparation in which comprises at least 98% of a single intramolecular disulfide bonding pattern in the purified polypeptide. In other embodiments, the single disulfide conformation in a preparation of purified polypeptide is at 99% homogeneous. In general, these Cysteine mutants will maintain some biological activity of the wildtype IL-28 or IL-29, as described herein. For example, the molecules of the present invention can bind to the IL-28 receptor with some specificity. Generally, a ligand binding to its cognate receptor is specific when the $K_D$ falls within the range of 100 nM to 100 pM. Specific binding in the range of 100 mM to 10 nM $K_D$ is low affinity binding. Specific binding in the range of 2.5 pM to 100 pM $K_D$ is high affinity binding. In another example, biological activity of IL-28 or IL-29 Cysteine mutants is present when the molecules are capable of some level of antiviral activity associated with wildtype IL-28 or IL-29. Determination of the level of antiviral activity is described in detail herein.

When referring to IL-28, the term shall mean both IL-28A and IL-28B. Previously IL-28A was designated zcyto20 (SEQ ID NOs:1 and 2), IL-29 was designated zcyto21 (SEQ ID NOs:3 and 4), and IL-28B was designated zcyto22 (SEQ ID NOs:5 and 6). (See, PCT application WO 02/086087 and Sheppard et al., supra.) The mouse orthologs for IL-28 were previously designated as zcyto24 (SEQ ID NOs:7 and 8), zcyto25 (SEQ ID NOs:9 and 10).

Wildtype IL-28A gene encodes a polypeptide of 200 amino acids, as shown in SEQ ID NO:2. The signal sequence for IL-28A can be predicted as comprising amino acid residue −25 (Met) through amino acid residue −1 (Ala) of SEQ ID NO:2. The mature peptide for IL-28A begins at amino acid residue 1 (Val) of SEQ ID NO:2. IL-28A helices are predicted as follow: helix A is defined by amino acid residues 31 (Ala) to 45 (Leu); helix B by amino acid residues 58 (Thr) to 65 (Gln); helix C by amino acid residues 69 (Arg) to 86 (Ala); helix D by amino acid residues 95 (Val) to 114 (Ala); helix E by amino acid residues 126 (Thr) to 142 (Lys); and helix F by amino acid residues 148 (Cys) to 169 (Ala); as shown in SEQ ID NO: 2.

Wildtype IL-29 gene encodes a polypeptide of 200 amino acids, as shown in SEQ ID NO:4. The signal sequence for IL-29 can be predicted as comprising amino acid residue −19 (Met) through amino acid residue −1 (Ala) of SEQ ID NO:4, SEQ ID NO:119, or SEQ ID NO:121. The mature peptide for IL-29 begins at amino acid residue 1 (Gly) of SEQ ID NO:4. IL-29 has been described in PCT application WO 02/02627. IL-29 helices are predicted as follows: helix A is defined by amino acid residues 30 (Ser) to 44 (Leu); helix B by amino acid residues 57 (Asn) to 65 (Val); helix C by amino acid residues 70 (Val) to 85 (Ala); helix D by amino acid residues 92 (Glu) to 111 (Gln); helix E by amino acid residues 118 (Thr) to 139 (Lys); and helix F by amino acid residues 144 (Gly) to 170 (Leu); as shown in SEQ ID NO:4.

Wildtype IL-28B gene encodes a polypeptide of 200 amino acids, as shown in SEQ ID NO:6. The signal sequence for IL-28B can be predicted as comprising amino acid residue −21 (Met) through amino acid residue −1 (Ala) of SEQ ID NO:6. The mature peptide for IL-28B begins at amino acid residue 1 (Val) of SEQ ID NO:6. IL-28B helices are predicted as follow: helix A is defined by amino acid residues 31 (Ala) to 45 (Leu); helix B by amino acid residues 58 (Thr) to 65 (Gln); helix C by amino acid residues 69 (Arg) to 86 (Ala); helix D by amino acid residues 95 (Gly) to 114 (Ala); helix E by amino acid residues 126 (Thr) to 142 (Lys); and helix F by amino acid residues 148 (Cys) to 169 (Ala); as shown in SEQ ID NO:6.

The present invention provides mutations in the IL-28 and IL-29 wildtype sequences as shown in SEQ ID NOs: 1, 2, 3, 4, 5, and 6, that result in expression of single forms of the IL-28 or IL-29 molecule. Because the heterogeneity of forms is believed to be a result of multiple intramolecular disulfide bonding patterns, specific embodiments of the present invention includes mutations to the cysteine residues within the wildtype IL-28 and IL-29 sequences. When IL-28 and IL-29 are expressed in *E. coli*, an N-terminal or amino-terminal Methionine is present. SEQ ID NOs:12-17, for example, show the nucleotide and amino acid residue numbering for IL-28A, IL-29 and IL-28B when the N-terminal Met is present. Table 1 shows the possible combinations of intramolecular disulfide bonded cysteine pairs for wildtype IL-28A, IL-28B, and IL-29.

TABLE 1

| | | | | | | | | | | |
|---|---|---|---|---|---|---|---|---|---|---|
| IL-28A SEQ ID NO: 2 | $C_{16}$-$C_{115}$ | $C_{48}$-$C_{148}$ | $C_{50}$-$C_{148}$ | $C_{167}$-$C_{174}$ | $C_{16}$-$C_{48}$ | $C_{16}$-$C_{50}$ | $C_{48}$-$C_{115}$ | $C_{50}$-$C_{115}$ | $C_{115}$-$C_{148}$ | |
| Met IL-28A SEQ ID NO: 13 | $C_{17}$-$C_{116}$ | $C_{49}$-$C_{149}$ | $C_{51}$-$C_{1498}$ | $C_{168}$-$C_{175}$ | $C_{17}$-$C_{49}$ | $C_{17}$-$C_{51}$ | $C_{49}$-$C_{116}$ | $C_{51}$-$C_{116}$ | $C_{116}$-$C_{149}$ | |
| IL-29 SEQ ID NO: 4 | $C_{15}$-$C_{112}$ | $C_{49}$-$C_{145}$ | $C_{112}$-$C_{171}$ | | | | | | | |
| Met IL-29 SEQ ID NO: 15 | $C_{16}$-$C_{113}$ | $C_{50}$-$C_{146}$ | $C_{113}$-$C_{172}$ | | | | | | | |
| IL-28B SEQ ID NO: 6 | $C_{16}$-$C_{115}$ | $C_{48}$-$C_{148}$ | $C_{50}$-$C_{148}$ | $C_{167}$-$C_{174}$ | $C_{16}$-$C_{48}$ | $C_{16}$-$C_{50}$ | $C_{48}$-$C_{115}$ | $C_{50}$-$C_{115}$ | $C_{115}$-$C_{148}$ | |
| Met IL-28B SEQ ID NO: 17 | $C_{17}$-$C_{116}$ | $C_{49}$-$C_{149}$ | $C_{51}$-$C_{149}$ | $C_{168}$-$C_{175}$ | $C_{17}$-$C_{49}$ | $C_{17}$-$C_{51}$ | $C_{49}$-$C_{116}$ | $C_{51}$-$C_{116}$ | $C_{116}$-$C_{149}$ | |

The polynucleotide and polypeptide molecules of the present invention have a mutation at one or more of the Cysteines present in the wildtype IL-28A, IL-29 or IL-28B molecules, yet retain some biological activity as described herein. Table 2 illustrates exemplary Cysteine mutants, in particular point mutations of cysteine (C) to serine (S).

TABLE 2

| | |
|---|---|
| IL-28A C48S | SEQ ID NO: 19 |
| Met IL-28A C49S | SEQ ID NO: 21 |
| IL-28A C50S | SEQ ID NO: 23 |
| Met IL-28A C51S | SEQ ID NO: 25 |
| IL-29 C171S | SEQ ID NO: 27 |
| Met IL-29 C172S | SEQ ID NO: 29 |

All the members of the family have been shown to bind to the same class II cytokine receptor, IL-28R. IL-28 α-subunit was previously designated zcytor19 receptor. While not wanting to be bound by theory, these molecules appear to all signal through IL-28R receptor via the same pathway. IL-28 receptor is described in a commonly assigned PCT patent application WO 02/44209, incorporated by reference herein; Sheppard et al., supra; Kotenko et al., *Nature Immunol.* 4:69-77, 2003; and PCT WO/03/040345. IL-28R is a member of the Class II cytokine receptors which is characterized by the presence of one or more cytokine receptor modules (CRM) in their extracellular domains. Other class TI cytokine receptors include zcytor11 (commonly owned U.S. Pat. No. 5,965,704), CRF2-4 (Genbank Accession No. Z17227), IL-10R (Genbank Accession No.s U00672 and NM_001558), DIRS1, zcytor7 (commonly owned U.S. Pat. No. 5,945,511), and tissue factor. IL-28 receptor, like all known class II receptors except interferon-alpha/beta receptor alpha chain, has only a single class II CRM in its extracellular domain.

Four-helical bundle cytokines are also grouped by the length of their component helices. "Long-helix" form cytokines generally consist of between 24-30 residue helices, and include IL-6, ciliary neutrotrophic factor (CNTF), leukemia inhibitory factor (LIF) and human growth hormone (hGH). "Short-helix" form cytokines generally consist of between 18-21 residue helices and include IL-2, IL-4 and GM-CSF. Studies using CNTF and IL-6 demonstrated that a CNTF helix can be exchanged for the equivalent helix in IL-6, conferring CTNF-binding properties to the chimera. Thus, it appears that functional domains of four-helical cytokines are determined on the basis of structural homology, irrespective of sequence identity, and can maintain functional integrity in a chimera (Kallen et al., *J. Biol. Chem.* 274:11859-11867, 1999). Therefore, Cysteine mutants IL-28 and IL-29 polypeptides will be useful for preparing chimeric fusion molecules, particularly with other interferons to determine and modulate receptor binding specificity. Of particular interest are fusion proteins that combine helical and loop domains from interferons and cytokines such as INF-$\alpha$, IL-10, human growth hormone.

The present invention provides polynucleotide molecules, including DNA and RNA molecules, that encode, for example, Cysteine mutant IL-28 or IL-29 polypeptides. For example, the present invention provides degenerate nucleotide sequences encoding IL-28A C48S, Met IL-28A C49S, IL-28A C50S, Met IL-28A C51S, IL-29 C171S and Met IL-29 C172S polypeptides disclose herein. Those skilled in the art will readily recognize that, in view of the degeneracy of the genetic code, considerable sequence variation is possible among these polynucleotide molecules. SEQ ID NOs: 30, 31, 32, 33, 34, and 35 are a degenerate DNA sequences that encompasses all DNAs that encode IL-28A C48S, Met IL-28A C49S, IL-28A C50S, Met IL-28A C51S, IL-29 C171S and IL-29 C172S, respectively. Those skilled in the art will recognize that the degenerate sequence of SEQ ID NOs: 30, 31, 32, 33, 34, and 35 also provides all RNA sequences encoding SEQ ID NOs: 30, 31, 32, 33, 34, and 35 by substituting U for T and are thus comtemplated by the present invention.

IL-28A polypeptides of the present invention also include a mutation at the second cysteine, C2, of the mature polypeptide. For example, C2 from the N-terminus or amino-terminus of the polypeptide of SEQ ID NO:2 is the cysteine at amino acid position 48, or position 49 (additional N-terminal Met) if expressed in *E coli* (see, for example, SEQ ID NO:13). This second cysteine (of which there are seven, like IL-28B) or C2 of IL-28A can be mutated, for example, to a serine, alanine, threonine, valine, or asparagine. IL-28A C2 mutant molecules of the present invention include, for example, polynucleotide molecules as shown in SEQ ID NOs:20 and 22, including DNA and RNA molecules, that encode IL-28A C2 mutant polypeptides as shown in SEQ ID NOs:21 and 23, respectively. SEQ ID NOs:36 and 37 are additional IL-28A C2 polypeptides of the present invention.

In addition to the IL-28A C2 mutants, the present invention also includes IL-28A polypeptides comprising a mutation at the third cysteine position, C3, of the mature polypeptide. For example, C3 from the N-terminus or amino-terminus of the polypeptide of SEQ ID NO:2, is the cysteine at position 50, or position 51 (additional N-terminal Met) if expressed in *E. coli* (see, for example, SEQ ID NO:13). IL-28A C3 mutant molecules of the present invention include, for example, polynucleotide molecules as shown in SEQ ID NOs:24 and 26, including DNA and RNA molecules, that encode IL-28A C3 mutant polypeptides as shown in SEQ ID NOs:25 and 27, respectively. SEQ ID NOs:38 and 39 are additional IL-28A C3 polypeptides of the present invention.

The IL-28A polypeptides of the present invention include, for example, SEQ ID NOs:2, 13, 19, 21, 23, and 25, which are encoded by IL-28A polynucleotide molecules as shown in SEQ ID NOs:1, 12, 18, 20, 22, and 24, respectively. Further IL-28A polypeptides of the present invention include, for example, SEQ ID NOs:36, 37, 38, and 39.

IL-28B polypeptides of the present invention also include a mutation at the second cysteine, C2, of the mature polypeptide. For example, C2 from the N-terminus or amino-terminus of the polypeptide of SEQ ID NO:6 is the cysteine at amino acid position 48, or position 49 (additional N-terminal Met) if expressed in *E coli* (see, for example, SEQ ID NO:17). This second cysteine (of which there are seven, like IL-28A) or C2 of IL-28B can be mutated, for example, to a serine, alanine, threonine, valine, or asparagine. IL-28B C2 mutant molecules of the present invention include, for example, polynucleotide molecules as shown in SEQ ID NOs:122 and 124, including DNA and RNA molecules, that encode IL-28B C2 mutant polypeptides as shown in SEQ ID NOs:123 and 125, respectively. Additional IL-28B C2 mutant molecules of the present invention include polynucleotide molecules as shown in SEQ ID NOs:130 and 132 including DNA and RNA molecules, that encode IL-28B C2 mutant polypeptides as shown in SEQ ID NOs: 131 and 133, respectively (PCT publication WO 03/066002 (Kotenko et al.)).

In addition to the IL-28B C2 mutants, the present invention also includes IL-28B polypeptides comprising a mutation at the third cysteine position, C3, of the mature polypeptide. For example, C3 from the N-terminus or amino-terminus of the polypeptide of SEQ ID NO:6, is the cysteine at position 50, or position 51 (additional N-terminal Met) if expressed in *E. coli* (see, for example, SEQ ID NO:17). IL-28B C3 mutant molecules of the present invention include, for example, polynucleotide molecules as shown in SEQ ID NOs:126 and 128, including DNA and RNA molecules, that encode IL-28B C3 mutant polypeptides as shown in SEQ ID NOs:127 and 129, respectively. Additional IL-28B C3 mutant molecules of the present invention include polynucleotide molecules as shown in SEQ ID NOs:134 and 136 including DNA and RNA molecules, that encode IL-28B C3 mutant polypeptides as shown in SEQ ID NOs: 135 and 137, respectively (PCT publication WO 03/066002 (Kotenko et al.)).

The IL-28B polypeptides of the present invention include, for example, SEQ ID NOs:6, 17, 123, 125, 127, 129, 131, 133, 135, and 137, which are encoded by IL-28B polynucleotide molecules as shown in SEQ ID NOs:5, 16, 122, 124, 126, 128, 130, 132, 134, and 136, respectively.

IL-29 polypeptides of the present invention also include, for example, a mutation at the fifth cysteine, C5, of the mature polypeptide. For example, C5 from the N-terminus of the polypeptide of SEQ ID NO:4, is the cysteine at position 171, or position 172 (additional N-terminal Met) if expressed in *E. coli.* (see, for example, SEQ ID NO:15). This fifth cysteine or C5 of IL-29 can be mutated, for example, to a serine, alanine, threonine, valine, or asparagine. These IL-29 C5 mutant polypeptides have a disulfide bond pattern of C1(Cys15 of SEQ ID NO:4)/C3(Cys112 of SEQ ID NO:4) and C2(Cys49 of SEQ ID NO:4)/C4(Cys145 of SEQ ID NO:4). Additional IL-29 C5 mutant molecules of the present invention include polynucleotide molecules as shown in SEQ ID NOs:26, 28, 82, 84, 138, 140, 142, 144, 146, 148, 150, 152, 154, 156, 158, and 160, including DNA and RNA molecules, that encode IL-29 C5 mutant polypeptides as shown in SEQ ID NOs:27, 29, 83, 85, 139, 141, 143, 145, 147, 149, 151, 153, 155, 157, 159, and 161, respectively. Additional IL-29 C5 mutant molecules of the present invention include polynucleotide molecules as shown in SEQ ID NOs:86, 88, 94, and 96, including DNA and RNA molecules, that encode IL-29 C5 mutant polypeptides as shown in SEQ ID NOs:87, 89, 95, and 97, respectively (PCT publication WO 03/066002 (Kotenko et al.)). Additional, IL-29 C5 mutant molecules of the present invention include polynucleotide molecules as shown in SEQ ID NOs:102, 104, 110, and 112, including DNA and RNA molecules, that encode IL-29 C5 mutant polypeptides as shown in SEQ ID NOs:103, 105, 111, and 113, respectively (PCT publication WO 02/092762 (Baum et al.)).

In addition to the IL-29 C5 mutants, the present invention also includes IL-29 polypeptides comprising a mutation at the first cysteine position, C1, of the mature polypeptide. For example, C1 from the N-terminus of the polypeptide of SEQ ID NO:4, is the cysteine at position 15, or position 16 (additional N-terminal Met) if expressed in *E. coli* (see, for example, SEQ ID NO:15). These IL-29 C1 mutant polypeptides will thus have a predicted disulfide bond pattern of C2(Cys49 of SEQ ID NO:4)/C4(Cys145 of SEQ ID NO:4) and C3(Cys112 of SEQ ID NO:4)/C5(Cys171 of SEQ ID NO:4). Additional IL-29 C1 mutant molecules of the present invention include polynucleotide molecules as shown in SEQ ID NOs:74, 76, 78, and 80, including DNA and RNA molecules, that encode IL-29 C1 mutant polypeptides as shown in SEQ ID NOs:75, 77, 79 and 81, respectively. Additional IL-29 C1 mutant molecules of the present invention include polynucleotide molecules as shown in SEQ ID NOs:90, 92, 98, and 100, including DNA and RNA molecules, that encode IL-29 C1 mutant polypeptides as shown in SEQ ID NOs:91, 93, 99, and 101, respectively (PCT publication WO 03/066002 (Kotenko et al.)). Additional, IL-29 C1 mutant molecules of the present invention include polynucleotide molecules as shown in SEQ ID NOs:106, 108, 114, and 116, including DNA and RNA molecules, that encode IL-29 C1 mutant polypeptides as shown in SEQ ID NOs:107, 109, 115, and 117, respectively (PCT publication WO 02/092762 (Baum et al.)).

The IL-29 polypeptides of the present invention, for example, SEQ ID NOs:4, 15, 27, 29, 75, 77, 79, 81, 83, 85, 87, 89, 91, 93, 95, 97, 99, 101, 103, 105, 107, 109, 111, 113, 115, 117, 139, 141, 143, 145, 147, 149, 151, 153, 155, 157, 159, and 161, which are encoded by IL-29 polynucleotide molecules as shown in SEQ ID NOs:3, 14, 26, 28, 74, 76, 78, 80, 82, 84, 86, 88, 90, 92, 94, 96, 98, 100, 102, 104, 106, 108, 110, 112, 114, 116, 138, 140, 142, 144, 146, 148, 150, 152, 154, 156, 158, and 160, may further include a signal sequence as shown in SEQ ID NO:119 or a signal sequence as shown in SEQ ID NO:121. In addition, the present invention also includes the IL-29 polypeptides as shown in SEQ ID NOs:40 and 41. A polynucleotide molecule encoding the signal sequence polypeptide of SEQ ID NO:119 is shown as SEQ ID NO:118. A polynucleotide molecule encoding the signal sequence polypeptide of SEQ ID NO:120 is shown as SEQ ID NO:121.

Within one aspect the present invention provides an isolated polypeptide comprising a sequence having at least 90 percent or 95 percent sequence identity to a sequence of amino acid residues selected from the group consisting of SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161. The polypeptide may optionally comprise at least 15, at least 30, at least 45, or at least 60 sequential amino acids of an amino acid sequence as shown in SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161. In another embodiment, the isolated polypeptide is an amino acid residues are selected from the group consisting of SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161. The polypeptide may have a conservative amino acid change, compared with the amino acid sequence selected from the group consisting of SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161.

Within a another aspect the present invention provides a fusion protein comprising a polypeptide that comprises a sequence of amino acid residues selected from the group consisting of SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161; and a polyalkyl oxide moiety. The polyalkyl oxcide moiety may optionally be polyethylene glycol, such as a 20 kD mPEG propionaldehyde or a 30 kD mPEG propionaldehyde. The polyethylene glycol may be linear or branched. The polyethylene glycol may be covalently attached N-terminally or C-terminally to the polypeptide.

Within a another aspect the present invention provides a fusion protein comprising a first polypeptide and a second polypeptide joined by a peptide bond, wherein the first polypeptide comprises a sequence of amino acid residues selected from the group consisting of SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161; and a second polypeptide. The second polypeptide may optionally be an antibody fragment. The antibody fragment may optionally be F(ab'), F(ab), Fab', Fab, Fv, scFv, and/or minimal recognition unit. The second polypeptide may optionally be human albumin. The second polypeptide may optionally be a polypeptide selected from the group consisting of affinity tags, toxins, radionucleotides, enzymes and fluorophores.

Table 3 sets forth the one-letter codes used within SEQ ID NOs:30, 31, 32, 33, 34, and 35 to denote degenerate nucleotide positions. "Resolutions" are the nucleotides denoted by a code letter. "Complement" indicates the code for the complementary nucleotide(s). For example, the code Y denotes either C or T, and its complement R denotes A or G, with A being complementary to T, and G being complementary to C.

TABLE 3

| Nucleotide | Resolution | Complement | Resolution |
|---|---|---|---|
| A | A | T | T |
| C | C | G | G |

TABLE 3-continued

| Nucleotide | Resolution | Complement | Resolution |
|---|---|---|---|
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOs:30, 31, 32, 33, 34, and 35, encompassing all possible codons for a given amino acid, are set forth in Table 4.

TABLE 4

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence, for example, of SEQ ID NOs:19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161. Variant sequences can be readily tested for functionality as described herein.

One of ordinary skill in the art will also appreciate that different species can exhibit "preferential codon usage." In general, see, Grantham, et al., *Nuc. Acids Res.* 8:1893-912, 1980; Haas, et al. *Curr. Biol.* 6:315-24, 1996; Wain-Hobson, et al., *Gene* 13:355-64, 1981; Grosjean and Fiers, *Gene* 18:199-209, 1982; Holm, *Nuc. Acids Res.* 14:3075-87, 1986; Ikemura, *J. Mol. Biol.* 158:573-97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 4). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NOs:30, 31, 32, 33, 34, and 35 serves as a template for optimizing expression of polynucleotides in various cell types and species commonly used in the art and disclosed herein. Sequences containing preferential codons can be tested and optimized for expression in various species, and tested for functionality as disclosed herein.

Within another aspect, the present invention provides an isolated polynucleotide selected from the group consisting of SEQ ID NOs:1, 3, 5, 7, 9, 12, 14, 16, 18, 20, 22, 24, 26, 28, 74, 76, 78, 80, 82, 84, 86, 88, 90, 92, 94, 96, 98, 100, 102, 104, 106, 108, 110, 112, 114, 116, 122, 124, 126, 128, 130, 132, 134, 136, 138, 140, 142, 144, 146, 148, 150, 152, 154, 156, 158, and 160.

Within another aspect, the present invention provides an isolated polynucleotide capable of hybridizing to a sequence selected from the group consisting of SEQ ID NOs:1, 3, 5, 7, 9, 12, 14, 16, 18, 20, 22, 24, 26, 28, 74, 76, 78, 80, 82, 84, 86, 88, 90, 92, 94, 96, 98, 100, 102, 104, 106, 108, 110, 112, 114, 116, 122, 124, 126, 128, 130, 132, 134, 136, 138, 140, 142, 144, 146, 148, 150, 152, 154, 156, 158, and 160, or a complement thereof, under hybridization conditions of 50% formamide, 5×SSC (1×SSC: 0.15 M sodium chloride and 15 mM sodium citrate), 50 mM sodium phosphate (pH 7.6), 5× Denhardt's solution (100× Denhardt's solution: 2% (w/v) Ficoll 400, 2% (w/v) polyvinylpyrrolidone, and 2% (w/v) bovine serum albumin, 10% dextran sulfate, and 20 mg/ml denatured, sheared salmon sperm DNA at about 42° C. to about 70° C., wherein the isolated polynucleotide encodes a polypeptide having antiviral activity. Optionally, the encoded polypeptide has antiviral activity to hepatitis B and/or hepatitis C. Optionally, the isolated polynucleotide may encode at least a portion of a sequence selected from the group of SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161. The isolated polynucleotide may encode a polypeptide represented by SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, or 161.

In another aspect, the present invention provides an isolated polynucleotide encoding a polypeptide wherein the encoded polypeptide is selected from the group consisting of SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161.

In another aspect, the present invention provides an isolated polynucleotide encoding a polypeptide wherein the encoded polypeptide has at least 90 percent or 95 percent sequence identity to a sequence selected from the group consisting of SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161, wherein the encoded polypeptide has antiviral activity. Optionally, the encoded polypeptide has antiviral activity to hepatitis B and/or hepatitis C.

As previously noted, the isolated polynucleotides of the present invention include DNA and RNA. Methods for preparing DNA and RNA are well known in the art. In general, RNA is isolated from a tissue or cell that produces large amounts of Cysteine mutant IL-28 or IL-29 RNA. Such tissues and cells are identified by Northern blotting (Thomas, *Proc. Natl. Acad. Sci. USA* 77:5201, 1980), or by screening conditioned medium from various cell types for activity on target cells or tissue. Once the activity or RNA producing cell or tissue is identified, total RNA can be prepared using guanidinium isothiocyanate extraction followed by isolation by centrifugation in a CsCl gradient (Chirgwin et al., *Biochemistry* 18:52-94, 1979). Poly (A)$^+$ RNA is prepared from total RNA using the method of Aviv and Leder (*Proc. Natl. Acad. Sci. USA* 69:1408-12, 1972). Complementary DNA (cDNA) is prepared from poly(A)$^+$ RNA using known methods. In the alternative, genomic DNA can be isolated. Polynucleotides encoding Cysteine mutant IL-28 or IL-29 polypeptides are then identified and isolated by, for example, hybridization or PCR.

A full-length clones encoding Cysteine mutant IL-28 or IL-29 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to IL-28 receptor fragments, or other specific binding partners.

Those skilled in the art will recognize that the sequence disclosed in, for example, SEQ ID NOs:1, 3, and 5, respectively, represent mutations of single alleles of human IL-28 and IL-29 bands, and that allelic variation and alternative splicing are expected to occur. For example, an IL-29 variant has been identified where amino acid residue 169 (Asn) as shown in SEQ ID NO:4 is an Arg residue, as described in WO 02/086087. Such allelic variants are included in the present invention. Allelic variants of this sequence can be cloned by probing cDNA or genomic libraries from different individuals according to standard procedures. Allelic variants of the DNA sequence shown in SEQ ID NO:1, 3 and 5, including those containing silent mutations and those in which mutations result in amino acid sequence changes, in addition to the cysteine mutations, are within the scope of the present invention, as are proteins which are allelic variants of SEQ ID NOs:2, 4, and 6. cDNAs generated from alternatively spliced mRNAs, which retain the properties of Cysteine mutant IL-28 or IL-29 polypeptides, are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art, and mutations to the polynucleotides encoding cysteines or cysteine residues can be introduced as described herein.

Within embodiments of the invention, isolated variant or Cysteine mutant IL-28- and IL-29-encoding nucleic acid molecules can hybridize under stringent conditions to nucleic acid molecules having the nucleotide sequence of SEQ ID NOs:18, 20, 22, 24, 26, 28, 74, 76, 78, 80, 82, 84, 86, 88, 90, 92, 94, 96, 98, 100, 102, 104, 106, 108, 110, 112, 114, 116, 122, 124, 126, 128, 130, 132, 134, 136, 138, 140, 142, 144, 146, 148, 150, 152, 154, 156, 158, and 160 or to nucleic acid molecules having a nucleotide sequence complementary to SEQ ID NOs:18, 20, 22, 24, 26, 28, 74, 76, 78, 80, 82, 84, 86, 88, 90, 92, 94, 96, 98, 100, 102, 104, 106, 108, 110, 112, 114, 116, 122, 124, 126, 128, 130, 132, 134, 136, 138, 140, 142, 144, 146, 148, 150, 152, 154, 156, 158, and 160. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1-1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases.

It is well within the abilities of one skilled in the art to adapt these conditions for use with a particular polynucleotide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al, *Molecular Cloning: A Laboratory Manual*, Second Edition (Cold Spring Harbor Press 1989); Ausubel et at., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20-25° C. below the calculated $T_m$. For smaller probes, <50 base pairs, hybridization is typically carried out at the $T_m$ or 5-10°

C. below the calculated $T_m$. This allows for the maximum rate of hybridization for DNA-DNA and DNA-RNA hybrids.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. That is, nucleic acid molecules encoding a variant or Cysteine mutant IL-28 or IL-29 polypeptides hybridize with a nucleic acid molecule having the nucleotide sequence of SEQ ID NOs:18, 20, 22, 24, 26, 28, 74, 76, 78, 80, 82, 84, 86, 88, 90, 92, 94, 96, 98, 100, 102, 104, 106, 108, 110, 112, 114, 116, 122, 124, 126, 128, 130, 132, 134, 136, 138, 140, 142, 144, 146, 148, 150, 152, 154, 156, 158, and 160, respectively (or its complement) under stringent washing conditions, in which the wash stringency is equivalent to 0.5×-2×SSC with 0.1% SDS at 55-65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×-0.2×SSC with 0.1% sodium dodecyl sulfate (SDS) at 50-65° C. In other words, nucleic acid molecules encoding a variant of a Cysteine mutant IL-28 or IL-29 polypeptide hybridize with a nucleic acid molecule having the nucleotide sequence of SEQ ID NOs:18, 20, 22, 24, 26, 28, 74, 76, 78, 80, 82, 84, 86, 88, 90, 92, 94, 96, 98, 100, 102, 104, 106, 108, 110, 112, 114, 116, 122, 124, 126, 128, 130, 132, 134, 136, 138, 140, 142, 144, 146, 148, 150, 152, 154, 156, 158, and 160 (or its complement) under highly stringent washing conditions, in which the wash stringency is equivalent to 0.1-0.2×SSC with 0.1% SDS at 50-65° C., including 0.1×SSC with 0.1% SDS at 50° C., or 0.2×SSC with 0.1% SDS at 65° C.

The present invention also provides isolated IL-28 or IL-29 polypeptides that have a substantially similar sequence identity to the polypeptides of the present invention, for example SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159 or 161. The term "substantially similar sequence identity" is used herein to denote polypeptides comprising at least 80%, at least 90%, at least 91%, at least 92%, at least 93%, at least 94%, at least 95%, at least 96%, at least 97%, at least 98%, at least 99%, or greater than 99% sequence identity to the sequences shown in SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159 or 161, or their orthologs. The present invention also includes polypeptides that comprise an amino acid sequence having at least 80%, at least 90%, at least 91%, at least 92%, at least 93%, at least 94%, at least 95%, at least 96%, at least 97%, at least 98%, at least 99%, or greater than 99% sequence identity to a polypeptide or fragment thereof of the present invention. The present invention further includes polynucleotides that encode such polypeptides. The IL-28 and IL-29 polypeptides of the present invention are preferably recombinant polypeptides. In another aspect, the IL-28 and IL-29 polypeptides of the present invention have at least 15, at least 30, at least 45, or at least 60 sequential amino acids. For example, an IL-28 or IL-29 polypeptide of the present invention relates to a polypeptide having at least 15, at least 30, at least 45, or at least 60 sequential amino acids from SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159 or 161. Methods for determining percent identity are described below.

The present invention also contemplates variant nucleic acid molecules that can be identified using two criteria: a determination of the similarity between the encoded polypeptide with the amino acid sequence of SEQ ID NOs:19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159 or 161 respectively, and/or a hybridization assay, as described above. Such variants include nucleic acid molecules: (1) that hybridize with a nucleic acid molecule having the nucleotide sequence of SEQ ID NOs:18, 20, 22, 24, 26, 28, 74, 76, 78, 80, 82, 84, 86, 88, 90, 92, 94, 96, 98, 100, 102, 104, 106, 108, 110, 112, 114, 116, 122, 124, 126, 128, 130, 132, 134, 136, 138, 140, 142, 144, 146, 148, 150, 152, 154, 156, 158, and 160, respectively (or its complement) under stringent washing conditions, in which the wash stringency is equivalent to 0.5×-2×SSC with 0.1% SDS at 55-65° C.; or (2) that encode a polypeptide having at least 80%, at least 90%, at least 91%, at least 92%, at least 93%, at least 94%, at least 95%, at least 96%, at least 97%, at least 98%, at least 99%, or greater than 99% sequence identity to the amino acid sequence of SEQ ID NOs:19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159 or 161. Alternatively, variants can be characterized as nucleic acid molecules: (1) that hybridize with a nucleic acid molecule having the nucleotide sequence of SEQ ID NOs:18, 20, 22, 24, 26, 28, 74, 76, 78, 80, 82, 84, 86, 88, 90, 92, 94, 96, 98, 100, 102, 104, 106, 108, 110, 112, 114, 116, 122, 124, 126, 128, 130, 132, 134, 136, 138, 140, 142, 144, 146, 148, 150, 152, 154, 156, 158, or 160, respectively (or its complement) under highly stringent washing conditions, in which the wash stringency is equivalent to 0.1×-0.2×SSC with 0.1% SDS at 50-65° C.; and (2) that encode a polypeptide having at least 80%, at least 90%, at least 91%, at least 92%, at least 93%, at least 94%, at least 95%, at least 96%, at least 97%, at least 98%, at least 99%, or greater than 99% sequence identity to the amino acid sequence of SEQ ID NOs:19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159 or 161, respectively.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 4 (amino acids are indicated by the standard one-letter codes).

$$\frac{\text{Total number of identical matches}}{\begin{bmatrix} \text{length of the longer sequence plus the} \\ \text{number of gaps introduced into the longer} \\ \text{sequence in order to align the two sequences} \end{bmatrix}} \times 100$$

modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

TABLE 5

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 |   |   |   |   |   |   |   |   |   |   |   |   |   |   |   |   |   |   |   |
| R | -1 | 5 |   |   |   |   |   |   |   |   |   |   |   |   |   |   |   |   |   |   |
| N | -2 | 0 | 6 |   |   |   |   |   |   |   |   |   |   |   |   |   |   |   |   |   |
| D | -2 | -2 | 1 | 6 |   |   |   |   |   |   |   |   |   |   |   |   |   |   |   |   |
| C | 0 | -3 | -3 | -3 | 9 |   |   |   |   |   |   |   |   |   |   |   |   |   |   |   |
| Q | -1 | 1 | 0 | 0 | -3 | 5 |   |   |   |   |   |   |   |   |   |   |   |   |   |   |
| E | -1 | 0 | 0 | 2 | -4 | 2 | 5 |   |   |   |   |   |   |   |   |   |   |   |   |   |
| G | 0 | -2 | 0 | -1 | -3 | -2 | -2 | 6 |   |   |   |   |   |   |   |   |   |   |   |   |
| H | -2 | 0 | 1 | -1 | -3 | 0 | 0 | -2 | 8 |   |   |   |   |   |   |   |   |   |   |   |
| I | -1 | -3 | -3 | -3 | -1 | -3 | -3 | -4 | -3 | 4 |   |   |   |   |   |   |   |   |   |   |
| L | -1 | -2 | -3 | -4 | -1 | -2 | -3 | -4 | -3 | 2 | 4 |   |   |   |   |   |   |   |   |   |
| K | -1 | 2 | 0 | -1 | -3 | 1 | 1 | -2 | -1 | -3 | -2 | 5 |   |   |   |   |   |   |   |   |
| M | -1 | -1 | -2 | -3 | -1 | 0 | -2 | -3 | -2 | 1 | 2 | -1 | 5 |   |   |   |   |   |   |   |
| F | -2 | -3 | -3 | -3 | -2 | -3 | -3 | -3 | -1 | 0 | 0 | -3 | 0 | 6 |   |   |   |   |   |   |
| P | -1 | -2 | -2 | -1 | -3 | -1 | -1 | -2 | -2 | -3 | -3 | -1 | -2 | -4 | 7 |   |   |   |   |   |
| S | 1 | -1 | 1 | 0 | -1 | 0 | 0 | 0 | -1 | -2 | -2 | 0 | -1 | -2 | -1 | 4 |   |   |   |   |
| T | 0 | -1 | 0 | -1 | -1 | -1 | -1 | -2 | -2 | -1 | -1 | -1 | -1 | -2 | -1 | 1 | 5 |   |   |   |
| W | -3 | -3 | -4 | -4 | -2 | -2 | -3 | -2 | -2 | -3 | -2 | -3 | -1 | 1 | -4 | -3 | -2 | 11 |   |   |
| Y | -2 | -2 | -2 | -3 | -2 | -1 | -2 | -3 | 2 | -1 | -1 | -2 | -1 | 3 | -3 | -2 | -2 | 2 | 7 |   |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant IL-28 or IL-29. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by Variant IL-28 or IL-29 Cysteine mutant polypeptides or polypeptides with substantially similar sequence identity are characterized as having one or more amino acid substitutions, deletions or additions. These changes are preferably of a minor nature, that is conservative amino acid substitutions (see Table 6) and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20-25 residues, or an affinity tag. The present invention thus includes polypeptides of from about 146 to 207 amino acid residues that comprise a sequence having at least 80%, at least 90%, at least 91%, at least 92%, at least 93%, at least 94%, at least 95%, at least 96%, at least 97%, at least 98%, at least 99%, or greater than 99% sequence identity to the corresponding region of SEQ ID NOs:19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159 or 161. Polypeptides comprising affinity tags can further comprise a proteolytic cleavage site between the IL-28 and IL-29 polypeptide and the affinity tag. Preferred such sites include thrombin cleavage sites and factor Xa cleavage sites.

TABLE 6

| Conservative amino acid substitutions | |
|---|---|
| Basic: | arginine |
|  | lysine |
|  | histidine |
| Acidic: | glutamic acid |
|  | aspartic acid |

TABLE 6-continued

Conservative amino acid substitutions

| | |
|---|---|
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Determination of amino acid residues that comprise regions or domains that are critical to maintaining structural integrity can be determined. Within these regions one can determine specific residues that will be more or less tolerant of change and maintain the overall tertiary structure of the molecule. Methods for analyzing sequence structure include, but are not limited to alignment of multiple sequences with high amino acid or nucleotide identity, secondary structure propensities, binary patterns, complementary packing and buried polar interactions (Barton, *Current Opin. Struct. Biol.* 5:372-376, 1995 and Cordes et al., *Current Opin. Struct. Biol.* 6:3-10, 1996). In general, when designing modifications to molecules or identifying specific fragments determination of structure will be accompanied by evaluating activity of modified molecules.

Amino acid sequence changes are made in Cysteine mutant IL-28 or IL-29 polypeptides so as to minimize disruption of higher order structure essential to biological activity. For example, where the Cysteine mutant IL-28 or IL-29 polypeptide comprises one or more helices, changes in amino acid residues will be made so as not to disrupt the helix geometry and other components of the molecule where changes in conformation abate some critical function, for example, binding of the molecule to its binding partners. The effects of amino acid sequence changes can be predicted by, for example, computer modeling as disclosed above or determined by analysis of crystal structure (see, e.g., Lapthorn et al., *Nat. Struct. Biol.* 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same cysteine pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance (NMR), digestive peptide mapping and epitope mapping are also known methods for analyzing folding and structurally similarities between proteins and polypeptides (Schaanan et al., *Science* 257:961-964, 1992).

A Hopp/Woods hydrophilicity profile of the Cysteine mutant IL-28 or IL-29 protein sequence as shown in SEQ ID NOs:19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159 or 161 can be generated (Hopp et al., *Proc. Natl. Acad. Sci.*78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. Those skilled in the art will recognize that hydrophilicity or hydrophobicity will be taken into account when designing modifications in the amino acid sequence of a Cysteine mutant IL-28 or IL-29 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp.

The identities of essential amino acids can also be inferred from analysis of sequence similarity between IFN-α and members of the family of IL-28A, IL-28B, and IL-29 (as shown in Tables 1 and 2). Using methods such as "FASTA" analysis described previously, regions of high similarity are identified within a family of proteins and used to analyze amino acid sequence for conserved regions. An alternative approach to identifying a variant polynucleotide on the basis of structure is to determine whether a nucleic acid molecule encoding a potential variant IL-28 or IL-29 gene can hybridize to a nucleic acid molecule as discussed above.

Other methods of identifying essential amino acids in the polypeptides of the present invention are procedures known in the art, such as site-directed mutagenesis or alanine-scanning mutagenesis (Cunningham and Wells, *Science* 244:1081 (1989), Bass et al., *Proc. Natl Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant Cysteine mutant molecules are tested for biological or biochemical activity as disclosed below to identify amino acid residues that are critical to the activity of the molecule. See also, Hilton et al, *J. Biol. Chem.* 271:4699 (1996).

The present invention also includes functional fragments of Cysteine mutant IL-28 or IL-29 polypeptides and nucleic acid molecules encoding such functional fragments. A "functional" Cysteine mutant IL-28 or IL-29 or fragment thereof as defined herein is characterized by its proliferative or differentiating activity, by its ability to induce or inhibit specialized cell functions, or by its ability to bind specifically to an anti-IL-28 or IL-29 antibody or IL-28 receptor (either soluble or immobilized). The specialized activities of Cysteine mutant IL-28 or IL-29 polypeptides and how to test for them are disclosed herein. As previously described herein, IL-28 and IL-29 polypeptides are characterized by a six-helical-bundle. Thus, the present invention further provides fusion proteins encompassing: (a) polypeptide molecules comprising one or more of the helices described above; and (b) functional fragments comprising one or more of these helices. The other polypeptide portion of the fusion protein may be contributed by another helical-bundle cytokine or interferon, such as IFN-α, or by a non-native and/or an unrelated secretory signal peptide that facilitates secretion of the fusion protein.

The Cysteine mutant IL-28 or IL-29 polypeptides of the present invention, including full-length polypeptides, biologically active fragments, and fusion polypeptides can be produced according to conventional techniques using cells into which have been introduced an expression vector encoding the polypeptide. As used herein, "cells into which have been introduced an expression vector" include both cells that have been directly manipulated by the introduction of exogenous DNA molecules and progeny thereof that contain the introduced DNA. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al., eds., *Current Protocols in Molecular Biology,* John Wiley and Sons, Inc., NY, 1987.

Within another aspect, the present invention provides an expression vector comprising the following operably linked elements: a transcription promoter; a DNA segment encoding a polypeptide as described herein; and a transcription terminator.

The present invention also provides an expression vector comprising an isolated and purified DNA molecule including the following operably linked elements: a transcription promoter; a DNA segment encoding a polypeptide having at least 90 percent or 95 percent sequence identity with a polypeptide selected from the group consisting of SEQ ID NOs:19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161; and a transcription terminator. The DNA molecule may further comprise a secretory signal sequence operably linked to the DNA segment. The encoding polypeptide may further comprise an affinity tag as described herein. The present invention also provides a cultured cell containing the above-described expression vector. The encoded polypeptide may optionally comprise at least 15, at least 30, at least 45, or at least 60 sequential amino acids of an amino acid sequence as shown in SEQ ID NOs:19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161. The encoded polypeptide may optionally have antiviral activity, e.g., hepatitis B and hepatitis C.

Within another aspect the present invention provides a cultured cell comprising an expression vector as disclosed above.

Within another aspect the present invention provides a method of producing a protein comprising: culturing a cell as disclosed above under conditions wherein the DNA segment is expressed; and recovering the protein encoded by the DNA segment.

In general, a DNA sequence encoding a Cysteine mutant IL-28 or IL-29 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a Cysteine mutant IL-28 or IL-29 polypeptide into the secretory pathway of a host cell, a secretory signal sequence (also known as a leader sequence, prepro sequence or pre sequence) is provided in the expression vector. The secretory signal sequence may be that of Cysteine mutant IL-28 or IL-29, e.g., SEQ ID NO:119 or SEQ ID NO:121, or may be derived from another secreted protein (e.g., t-PA; see, U.S. Pat. No. 5,641,655) or synthesized de novo. The secretory signal sequence is operably linked to the Cysteine mutant IL-28 or IL-29 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

A wide variety of suitable recombinant host cells includes, but is not limited to, gram-negative prokaryotic host organisms. Suitable strains of *E. coli* include W3110, K12-derived strains MM294, TG-1, JM-107, BL21, and UT5600. Other suitable strains include: BL21(DE3), BL21(DE3)pLysS, BL21(DE3)pLysE, DH1, DH4T, DH5, DH5T, DH5IF', DH5IMCR, DH10B, DH10B/p3, DH11S, C600, HB101, JM101, JM105, JM109, JM110, K38, RR1, Y1088, Y1089, CSH18, ER1451, ER1647, *E. coli* K12, *E. coli* K12 RV308, *E. coli* K12 C600, *E. coli* HB101, *E. coli* K12 C600 R.sub.k-M.sub.k-, *E. coli* K12 RR1 (see, for example, Brown (ed.), *Molecular Biology Labfax* (Academic Press 1991)). Other gram-negative prokaryotic hosts can include *Serratia, Pseudomonas, Caulobacter*. Prokaryotic hosts can include gram-positive organisms such as *Bacillus*, for example, *B. subtilis* and *B. thuringienesis*, and *B. thuringienesis* var. israelensis, as well as *Streptomyces*, for example, *S. lividans, S. ambofaciens, S. fradiae*, and *S. griseofuscus*. Suitable strains of *Bacillus subtilus* include BR151, YB886, MI119, M1120, and B170 (see, for example, Hardy, "Bacillus Cloning Methods," in *DNA Cloning: A Practical Approach*, Glover (ed.) (IRL Press 1985)). Standard techniques for propagating vectors in prokaryotic hosts are well-known to those of skill in the art (see, for example, Ausubel et al (eds.), *Short Protocols in Molecular Biology*, 3$^{rd}$ *Edition* (John Wiley & Sons 1995); Wu et al, *Methods in Gene Biotechnology* (CRC Press, Inc. 1997)). In one embodiment, the methods of the present invention use Cysteine mutant IL-28 or IL-29 expressed in the W3110 strain, which has been deposited at the American Type Culture Collection (ATCC) as ATCC # 27325.

When large scale production of Cysteine mutant IL-28 or IL-29 using the expression system of the present invention is required, batch fermentation can be used. Generally, batch fermentation comprises that a first stage seed flask is prepared by growing *E. coli* strains expressing Cysteine mutant IL-28 or IL-29 in a suitable medium in shake flask culture to allow for growth to an optical density (OD) of between 5 and 20 at 600 nm. A suitable medium would contain nitrogen from a source(s) such as ammonium sulfate, ammonium phosphate, ammonium chloride, yeast extract, hydrolyzed animal proteins, hydrolyzed plant proteins or hydrolyzed caseins. Phosphate will be supplied from potassium phosphate, ammonium phosphate, phosphoric acid or sodium phosphate. Other components would be magnesium chloride or magnesium sulfate, ferrous sulfate or ferrous chloride, and other trace elements. Growth medium can be supplemented with carbohydrates, such as fructose, glucose, galactose, lactose, and glycerol, to improve growth. Alternatively, a fed batch culture is used to generate a high yield of Cysteine mutant IL-28 or IL-29 protein. The Cysteine mutant IL-28 or IL-29 producing *E. coli* strains are grown under conditions similar to those described for the first stage vessel used to inoculate a batch fermentation.

Following fermentation the cells are harvested by centrifugation, re-suspended in homogenization buffer and homogenized, for example, in an APV-Gaulin homogenizer (Invensys APV, Tonawanda, N.Y.) or other type of cell disruption equipment, such as bead mills or sonicators. Alternatively, the cells are taken directly from the fermentor and homogenized in an APV-Gaulin homogenizer. The washed inclusion body prep can be solubilized using guanidine hydrochloride (5-8 M) or urea (7-8 M) containing a reducing agent such as beta mercaptoethanol (10-100 mM) or dithiothreitol (5-50 mM). The solutions can be prepared in Tris, phopshate, HEPES or other appropriate buffers. Inclusion bodies can also be solubilized with urea (2-4 M) containing sodium lauryl sulfate (0.1-2%). In the process for recovering purified Cysteine mutant IL-28 or IL-29 from transformed *E. coli* host strains in which the Cysteine mutant IL-28 or IL-29 is accumulates as refractile inclusion bodies, the cells are disrupted and the inclusion bodies are recovered by centrifugation. The inclusion bodies are then solubilized and denatured in 6 M guanidine hydrochloride containing a reducing agent. The reduced Cysteine mutant IL-28 or IL-29 is then oxidized in a controlled renaturation step. Refolded Cysteine mutant IL-28 or IL-29 can be passed through a filter for clarification and removal of insoluble protein. The solution is then passed through a filter for clarification and removal of insoluble protein. After the Cysteine mutant IL-28 or IL-29 protein is refolded and concentrated, the refolded Cysteine mutant IL-28 or IL-29 protein is captured in dilute buffer on a cation exchange column and purified using hydrophobic interaction chromatography.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-5, 1982), DEAE-dextran mediated transfection (Ausubel et al., *ibid.*), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980-90, 1989; Wang and Finer, *Nature Med.* 2:714-6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al, U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols, Methods in Molecular Biology*, Totowa, N.J., Humana Press, 1995. The second method of making recombinant baculovirus utilizes a transposon-based system described by Luckow (Luckow, V. A, et al., *J Virol* 67:4566-79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the Cysteine mutant IL-28 or IL-29 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case Cysteine mutant IL-28 or IL-29. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971-6, 1990; Bonning, B. C. et al., *J. Gen. Virol.* 75:1551-6, 1994; and, Chazenbalk, G. D., and Rapoport, B., *J. Biol. Chem.* 270: 1543-9, 1995. In such transfer vector constructs, a short or long version of the basic protein promoter can be used. Moreover, transfer vectors can be constructed which replace the native IL-28 or IL-29 secretory signal sequences with secretory signal sequences derived from insect proteins. For example, a secretory signal sequence from Ecdysteroid Glucosyltransferase (EGT), honey bee Meliffin (Invitrogen, Carlsbad, Calif.), or baculovirus gp67 (PharMingen, San Diego, Calif.) can be used in constructs to replace the native IL-28 or IL-29 secretory signal sequence. In addition, transfer vectors can include an in-frame fusion with DNA encoding an epitope tag at the C— or N-terminus of the expressed Cysteine mutant IL-28 or IL-29 polypeptide, for example, a Glu-Glu epitope tag (Grussenmeyer, T. et al., *Proc. Natl. Acad. Sci.* 82:7952-4, 1985). Using techniques known in the art, a transfer vector containing Cysteine mutant IL-28 or IL-29 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses Cysteine mutant IL-28 or IL-29 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435).

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al, U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Ktuyveromyces lactis, Ktuyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459-65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. The use of *Pichia methanotica* as host for the production of recombinant proteins is disclosed in U.S. Pat. Nos. 5,955,349, 5,888,768 and 6,001,597, U.S. Pat. No. 5,965,389, U.S. Pat. No. 5,736,383, and U.S. Pat. No. 5,854,039.

It is preferred to purify the polypeptides and proteins of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide or protein is substantially free of other polypeptides or proteins, particularly those of animal origin.

Expressed recombinant Cysteine mutant IL-28 or IL-29 proteins (including chimeric polypeptides and multimeric proteins) are purified by conventional protein purification methods, typically by a combination of chromatographic techniques. See, in general, *Affinity Chromatoiraphy: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321-1325, 1988. Proteins comprising a glu-glu tag can be purified by immunoaffinity chromatography according to conventional procedures. See, for example, Grussenmeyer et al., supra. Maltose binding protein fusions are purified on an amylose column according to methods known in the art.

Cysteine mutant IL-28 or IL-29 polypeptides can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Pelptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989. In vitro synthesis is particularly advantageous for the preparation of smaller polypeptides.

Using methods known in the art, Cysteine mutant IL-28 or IL-29 proteins can be prepared as monomers or multimers; glycosylated or non-glycosylated; pegylated or non-pegylated; fusion proteins; and may or may not include an initial methionine amino acid residue. Cysteine mutant IL-28 or IL-29 conjugates used for therapy may comprise pharmaceutically acceptable water-soluble polymer moieties. Conjugation of interferons with water-soluble polymers has been shown to enhance the circulating half-life of the interferon, and to reduce the immunogenicity of the polypeptide (see, for example, Nieforth et al, *Clin. Pharmacol. Ther.* 59:636 (1996), and Monkarsh et al, *Anal. Biochem.* 247:434 (1997)).

Suitable water-soluble polymers include polyethylene glycol (PEG), monomethoxy-PEG, mono-(C1-C10)alkoxy-PEG, aryloxy-PEG, poly-(N-vinyl pyrrolidone)PEG, tresyl monomethoxy PEG, monomethoxy-PEG propionaldehyde, PEG propionaldehyde, bis-succinimidyl carbonate PEG, propylene glycol homopolymers, a polypropylene oxide/ethylene oxide co-polymer, polyoxyethylated polyols (e.g., glycerol), monomethoxy-PEG butyraldehyde, PEG butyraldehyde, monomethoxy-PEG acetaldehyde, PEG acetaldehyde, methoxyl PEG-succinimidyl propionate, methoxyl PEG-succinimidyl butanoate, polyvinyl alcohol, dextran, cellulose, or other carbohydrate-based polymers. Suitable PEG may have a molecular weight from about 600 to about 60,000, including, for example, 5,000 daltons, 12,000 daltons, 20,000 daltons, 30,000 daltons, and 40,000 daltons, which can be linear or branched. A Cysteine mutant IL-28 or IL-29 conjugate can also comprise a mixture of such water-soluble polymers.

One example of a Cysteine mutant IL-28 or IL-29 conjugate comprises a Cysteine mutant IL-28 or IL-29 moiety and a polyalkyl oxide moiety attached to the N-terminus of the Cysteine mutant IL-28 or IL-29 moiety. PEG is one suitable polyalkyl oxide. As an illustration, Cysteine mutant IL-28 or IL-29 can be modified with PEG, a process known as "PEGylation." PEGylation of Cysteine mutant IL-28 or IL-29 can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, Cysteine mutant IL-28 or IL-29 conjugates are formed by condensing activated PEG, in which a terminal hydroxy or amino group of PEG has been replaced by an activated linker (see, for example, Karasiewicz et at., U.S. Pat. No. 5,382,657).

PEGylation by acylation typically requires reacting an active ester derivative of PEG with a Cysteine mutant IL-28 or IL-29 polypeptide. An example of an activated PEG ester is PEG esterified to N-hydroxysuccinimide. As used herein, the term "acylation" includes the following types of linkages between Cysteine mutant IL-28 or IL-29 and a water-soluble polymer: amide, carbamate, urethane, and the like. Methods for preparing PEGylated Cysteine mutant IL-28 or IL-29 by acylation will typically comprise the steps of (a) reacting an Cysteine mutant IL-28 or IL-29 polypeptide with PEG (such as a reactive ester of an aldehyde derivative of PEG) under conditions whereby one or more PEG groups attach to Cysteine mutant IL-28 or IL-29, and (b) obtaining the reaction product(s). Generally, the optimal reaction conditions for acylation reactions will be determined based upon known parameters and desired results. For example, the larger the ratio of PEG: Cysteine mutant IL-28 or IL-29, the greater the percentage of polyPEGylated Cysteine mutant IL-28 or IL-29 product.

PEGylation by alkylation generally involves reacting a terminal aldehyde, e.g., propionaldehyde, butyraldehyde, acetaldehyde, and the like, derivative of PEG with Cysteine mutant IL-28 or IL-29 in the presence of a reducing agent. PEG groups are preferably attached to the polypeptide via a $—CH_2—NH_2$ group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the $\epsilon$-amino groups of the lysine residues and the $\alpha$-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups.

Reductive alkylation to produce a substantially homogenous population of monopolymer Cysteine mutant IL-28 or IL-29 conjugate molecule can comprise the steps of: (a) reacting a Cysteine mutant IL-28 or IL-29 polypeptide with a reactive PEG under reductive alkylation conditions at a pH suitable to permit selective modification of the $\alpha$-amino group at the amino terminus of the Cysteine mutant IL-28 or IL-29, and (b) obtaining the reaction product(s). The reducing agent used for reductive alkylation should be stable in aqueous solution and preferably be able to reduce only the Schiff base formed in the initial process of reductive alkylation. Preferred reducing agents include sodium borohydride, sodium cyanoborohydride, dimethylamine borane, trimethylamine borane, and pyridine borane.

For a substantially homogenous population of monopolymer Cysteine mutant IL-28 or IL-29 conjugates, the reductive alkylation reaction conditions are those that permit the selective attachment of the water-soluble polymer moiety to the N-terminus of Cysteine mutant IL-28 or IL-29. Such reaction conditions generally provide for pKa differences between the lysine amino groups and the $\alpha$-amino group at the N-terminus. The pH also affects the ratio of polymer to protein to be used. In general, if the pH is lower, a larger excess of polymer to protein will be desired because the less reactive the N-terminal $\alpha$-group, the more polymer is needed to achieve optimal conditions. If the pH is higher, the polymer: Cysteine mutant IL-28 or IL-29 need not be as large because more reactive groups are available. Typically, the pH will fall within the range of 3-9, or 3-6. Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, about 12 kDa to about 40 kDa, or about 20 kDa to about 30 kDa. The molar ratio of water-soluble polymer to Cysteine mutant IL-28 or IL-29 will generally be in the range of 1:1 to 100:1. Typically, the molar ratio of water-soluble polymer to Cysteine mutant IL-28 or IL-29 will be 1:1 to 20:1 for polyPEGylation, and 1:1 to 5:1 for monoPEGylation.

General methods for producing conjugates comprising interferon and water-soluble polymer moieties are known in the art. See, for example, Karasiewicz et at., U.S. Pat. No. 5,382,657, Greenwald et at., U.S. Pat. No. 5,738, 846, Nieforth et al, *Clin. Pharmacol. Ther.* 59:636 (1996), Monkarsh et al, *Anal. Biochem.* 247:434 (1997). PEGylated species can be separated from unconjugated Cysteine mutant IL-28 or IL-29 polypeptides using standard purification methods, such as dialysis, ultrafiltration, ion exchange chromatography, affinity chromatography, size exclusion chromatography, and the like.

The Cysteine mutant IL-28 or IL-29 molecules of the present invention are capable of specifically binding the IL-28 receptor and/or acting as an antiviral agent. The binding of Cysteine mutant IL-28 or 11-29 polypeptides to the IL-28 receptor can be assayed using established approaches. Cysteine mutant IL-28 or IL-29 can be iodinated using an iodobead (Pierce, Rockford, Ill.) according to manufacturer's directions, and the $^{125}$I-IL-28 or $^{125}$I-IL-29 can then be used as described below.

In a first approach fifty nanograms of $^{125}$I-IL-28 or $^{125}$I-IL-29 can be combined with 1000 ng of IL-28 receptor human IgG fusion protein, in the presence or absence of possible binding competitors including unlabeled cysteine mutant IL-28, cysteine mutant IL-29, IL-28, or IL-29. The same binding reactions would also be performed substituting other cytokine receptor human IgG fusions as controls for specificity. Following incubation at 4° C., protein-G (Zymed, San Fransisco, Calif.) is added to the reaction, to capture the receptor-IgG fusions and any proteins bound to them, and the reactions are incubated another hour at 4° C. The protein-G sepharose is then collected, washed three times with PBS and $^{125}$I-IL-28 or $^{125}$I-IL-29 bound is measure by gamma counter (Packard Instruments, Downers Grove, Ill.).

In a second approach, the ability of molecules to inhibit the binding of $^{125}$I-IL-28 or $^{125}$I-IL-29 to plate bound receptors can be assayed. A fragment of the IL-28 receptor, representing the extracellular, ligand binding domain, can be adsorbed to the wells of a 96 well plate by incubating 100 µl of 1 g/mL solution of receptor in the plate overnight. In a second form, a receptor-human IgG fusion can be bound to the wells of a 96 well plate that has been coated with an antibody directed against the human IgG portion of the fusion protein. Following coating of the plate with receptor the plate is washed, blocked with SUPERBLOCK (Pierce, Rockford, Ill.) and washed again. Solutions containing a fixed concentration of $^{125}$I-IL-28 or $^{125}$I-IL-29 with or without increasing concentrations of potential binding competitors including, Cystein mutant IL-28, cysteine mutant IL-29, IL-28 and IL-29, and 100 μl of the solution added to appropriate wells of the plate. Following a one hour incubation at 4° C. the plate is washed and the amount $^{125}$I-IL-28 or $^{125}$I-IL-29 bound determined by counting (Topcount, Packard Instruments, Downers grove, Ill.). The specificity of binding of $^{125}$I-IL-28 or $^{125}$I-IL-29 can be defined by receptor molecules used in these binding assays as well as by the molecules used as inhibitors.

In addition to pegylation, human albumin can be genetically coupled to a polypeptide of the present invention to prolong its half-life. Human albumin is the most prevalent naturally occurring blood protein in the human circulatory system, persisting in circulation in the body for over twenty days. Research has shown that therapeutic proteins genetically fused to human albumin have longer half-lives. An IL28 or IL29 albumin fusion protein, like pegylation, may provide patients with long-acting treatment options that offer a more convenient administration schedule, with similar or improved efficacy and safety compared to currently available treatments (U.S. Pat. No. 6,165,470; Syed et al., *Blood,* 89(9): 3243-3253 (1997); Yeh et al., *Proc. Natl. Acad. Sci. USA,* 89:1904-1908 (1992); and Zeisel et al., *Horm. Res.,* 37:5-13 (1992)).

Like the aforementioned peglyation and human albumin, an Fc portion of the human IgG molecule can be fused to a polypeptide of the present invention. The resultant fusion protein may have an increased circulating half-life due to the Fc moiety (U.S. Pat. No. 5,750,375, U.S. Pat. No. 5843,725, U.S. Pat. No. 6,291,646; Barouch et al., *Journal of Immunology,* 61:1875-1882 (1998); Barouch et al., *Proc. Natl. Acad. Sci. USA,* 97(8):4192-4197 (Apr. 11, 2000); and Kim et al., *Transplant Proc.,* 30(8):4031-4036 (Dec. 1998)).

Methods for detection and diagnosis of viral infections are well known to those skilled in the art. The exact method used for measuring a reduction in virus in response to administration of molecules of the present invention will be dependent upon the species of virus and whether the infection is in vitro or in vivo. If the infection is in vivo, measurement and detection of infection and changes in the levels of infection, can vary depending on subject infected, type of viral infection, and the like. For example, methods include, but are not limited to, measuring changes in CD4 cell counts, serologic tests, measuring the DNA of the virus and RNA of the virus by conventional and real-time quantitative polymerase chain reaction assays, viral induced antibody levels, immunofluorescence and enzyme-linked immunosorbant assays, cytopathic effects, and histology.

Antiviral effects may be direct or indirect. An example of a direct antiviral effect is, for example, where Cysteine mutant IL-28 or IL-29 polypeptide competes for a viral receptor or co-receptor to block viral infection. Cysteine mutant IL-28 or IL-29 may be given parentally to prevent viral infection or to reduce ongoing viral replication and re-infection (Gayowski, T. et al., *Transiplantation* 64:422-426, 1997). An example of an indirect antiviral effect is, for example, where a Cysteine mutant IL-28 or IL-29 may bind CD4 or another leukocyte receptor and exhibit antiviral effects by modulating the effects of the immune response.

Of particular interest is the use of Cysteine mutant IL-28 or IL-29 as an antiviral therapeutic for viral leukemias (HTLV), AIDS (HIV), or gastrointestinal viral infections caused by, for example, rotavirus, calicivirus (e.g., Norwalk Agent) and certain strains of pathogenic adenovirus, Hepatitis B and C.

Additional types of viral infections for Cysteine mutant IL-28 or IL-29 use include, but are not limited to: infections caused by DNA Viruses (e.g., Herpes Viruses such as Herpes Simplex viruses, Epstein-Barr virus, Cytomegalovirus; Pox viruses such as Variola (small pox) virus; Hepadnaviruses (e.g, Hepatitis B virus); Papilloma viruses; Adenoviruses); RNA Viruses (e.g., HIV I, II; HTLV I, II; Poliovirus; Hepatitis A; coronoviruses, such as sudden acute respiratory syndrome (SARS); Orthomyxoviruses (e.g., Influenza viruses); Paramyxoviruses (e.g., Measles virus); Rabies virus; Hepatitis C virus), Flaviviruses, Influenza viruses; caliciviruses; rabies viruses, rinderpest viruses, Arena virus, and the like. Moreover, examples of the types of virus-related diseases for which Cysteine mutant IL-28 or IL-29 could be used include, but are not limited to: Acquired immunodeficiency; Severe Acute Respiratory Syndrome (SARS); Hepatitis; Gastroenteritis; Hemorrhagic diseases; Enteritis; Carditis; Encephalitis; Paralysis; Brochiolitis; Upper and lower respiratory disease; Respiratory Papillomatosis; Arthritis; Disseminated disease, Meningitis, Mononucleosis. In addition, Cysteine mutant IL-28 or IL-29 can be used in various applications for antiviral immunotherapy, and in conjunction with other cytokines, other protein or small molecule antivirals, and the like.

Clinically, diagnostic tests for HCV include serologic assays for antibodies and molecular tests for viral particles. Enzyme immunoassays are available (Vrielink et al., *Transfusion* 37:845-849, 1997), but may require confirmation using additional tests such as an immunoblot assay (Pawlotsky et al., *Hepatology* 27:1700-1702, 1998). Qualitative and quantitative assays generally use polymerase chain reaction techniques, and are preferred for assessing viremia and treatment response (Poynard et al., *Lancet* 352:1426-1432, 1998; McHutchinson et al., *N. Engl. J. Med.* 339:1485-1492, 1998). Several commercial tests are available, such as, quantitative RT-PCR (Amplicor HCV Monitor™, Roche Molecular Systems, Branchburg, N.J.) and a branched DNA (deoxyribonucleic acid) signal amplification assay (Quantiplex™ HCV RNA Assay [bDNA], Chiron Corp., Emeryville, Calif.). A non-specific laboratory test for HCV infection measures alanine aminotransferase level (ALT) and is inexpensive and readily available (National Institutes of Health Consensus Development Conference Panel, *Hepatology* 26 (*Suppl.* 1):2S-10S, 1997). Histologic evaluation of liver biopsy is generally considered the most accurate means for determining HCV progression (Yano et al., *Hepatology* 23:1334-1340, 1996.) For a review of clinical tests for HCV, see, Lauer et al., *N. Engl. J. Med.* 345:41-52, 2001.

There are several in vivo models for testing HBV and HCV that are known to those skilled in art. With respect to HCV, for example, the HCV Replicon model is a cell-based system to study the effectiveness of a drug to inhibit HCV replication (Blight et al., *Science,* 290(5498):1972-1974 (Dec. 8, 2000); and Lohmann et al., *Science,* 285(5424):110-113 (Jul. 2, 1999)). A well-known and accepted in vitro HBV model to one of skill in the art can be used to determine the anti-HBV activity of a test molecule is disclosed in Korba et al., *Antiviral Res.,* 19(1):55-70 (1992) and Korba et al., *Antiviral Res.,* 15(3):217-228 (1991).

For example, the effects of Cysteine mutant IL-28 or IL-29 on mammals infected with HBV can accessed using a woodchuck model. Briefly, woodchucks chronically infected with woodchuck hepatitis virus (WHV) develop hepatitis and hepatocellular carcinoma that is similar to disease in humans chronically infected with HBV. The model has been used for the preclinical assessment of antiviral activity. A chronically infected WHV strain has been established and neonates are inoculated with serum to provide animals for studying the effects of certain compounds using this model. (For a review, see, Tannant et al., *ILAR J.* 42 (2):89-102, 2001). Chimpanzees may also be used to evaluate the effect of Cysteine mutant IL-28 or IL-29 on HBV infected mammals. Using chimpanzees, characterization of HBV was made and these studies demonstrated that the chimpanzee disease was remarkably similar to the disease in humans (Barker et al., *J. Infect. Dis.* 132:451-458, 1975 and Tabor et al., *J. Infect. Dis.* 147:531-534, 1983.) The chimpanzee model has been used in evaluating vaccines (Prince et al., In: *Vaccines* 97 Cold Spring Harbor Laboratory Press, 1997.) Therapies for HIV are routinely tested using non-human primates infected with simian immunodeficiency viruses (for a review, see, Hirsch et al., *Adv. Pharmcol.* 49:437-477, 2000 and Nathanson et al., *AIDS* 13 (*suppl. A*):S113-S120, 1999.) For a review of use of non-human primates in HIV, hepatitis, malaria, respiratory syncytial virus, and other diseases, see, Sibal et al., *ILAR J.* 42 (2):74-84, 2001. A recently developed transgenic mouse model (Guidotti et al., *Journal of Virology* 69:6158-6169, 1995) supports the replication of high levels of infectious HBV and has been used as a chemotherapeutic model for HBV infection. Transgenic mice are treated with antiviral drugs and the levels of HBV DNA and RNA are measured in the transgenic mouse liver and serum following treatment. HBV protein levels can also be measured in the transgenic mouse serum following treatment. This model has been used to evaluate the effectiveness of lamivudine and IFN-alpha in reducing HBV viral titers (Morrey et al., *Antiviral Therapy* 3 :59-68, 1998).

Moreover, Cysteine mutant IL-28 or IL-29 polypeptides and proteins of the present invention can be characterized by their activity, that is, modulation of the proliferation, differentiation, migration, adhesion, gene expression or metabolism of responsive cell types. Biological activity of Cysteine mutant IL-28 or IL-29 polypeptides and proteins is assayed using in vitro or in vivo assays designed to detect cell proliferation, differentiation, migration or adhesion; or changes in gene expression or cellular metabolism (e.g., production of other growth factors or other macromolecules). Many suitable assays are known in the art, and representative assays are disclosed herein. Assays using cultured cells are most convenient for screening, such as for determining the effects of amino acid substitutions, deletions, or insertions.

Activity of Cysteine mutant IL-28 or IL-29 proteins can be measured in vitro using cultured cells or in vivo by administering molecules of the claimed invention to an appropriate animal model. Assays measuring cell proliferation or differentiation are well known in the art. For example, assays measuring proliferation include such assays as chemosensitivity to neutral red dye (Cavanaugh et al., *Investigational New Drugs* 8:347-354, 1990), incorporation of radiolabelled nucleotides (as disclosed by, e.g., Raines and Ross, *Methods Enzymol.* 109:749-773, 1985; Wahl et al., *Mol. Cell Biol.* 8:5016-5025, 1988; and Cook et al., *Analytical Biochem.* 179:1-7, 1989), incorporation of 5-bromo-2'-deoxyuridine (BrdU) in the DNA of proliferating cells (Porstmann et al., *J. Immunol. Methods* 82:169-179, 1985), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988). Differentiation can be assayed using suitable precursor cells that can be induced to differentiate into a more mature phenotype. Assays measuring differentiation include, for example, measuring cell-surface markers associated with stage-specific expression of a tissue, enzymatic activity, functional activity or morphological changes (Watt, *FASEB,* 5:281-284, 1991; Francis, *Differentiation* 57:63-75, 1994; Raes, *Adv. Anim. Cell Biol. Technol. Bioprocesses,* 161-171, 1989; all incorporated herein by reference).

Cysteine mutant IL-28 or IL-29 polypeptide activity may also be detected using assays designed to measure IL-28- and IL-29-induced production of one or more additional growth factors or other macromolecules. Certain members of the protein family comprising IL-28 and IL-29 have been shown to increase circulating monocyte numbers in vivo. Monocyte activation is important in both innate and adaptive immunity. For example, activation of monocytes has been shown to stimulate antigen presentation by several mechanisms. Antigen presentation promotes activation and proliferation of T-cells, both cytotoxic and helper T cells. The maturation and activation of dendritic cells also promotes activation of T cells and both innate and adaptive immunity. Increases in activated monocytes and macrophages have also been shown to increase cytolytic activity. Therefore, Cysteine mutant IL-28 or IL-29 will be useful as an anti-infectious agent, enhancing innate, cell-mediated and humoral immune responses. Increases in ICAM staining in CD 14+ monocytes was seen suggesting that IL-28 and IL-29 play a role in monocyte activation. While data show that family members promote an anti-viral response to virus, bacteria and parasites may also be affected.

Monocyte activation assays are carried out (1) to look for the ability of Cysteine mutant IL-28 or IL-29 proteins to further stimulate monocyte activation, and (2) to examine the ability of Cysteine mutant IL-28 or IL-29 proteins to modulate attachment-induced or endotoxin-induced monocyte activation (Fuhlbrigge et al., *J. Immunol.* 138: 3799-3802, 1987). IL-1α and TNFα levels produced in response to activation are measured by ELISA (Biosource, Inc. Camarillo, Calif.). Monocyte/macrophage cells, by virtue of CD14 (LPS receptor), are exquisitely sensitive to endotoxin, and proteins with moderate levels of endotoxin-like activity will activate these cells.

Increased levels of monocytes suggest that Cysteine mutant IL-28 or IL-29 may have a direct effect on myeloid progenitor cells in the bone marrow. Increasing differentiation of myeloid progenitor cells to monocytes is essential in restoring immnunocompetency, for example, after chemotherapy. Thus, administration of Cysteine mutant IL-28 or IL-29 to patients receiving chemotherapy could promote their recovery and ability to resist infection commonly associated with chemotherapy regimens. Thus, methods for expanding the numbers of monocytes or monocyte progenitor cells by either culturing bone marrow or peripheral blood cells with the molecules of the present invention such that there is an increase in the monocyte or monocyte progenitor cells for achieving this effect in vitro or ex vivo. The present invention also provides for the in vivo administration of the molecules of the present invention to a mammal needing increased monocyte or monocyte progenitor cells. Increased monocyte and monocyte progenitor cells can be measured using methods well known to clinicians, physicians, and other persons skilled the art. Monocyte cells are included in the myeloid lineage of hematopoietic cells, so affects on other cells in that lineage would not be unusual. For example, when a factor facilitates the differentiation or proliferation of one type of cell in the myeloid or lymphoid lineage, this can affect production of other cells with a common progenitor or stem cell.

Hematopoietic activity of Cysteine mutant IL-28 or IL-29 proteins can be assayed on various hematopoietic cells in culture. Preferred assays include primary bone marrow colony assays and later stage lineage-restricted colony assays, which are known in the art (e.g., Holly et al., WIPO Publication WO 95/21920). Marrow cells plated on a suitable semi-solid medium (e.g., 50% methylcellulose containing 15% fetal bovine serum, 10% bovine serum albumin, and 0.6% PSN antibiotic mix) are incubated in the presence of test polypeptide, then examined microscopically for colony formation. Known hematopoietic factors are used as controls. Mitogenic activity of Cysteine mutant IL-28 or IL-29 polypeptides on hematopoietic cell lines can be measured as disclosed above.

Cell migration is assayed essentially as disclosed by Kahler et al. (*Arteriosclerosis Thrombosis, and Vascular Biology* 17:932-939, 1997). A protein is considered to be chemotactic if it induces migration of cells from an area of low protein concentration to an area of high protein concentration. A typical assay is performed using modified Boyden chambers with a polystryrene membrane separating the two chambers (Transwell; Corning Costar Corp.). The test sample, diluted in medium containing 1% BSA, is added to the lower chamber of a 24-well plate containing Transwells. Cells are then placed on the Transwell insert that has been pretreated with 0.2% gelatin. Cell migration is measured after 4 hours of incubation at 37° C. Non-migrating cells are wiped off the top of the Transwell membrane, and cells attached to the lower face of the membrane are fixed and stained with 0.1% crystal violet. Stained cells are then extracted with 10% acetic acid and absorbance is measured at 600 nm. Migration is then calculated from a standard calibration curve. Cell migration can also be measured using the matrigel method of Grant et al. ("Angiogenesis as a component of epithelial-mesenchymal interactions" in Goldberg and Rosen, *Epithelial-Mesenchymal Interaction in Cancer*, Birkhäuser Verlag, 1995, 235-248; Baatout, *Anticancer Research* 17:451-456, 1997).

Cell adhesion activity is assayed essentially as disclosed by LaFleur et al. (*J. Biol. Chem.* 272:32798-32803, 1997). Briefly, microtiter plates are coated with the test protein, non-specific sites are blocked with BSA, and cells (such as smooth muscle cells, leukocytes, or endothelial cells) are plated at a density of approximately $10^4$-$10^5$ cells/well. The wells are incubated at 37° C. (typically for about 60 minutes), then non-adherent cells are removed by gentle washing. Adhered cells are quantitated by conventional methods (e.g., by staining with crystal violet, lysing the cells, and determining the optical density of the lysate). Control wells are coated with a known adhesive protein, such as fibronectin or vitronectin.

Expression of Cysteine mutant IL-28 or IL-29 polynucleotides in animals provides models for further study of the biological effects of overproduction or inhibition of protein activity in vivo. IL-28- or IL-29-encoding polynucleotides and antisense polynucleotides can be introduced into test animals, such as mice, using viral vectors or naked DNA, or transgenic animals can be produced.

One in vivo approach for assaying proteins of the present invention utilizes viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., *Meth. Cell Biol.* 43:161-89, 1994; and Douglas and Curiel, *Science & Medicine* 4:44-53, 1997. The adenovirus system offers several advantages. Adenovirus can (i) accommodate relatively large DNA inserts; (ii) be grown to high-titer; (iii) infect a broad range of mammalian cell types; and (iv) be used with many different promoters including ubiquitous, tissue specific, and regulatable promoters. Because adenoviruses are stable in the bloodstream, they can be administered by intravenous injection. Also see, Wu et al., *J. Biol. Chem.* 263:14621-14624, 1988; Wu et al., *J. Biol. Chem.* 267:963-967, 1992; and Johnston and Tang, *Meth. Cell Biol.* 43:353-365, 1994.

Transgenic mice, engineered to express a Cysteine mutant IL-28 or IL-29 gene, and mice that exhibit a complete absence of Cysteine mutant IL-28 or IL-29 gene function, referred to as "knockout mice" (Snouwaert et al., *Science* 257:1083, 1992), can also be generated (Lowell et al., *Nature* 366:740-742, 1993). These mice can be employed to study the Cysteine mutant IL-28 or IL-29 gene and the protein encoded thereby in an in vivo system. Preferred promoters for transgenic expression include promoters from metallothionein and albumin genes.

Most cytokines as well as other proteins produced by activated lymphocytes play an important biological role in cell differentiation, activation, recruitment and homeostasis of cells throughout the body. Cysteine mutant IL-28 or IL-29 and inhibitors of their activity are expected to have a variety of therapeutic applications. These therapeutic applications include treatment of diseases which require immune regulation, including autoimmune diseases such as rheumatoid arthritis, multiple sclerosis, myasthenia gravis, systemic lupus erythematosis, and diabetes. IL-28 or IL-29 may be important in the regulation of inflammation, and therefore would be useful in treating rheumatoid arthritis, asthma and sepsis. There may be a role of IL-28 or IL-29 in mediating tumorgenesis, whereby a Cysteine mutant IL-28 or IL-29 antagonist would be useful in the treatment of cancer. IL-28 or IL-29 may be useful in modulating the immune system, whereby Cysteine mutant IL-28 or IL-29 antagonists may be used for reducing graft rejection, preventing graft-vs-host disease, boosting immunity to infectious diseases, treating immunocompromised patients (e.g., HIV patients), or in improving vaccines.

Members of the protein family of the present invention have been shown to have an antiviral effect that is similar to interferon-α. Interferon has been approved in the United States for treatment of autoimmune diseases, condyloma acuminatum, chronic hepatitis C, bladder carcinoma, cervical carcinoma, laryngeal papillomatosis, fungoides mycosis, chronic hepatitis B, Kaposi's sarcoma in patients infected with human immunodeficiency virus, malignant melanoma, hairy cell leukemia, and multiple sclerosis. In addition, Cysteine mutant IL-28 or IL-29 may be used to treat forms of arteriosclerosis, such as atherosclerosis, by inhibiting cell proliferation. Accordingly, the present invention contemplates the use of Cysteine mutant IL-28 or IL-29 proteins, polypeptides, and peptides having IL-28 and IL-29 activity to treat such conditions, as well as to treat retinopathy. The present invention also contemplates the use of Cysteine mutant IL-28 or IL-29 proteins, polypeptides, and peptides having IL-28 and IL-29 activity to treat lymphoproliferative disorders, including B-cell lymphomas, chronic lymphocytic leukemia, acute lymphocytic leukemia, Non-Hodkin's lymphomas, multiple myeloma, acute myelocytic leukemia, chronic myelocytic leukemia.

Interferons have also been shown to induce the expression of antigens by cultured cells (see, for example, Auth et al, *Hepatology* 18:546 (1993), Guadagni et al, *Int. J. Biol. Markers* 9:53 (1994), Girolomoni et al, *Eur. J. Immunol.* 25:2163 (1995), and Maciejewski et al, *Blood* 85:3183 (1995). This activity enhances the ability to identify new tumor associated antigens in vitro. Moreover, the ability of interferons to augment the level of expression of human tumor antigens indicates that interferons can be useful in an adjuvant setting for immunotherapy or enhance immunoscintigraphy using anti-tumor antigen antibodies (Guadagni et al, *Cancer Immunol. Immunother.* 26:222 (1988); Guadagni et al, *Int. J. Biol. Markers* 9:53 (1994)). Thus, the present invention includes the use of Cysteine mutant IL-28 or IL-29 proteins, polypeptides and peptides having IL-28 and IL-29 activity as an adjuvant for immunotherapy or to improve immunoscintigraphy using anti-tumor antigen antibodies.

The activity and effect of Cysteine mutant IL-28 or IL-29 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly M S, et al. *Cell* 79: 315-328,1994). C57BL6/J mice are treated with an experimental agent either through daily injection of recombinant protein, agonist or antagonist or a one-time injection of recombinant adenovirus. Three days following this treatment, 105 to 106 cells are implanted under the dorsal skin. Alternatively, the cells themselves may be infected with recombinant adenovirus, such as one expressing Cysteine mutant IL-28 and IL-29, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500-1800 mm$^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., Cysteine mutant IL-28 and IL-29, on the ability of the tumor to recruit vasculature and undergo metastasis can thus be assessed. In addition, aside from using adenovirus, the implanted cells can be transiently transfected with Cysteine mutant IL-28 and IL-29. Use of stable Cysteine mutant IL-28 or IL-29 transfectants as well as use of induceable promoters to activate Cysteine mutant IL-28 or IL-29 expression in vivo are known in the art and can be used in this system to assess induction of metastasis. Moreover, purified Cysteine mutant IL-28 or IL-29 conditioned media can be directly injected in to this mouse model, and hence be used in this system. For general reference see, O'Reilly M S, et al. *Cell* 79:315-328, 1994; and Rusciano D, et al. Murine Models of Liver Metastasis. *Invasion Metastasis* 14:349-361, 1995.

Cysteine mutant IL-28 or IL-29 can also be used to treat myocarditis, a disorder that arises when the heart is involved in an inflammatory process. The infiltration of lymphocytes and myocytolysis is thought to result after infection by virus, bacteria, fungi or parasites (see, for example, Brodison et al., *J. Infection* 37:99 (1998)). Cysteine mutant IL-28 or IL-29 can be injected intravenously or subcutaneously to treat infections associated with myocarditis. Cysteine mutant IL-28 or IL-29 can also be administered intravenously as an immunoregulatory cytokine in the treatment of autoimmune myocarditis. Interferon dosages can be extrapolated using a autoimmune model of myocarditis in the A/J mouse (Donermeyer, et al., *J. Exp. Med.* 182:1291 (1995)).

Recent reports have highlighted the role of type I interferons in the prevention of viral-induced diabetes by inducing a strong antiviral state in pancreatic beta cells early during viral infection (Flodstroem et al., *Nature Immunology* 3, 373-382 (2002)). This prevents the loss of beta cells due to viral-induced cell death and autoimmunity that accompanies it. Cysteine mutant IL-28 or IL-29 also induce an antiviral state in cells that express the IL-28 receptor. IL-28 receptor is highly expressed in pancreatic tissue and therefore IL-28 and IL-29 may play a role in prevention of viral-induced diabetes due to beta cell death. In addition, the role of type I interferons in prevention of viral-induced diabetes may be extended to other viral-induced autoimmune diseases and therefore, IL-28 and IL-29 may also play a role in prevention of other diseases such as muscular sclerosis, lupus, and viral-induced autoimmune diseases in tissues that express the IL-28 receptor.

Cysteine mutant IL-28 or IL-29 polypeptides can be administered alone or in combination with other vasculogenic or angiogenic agents, including VEGF. When using Cysteine mutant IL-28 or IL-29 in combination with an additional agent, the two compounds can be administered simultaneously or sequentially as appropriate for the specific condition being treated.

Cysteine mutant IL-28 or IL-29 will be useful in treating tumorgenesis, and therefore would be useful in the treatment of cancer. An IL-28 may inhibit B-cell tumor lines suggesting that there may be therapeutic benefit in treating patients with Cysteine mutant IL-28 or IL-29 in order to induce the B cell tumor cells into a less proliferative state. The ligand could be administered in combination with other agents already in use including both conventional chemotherapeutic agents as well as immune modulators such as interferon alpha. Alpha/beta interferons have been shown to be effective in treating some leukemias and animal disease models, and the growth inhibitory effects of interferon-alpha and Cysteine mutant IL-28 or IL-29 may be additive for B-cell tumor-derived cell lines.

Within another aspect, the present invention provides a pharmaceutical formulation comprising an isolated polypeptide selected from the group consisting of SEQ ID NOs:2, 4, 6, 8, 10, 13, 15, 17, 19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161, and a pharmaceutically acceptable vehicle.

For pharmaceutical use, Cysteine mutant IL-28 or IL-29 proteins are formulated for topical or parenteral, particularly intravenous or subcutaneous, delivery according to conventional methods. In general, pharmaceutical formulations will include Cysteine mutant IL-28 or IL-29 polypeptide in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in Remington: The Science and Practice of Pharmacy, Gennaro, ed., Mack Publishing Co., Easton, Pa., 19th ed., 1995. Cysteine mutant IL-28 or IL-29 will preferably be used in a concentration of about 10 to 100 µg/ml of total volume, although concentrations in the range of 1 ng/ml to 1000 µg/ml may be used. For topical application, such as for the promotion of wound healing, the protein will be applied in the range of 0.1-10 µg/cm² of wound area, with the exact dose determined by the clinician according to accepted standards, taking into account the nature and severity of the condition to be treated, patient traits, etc. Determination of dose is within the level of ordinary skill in the art. Dosing is daily or intermittently over the period of treatment. Intravenous administration will be by bolus injection or infusion over a typical period of one to several hours. Sustained release formulations can also be employed. In general, a therapeutically effective amount of IL-28 or IL-29 Cysteine mutant is an amount sufficient to produce a clinically significant change in the treated condition, such as a clinically significant change in viral load or immune function, a significant reduction in morbidity, or a significantly increased histological score.

As an illustration, pharmaceutical formulations may be supplied as a kit comprising a container that comprises a IL-28 or IL29 polypeptide of the present invention. Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise writen information on indications and usage of the pharmaceutical composition. Moreover, such information may include a statement that the IL-28 or IL29 polypeptide formulation is contraindicated in patients with known hypersensitivity to IL-28 or IL29 polypeptide.

Within another aspect the present invention provides a method of producing an antibody to a polypeptide comprising: inoculating an animal with a polypeptide selected from the group consisting of SEQ ID NOs:19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161, wherein the polypeptide elicits an immune response in the animal to produce the antibody; and isolating the antibody from the animal. Within another aspect the present invention provides an antibody (e.g., neutralizing antibody) produced by the method as disclosed above, wherein the antibody binds to a polypeptide selected from the group consisting of SEQ ID NOs:19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161. In one embodiment, the antibody disclosed above specifically binds to a polypeptide polypeptide selected from the group consisting of SEQ ID NOs:19, 21, 23, 25, 27, 29, 36, 37, 38, 39, 40, 41, 75, 77, 79, 81, 83, 85, 87, 89, 91, 93, 95, 97, 99, 101, 103, 105, 107, 109, 111, 113, 115, 117, 123, 125, 127, 129, 131, 133, 135, 137, 139, 141, 143, 145, 147, 149, 151, 153, 155, 157, 159, and 161. Within another aspect, the present invention provides an antibody or antibody fragment that specifically binds to a polypeptide as described herein. In one embodiment, the antibody is selected from the group consisting of a polyclonal antibody, a murine monoclonal antibody a humanized antibody derived from a murine monoclonal antibody, an antibody fragment, and human monoclonal antibody. In one embodiment, the antibody fragment is as described herein, wherein said antibody fragment is selected from the group consisting of F(ab'), F(ab), Fab', Fab, Fv, scFv, and minimal recognition unit.

Within another aspect, the present invention provides an anti-idiotype antibody that specifically binds to the antibody as described herein.

As used herein, the term "antibodies" includes polyclonal antibodies, monoclonal antibodies, antigen-binding fragments thereof such as F(ab')$_2$ and Fab fragments, single chain antibodies, and the like, including genetically engineered antibodies. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. One skilled in the art can generate humanized antibodies with specific and different constant domains (i.e., different Ig subclasses) to facilitate or inhibit various immune functions associated with particular antibody constant domains. Antibodies are defined to be specifically binding if they bind to Cysteine mutant IL-28 or IL-29 polypeptide or protein with an affinity at least 10-fold greater than the binding affinity to control (non-Cysteine mutant IL-28 and IL-29) polypeptide or protein. The affinity of a monoclonal antibody can be readily determined by one of ordinary skill in the art (see, for example, Scatchard, Ann. NY Acad. Sci. 51: 660-672, 1949).

Methods for preparing polyclonal and monoclonal antibodies are well known in the art (see for example, Hurrell, J. G. R., Ed., Monoclonal Hybridoma Antibodies: Techniques and Applications, CRC Press, Inc., Boca Raton, Fla., 1982, which is incorporated herein by reference). The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

A variety of assays known to those skilled in the art can be utilized to detect antibodies which specifically bind to Cysteine mutant IL-28 or IL-29 polypeptides. Exemplary assays are described in detail in Using Antibodies: A Laboratory Manual, Harlow and Lane (Eds.), Cold Spring Harbor Laboratory Press, 1999. Representative examples of such assays include: concurrent immunoelectrophoresis, radio-immunoassays, radio-immunoprecipitations, enzyme-linked immunosorbent assays (ELISA), dot blot assays, Western blot assays, inhibition or competition assays, and sandwich assays.

For certain applications, including in vitro and in vivo diagnostic uses, it is advantageous to employ labeled antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies of the present invention may also be directly or indirectly conjugated to drugs, toxins, radionuclides and the like, and these conjugates used for in vivo diagnostic or therapeutic applications (e.g., inhibition of cell proliferation). See, in general, Ramakrishnan et al., *Cancer Res.* 56:1324-1330, 1996.

The present invention is further illustrated by the following non-limiting examples.

EXAMPLES

Example 1

Mammalian Expression Plasmids

An expression plasmid containing zcyto20 and zcyto21 was constructed via homologous recombination. Fragments of zcyto20 and zcyto21 cDNA were generated using PCR amplification. The primers for PCR were as follows:

zcyto20/pZMP21: zc40923, and zc43152 SEQ ID NOs:42 and 43, respectively; and zcyto21/pZMP21: zc40922, and zc43153 SEQ ID NOs:2 and 73, respectively.

The PCR reaction mixture was run on a 1% agarose gel and a band corresponding to the size of the insert was gel-extracted using a QIAquick™ Gel Extraction Kit (Qiagen, Valencia, Calif.).

The plasmid pZMP21, which was cut with BglII, was used for recombination with the PCR insert fragment. Plasmid pZMP21 is a mammalian expression vector containing an expression cassette having the MPSV promoter, and multiple restriction sites for insertion of coding sequences; an *E. coli* origin of replication; a mammalian selectable marker expression unit comprising an SV40 promoter, enhancer and origin of replication, a DHFR gene, and the SV40 terminator; and URA3 and CEN-ARS sequences required for selection and replication in *S. cerevisiae*. It was constructed from pZP9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain.

One hundred microliters of competent yeast (S. cerevisiae) cells were independently combined with 10 μl of the insert DNA and 100 ng of the cut pZMP21 vector above, and the mix was transferred to a 0.2-cm electroporation cuvette. The yeast/DNA mixture was electropulsed using power supply (BioRad Laboratories, Hercules, Calif.) settings of 0.75 kV (5 kV/cm), ∞ ohms, and 25 μF. Six hundred μl of 1.2 M sorbitol was added to the cuvette, and the yeast was plated in a 100-μl and 300 μl aliquot onto two URA-D plates and incubated at 30° C. After about 72 hours, the Ura$^+$ yeast transformants from a single plate were resuspended in 1 ml H$_2$O and spun briefly to pellet the yeast cells. The cell pellet was resuspended in 0.5 ml of lysis buffer (2% Triton X-100, 1% SDS, 100 mM NaCl, 10 mM Tris, pH 8.0, 1 mM EDTA). The five hundred microliters of the lysis mixture was added to an Eppendorf tube containing 250 μl acid-washed glass beads and 300 μl phenol-chloroform, was vortexed for 3 minutes, and spun for 5 minutes in an Eppendorf centrifuge at maximum speed. Three hundred microliters of the aqueous phase was transferred to a fresh tube, and the DNA was precipitated with 600 μl ethanol (EtOH) and 30 μl 3M sodium acetate, followed by centrifugation for 30 minutes at maximum speed. The DNA pellet was resuspended in 30 μl TE.

Transformation of electrocompetent *E. coli* host cells (MC1061) was done using 5 μl of the yeast DNA prep and 50 μl of cells. The cells were electropulsed at 2.0 kV, 25 μF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) was added and then the cells were plated in a 50 μl and 200 μl aliquot on two LB AMP plates (LB broth (Lennox), 1.8% Bacto™ Agar (Difco), 100 mg/L Ampicillin).

The inserts of three clones for each construct were subjected to sequence analysis and one clone for each construct, containing the correct sequence, was selected. Larger scale plasmid DNA was isolated using a commercially available kit (QIAGEN Plasmid Mega Kit, Qiagen, Valencia, Calif.) according to manufacturer's instructions. The correct constructs were designated zcyto20/pZMP21 and zcyto21/pZMP21.

Example 2

Expression of Mammalian Constructs in CHO Cells

200 μg of a zcyto20/pZMP21 and zcyto21/pZMP21 construct were digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was aspirated off the pellet. The pellet was then resuspended in 750 μl of PF-CHO media in a sterile environment, and allowed to incubate at 60° C. for 30 minutes. CHO cells were spun down and resuspended using the DNA-media solution. The DNA/cell mixture was placed in a 0.4 cm gap cuvette and electroporated using the following parameters: 950 μF, high capacitance, and 300 V. The contents of the cuvette were then removed and diluted to 25 mLs with PF-CHO media and placed in a 125 mL shake flask. The flask was placed in an incubator on a shaker at 37° C., 6% CO$_2$, and shaking at 120 RPM.

Example 3

Purification and Analysis of zcyto20-CHO Protein

A. Purification of Zcyto20-CHO Protein

Recombinant zcyto20 (IL-28A) protein was produced from a pool of DXB11-CHO cell lines. Cultures were harvested, and the media were sterile filtered using a 0.2 μm filter.

The purification of zcyto20-CHO protein was achieved by the sequential use of a Poros HS 50 column (Applied Biosystems, Framingham, Mass.), a Monolithic WCX column (Isco, Inc., Lincoln, Nebr.), a ToyoPearl Butyl 650S column (TosoH, Montgomeryville, Pa.), and a Superdex 75 column (Amersham Biosciences, Piscataway, N.J.). Culture media from DXB111-CHO were adjusted to pH 6.0 before loading onto a Poros 50 HS column. The column was washed with 50 mM MES (2-Morpholinoethanesulfonic acid), 100 mM NaCl, pH 6 and the bound protein was eluted with a 10 column volumes (CV) linear gradient to 60% of 50 mM MES, 2 M NaCl, pH 6. The eluting fractions were collected and the presence of zcyto20 protein was confirmed by SDS-PAGE with a Coomassie staining. This fractions containing zcyto20 protein were pooled, diluted with double distilled water to a conductivity of about 20 mS, and loaded onto a Monolithic WCX column. The column was washed with 93% of 50 mM MES, 100 mM NaCl, pH 6, and 7% of 50 mM MES, 2 M NaCl, pH 6. The bound protein was eluted with a 25-CV linear gradient from 7% to 50% of 50 mM MES, 2 M NaCl, pH 6. The eluting fractions were collected and the presence of zcyto20 protein was confirmed by SDS-PAGE with a Coomassie staining. The fractions containing zcyto20 protein were pooled, adjusted to 1 M ammonium sulfate and loaded onto a ToyoPearl Butyl 650S column. Zcyto20 was eluted with a decreasing ammonium sulfate gradient and the fractions containing the pure zcyto20 were pooled and concentrated for injection into a Superdex 75 column. Fractions containing zcyto20 protein from the gel filtration column was pooled, concentrated, filtered through a 0.2 μm filter and frozen at −80° C. The concentration of the final purified protein was determined by a BCA assay (Pierce Chemical Co., Rockford, Ill.) and HPLC-amino acid analysis.

B. SDS-PAGE and Western Blotting Analysis of zcyto20-CHO Protein

Recombinant zcyto20 protein was analyzed by SDS-PAGE (Nupage 4-12% Bis-Tris, Invitrogen, Carlsbad, Calif.) and Western blot using rabbit anti-zcyto21-CEE-BV IgG as the primary antibody that cross-reacts to zcyto20-CHO protein. The gel was electrophoresed using Invitrogen's Xcell II mini-cell (Carlsbad, Calif.) and transferred to a 0.2 μm nitrocellulose membrane (Bio-Rad Laboratories, Hercules, Calif.) using Invitrogen's Xcell II blot module according to directions provided in the instrument manual. The transfer was run at 500 mA for 50 minutes in a buffer containing 25 mM Tris base, 200 mM glycine, and 20% methanol. The membrane was blocked with 10% non-fat dry milk in 1× PBS for 10 minutes then probed with the primary antibody in 1× PBS containing 2.5% non-fat dry milk. The blot was labeled for one hour at room temperature while shaking. For the secondary antibody labeling, blot was washed three times for 10 minutes each with PBS and then probed with goat anti-rabbit IgG-HRP (Pierce Chemical Co., Rockford, Ill.) for one hour. The blot was washed three times with 1× PBS for 10 minutes each and developed using a 1:1 mixture of SuperSignal® ULTRA reagents (Pierce Chemical Co., Rockford, Ill.) and the signal was captured using a Lumi-Imager (Boehringer Mannheim GmbH, Germany).

C. Summary of Protein Purification and Analysis

The purified zcyto20 protein from the CHO media migrated predominantly as a doublet at approximately 20 kDa and a minor triplet dimer at about 38 kDa on a 4-12% Bis-Tris gel under non-reducing conditions. They all collapsed into a single 20 kDa band under reducing conditions. MS peptide mapping indicated a mixture of two isomers with respect to disulfide linkage and the presence of O-linked glycosylation site.

Example 4

Purification and Analysis of zcyto21-CHO Protein

A. Purification of Zcyto21-CHO Protein

Recombinant zcyto21 was produced from stable DXB11-CHO cell lines. Cultures were harvested, and the media were sterile filtered using a 0.2 μm filter. Proteins were purified from the conditioned media by starting with a combination of cationic and anionic exchange chromatography followed by a hydrophobic interaction chromatography and a size exclusion chromatography. DXB111-CHO culture media were adjusted to pH 6.0 before loading onto a Poros 50 HS column (Applied Biosystems, Framingham, Mass.). The column was washed with 1× PBS, pH 6 and the bound protein was eluted with 5× PBS, pH 8.4. The eluting fraction was collected and the presence of zcyto21 protein was confirmed by SDS-PAGE with a Coomassie stain. This fraction was then diluted to a conductivity of 13 mS and its pH adjusted to 8.4 and flowed through a Poros 50 HQ column (Applied Biosystems, Framingham, Mass.). The flow-through containing zcyto21 protein were then adjusted to about 127 mS with ammonium sulfate and loaded onto a Toyopearl Phenyl 650S column (TosoH, Montgomeryville, Pa.). Zcyto21 protein was eluted with a decreasing ammonium sulfate gradient and the fractions containing the pure zcyto21 were pooled and concentrated for injection into a Superdex 75 column (Amersham Biosciences, Piscataway, N.J.). The concentration of the final purified protein was determined by a BCA assay (Pierce Chemical Co., Rockford, Ill.) and HPLC-amino acid analysis.

B. SDS-PAGE and Western Blotting Analysis of zcyto21-CHO Protein

Recombinant zcyto21 protein was analyzed by SDS-PAGE (Nupage 4-12% Bis-Tris, Invitrogen, Carlsbad, Calif.) and Western blot using rabbit anti-zcyto21-CEE-BV IgG as the primary antibody. The gel was electrophoresed using Invitrogen's Xcell II mini-cell (Carlsbad, Calif.) and transferred to a 0.2 μm nitrocellulose membrane (Bio-Rad Laboratories, Hercules, Calif.) using Invitrogen's Xcell II blot module according to directions provided in the instrument manual. The transfer was run at 500 mA for 50 minutes in a buffer containing 25 mM Tris base, 200 mM glycine, and 20% methanol. The transferred blot was blocked with 10% non-fat dry milk in 1× PBS for 10 minutes then probed with the primary antibody in 1× PBS containing 2.5% non-fat dry milk. The blot was labeled for one hour at room temperature while shaking. For the secondary antibody labeling, blot was washed three times for 10 minutes each with PBS and then probed with goat anti-rabbit IgG-HRP (Pierce Chemical Co., Rockford, Ill.) for one hour. The blot was washed three times with 1× PBS for 10 minutes each and developed using a 1:1 mixture of SuperSignal® ULTRA reagents (Pierce Chemical Co., Rockford, Ill.) and the signal was captured using a Lumi-Imager (Boehringer Mannheim GmbH, Germany).

C. Summary of Protein Purification and Analysis

The purified zcyto21 protein from the CHO media migrated as two or more approximately 28 kDa bands on a 4-12% Bis-Tris gel under both reducing and non-reducing conditions. MS peptide mapping indicated a mixture of two isomers with respect to disulfide linkage and the presence of one N-linked glycosylation and several O-linked glycosylation sites.

Example 5

Identification of IL-29 Forms

Peak fractions from purified pools of IL-29 were digested overnight at 37° C. with sequencing grade trypsin (Roche Applied Science, Indianapolis, Ind.) in phosphate buffer at approximately pH 6.3 to limit disulfide re-arrangement. Each digest was analyzed by reversed-phase HPLC (Agilent, Palo Alto, Calif.) connected in-line to a quadrupole-time of flight hybrid mass spectrometer (Micromass, Milford Mass.). Spectra were collected, converted from mass to charge ratio to mass, and compared to all theoretical peptides and disulfide-linked peptide combinations resulting from trypsin digestion of IL-29. Disulfides were assigned by comparing spectra before and after reduction with assignment of appropriate masses to disulfide linked peptides in IL-29. The material from fraction #20 showed the disulfide pattern C15-C112 and C49-C145 with C171 observed as a S-glutathionyl cysteine (all referring to SEQ ID NO:4). The material from fraction #51 showed the disulfide pattern C49-C145 and C112-C171 with C15 observed as an S-glutathionyl cysteine (referring to SEQ ID NO:4).

Example 6

E. coli Expression Plasmids

Construction of Expression Vector, pTAP237

Plasmid pTAP237 was generated by inserting a PCR-generated linker into the SmaI site of pTAP186 by homologous recombination. Plasmid pTAP186 was derived from the plasmids pRS316 (a *Saccharomyces cerevisiae* shuttle vector) and pMAL-c2, an *E. coli* expression plasmid derived from pKK223-3 and comprising the tac promoter and the rrnB terminator. Plasmid pTAP186 contains a kanamycin resistance gene in which the Sma I site has been destroyed and has NotI and SfiI sites flanking the yeast ARS-CEN6 and URA3 sequences, facilitating their removal from the plasmid by digestion with NotI. The PCR-generated linker replaced the expression coupler sequence in pTAP186 with the synthetic RBS II sequence. It was prepared from 100 pmoles each of oligonucleotides zc29,740 and zc29,741, as shown in SEQ ID NOS: 44 and 45, respectively, and approximately 5 pmoles each of oligonucleotides zc29,736 and zc29,738, as shown in SEQ ID NOs:46 and 47, respectively. These oligonucleotides were combined by PCR for ten cycles of 94° C. for 30 seconds, 50° C. for 30 seconds, and 72° C. for 30 seconds, followed by 4° C. soak. The resulting PCR products were concentrated by precipitation with two times the volume of 100% ethanol. Pellet was resuspended in 10 µL water to be used for recombining into the recipient vector pTAP186 digested with SmaI to produce the construct containing the synthetic RBS II sequence. Approximately 1 µg of the PCR-generated linker and 100 ng of pTAP186 digested with SmaI were mixed together and transformed into competent yeast cells (*S. cerevisiae*). The yeast was then plated onto –URA D plates and left at room temperature for about 72 hours. Then the Ura+ transformants from a single plate were resuspended in 1 mL $H_2O$ and spun briefly to pellet the yeast cells. The cell pellet was resuspended in 0.5 mL of lysis buffer. DNA was recovered and transformed into *E. coli* MC1061. Clones were screened by colony PCR as disclosed above using 20 pmoles each of oligonucleotides zc29,740 and zc29,741, as shown in SEQ ID NOS: 44 and 45, respectively. Clones displaying the correct size band on an agarose gel were subject to sequence analysis. The correct plasmid was designated pTAP237.

Example 7

Codon Optimization of IL-29 Cysteine Mutant

A. Codon Optimization Generation of the IL-29 Wildtype Expression Construct

Native human IL-29 gene sequence was not well expressed in *E. coli* strain W3110. Examination of the codons used in the IL-29 coding sequence indicated that it contained an excess of the least frequently used codons in *E. coli* with a CAI value equal to 0.206. The CAI is a statistical measure of synonymous codon bias and can be used to predict the level of protein production (Sharp et al., *Nucleic Acids Res.* 15(3):1281-95, 1987). Genes coding for highly expressed proteins tend to have high CAI values (>0.6), while proteins encoded by genes with low CAI values (<0.2) are generally inefficiently expressed. This suggested a reason for the poor production of IL-29 in *E. coli*. Additionally, the rare codons are clustered in the second half of the message leading to higher probability of translational stalling, premature termination of translation, and amino acid misincorporation (Kane J F. *Curr. Opin. Biotechnol.* 6(5):494-500, 1995).

It has been shown that the expression level of proteins whose genes contain rare codons can be dramatically improved when the level of certain rare tRNAs is increased within the host (Zdanovsky et al., *Applied Enviromental Microb.* 66:3166-3173, 2000; You et al,. *Biotechniques* 27:950-954, 1999). The pRARE plasmid carries genes encoding the tRNAs for several codons that are rarely used *E. coli* (argU, argW, leuW, proL, ileX and glyT). The genes are under the control of their native promoters (Novy, ibid.). Co-expression with pRARE enhanced IL-29 production in *E. coli* and yield approximately 200 mg/L. These data suggest that re-resynthesizing the gene coding for IL-29 with more appropriate codon usage provides an improved vector for expression of large amounts of IL-29.

The codon optimized IL-29 coding sequence was constructed from sixteen overlaping oligonucleotides: zc44,566 (SEQ ID NO:48), zc44,565 (SEQ ID NO:49), zc44,564 (SEQ ID NO:50), zc44,563 (SEQ ID NO:51), zc44,562 (SEQ ID NO:52), zc44,561 (SEQ ID NO:53), zc44,560 (SEQ ID NO:54), zc244,559 (SEQ ID NO:55), zc44,558 (SEQ ID NO:56), zc44,557 (SEQ ID NO:57). Primer extension of these overlapping oligonucleotides followed by PCR amplication produced a full length IL-29 gene with codons optimized for expression in *E. coli*. The final PCR product was inserted into expression vector pTAP237 by yeast homologous recombination. The expression construct was extracted from yeast and transformed into competent *E. coli* MC1061. Clones resistance to kanamycin were identified by colony PCR. A positive clone was verified by sequencing and subsequently transformed into production host strain W3110. The expression vector with the optimized IL-29 sequence was named pSDH184. The resulting gene was expressed very well in *E. coli*. expression levels with the new construct increased to around 250 mg/L.

B. Generation of the Codon Optimized zcyto21 C172S Cysteine Mutant Expression Construct The strategy used to generate the zcyto21 C172S Cysteine mutant is based on the QuikChange Site-Directed Mutagenesis Kit (Stratagene). Primers were designed to introduce the C172S mutation based on manufacturer's suggestions. These primers were designated ZG44,340 (SEQ ID NO:58) and ZG44,341 (SEQ ID NO:59). PCR was performed to generate the zcyto21 C172S Cysteine mutant according to QuikChange Mutagenesis instructions. Five identical 50 µl reactions were set-up. 2.5 µl pSDH175 (missing yeast vector backbone sequence) DNA was used as template per reaction. A PCR cocktail was made up using the following amounts of reagents: 30 µl 10× PCR buffer, 125 ng (27.42 µl) ZG44,340, 125 ng (9.18 µl) ZG44,341, 6 µl dNTP, 6 µl Pfu Turbo polymerase (Stratagene, La Jolla, Calif.), and 206.4 µl water. 47.5 µl of the cocktail was aliquotted into each reaction. The PCR conditions were as follows: 1 cycle of 95° C. for 30 seconds followed by 16 cycles of 95° C. for 30 seconds, 55° C. for 1 minute, 68° C. for 7 minutes, followed by 1 cycle at 68° C. for 7 minutes, and ending with a 4° C. hold. All five PCR reactions were consolidated into one tube. As per manufacturer's instructions, 5 µl DpnI restriction enzyme was added to the PCR reaction and incubated at 37° C. for 2 hours. DNA was precipitated my adding 10% 3 Molar Sodium Acetate and two volumes of 100% ethanol. Precipitation was carried-out at −20° C. for 20 minutes. DNA was spun at 14,000 rpm for 5 minutes and pellet was speed-vac dried. DNA pellet was resuspended in 20 µl water. DNA resulting from PCR was transformed into E. coli strain DH10B. 5 µl DNA was mixed with 40 µl ElectroMAX DH10B cells (Invitrogen). Cells and DNA mixture were then electroporated in a 0.1 cm cuvette (Bio-Rad) using a Bio-Rad Gene Pulser II™ set to 1.75 kV, 100 Ω, and 25 µF. Electroporated cells were then outgrown at 37° C. for 1 hour. Mixture was plated on an LB+25 µg/ml kanamycin plate and incubated at 37° C. overnight. Ten clones were screened for presence of zcyto21 C172S insert. DNA was isolated from all ten clones using the QIAprep™ Spin Miniprep Kit (Qiagen, Valencia, Calif.) and analyzed for presence of insert by cutting with XbaI and PstI restriction enzymes. Nine clones contained insert and were sequenced to insure the zcyto21 C172S mutation had been introduced. A clone was sequence verified and was subsequently labeled pSDH188.

Example 8

E. coli IL-29 Expression Construct

A DNA fragment of IL-29 containing the wildtype sequence was isolated using PCR. Primers zc41,212 (SEQ ID NO: 60) containing 41 base pair (bp) of vector flanking sequence and 24 bp corresponding to the amino terminus of IL-29, and primer zc41,041 (SEQ ID NO:61) contained 38 bp corresponding to the 3' end of the vector which contained the zcyto21 insert were used in the reaction. The PCR conditions were as follows: 25 cycles of 94° C. for 30 seconds, 50° C. for 30 seconds, and 72° C. for 1 minute; followed by a 4° C. soak. A small sample (2-4 µL) of the PCR sample was run on a 1% agarose gel with 1× TBE buffer for analysis, and the expected band of approximately 500 bp fragment was seen. The remaining volume of the 100 µL reaction was precipitated with 200 µL absolute ethanol. The pellet was resuspended in 10 µL water to be used for recombining into recipient vector pTAP238 cut with SmaI to produce the construct encoding the zcyto21 as disclosed above. The clone with correct sequence was designated as pTAP377. Clone pTAP377 was digested with NotI/NcoI (10 µl DNA, 5 µl buffer 3 New England BioLabs, 2 µL Not 1, 2 µL NcoI, 31 µL water for 1 hour at 37° C.) and religated with T4 DNA ligase buffer (7 µL of the previous digest, 2 µL of 5× buffer, 1 µL of T4 DNA ligase). This step removed the yeast sequence, CEN-ARS, to streamline the vector. The pTAP337 DNA was diagnostically digested with Pvu2 and Pst1 to confirm the absence of the yeast sequence. P/taP377 DNA was transformed into E. coli strain W3110/pRARE, host strain carrying extra copies of rare E. coli tRNA genes.

Example 9

E. coli IL-28A Expression Construct

A DNA fragment containing the wildtype sequence of zcyto20 (as shown in SEQ ID NO: 1) was isolated using PCR. Primers zc43,431 (SEQ ID NO:62) containing 41 bp of vector flanking sequence and 24 bp corresponding to the amino terminus of zcyto2o, and primer zc43,437 (SEQ ID NO:63) contained 38 bp corresponding to the 3' end of the vector which contained the zcyto20 insert. The PCR conditions were as follows: 25 cycles of 94° C. for 30 seconds, 50° C. for 30 seconds, and 72° C. for 1 minute; followed by a 4° C. soak. A small sample (2-4 µL) of the PCR sample was run on a 1% agarose gel with 1× TBE buffer for analysis, and the expected band of approximately 500 bp fragment was seen. The remaining volume of the 100 µL reaction was precipitated with 200 µL absolute ethanol. The pellet was resuspended in 10 µL water to be used for recombining into recipient vector pTAP238 cut with SmaI to produce the construct encoding the zcyto20 as disclosed above. The clone with correct sequence was designated as pYEL7. It was digested with NotI/NcoI (10 µl DNA, 5 µl buffer 3 New England BioLabs, 2 µL NotI, 2 µL NcoI, 31 µL water for 1 hour at 37° C.) and religated with T4 DNA ligase buffer (7 µL of the previous digest, 2 µL of 5×buffer, 1 µL of T4 DNA ligase). This step removed the yeast sequence, CEN-ARS, to streamline the vector. The relegated pYEL7 DNA was diagnostically digested with Pvu2 and Pst1 to confirm the absence of the yeast sequence. PYEL7 DNA was transformed into E. coli strain W3110/pRARE.

Example 10 zcyto21 C172S Cysteine Mutant Expression Construct

The strategy used to generate the zcyto21 C172S Cysteine mutant (SEQ ID NO: 28) is based on the QuikChange® Site-Directed Mutagenesis Kit (Stratagene, La Jolla, Calif.). Primers were designed to introduce the C172S mutation based on manufacturer's suggestions. These primers were designated ZG44,327 and ZG44,328 (SEQ ID NOs:64 and 65, respectively). PCR was performed to generate the zcyto21 C172S Cysteine mutant according to QuikChange Mutagenesis instructions. Five identical 50 µl reactions were set-up. 2.5 µl pTAP377 (missing yeast vector backbone sequence) DNA was used as template per reaction. A PCR cocktail was made up using the following amounts of reagents: 30 µl 10× PCR buffer, 125 ng (27.42 µl) ZG44,327 (SEQ ID NO: 64), 125 ng (9.18 µl) ZG44,328 (SEQ ID NO: 65), 6 µl dNTP, 6 1 Pfu Turbo polymerase (Strategene), and 206.4 µl water. 47.5 µl of the cocktail was aliquotted into each reaction. The PCR conditions were as follows: 1 cycle of 95° C. for 30 seconds followed by 16 cycles of 95° C. for 30 seconds, 55° C. for 1 minute, 68° C. for 7 minutes, followed by 1 cycle at 68° C. for 7 minutes, and ending with a 4° C. hold. All five PCR reactions were consolidated into one tube. As per manufacturer's instructions, 5 µl DpnI restriction enzyme was added to the PCR reaction and incubated at 37° C. for 2 hours. DNA was precipitated my adding 10% 3 Molar Sodium Acetate and two volumes of 100% ethanol (Aaper Alcohol, Shelbyville, Ky.). Precipitation was carried-out at −20° C. for 20 minutes. DNA was spun at 14,000 rpm for 5 minutes and pellet was speed-vac dried. DNA pellet was resuspended in 20 µl water. DNA resulting from PCR was transformed into E. coli strain DH10B. 5 µl DNA was mixed with 40 µl ElectroMAX DH10B cells (Invitrogen, Carlsbad, Calif.). Cells and DNA mixture were then electroporated in a 0.1 cm cuvette (Bio-Rad, Hercules, Calif.) using a Bio-Rad Gene Pulser II™ set to 1.75 kV, 100 Ω, and 25 µF. Electroporated cells were then outgrown at 37° C. for 1 hour. Mixture was plated on an LB+25 µg/ml kanamycin plate and incubated at 37° C. overnight. Ten clones were screened for presence of IL-29 insert. DNA was isolated from all ten clones using the QIAprep™ Spin Miniprep Kit (Qiagen) and analyzed for presence of insert by cutting with XbaI (Roche) and PstI (New England Biolabs) restriction enzymes. Nine clones contained insert and were sequenced to insure the zcyto21 C172S mutation had been introduced. A clone (isolet #6) was sequence verified and was subsequently labeled pSDH171. A similar strategy can be implemented to generate a zcyto21 C15S mutant.

Example 11 zcyto20 C49S Cysteine Mutant Expression Construct

The zcyto20 C49S Cysteine mutant coding sequence was generated by overlap PCR (SEQ ID NO:20). The first 187 bases of the wildtype IL-28A sequence (SEQ ID NO:1) was generated by PCR amplification using pYEL7 (SEQ ID NO:67) as template and oligonucleotide primers zc43,431 (SEQ ID NO: 62) and zc45,399 (SEQ ID NO:66). The second DNA fragment from base 105 to 531 was generated by PCR amplification using pYEL7 (SEQ ID NO:67) as template and oligonucleotide primers zc45,398 (SEQ ID NO: 68) and zc43,437 (SEQ ID NO:63). Primers zc45,399 (SEQ ID NO:66) and zc45,398 (SEQ ID NO:68) contained the specific modified sequence which changed the cysteine 49 to a serine. These two PCR products were combined and PCR overlap amplified using oligonucleotide primers zc43,431 (SEQ ID NO:62) and zc43,437 (SEQ ID NO:63). The final PCR product was inserted into expression vector pTAP238 by yeast homologous recombination (Raymond et al. *Biotechniques*. Jan. 26(1):134-8, 140-1, 1999). The expression construct was extracted from yeast and transformed into competent *E. coli* DH10B. Kanamycin resistant clones were screened by colony PCR. A positive clone was verified by sequencing and subsequently transformed into production host strain W3110/pRARE. The expression construct with the zcyto20 C49S Cysteine mutant coding sequence was named pCHAN9.

Example 12 zcyto20 C51S Cysteine Mutant Expression Construct

The zcyto20 C51S Cysteine mutant coding sequence was generated by overlap PCR (SEQ ID NO:24). The first 193 bases of the wildtype IL-28A sequence was generated by PCR amplification using pYEL7 (SEQ ID NO:67) as template and oligonucleotide primers zc43,431 (SEQ ID NO:62) and zc45,397 (SEQ ID NO:63). The second DNA fragment from base 111 to 531 was generated by PCR amplification using pYEL7 (SEQ ID NO:67) as template and oligonucleotide primers zc45,396 (SEQ ID NO:70) and zc43,437 (SEQ ID NO:63). Primers zc45,397 (SEQ ID NO:69) and zc45,396 (SEQ ID NO:70) contained the specific modified sequence which changed the cysteine51 to a serine. These two PCR products were combined and PCR overlap amplified using oligonucleotide primers zc43,431 (SEQ ID NO:62) and zc43,437 (SEQ ID NO:63). The final PCR product was inserted into our in-house expression vector pTAP238 by yeast homologous recombination (Raymond et al. supra). The expression construct was extracted from yeast and transformed into competent *E. coli* DH10B. Kanamycin resistant clones were screened by colony PCR. A positive clone was verified by sequencing and subsequently transformed into production host strain W3110/pRARE. The expression construct with the zcyto20 C50S Cysteine mutant coding sequence was named pCHAN10.

Example 13

Expression of Il-28A, IL-29 and Cys to Ser Cysteine Mutants in *E. coli*

In separate experiments, *E. coli* transformed with each of the expression vectors described in Examples 6-9 were inoculated into 100 mL Superbroth II medium (Becton Dickinson, San Diego, Calif.) with 0.01% Antifoam 289 (Sigma Aldrich, St. Louis, Mo.), 30 tg/ml kanamycin, 35 µg/ml chloramphenicol and cultured overnight at 37° C. A 5 mL inoculum was added to 500 mL of same medium in a 2 L culture flask which was shaken at 250 rpm at 37° C. until the culture attained an OD600 of 4. IPTG was then added to a final concentration of 1 mM and shaking was continued for another 2.5 hours. The cells were centrifuged at 4,000×g for 10 min at 4° C. The cell pellets were frozen at −80° C. until use at a later time.

Example 14

Refolding and Purification of IL-28

A. Inclusion Body Preparation

Human wildtype IL-29 was expressed in *E. coli* strain W3110 as inclusion bodies as described above. A cell pellet from a fed-batch fermentation was resuspended in 50 mM Tris, pH 7.3. The suspension was passed through an APV-Gaulin homogenizer (Invensys APV, Tonawanda, N.Y.) three times at 8000 psi. The insoluble material was recovered by centrifugation at 15,000 g for 30 minutes. The pellet was washed consecutively with 50 mM Tris, 1% (v/v) Triton X100, pH 7.3 and 4 M Urea. The inclusion body was then dispersed in 50 mM Tris, 6 M guanidine hydrochloride, 5 mM DTT at room temperature for 1 hour. The material was then centrifuged at 15,000 g for 1 hour. The supernatant from this step contains reduced soluble IL-29.

B. Refolding

The solubilized IL-29 was diluted slowly into 50 mM Tris, pH 8, 0.75 M Arginine, 0.05% PEG3350, 2 mM $MgCl_2$, 2 mM $CaCl_2$, 0.4 mM KCl, 10 mM NaCl, 4 mM reduced Glutathione, 0.8 mM oxidized Glutathione at room temperature while stirring. The final concentration of IL-29 in the refolding buffer was 0.1 mg/ml. The refolding mixture was left at room temperature overnight. Concentrated acetic acid was then used to adjust the pH of the suspension to 5. The suspension was then filtered through a 0.2 µm filter. RP-HPLC analysis of the refolding mixture showed two prominent peaks.

C. Purification

The refolding mixture was in-line diluted (1:2) with 50 mM NaOAc at pH 5 and loaded onto a Pharmacia SP Sepharose Fast Flow cation exchange column (North Peapack, N.J.). The column was washed with 3 column volumes of 50 mM NaOAc, 400 mM NaCl, pH 5. The bound IL-29 was eluted with 50 mM NaOAc, 1.4 M NaCl, pH 5. Solid $(NH_4)_2SO_4$ was added to the elute pool of the cation exchange step so that the final concentration of $(NH_4)_2SO_4$ was 0.5 M. The material was then loaded onto a ToyoPearl Phenyl 650S HIC column (Tosoh Biosep, Montgomery, Pa.). The column was washed with 3 column volumes of 50 mM NaOAc, 1 M $(H_4)_2SO_4$, pH 5. A linear gradient of 10 column volumes from 50 mM NaOAc, 1 M $(NH_4)_2SO_4$, pH 5 to 50 mM NaOAc, pH 5 was used to elute the bound zcyto21. Fractions were collected of the elute. Two prominent peaks were observed in this step. RP-HPLC analysis of the elute fractions was performed. Two products corresponding to two disulfide bond isomers were produced after final buffer exchange into PBS, pH 7.3.

Example 15

Refolding and Purification of IL-29 Cysteine Mutant

As described in Example 3, purification of IL-29 produced two disulfide bond isomers. A HIC FPLC step was employed to separate the two forms. The separation was not baseline resolved. Severe "Peak Shaving" had to be used to obtain substantially pure isomers (>95%). The yield for this step and by extension for the whole process suffered. The final yields were 8% and 9% for the C15-C112 form and C12-C171 form respectively. Wildtype IL-29 produced in CHO and baculovirus (BV) systems also showed similar phenomena. It was established that the C15-C112 form of the isomer is homologous to type I INF's in disulfide bond patterns. The C15-C112 form also demonstrated 30-fold higher bioactivity than the C112-C171 form in an ISRE assay (see below).

Refolding and Purification of zcyto21 Cys172Ser Mutein

The inclusion body preparation, refolding and purification of zcyto21 C172S polypeptide (SEQ ID NO:29) is essentially the same as those of IL-29 wild-type (SEQ ID NO:4). RP-HPLC analysis of the refolding mixture of the mutein showed only one prominent peak corresponding to the C15-C112 form of the wild-type IL-29. Subsequent HIC chromatography show only a single peak. It was therefore unnecessary to employ severe "peak shaving". The final yield for the entire process is close to 50%. The zcyto2l Cys172Ser polypeptide (SEQ ID NO:29) showed equivalent bioactivity to the C15-C112 form of wild-type IL-29 in ISRE assay shown in Example 16.

Example 16

Antiviral Activity: Cytopathic Effect in Hela and L929 Cells

Initial functional assays for antiviral activity were conducted using conditioned media from transiently transfected human embryonal kidney (HEK) cells. Production of this conditioned medium is described as follows. A full-length cDNA for human or murine IL-28A, IL-28B, or IL-29 was cloned into the pzp7Z vector using standard procedures. The human or murine IL-28A, IL-28B, or IL-29 constructs were transfected into 293 HEK cells. Briefly, for each construct 700,000 cells/well (6 well plates) were plated approximately 18 h prior to transfection in 2 milliliters DMEM +10% fetal bovine serum. Per well, 1.5 micrograms human or murine IL-28A, IL-28B, or IL-29 DNA and 0.5 micrograms pIRES2-EGFP DNA (Clontech) were added to 6 microliters Fugene 6 reagent (Roche Biochemicals) in a total of 100 microliters DMEM. Two micrograms pIRES2-EGFP DNA alone was used as a negative control. These transfection mixtures were added 30 minutes later to the pre-plated 293 cells. Twenty-four hours later the cell media were removed and DMEM +0.1% bovine serum albumin was added. Conditioned media was collected after 48 hours, filtered through a 0.45 micron filter and used for antiviral and reporter assays.

Antiviral Assays were carried out using human cervical carcinoma cells (HeLa) and mouse fibroblast cells (L929). On the first day, conditioned medium containing human or murine IL-28A, IL-28B, or IL-29 was diluted and plated with 50,000 cells in a 96-well flat bottom microtiter plate. Following a 24-hour incubation at 37° C., the medium was removed and replaced with medium containing encephelomyocarditis virus at a multiplicity of infection of 0.1. The cells were again incubated for 24 hours at 37° C. Culture wells were then scored visually on a 4-point scale for the presence of cytopathic effect, which was then converted to % CPE as shown in Table 7. Conditioned medium from cells transfected with GFP alone and purified human interferon-a-2a or murine interferon-alpha were included as controls.

TABLE 7

Determination of Cytopathic Effect

| Designation | Observation of Cytopathic Effect (CPE) |
|---|---|
| − | No CPE |
| +/− | Possible CPE (about 1% of monolayer surface) |
| + | CPE limited to one plaque (about 5% of the surface) |
| +1 | CPE is limited to three plaques, affecting less than 25% of the monolayer |
| 1 | 25% CPE |
| 1-2 | 37% CPE |
| 2 | 50% CPE |
| 2-3 | 62% CPE |
| 3 | 75% CPE |
| 3-4 | 87% CPE |
| 4 | 100% CPE |

Table 8 shows that conditioned medium containing human or murine IL-28A, IL-28B, or IL-29 inhibited viral infection (% CPE) in HeLa cells in a dose-dependent manner, while control GFP conditioned medium failed to significantly block the appearance of cytopathic effect. As shown in Table 9, conditioned medium containing human or murine IL-28A, IL-28B, or IL-29 did not inhibit viral infection in L929 cells. In both experiments purified interferon showed positive antiviral activity.

TABLE 8

Percentage Cytopathic Effect of human or murine IL-28A, IL-28B, or IL-29 in HeLa Cells using Conditioned Medium (CM)

| Relative CM Concentration | Control GFP | zcyto20 IL-28A (CM) | zcyto21 IL-29 (CM) | zcyto22 IL-28B (CM) | zcyto24 mouse IL-28 (CM) | zcyto25 mouse IL-28 (CM) | hIFN-a-2a | hIFN-a-2a Concentration |
|---|---|---|---|---|---|---|---|---|
| No Add | 87 | 87 | 87 | 87 | 87 | 87 | 87 | 0 ng/ml |
| .008X | 87 | 10 | 56 | 0 | 0 | 10 | 15 | .0001 ng/ml |
| .0156X | 87 | 2.5 | 31 | 0 | 0 | 5 | 8.3 | .001 ng/ml |
| .0325X | 87 | 5 | 10 | 0 | 0 | 5 | 1.7 | .01 ng/ml |
| .0625X | 87 | 2.5 | 10 | 0 | 0 | 0 | 0 | .1 ng/ml |

TABLE 8-continued

Percentage Cytopathic Effect of human or murine IL-28A, IL-28B, or IL-29 in HeLa Cells using Conditioned Medium (CM)

| Relative CM Concentration | Control GFP | zcyto20 IL-28A (CM) | zcyto21 IL-29 (CM) | zcyto22 IL-28B (CM) | zcyto24 mouse IL-28 (CM) | zcyto25 mouse IL-28 (CM) | hIFN-a-2a | hIFN-a-2a Concentration |
|---|---|---|---|---|---|---|---|---|
| .125X | 87 | 0 | 5 | 0 | 0 | 0 | 0 | 1 ng/ml |
| .25X | 87 | 0 | 0 | 0 | 0 | 0 | 0 | 10 ng/ml |
| .5X | 87 | 0 | 0 | 0 | 0 | 0 | 0 | 100 ng/ml |

TABLE 9

Percentage Cytopathic Effect of human or murine IL-28A, IL-28B, or IL-29 in L929 Cells using Conditioned Medium (CM)

| Relative CM Conc. | Control GFP | zcyto20 (CM) | zcyto21 (CM) | zcyto22 (CM) | zcyto24 (CM) | zcyto25 (CM) | mIFN-alpha | mIFN-alpha Conc. |
|---|---|---|---|---|---|---|---|---|
| No Add | 87 | 87 | 87 | 87 | 87 | 87 | 87 | 0 ng/ml |
| .008X | 87 | 87 | 87 | 87 | 87 | 87 | 87 | .0001 ng/ml |
| .0156X | 87 | 87 | 87 | 87 | 87 | 87 | 87 | .001 ng/ml |
| .0325X | 87 | 87 | 87 | 87 | 87 | 87 | 87 | .01 ng/ml |
| .0625X | 87 | 87 | 87 | 87 | 87 | 87 | 58 | .1 ng/ml |
| .125X | 87 | 87 | 87 | 87 | 87 | 87 | 6.7 | 1 ng/ml |
| .25X | 87 | 87 | 87 | 87 | 87 | 87 | 0 | 10 ng/ml |
| .5X | 87 | 87 | 87 | 87 | 87 | 87 | 0 | 100 ng/ml |

Example 17

Signaling Via Interferon-Response Pathway

Interaction of type 1 interferons with their specific receptor leads to induction of a number of genes responsible for their antiviral/antiproliferative activity. These include 2'-5' oligoadenylate synthetase (2-5 OAS), double-stranded RNA dependent Pkr kinase (Pkr), phospholipid scramblase, and intercellular adhesion molecule-1 (ICAM-1). Induction of genes with as yet unknown function, such as a 56 kDa interferon stimulated gene product (ISG-56 k), also occurs. To determine if some or all of these genes are induced upon treatment of cells with IL-28A, human Daudi B lymphoid cells were treated for 72 hours with conditioned medium from Sf9 cells infected with baculovirus expressing IL-28A. Conditioned medium from Sf9 cells infected with wild-type baculovirus was used as a negative control. Following treatment cells were collected and lysed for isolation of total RNA. One microgram of total RNA was converted to cDNA using reverse transcriptase and used as a template for polymerase chain reaction using oligonucleotide primers specific for the human interferon-stimulated genes described above. Oligonucleotide primers for human glycerol-3-phosphate dehydrogenase (G3PDH) were used as a non-interferon stimulated gene control. The results show clear induction of ISG-56 k, Pkr, 2-5 OAS and phospholipid scramblase following treatment of cells with IL-28A. No induction was seen for ICAM-1 or the non-interferon stimulated gene control, G3PDH.

Example 18

Signal Transduction Reporter Assay

A signal transduction reporter assay can be used to determine the functional interaction of human and mouse IL-28 and IL-29 with the IL-28 receptor. Human embryonal kidney (HEK) cells are transfected with a reporter plasmid containing an interferon-stimulated response element (ISRE) driving transcription of a luciferase reporter gene in the presence or absence of pZP7 expression vectors containing cDNAs for class II cytokine receptors (including human DIRS1, IFNαR1, IFNαR2 and IL-28 receptor). Luciferase activity following stimulation of transfected cells with class II ligands (including IL-28A (SEQ ID NO:2), IL-29 (SEQ ID NO:4), IL-28B (SEQ ID NO:6), zcyto10, huIL10 and huIFNa-2a) reflects the interaction of the ligand with transfected and native cytokine receptors on the cell surface. The results and methods are described below.

Cell Transfections

293 HEK cells were transfected as follows: 700,000 293 cells/well (6 well plates) were plated approximately 18 h prior to transfection in 2 milliliters DMEM +10% fetal bovine serum. Per well, 1 microgram pISRE-Luciferase DNA (Stratagene), 1 microgram cytokine receptor DNA and 1 microgram pIRES2-EGFP DNA (Clontech,) were added to 9 microliters Fugene 6 reagent (Roche Biochemicals) in a total of 100 microliters DMEM. Two micrograms pIRES2-EGFP DNA was used when cytokine receptor DNA was not included. This transfection mix was added 30 minutes later to the pre-plated 293 cells. Twenty-four hours later the transfected cells were removed from the plate using trypsin-EDTA and replated at approximately 25,000 cells/well in 96 well microtiter plates. Approximately 18 h prior to ligand stimulation, media was changed to DMEM +0.5% FBS.

Signal Transduction Reporter Assays

The signal transduction reporter assays were done as follows: Following an 18 h incubation at 37° C. in DMEM +0.5% FBS, transfected cells were stimulated with dilutions (in DMEM +0.5% FBS) of the following class II ligands; IL-28A, IL-29, IL-28B, zcyto10, huIL10 and huIFNa-2a.

Following a 4-hour incubation at 37° C., the cells were lysed, and the relative light units (RLU) were measured on a luminometer after addition of a luciferase substrate. The results obtained are shown as the fold induction of the RLU of the experimental samples over the medium alone control (RLU of experimental samples/RLU of medium alone=fold induction). Table 10 shows that IL-28A, IL-29, and IL-28B induce ISRE signaling in 293 cells transfected with ISRE-luciferase giving a 15 to 17-fold induction in luciferase activity over medium alone. The addition of IL-28 receptor alpha subunit DNA (SEQ ID NO:11), using the endogenous CRF2-4 (SEQ ID NO:71) to the transfection mix results in a 6 to 8-fold further induction in ISRE signaling by IL-28A, IL-29, and IL-28B giving a 104 to 125-fold total induction. None of the other transfected class II cytokine receptor DNAs resulted in increased ISRE signaling. These results indicate that IL-28A, IL-29, and IL-28B functionally interact with the IL-28 cytokine receptor. Table 10 also shows that huIFNa-2a can induce ISRE signaling in ISRE-luciferase transfected 293 cells giving a 205-fold induction of luciferase activity compared to medium alone. However, the addition of IL-28 receptor DNA to the transfection leads to an 11-fold reduction in ISRE-signaling (compared to ISRE-luciferase DNA alone), suggesting that IL-28 receptor over-expression negatively effects interferon signaling, in contrast to the positive effects of IL-28 receptor over-expression on IL-28A, IL-29, and IL-28B signaling.

TABLE 10

Interferon Stimulated Response Element (ISRE) Signaling of Transfected 293 Cells Following Class II Cytokine Stimulation (Fold Induction)

| Ligand | ISRE-Luc. | ISRE-Luc./IL-28R |
|---|---|---|
| IL-28A (125 ng/ml) | 15 | 125 |
| IL-29 (125 ng/ml) | 17 | 108 |
| IL-28B (125 ng/ml) | 17 | 104 |
| HuIFNa-2a (100 ng/ml) | 205 | 18 |
| Zcyto 10 (125 ng/ml) | 1.3 | 1 |
| HuIL 10 (100 ng/ml) | 1 | 0.5 |

Example 19

Signal Transduction Assays with IL-29 Cysteine Mutants

Cell Transfections

To produce 293 HEK cells stably overexpressing human IL-28 receptor, 293 cells were transfected as follows: 300,000 293 cells/well (6 well plates) were plated approximately 6 h prior to transfection in 2 milliliters DMEM +10% fetal bovine serum. Per well, 2 micrograms of a pZP7 expression vector containing the cDNA of human IL-28 receptor alpha subunit (SEQ ID NO: 11) was added to 6 microliters Fugene 6 reagent (Roche Biochemicals) in a total of 100 microliters DMEM. This transfection mix was added 30 minutes later to the pre-plated 293 cells. Forty-eight hours later the transfected cells were placed under 2 microgram/milliliter puromicin selection. Puromycin resistant cells were carried as a population of cells.

The 293 HEK cells overexpressing human IL-28 receptor were transfected as follows: 700,000 293 cells/well (6 well plates) were plated approximately 18 h prior to transfection in 2 milliliters DMEM +10% fetal bovine serum. Per well, 1 microgram KZ 157 containing an interferon-stimulated response element (ISRE) driving transcription of a luciferase reporter gene were added to 3 microliters Fugene 6 reagent (Roche Biochemicals) in a total of 100 microliters DMEM. This transfection mix was added 30 minutes later to the pre-plated 293 HEK cells. Forty-eight hours later the transfected cells were removed from the plate using trypsin-EDTA and replated in 500 micrograms/ml G418 (Geneticin, Life Technologies). Puromycin and G418 resistant cells were carried as a population of cells.

Signal Transduction Reporter Assays

The signal transduction reporter assays were done as follows: 293HEK cells overexpressing human IL-28 receptor and containing KZ157 were treated with trypsin-EDTA and replated at approximately 25,000 cells/well in 96 well microtiter plates. Approximately 18 h prior to ligand stimulation, media was changed to DMEM +0.5% FBS.

Following an 18 h incubation at 37° C. in DMEM +0.5% FBS, transfected cells were stimulated with dilutions (in DMEM +0.5% FBS) of the different forms of E. coli-derived zcyto21 containing different cysteine binding patterns. Following a 4-hour incubation at 37° C., the cells were lysed, and the relative light units (RLU) were measured on a luminometer after addition of a luciferase substrate. The results obtained are shown as the fold induction of the RLU of the experimental samples over the medium alone control (RLU of experimental samples/RLU of medium alone=fold induction).

Table 11 shows that C1-C3 form (C16-C113) of wild-type E. coli-derived IL-29 is better able to induce ISRE signaling than wild-type C3-C5 form (C113-C172) or a mixture of wild-type C1-C3 form and C3-C5 form (C16-C113, C113-C172), all referring to SEQ ID NO:15.

Table 12 shows that C1-C3 (C16-C113) of wild-type E. coli-derived IL-29 and C1-C3 (C16-C113; SEQ ID NO:15) of Cysteine mutant (C172S) E. coli-derived IL-29 (SEQ ID NO:29) are equally able to induce ISRE signaling in 293 HEK cells overexpressing human IL-28 receptor.

TABLE 11

ISRE Signaling by different forms of E. coli-derived IL-29 (Fold Induction)

| Cytokine Concentration (ng/ml) | C1-C3 form (C16-C113) | C3-C5 form (C113-C172) | Mixture of C1-C3 and C3-C5 |
|---|---|---|---|
| 100 | 36 | 29 | 34 |
| 10 | 38 | 25 | 35 |
| 1 | 32 | 12 | 24 |
| 0.1 | 10 | 2 | 5 |
| 0.01 | 3 | 1 | 1 |
| 0.001 | 1 | 1 | 1 |

TABLE 12

ISRE Signaling by different forms of E. coli-derived IL-29 (Fold Induction)

| Cytokine Concentration (ng/ml) | Wild-type C1-C3 | Cysteine mutant C172S C1-C3 |
|---|---|---|
| 1000 | 9.9 | 8.9 |
| 100 | 9.3 | 8.7 |
| 10 | 9.3 | 8.1 |
| 1 | 7.8 | 7 |
| 0.1 | 4.6 | 3.3 |
| 0.01 | 1.9 | 1.5 |
| 0.001 | 1.3 | 0.9 |

Example 20

Induction of IL-28A, IL-29 IL-28B by poly I:C and Viral Infection

Freshly isolated human peripheral blood mononuclear cells were grown in the presence of polyinosinic acid-polycytidylic acid (poly I:C; 100 μg/ml) (SIGMA; St. Louis, Mo.), encephalomyocarditis virus (EMCV) with an MOI of 0.1, or in medium alone. After a 15 h incubation, total RNA was isolated from cells and treated with RNase-free DNase. 100 ng total RNA was used as template for one-step RT-PCR using the Superscript One-Step RT-PCR with Platinum Taq kit and gene-specific primers as suggested by the manufacturer (Invitrogen).

Low to undetectable amounts of human IL-28A, IL-28B, and IL-29, IFN-α and IFN-β RNA were seen in untreated cells. In contrast, the amount of IL-28A, IL-29, IL-28B RNA was increased by both poly I:C treatment and viral infection, as was also seen for the type I interferons. These experiments indicate that IL-28A, IL-29, IL-28B, like type I interferons, can be induced by double-stranded RNA or viral infection.

Example 21

IL-28, IL-29 Signaling Activity Compared to IFNα in HepG2 Cells

A. Cell Transfections

HepG2 cells were transfected as follows: 700,000 HepG2 cells/well (6 well plates) were plated approximately 18 h prior to transfection in 2 milliliters DMEM +10% fetal bovine serum. Per well, 1 microgram pISRE-Luciferase DNA (Stratagene) and 1 microgram pIRES2-EGFP DNA (Clontech,) were added to 6 microliters Fugene 6 reagent (Roche Biochemicals) in a total of 100 microliters DMEM. This transfection mix was added 30 minutes later to the pre-plated HepG2 cells. Twenty-four hours later the transfected cells were removed from the plate using trypsin-EDTA and replated at approximately 25,000 cells/well in 96 well microtiter plates. Approximately 18 h prior to ligand stimulation, media was changed to DMEM +0.5% FBS.

B. Signal Transduction Reporter Assays

The signal transduction reporter assays were done as follows: Following an 18 h incubation at 37° C. in DMEM +0.5% FBS, transfected cells were stimulated with 100 ng/ml IL-28A, IL-29, IL-28B, zcyto24, zcyto25 and huIFN-α2a ligands. Following a 4-hour incubation at 37° degrees, the cells were lysed, and the relative light units (RLU) were measured on a luminometer after addition of a luciferase substrate. The results obtained are shown as the fold induction of the RLU of the experimental samples over the medium alone control (RLU of experimental samples/RLU of medium alone=fold induction). Table 13 shows that IL-28A, IL-29, IL-28B, zcyto24 and zcyto25 induce ISRE signaling in human HepG2 liver cells transfected with ISRE-luciferase.

TABLE 13

Fold Induction of Cytokine-dependent ISRE Signaling in HepG2 Cells

| Cytokine | Fold Induction |
|---|---|
| IL-28A | 5.6 |
| IL-29 | 4 |
| IL-28B | 5.8 |

TABLE 13-continued

Fold Induction of Cytokine-dependent ISRE Signaling in HepG2 Cells

| Cytokine | Fold Induction |
|---|---|
| Zcyto24 | 4.7 |
| Zcyto25 | 3 |
| HuIFN-a2a | 5.8 |

Example 22

IL-29 Antiviral Activity Compared to IFNα in HepG2 Cells

An antiviral assay was adapted for EMCV (American Type Culture Collection # VR-129B, Manassas, Va.) with human cells (Familletti, P., et al., *Methods Enzym.* 78: 387-394, 1981). Cells were plated with cytokines and incubated 24 hours prior to challenge by EMCV at a multiplicity of infection of 0.1 to 1. The cells were analyzed for viability with a dye-uptake bioassay 24 hours after infection (Berg, K., et al., *Apmis* 98: 156-162, 1990). Target cells were given MTT and incubated at 37° C. for 2 hours. A solubiliser solution was added, incubated overnight at 37° C. and the optical density at 570 nm was determined. OD570 is directly proportional to antiviral activity.

The results show the antiviral activity when IL-29 and IFN on were tested with HepG2 cells: IL-29, IFN-β and IFN α-2a were added at varying concentration to HepG2 cells prior to EMCV infection and dye-uptake assay. The mean and standard deviation of the OD570 from triplicate wells is plotted. OD570 is directly proportional to antiviral activity. For IL-29, the EC50 was 0.60 ng/ml; for IFN-α2a, the EC50 was 0.57 ng/ml; and for IFN-β, the EC50 was 0.46 ng/ml.

Example 23

IL-28RA mRNA Expression in Liver and Lymphocyte Subsets

In order to further examine the mRNA distribution for IL-28RA, semi-quantitative RT-PCR was performed using the SDS 7900HT system (Applied Biosystems, Calif.). One-step RT-PCR was performed using 100 ng total RNA for each sample and gene-specific primers. A standard curve was generated for each primer set using Bjab RNA and all sample values were normalized to HPRT. The normalized results are summarized in Tables 14-17. The normalized values for IFNAR2 and CRF2-4 are also shown.

Table 14: B and T cells express significant levels of IL-28RA mRNA. Low levels are seen in dendritic cells and most monocytes.

TABLE 14

| Cell/Tissue | IL-28RA | IFNAR2 | CRF2-4 |
|---|---|---|---|
| Dendritic Cells unstim | .04 | 5.9 | 9.8 |
| Dendritic Cells + IFNg | .07 | 3.6 | 4.3 |
| Dendritic Cells | .16 | 7.85 | 3.9 |
| CD14+ stim'd with LPS/IFNg | .13 | 12 | 27 |
| CD14+ monocytes resting | .12 | 11 | 15.4 |
| Hu CD14+ Unact. | 4.2 | TBD | TBD |
| Hu CD14+ 1 ug/ml LPS act. | 2.3 | TBD | TBD |
| H. Inflamed tonsil | 3 | 12.4 | 9.5 |
| H. B-cells + PMA/Iono 4 & 24 hrs | 3.6 | 1.3 | 1.4 |
| Hu CD19+ resting | 6.2 | TBD | TBD |

TABLE 14-continued

| Cell/Tissue | IL-28RA | IFNAR2 | CRF2-4 |
|---|---|---|---|
| Hu CD19+ 4 hr. PMA/Iono | 10.6 | TBD | TBD |
| Hu CD 19+ 24 hr Act. PMA/Iono | 3.7 | TBD | TBD |
| IgD+ B-cells | 6.47 | 13.15 | 6.42 |
| IgM+ B-cells | 9.06 | 15.4 | 2.18 |
| IgD− B-cells | 5.66 | 2.86 | 6.76 |
| NKCells + PMA/Iono | 0 | 6.7 | 2.9 |
| Hu CD3+ Unactivated | 2.1 | TBD | TBD |
| CD4+ resting | .9 | 8.5 | 29.1 |
| CD4+ Unstim 18 hrs | 1.6 | 8.4 | 13.2 |
| CD4+ + Poly I/C | 2.2 | 4.5 | 5.1 |
| CD4+ + PMA/Iono | .3 | 1.8 | .9 |
| CD3 neg resting | 1.6 | 7.3 | 46 |
| CD3 neg unstim 18 hrs | 2.4 | 13.2 | 16.8 |
| CD3 neg + Poly I/C 18 hrs | 5.7 | 7 | 30.2 |
| CD3 neg + LPS 18 hrs | 3.1 | 11.9 | 28.2 |
| CD8+ unstim 18 hrs | 1.8 | 4.9 | 13.1 |
| CD8+ stim'd with PMA/Ion 18 hrs | .3 | .6 | 1.1 |

As shown in Table 14, normal liver tissue and liver derived cell lines display substantial levels of IL-28RA and CRF2-4 mRNA.

TABLE 15

| Cell/Tissue | IL-28RA | IFNAR2 | CRF2-4 |
|---|---|---|---|
| HepG2 | 1.6 | 3.56 | 2.1 |
| HepG2 UGAR 5/10/02 | 1.1 | 1.2 | 2.7 |
| HepG2, CGAT HKES081501C | 4.3 | 2.1 | 6 |
| HuH7 5/10/02 | 1.63 | 16 | 2 |
| HuH7 hepatoma - CGAT | 4.2 | 7.2 | 3.1 |
| Liver, normal - CGAT #HXYZ020801K | 11.7 | 3.2 | 8.4 |
| Liver, NAT—Normal adjacent tissue | 4.5 | 4.9 | 7.7 |
| Liver, NAT—Normal adjacent tissue | 2.2 | 6.3 | 10.4 |
| Hep SMVC hep vein | 0 | 1.4 | 6.5 |
| Hep SMCA hep. Artery | 0 | 2.1 | 7.5 |
| Hep. Fibro | 0 | 2.9 | 6.2 |
| Hep. Ca. | 3.8 | 2.9 | 5.8 |
| Adenoca liver | 8.3 | 4.2 | 10.5 |
| SK-Hep-1 adenoca. Liver | .1 | 1.3 | 2.5 |
| AsPC-1 Hu. Pancreatic adenocarc. | .7 | .8 | 1.3 |
| Hu. Hep. Stellate cells | .025 | 4.4 | 9.7 |

As shown in Table 15, primary airway epithelial cells contain abundant levels of IL-28RA and CRF2-4.

TABLE 16

| Cell/Tissue | IL-28RA | IFNAR2 | CRF2-4 |
|---|---|---|---|
| U87MG - glioma | 0 | .66 | .99 |
| NHBE unstim | 1.9 | 1.7 | 8.8 |

TABLE 16-continued

| Cell/Tissue | IL-28RA | IFNAR2 | CRF2-4 |
|---|---|---|---|
| NHBE + TNF-alpha | 2.2 | 5.7 | 4.6 |
| NHBE + poly I/C | 1.8 | nd | nd |
| Small Airway Epithelial Cells | 3.9 | 3.3 | 27.8 |
| NHLF—Normal human lung fibroblasts | 0 | nd | nd |

As shown in Table 16, IL-28RA is present in normal and diseased liver specimens, with increased expression in tissue from Hepatitis C and Hepatitis B infected specimens.

TABLE 17

| Cell/Tissue | IL-28RA | CRF2-4 | IFNAR2 |
|---|---|---|---|
| Liver with Coagulation Necrosis | 8.87 | 15.12 | 1.72 |
| Liver with Autoimmune Hepatitis | 6.46 | 8.90 | 3.07 |
| Neonatal Hepatitis | 6.29 | 12.46 | 6.16 |
| Endstage Liver disease | 4.79 | 17.05 | 10.58 |
| Fulminant Liver Failure | 1.90 | 14.20 | 7.69 |
| Fulminant Liver failure | 2.52 | 11.25 | 8.84 |
| Cirrhosis, primary biliary | 4.64 | 12.03 | 3.62 |
| Cirrhosis Alcoholic (Laennec's) | 4.17 | 8.30 | 4.14 |
| Cirrhosis, Cryptogenic | 4.84 | 7.13 | 5.06 |
| Hepatitis C+, with cirrhosis | 3.64 | 7.99 | 6.62 |
| Hepatitis C+ | 6.32 | 11.29 | 7.43 |
| Fulminant hepatitis secondary to Hep A | 8.94 | 21.63 | 8.48 |
| Hepatitis C+ | 7.69 | 15.88 | 8.05 |
| Hepatitis B+ | 1.61 | 12.79 | 6.93 |
| Normal Liver | 8.76 | 5.42 | 3.78 |
| Normal Liver | 1.46 | 4.13 | 4.83 |
| Liver NAT | 3.61 | 5.43 | 6.42 |
| Liver NAT | 1.97 | 10.37 | 6.31 |
| Hu Fetal Liver | 1.07 | 4.87 | 3.98 |
| Hepatocellular Carcinoma | 3.58 | 3.80 | 3.22 |
| Adenocarcinoma Liver | 8.30 | 10.48 | 4.17 |
| hep. SMVC, hep. Vein | 0.00 | 6.46 | 1.45 |
| Hep SMCA hep. Artery | 0.00 | 7.55 | 2.10 |
| Hep. Fibroblast | 0.00 | 6.20 | 2.94 |
| HuH7 hepatoma | 4.20 | 3.05 | 7.24 |
| HepG2 Hepatocellular carcinoma | 3.40 | 5.98 | 2.11 |
| SK-Hep-1 adenocar. Liver | 0.03 | 2.53 | 1.30 |
| HepG2 Unstim | 2.06 | 2.98 | 2.28 |
| HepG2 + zcyto21 | 2.28 | 3.01 | 2.53 |
| HepG2 + IFNα | 2.61 | 3.05 | 3.00 |
| Normal Female Liver - degraded | 1.38 | 6.45 | 4.57 |
| Normal Liver - degraded | 1.93 | 4.99 | 6.25 |
| Normal Liver - degraded | 2.41 | 2.32 | 2.75 |
| Disease Liver - degraded | 2.33 | 3.00 | 6.04 |
| Primary Hepatocytes from Clonetics | 9.13 | 7.97 | 13.30 |

As shown in Tables 18-22, IL-28RA is detectable in normal B cells, B lymphoma cell lines, T cells, T lymphoma cell lines (Jurkat), normal and transformed lymphocytes (B cells and T cells) and normal human monocytes.

TABLE 18

| | HPRT Mean | IL-28RA Mean | IL-28RA norm | IFNAR2 | IFNR2 norm | CRF2-4 | CRF2-4 Norm |
|---|---|---|---|---|---|---|---|
| CD14+ 24 hr unstim #A38 | 13.1 | 68.9 | 5.2 | 92.3 | 7.0 | 199.8 | 15.2 |
| CD14+ 24 hr stim #A38 | 6.9 | 7.6 | 1.1 | 219.5 | 31.8 | 276.6 | 40.1 |
| CD14+ 24 hr unstim #A112 | 17.5 | 40.6 | 2.3 | 163.8 | 9.4 | 239.7 | 13.7 |
| CD14+ 24 hr stim #A112 | 11.8 | 6.4 | 0.5 | 264.6 | 22.4 | 266.9 | 22.6 |
| CD14+ rest #X | 32.0 | 164.2 | 5.1 | 1279.7 | 39.9 | 699.9 | 21.8 |

TABLE 18-continued

|  | HPRT Mean | IL-28RA Mean | IL-28RA norm | IFNAR2 | IFNR2 norm | CRF2-4 | CRF2-4 Norm |
|---|---|---|---|---|---|---|---|
| CD14+ + LPS #X | 21.4 | 40.8 | 1.9 | 338.2 | 15.8 | 518.0 | 24.2 |
| CD14+ 24 hr unstim #A39 | 26.3 | 86.8 | 3.3 | 297.4 | 11.3 | 480.6 | 18.3 |
| CD14+ 24 hr stim #A39 | 16.6 | 12.5 | 0.8 | 210.0 | 12.7 | 406.4 | 24.5 |
| HL60 Resting | 161.2 | 0.2 | 0.0 | 214.2 | 1.3 | 264.0 | 1.6 |
| HL60 + PMA | 23.6 | 2.8 | 0.1 | 372.5 | 15.8 | 397.5 | 16.8 |
| U937 Resting | 246.7 | 0.0 | 0.0 | 449.4 | 1.8 | 362.5 | 1.5 |
| U937 + PMA | 222.7 | 0.0 | 0.0 | 379.2 | 1.7 | 475.9 | 2.1 |
| Jurkat Resting | 241.7 | 103.0 | 0.4 | 327.7 | 1.4 | 36.1 | 0.1 |
| Jurkat Activated | 130.7 | 143.2 | 1.1 |  |  |  |  |
| Colo205 | 88.8 | 43.5 | 0.5 |  |  |  |  |
| HT-29 | 26.5 | 30.5 | 1.2 |  |  |  |  |

TABLE 19

|  | HPRT SD | IL-28RA SD |
|---|---|---|
| Mono 24 hr unstim #A38 | 0.6 | 2.4 |
| Mono 24 hr stim #A38 | 0.7 | 0.2 |
| Mono 24 hr unstim #A112 | 2.0 | 0.7 |
| Mono 24 hr stim #A112 | 0.3 | 0.1 |
| Mono rest #X | 5.7 | 2.2 |
| Mono + LPS #X | 0.5 | 1.0 |
| Mono 24 hr unstim #A39 | 0.7 | 0.8 |
| Mono 24 hr stim #A39 | 0.1 | 0.7 |
| HL60 Resting | 19.7 | 0.1 |
| HL60 + PMA | 0.7 | 0.4 |
| U937 Resting | 7.4 | 0.0 |
| U937 + PMA | 7.1 | 0.0 |
| Jurkat Resting | 3.7 | 1.1 |
| Jurkat Activated | 2.4 | 1.8 |
| Colo205 | 1.9 | 0.7 |
| HT-29 | 2.3 | 1.7 |

TABLE 20

|  | Mean Hprt | Mean IFNAR2 | Mean IL-28RA | Mean CRF |
|---|---|---|---|---|
| CD3+/CD4+ 0 | 10.1 | 85.9 | 9.0 | 294.6 |
| CD4/CD3+ Unstim 18 hrs | 12.9 | 108.7 | 20.3 | 170.4 |
| CD4+/CD3+ + Poly I/C 18 hrs | 24.1 | 108.5 | 52.1 | 121.8 |
| CD4+/CD3+ + PMA/Iono 18 hrs | 47.8 | 83.7 | 16.5 | 40.8 |
| CD3 neg 0 | 15.4 | 111.7 | 24.8 | 706.1 |
| CD3 neg unstim 18 hrs | 15.7 | 206.6 | 37.5 | 263.0 |
| CD3 neg + Poly I/C 18 hrs | 9.6 | 67.0 | 54.7 | 289.5 |
| CD3 neg + LPS 18 hrs | 14.5 | 173.2 | 44.6 | 409.3 |
| CD8+ Unstim. 18 hrs | 6.1 | 29.7 | 11.1 | 79.9 |
| CD8+ + PMA/Iono 18 hrs | 78.4 | 47.6 | 26.1 | 85.5 |
| 12.8.1 – NHBE Unstim | 47.4 | 81.1 | 76.5 | 415.6 |
| 12.8.2 – NHBE + TNF-alpha | 42.3 | 238.8 | 127.7 | 193.9 |
| SAEC | 15.3 | 49.9 | 63.6 | 426.0 |

TABLE 21

|  | IL-28RA Norm | CRF Norm | IFNAR2 Norm | IL-28RA SD | CRF SD | IFNAR2 SD |
|---|---|---|---|---|---|---|
| CD3+/CD4+ 0 | 0.9 | 29.1 | 8.5 | 0.1 | 1.6 | 0.4 |
| CD4/CD3+ Unstim 18 hrs | 1.6 | 13.2 | 8.4 | 0.2 | 1.6 | 1.4 |
| CD4+/CD3+ + Poly I/C 18 hrs | 2.2 | 5.1 | 4.5 | 0.1 | 0.3 | 0.5 |
| CD4+/CD3+ + PMA/Iono 18 hrs | 0.3 | 0.9 | 1.8 | 0.0 | 0.1 | 0.3 |
| CD3 neg 0 | 1.6 | 46.0 | 7.3 | 0.2 | 4.7 | 1.3 |
| CD3 neg unstim 18 hrs | 2.4 | 16.8 | 13.2 | 0.4 | 2.7 | 2.3 |
| CD3 neg + Poly I/C 18 hrs | 5.7 | 30.2 | 7.0 | 0.3 | 1.7 | 0.8 |
| CD3 neg + LPS 18 hrs | 3.1 | 28.2 | 11.9 | 0.4 | 5.4 | 2.9 |
| CD8+ Unstim. 18 hrs | 1.8 | 13.1 | 4.9 | 0.1 | 1.1 | 0.3 |
| CD8+ + PMA/Iono 18 hrs | 0.3 | 1.1 | 0.6 | 0.0 | 0.1 | 0.0 |
| 12.8.1 - NHBE Unstim | 1.6 | 8.8 | 1.7 | 0.1 | 0.4 | 0.1 |
| 12.8.2 - NHBE + TNF-alpha | 3.0 | 4.6 | 5.7 | 0.1 | 0.1 | 0.1 |
| SAEC | 4.1 | 27.8 | 3.3 | 0.2 | 1.1 | 0.3 |

TABLE 22

|  | SD Hprt | SD IFNAR2 | SD IL-28RA | SD CRF |
|---|---|---|---|---|
| CD3+/CD4+ 0 | 0.3 | 3.5 | 0.6 | 12.8 |
| CD4/CD3+ Unstim 18 hrs | 1.4 | 13.7 | 1.1 | 8.5 |
| CD4+/CD3+ + Poly I/C 18 hrs | 1.3 | 9.8 | 1.6 | 3.4 |
| CD4+/CD3+ + PMA/Iono 18 hrs | 4.0 | 10.3 | 0.7 | 3.7 |
| CD3 neg 0 | 1.4 | 16.6 | 1.6 | 28.6 |
| CD3 neg unstim 18 hrs | 2.4 | 16.2 | 2.7 | 12.6 |
| CD3 neg + Poly I/C 18 hrs | 0.5 | 7.0 | 1.0 | 8.3 |
| CD3 neg + LPS 18 hrs | 1.0 | 39.8 | 5.6 | 73.6 |
| CD8+ Unstim. 18 hrs | 0.2 | 1.6 | 0.5 | 6.1 |
| CD8+ + PMA/Iono 18 hrs | 1.3 | 1.7 | 0.2 | 8.1 |
| 12.8.1 – NHBE Unstim | 2.4 | 5.6 | 2.7 | 2.8 |
| 12.8.2 – NHBE + TNF-alpha | 0.5 | 3.4 | 3.5 | 3.4 |
| SAEC | 0.5 | 4.8 | 1.8 | 9.9 |

Example 24

Mouse IL-28 Does Not Effect Daudi Cell Proliferation

Human Daudi cells were suspended in RPMI +10% FBS at 50,000 cells/milliliter and 5000 cells were plated per well in a 96 well plate. IL-29-CEE (IL-29 conjugated with glu tag), IFN-γ or IFN-α2a was added in 2-fold serial dilutions to each well. IL-29-CEE was used at a concentration range of from 1000 ng/ml to 0.5 ng/ml. IFN-γ was used at a concentration range from 125 ng/ml to 0.06 ng/ml. IFN-α2a was used at a concentration range of from 62 ng/ml to 0.03 ng/ml. Cells were incubated for 72 h at 37° C. After 72 hrs Alamar Blue (Accumed, Chicago, Ill.) was added at 20 microliters/well. Plates were further incubated at 37° C., 5% CO, for 24 hours. Plates were read on the Fmax™ plate reader (Molecular Devices, Sunnyvale, Calif.) using the SoftMax™ Pro program, at wavelengths 544 (Excitation) and 590 (Emission). Alamar Blue gives a fluourometric readout based on the metabolic activity of cells, and is thus a direct measurement of cell proliferation in comparison to a negative control. The results indicate that IL-29-CEE, in contrast to IFN-α2a, has no significant effect on proliferation of Daudi cells.

Example 25

Mouse IL-28 Does Not Have Antiproliferative Effect on Mouse B Cells

Mouse B cells were isolated from 2 Balb/C spleens (7 months old) by depleting CD43+ cells using MACS magnetic beads. Purified B cells were cultured in vitro with LPS, anti-IgM or anti-CD40 monoclonal antibodies. Mouse IL-28 or mouse IFNA was added to the cultures and $^3$H-thymidine was added at 48 hrs. and $^3$H-thymidine incorporation was measured after 72 hrs. culture.

IFNα at 10 ng/ml inhibited $^3$H-thymidine incorporation by mouse B cells stimulated with either LPS or anti-IgM. However mouse IL-28 did not inhibit $^3$H-thymidine incorporation at any concentration tested including 1000 ng/ml. In contrast, both mIFNa and mouse IL-28 increased $^3$H thymidine incorporation by mouse B cells stimulated with anti-CD40 MAb.

These data demonstrate that mouse IL-28 unlike IFNa displays no antiproliferative activity even at high concentrations. In addition, zcyto24 enhances proliferation in the presence of anti-CD40 MAbs. The results illustrate that mouse IL-28 differs from IFNA, in that mouse IL-28 does not display antiproliferative activity on mouse B cells, even at high concentrations. In addition, mouse IL-28 enhances proliferation in the presence of anti-CD40 monoclonal antibodies.

Example 26

Bone Marrow Expansion Assay

Fresh human marrow mononuclear cells (Poietic Technologies, Gaithersburg, Md.) were adhered to plastic for 2 hrs in αMEM, 10% FBS, 50 micromolar Omercaptoethanol, 2 ng/ml FLT3L at 37° C. Non adherent cells were then plated at 25,000 to 45,000 cells/well (96 well tissue culture plates) in αMEM, 10% FBS, 50 micromolar βmercaptoethanol, 2 ng/ml FLT3L in the presence or absence of 1000 ng/ml IL-29-CEE, 100 ng/ml IL-29-CEE, 10 ng/ml IL-29-CEE, 100 ng/ml IFN-α2a, 10 ng/ml IFN-α2a or 1 ng/ml IFN-α2a. These cells were incubated with a variety of cytokines to test for expansion or differentiation of hematopoietic cells from the marrow (20 ng/ml IL-2, 2 ng/ml IL-3, 20 ng/ml IL-4, 20 ng/ml IL-5, 20 ng/ml IL-7, 20 ng/ml IL-10, 20 ng/ml IL-12, 20 ng/ml IL-15, 10 ng/ml IL-21 or no added cytokine). After 8 to 12 days Alamar Blue (Accumed, Chicago, Ill.) was added at 20 microliters/well. Plates were further incubated at 37° C., 5% CO, for 24 hours. Plates were read on the Fmax™ plate reader (Molecular Devices Sunnyvale, Calif.) using the SoftMax™ Pro program, at wavelengths 544 (Excitation) and 590 (Emission). Alamar Blue gives a fluourometric readout based on the metabolic activity of cells, and is thus a direct measurement of cell proliferation in comparison to a negative control.

IFN-α2a caused a significant inhibition of bone marrow expansion under all conditions tested. In contrast, IL-29 had no significant effect on expansion of bone marrow cells in the presence of IL-3, IL-4, IL-5, IL-7, IL-10, IL-12, IL-21 or no added cytokine. A small inhibition of bone marrow cell expansion was seen in the presence of IL-2 or IL-15.

Example 27

Inhibition of IL-28 and IL-29 Signaling with Soluble Receptor (zcytoR19/CRF2-4)

A. Signal Transduction Reporter Assay

A signal transduction reporter assay can be used to show the inhibitor properties of zcytor19-Fc4 homodimeric and zcytor19-Fc/CRF2-4-Fc heterodimeric soluble receptors on zcyto20, zcyto21 and zcyto24 signaling. Human embryonal kidney (HEK) cells overexpressing the zcytor19 receptor are transfected with a reporter plasmid containing an interferon-stimulated response element (ISRE) driving transcription of a luciferase reporter gene. Luciferase activity following stimulation of transfected cells with ligands (including zcyto20 (SEQ ID NO:2), zcyto21 (SEQ ID NO:4), zcyto24 (SEQ ID NO:8)) reflects the interaction of the ligand with soluble receptor.

B. Cell Transfections

293 HEK cells overexpressing zcytor19 were transfected as follows: 700,000 293 cells/well (6 well plates) were plated approximately 18 h prior to transfection in 2 milliliters DMEM +10% fetal bovine serum. Per well, 1 microgram pISRE-Luciferase DNA (Stratagene) and 1 microgram pIRES2-EGFP DNA (Clontech,) were added to 6 microliters Fugene 6 reagent (Roche Biochemicals) in a total of 100 microliters DMEM. This transfection mix was added 30 minutes later to the pre-plated 293 cells. Twenty-four hours later the transfected cells were removed from the plate using trypsin-EDTA and replated at approximately 25,000 cells/ well in 96 well microtiter plates. Approximately 18 h prior to ligand stimulation, media was changed to DMEM +0.5% FBS.

C. Signal Transduction Reporter Assays

The signal transduction reporter assays were done as follows: Following an 18 h incubation at 37° C. in DMEM +0.5% FBS, transfected cells were stimulated with 10 ng/ml zcyto20, zcyto21 or zcyto24 and 10 micrograms/ml of the following soluble receptors; human zcytor19-Fc homodimer, human zcytor19-Fc/human CRF2-4-Fc heterodimer, human CRF2-4-Fc homodimer, murine zcytor19-Ig homodimer. Following a 4-hour incubation at 37° C., the cells were lysed, and the relative light units (RLU) were measured on a luminometer after addition of a luciferase substrate. The results obtained are shown as the percent inhibition of ligand-induced signaling in the presence of soluble receptor relative to the signaling in the presence of PBS alone. Table 23 shows that the human zcytor19-Fc/human CRF2-4 heterodimeric soluble receptor is able to inhibit zcyto20, zcyto21 and zcyto24-induced signaling between 16 and 45% of control. The human zcytor19-Fc homodimeric soluble receptor is also able to inhibit zcyto2 1-induced signaling by 45%. No significant effects were seen with huCRF2-4-Fc or muzcytor19-Ig homodimeric soluble receptors.

TABLE 23

Percent Inhibition of Ligand-induced Interferon Stimulated Response Element (ISRE) Signaling by Soluble Receptors

| Ligand | Huzcytor19-Fc/huCRF2-4-Fc | Huzcytor19-Fc | HuCRF2-4-Fc | Muzcytor19-Ig |
|---|---|---|---|---|
| Zcyto20 | 16% | 92% | 80% | 91% |
| Zcyto21 | 16% | 45% | 79% | 103% |
| Zcyto24 | 47% | 90% | 82% | 89% |

Example 28

IL-28 and IL-29 Inhibit HIV Replication in Fresh Human PBMCs

Human immunodeficiency virus (HIV) is a pathogenic retrovirus that infects cells of the immune system. CD4 T cells and monocytes are the primary infected cell types. To test the ability of IL-28 and IL-29 to inhibit HIV replication in vitro, PBMCs from normal donors were infected with the HIV virus in the presence of IL-28, IL-29 and MetIL-29C172S-PEG.

Fresh human peripheral blood mononuclear cells (PBMCs) were isolated from whole blood obtained from screened donors who were seronegative for HIV and HBV. Peripheral blood cells were pelleted/washed 2-3 times by low speed centrifugation and resuspended in PBS to remove contaminating platelets. The washed blood cells were diluted 1:1 with Dulbecco's phosphate buffered saline (D-PBS) and layered over 14 mL of Lymphocyte Separation Medium ((LSM; cellgro™ by Mediatech, Inc. Herndon, Va.); density 1.078+/−0.002 g/ml) in a 50 mL centrifuge tube and centrifuged for 30 minutes at 600×G. Banded PBMCs were gently aspirated from the resulting interface and subsequently washed 2× in PBS by low speed centrifugation. After the final wash, cells were counted by trypan blue exclusion and resuspended at $1\times10^7$ cells/mL in RPMI 1640 supplemented with 15% Fetal Bovine Serum (FBS), 2 mM L-glutamine, 4 μg/mL PHA-P.

The cells were allowed to incubate for 48-72 hours at 37° C. After incubation, PBMCs were centrifuged and resuspended in RPMI 1640 with 15% FBS, 2 mM L-glutamine, 100 U/mL penicillin, 100 μg/mL streptomycin, 10 μg/mL gentamycin, and 20 U/mL recombinant human IL-2. PBMCs were maintained in the medium at a concentration of $1-2\times10^6$ cells/mL with biweekly medium changes until used in the assay protocol. Monocytes were depleted from the culture as the result of adherence to the tissue culture flask.

For the standard PBMC assay, PHA-P stimulated cells from at least two normal donors were pooled, diluted in fresh medium to a final concentration of $1\times10^6$ cells/mL, and plated in the interior wells of a 96 well round bottom microplate at 50 μL/well ($5\times10^4$ cells/well). Test dilutions were prepared at a 2× concentration in microtiter tubes and 100 μL of each concentration was placed in appropriate wells in a standard format. IL-28, IL-29 and MetIL-29C172S-PEG were added at concentrations from 0-10 μg/ml, usually in ½ log dilutions. 50 μL of a predetermined dilution of virus stock was placed in each test well (final MOI of 0.1). Wells with only cells and virus added were used for virus control. Separate plates were prepared identically without virus for drug cytotoxicity studies using an MTS assay system. The PBMC cultures were maintained for seven days following infection, at which time cell-free supernatant samples were collected and assayed for reverse transcriptase activity and p24 antigen levels.

A decrease in reverse transcriptase activity or p24 antigen levels with IL-28, IL-29 and MetIL-29C172S-PEG would be indicators of antiviral activity. Result would demonstrate that IL-28 and IL-29 may have therapeutic value in treating HIV and AIDS.

Example 29

IL-28 and IL-29 Inhibit GBV-B Replication in Marmoset Liver Cells

HCV is a member of the *Flaviviridae* family of RNA viruses. HCV does not replicate well in either ex-vivo or in vitro cultures and therefore, there are no satisfactory systems to test the anti-HCV activity of molecules in vitro. GB virus B (GBV-B) is an attractive surrogate model for use in the development of anti-HCV antiviral agents since it has a relatively high level of sequence identity with HCV and is a hepatotropic virus. To date, the virus can only be grown in the primary hepatocytes of certain non-human primates. This is accomplished by either isolating hepatocytes in vitro and infecting them with GBV-B, or by isolating hepatocytes from GBV-B infected marmosets and directly using them with antiviral compounds.

The effects of IL-28, IL-29 and MetIL-29C172S-PEG are assayed on GBV-B extracellular RNA production by TaqMan RT-PCR and on cytotoxicity using CellTiter96® reagent (Promega, Madison, Wis.) at six half-log dilutions IL-28, IL-29 or MetIL-29C172S-PEG polypeptide in triplicate. Untreated cultures serve as the cell and virus controls. Both RIBAVIRIN® (200 μg/ml at the highest test concentration) and IFN-α (5000 IU/ml at the highest test) are included as positive control compounds. Primary hepatocyte cultures are isolated and plated out on collagen-coated plates. The next day the cultures are treated with the test samples (IL-28, IL-29, MetIL-29C172S-PEG, IFNα, or RIBAVIRIN®) for 24 hr before being exposed to GBV-B virions or treated directly with test samples when using in vivo infected hepatocytes. Test samples and media are added the next day, and replaced three days later. Three to four days later (at day 6-7 post test sample addition) the supernatant is collected and the cell numbers quantitated with CellTiter96®. Viral RNA is extracted from the supernatant and quantified with triplicate replicates in a quantitative TaqMan RT-PCR assay using an in vitro transcribed RNA containing the RT-PCR target as a standard. The average of replicate samples is computed. Inhibition of virus production is assessed by plotting the average RNA and cell number values of the triplicate samples relative to the untreated virus and cell controls. The inhibitory concentration of drug resulting in 50% inhibition of GBV-B RNA production (IC50) and the toxic concentration resulting in destruction of 50% of cell numbers relative to control values (TC50) are calculated by interpolation from graphs created with the data.

Inhibition of the GBV-B RNA production by IL-28 and 29 is an indication of the antiviral properties of IL-28 and IL-29 on this Hepatitis C-like virus on hepatocytes, the primary organ of infection of Hepatitis C, and positive results suggest that IL-28 or IL-29 may be useful in treating HCV infections in humans.

Example 30

IL-28, IL-29 and MetIL-29C172S-PEG Inhibit HBV Replication in WT10 Cells

Chronic hepatitis B (HBV) is one of the most common and severe viral infections of humans belonging to the *Hepadnaviridae* family of viruses. To test the antiviral activities of IL-28 and IL-29 against HBV, IL-28, IL-29 and MetIL-29C172S-PEG were tested against HBV in an in vitro infection system using a variant of the human liver line HepG2. IL-28, IL-29 and MetIL-29C172S-PEG inhibited viral replication in this system, suggesting therapeutic value in treating HBV in humans.

WT10 cells are a derivative of the human liver cell line HepG2 2.2.15. WT10 cells are stably transfected with the HBV genome, enabling stable expression of HBV transcripts in the cell line (Fu and Cheng, *Antimicrobial Agents Chemother.* 44(12):3402-3407, 2000). In the WT10 assay the drug in question and a 3TC control will be assayed at five concentrations each, diluted in a half-log series. The endpoints are TaqMan PCR for extracellular HBV DNA (IC50) and cell numbers using CellTiter96 reagent (TC50). The assay is similar to that described by Korba et al. *Antiviral Res.* 15(3):217-228, 1991 and Korba et al., *Antiviral Res.* 19(1): 55-70, 1992. Briefly, WT10 cells are plated in 96-well microtiter plates. After 16-24 hours the confluent monolayer of HepG2-2.2.15 cells is washed and the medium is replaced with complete medium containing varying concentrations of a test samples in triplicate. 3TC is used as the positive control, while media alone is added to cells as a negative control (virus control, VC). Three days later the culture medium is replaced with fresh medium containing the appropriately diluted test samples. Six days following the initial addition of the test compound, the cell culture supernatant is collected, treated with pronase and DNAse, and used in a real-time quantitative TaqMan PCR assay. The PCR-amplified HBV DNA is detected in real-time by monitoring increases in fluorescence signals that result from the exonucleolytic degradation of a quenched fluorescent probe molecule that hybridizes to the amplified HBV DNA. For each PCR amplification, a standard curve is simultaneously generated using dilutions of purified HBV DNA. Antiviral activity is calculated from the reduction in HBV DNA levels ($IC_{50}$). A dye uptake assay is then employed to measure cell viability which is used to calculate toxicity ($TC_{50}$). The therapeutic index (TI) is calculated as $TC_{50}/IC_{50}$.

IL-28, IL-29 and MetIL-29C172S-PEG inhibited HepB viral replication in WT10 cells with an IC50 <0.032 ug/ml. This demonstrates antiviral activity of IL-28 and IL-29 against HBV grown in liver cell lines, providing evidence of therapeutic value for treating HBV in human patients.

Example 31

IL-28, IL-29 and MetIL-29C172S-PEG Inhibit BVDV Replication in Bovine Kidney Cells HCV is a member of the *Flaviviridae* family of RNA viruses. Other viruses belonging to this family are the bovine viral diarrhea virus (BVDV) and yellow fever virus (YFV). HCV does not replicate well in either ex vivo or in vitro cultures and therefore there are no systems to test anti-HCV activity in vitro. The BVDV and YFV assays are used as surrogate viruses for HCV to test the antiviral activities against the *Flavivirida* family of viruses.

The antiviral effects of IL-28, IL-29 and MetIL-29C172S-PEG were assessed in inhibition of cytopathic effect assays (CPE). The assay measured cell death using Madin-Darby bovine kidney cells (MDBK) after infection with cytopathic BVDV virus and the inhibition of cell death by addition of IL-28, IL-29 and MetIL-29C172S-PEG. The MDBK cells were propagated in Dulbecco's modified essential medium (DMEM) containing phenol red with 10% horse serum, 1% glutamine and 1% penicillin-streptomycin. CPE inhibition assays were performed in DMEM without phenol red with 2% FBS, 1% glutamine and 1% Pen-Strep. On the day preceding the assays, cells were trypsinized (1% trypsin-EDTA), washed, counted and plated out at $10^4$ cells/well in a 96-well flat-bottom BioCoat® plates (Fisher Scientific, Pittsburgh, Pa.) in a volume of 100 µl/well. The next day, the medium was removed and a pre-titered aliquot of virus was added to the cells. The amount of virus was the maximum dilution that would yield complete cell killing (>80%) at the time of maximal CPE development (day 7 for BVDV). Cell viability was determined using a CellTiter96® reagent (Promega) according to the manufacturer's protocol, using a Vmax plate reader (Molecular Devices, Sunnyvale, Calif.). Test samples were tested at six concentrations each, diluted in assay medium in a half-log series. IFNA. and RIBAVIRIN® were used as positive controls. Test sample were added at the time of viral infection. The average background and sample color-corrected data for percent CPE reduction and percent cell viability at each concentration were determined relative to controls and the $IC_{50}$ calculated relative to the $TC_{50}$.

IL-28, IL-29 and MetIL-29C172S-PEG inhibited cell death induced by BVDV in MDBK bovine kidney cells. IL-28 inhibited cell death with an $IC_{50}$ of 0.02 µg/ml, IL-29 inhibited cell death with an $IC_{50}$ of 0.19 µg/ml, and MetIL-29C172S-PEG inhibited cell death with an $IC_{50}$ of 0.45 µg/ml. This demonstrated that IL-28 and IL-29 have antiviral activity against the *Flavivirida* family of viruses.

Example 32

Induction of Interferon Stimulated Genes by IL-28 and IL-29

A. Human Peripheral Blood Mononuclear Cells

Freshly isolated human peripheral blood mononuclear cells were grown in the presence of IL-29 (20 ng/mL), IFNα2a (2 ng/ml) (PBL Biomedical Labs, Piscataway, N.J.), or in medium alone. Cells were incubated for 6, 24, 48, or 72 hours, and then total RNA was isolated and treated with RNase-free DNase. 100 ng total RNA was used as a template for One-Step Semi-Quantitative RT-PCR® using Taqman One-Step RT-PCR Master Mix® Reagents and gene specific primers as suggested by the manufacturer. (Applied Biosystems, Branchburg, N.J.) Results were normalized to HPRT and are shown as the fold induction over the medium alone control for each time-point. Table 24 shows that IL-29 induces Interferon Stimulated Gene Expression in human peripheral blood mononuclear cells at all time-points tested.

TABLE 24

| | MxA Fold induction | Pkr Fold Induction | OAS Fold Induction |
|---|---|---|---|
| 6 hr IL29 | 3.1 | 2.1 | 2.5 |
| 6 hr IFNα2a | 17.2 | 9.6 | 16.2 |
| 24 hr IL29 | 19.2 | 5.0 | 8.8 |
| 24 hr IFNα2a | 57.2 | 9.4 | 22.3 |
| 48 hr IL29 | 7.9 | 3.5 | 3.3 |
| 48 hr IFNα2a | 18.1 | 5.0 | 17.3 |
| 72 hr IL29 | 9.4 | 3.7 | 9.6 |
| 72 hr IFNα2a | 29.9 | 6.4 | 47.3 |

B. Activated Human T Cells

Human T cells were isolated by negative selection from freshly harvested peripheral blood mononuclear cells using the Pan T-cell IsolationiR kit according to manufacturer's instructions (Miltenyi, Auburn, Calif.). T cells were then activated and expanded for 5 days with plate-bound anti-CD3, soluble anti-CD28 (0.5 ug/ml), (Pharmingen, San Diego, Calif.) and Interleukin 2 (IL-2; 100 U/ml) (R&D Systems, Minneapolis, Minn.), washed and then expanded for a further 5 days with IL-2. Following activation and expansion, cells were stimulated with IL-28A (20 ng/ml), IL-29 (20 ng/ml), or medium alone for 3, 6, or 18 hours. Total RNA was isolated and treated with RNase-Free DNase. One-Step Semi-Quantitative RT-PCR® was performed as described in the example above. Results were normalized to HPRT and are shown as the fold induction over the medium alone control for each time-point. Table 25 shows that IL-28 and IL-29 induce Interferon Stimulated Gene expression in activated human T cells at all time-points tested.

TABLE 25

| | MxA Fold Induction | Pkr Fold Induction | OAS Fold Induction |
|---|---|---|---|
| Donor #1 3 hr IL28 | 5.2 | 2.8 | 4.8 |
| Donor #1 3 hr IL29 | 5.0 | 3.5 | 6.0 |
| Donor #1 6 hr IL28 | 5.5 | 2.2 | 3.0 |
| Donor #1 6 hr IL29 | 6.4 | 2.2 | 3.7 |
| Donor #1 18 hr IL28 | 4.6 | 4.8 | 4.0 |
| Donor #1 18 hr IL29 | 5.0 | 3.8 | 4.1 |
| Donor #2 3 hr IL28 | 5.7 | 2.2 | 3.5 |
| Donor #2 3 hr IL29 | 6.2 | 2.8 | 4.7 |
| Donor #2 6 hr IL28 | 7.3 | 1.9 | 4.4 |
| Donor #2 6 hr IL29 | 8.7 | 2.6 | 4.9 |
| Donor #2 18 hr IL28 | 4.7 | 2.3 | 3.6 |
| Donor #2 18 hr IL29 | 4.9 | 2.1 | 3.8 |

C. Primary Human Hepatocytes

Freshly isolated human hepatocytes from two separate donors (Cambrex, Baltimore, Md. and CellzDirect, Tucson, Ariz.) were stimulated with IL-28A (50 ng/ml), IL-29 (50 ng/ml), IFNα2a (50 ng/ml), or medium alone for 24 hours. Following stimulation, total RNA was isolated and treated with RNase-Free DNase. One-step semi-quantitative RT-PCR was performed as described previously in the example above. Results were normalized to HPRT and are shown as the fold induction over the medium alone control for each time-point. Table 26 shows that IL-28 and IL-29 induce Interferon Stimulated Gene expression in primary human hepatocytes following 24-hour stimulation.

TABLE 26

| | MxA Fold Induction | Pkr Fold Induction | OAS Fold Induction |
|---|---|---|---|
| Donor #1 IL28 | 31.4 | 6.4 | 30.4 |
| Donor #1 IL29 | 31.8 | 5.2 | 27.8 |
| Donor #1 IFN-α2a | 63.4 | 8.2 | 66.7 |
| Donor #2 IL28 | 41.7 | 4.2 | 24.3 |
| Donor #2 IL29 | 44.8 | 5.2 | 25.2 |
| Donor #2 IFN-α2a | 53.2 | 4.8 | 38.3 |

D. HepG2 and HuH7: Human Liver Hepatoma Cell Lines

HepG2 and HuH7 cells (ATCC NOS. 8065, Manassas, Va.) were stimulated with IL-28A (10 ng/ml), IL-29 (10 ng/ml), IFNα2a (10 ng/ml), IFNB (1 ng/ml) (PBL Biomedical, Piscataway, N.J.), or medium alone for 24 or 48 hours. In a separate culture, HepG2 cells were stimulated as described above with 20 ng/ml of MetIL-29C172S-PEG or MetIL-29-PEG. Total RNA was isolated and treated with RNase-Free DNase. 100 ng Total RNA was used as a template for one-step semi-quantitative RT-PCR as described previously. Results were normalized to HPRT and are shown as the fold induction over the medium alone control for each time-point. Table 27 shows that IL-28 and IL-29 induce ISG expression in HepG2 and HuH7 liver hepatoma cell lines after 24 and 48 hours.

TABLE 27

| | MxA Fold Induction | Pkr Fold Induction | OAS Fold Induction |
|---|---|---|---|
| HepG2 24 hr IL28 | 12.4 | 0.7 | 3.3 |
| HepG2 24 hr IL29 | 36.6 | 2.2 | 6.4 |
| HepG2 24 hr IFNα2a | 12.2 | 1.9 | 3.2 |
| HepG2 24 hr IFNβ | 93.6 | 3.9 | 19.0 |
| HepG2 48 hr IL28 | 2.7 | 0.9 | 1.1 |
| HepG2 48 hr IL29 | 27.2 | 2.1 | 5.3 |
| HepG2 48 hr IFNα2a | 2.5 | 0.9 | 1.2 |
| HepG2 48 hr IFNβ | 15.9 | 1.8 | 3.3 |
| HuH7 24 hr IL28 | 132.5 | 5.4 | 52.6 |
| HuH7 24 hr IL29 | 220.2 | 7.0 | 116.6 |
| HuH7 24 hr IFNα2a | 157.0 | 5.7 | 67.0 |
| HuH7 24 hr IFNβ | 279.8 | 5.6 | 151.8 |
| HuH7 48 hr IL28 | 25.6 | 3.4 | 10.3 |
| HuH7 48 hr IL29 | 143.5 | 7.4 | 60.3 |
| HuH7 48 hr IFNα2a | 91.3 | 5.8 | 32.3 |
| HuH7 48r IFNβ | 65.0 | 4.2 | 35.7 |

TABLE 28

| | MxA Fold Induction | OAS Fold Induction | Pkr Fold Induction |
|---|---|---|---|
| MetIL-29-PEG | 36.7 | 6.9 | 2.2 |
| MetIL-29C172S-PEG | 46.1 | 8.9 | 2.8 |

Data shown is for 20 ng/ml metIL-29-PEG and metIL-29C172S-PEG versions of IL-29 after culture for 24 hours.

Example 33

Antiviral Activity of IL-28 and IL-29 in HCV Replicon System

The ability of antiviral drugs to inhibit HCV replication can be tested in vitro with the HCV replicon system. The replicon system consists of the Huh7 human hepatoma cell line that has been transfected with subgenomic RNA replicons that direct constitutive replication of HCV genomic RNAs (Blight, K. J. et al. *Science* 290:1972-1974, 2000). Treatment of replicon clones with IFNα at 10 IU/ml reduces the amount of HCV RNA by 85% compared to untreated control cell lines. The ability of IL-28A and IL-29 to reduce the amount of HCV RNA produced by the replicon clones in 72 hours indicates the antiviral state conferred upon Huh7 cells by IL-28A/IL-29 treatment is effective in inhibiting HCV replicon replication, and thereby, very likely effective in inhibiting HCV replication.

The ability of IL-28A and IL-29 to inhibit HCV replication as determined by Bayer Branched chain DNA kit, is be done under the following conditions:

IL28 alone at increasing concentrations (6)* up to 1.0 μg/ml

IL29 alone at increasing concentrations (6)* up to 1.0 μg/ml

PEGIL29 alone at increasing concentrations (6)* up to 1.0 μg/ml

IFNα2A alone at 0.3, 1.0, and 3.0 IU/ml

Ribavirin alone.

The positive control is IFNα and the negative control is ribavirin.

The cells are stained after 72 hours with Alomar Blue to assess viablility.

*The concentrations for conditions 1-3 are:

μg/ml, 0.32 μg/ml, 0.10 μg/ml, 0.032 μg/ml, 0.010 μg/ml, 0.0032 μg/ml.

The replicon clone (BB7) is treated 1× per day for 3 consecutive days with the doses listed above. Total HCV RNA is measured after 72 hours.

Example 34

IL-28 and IL-29 Have Antiviral Activity Against Pathogenic Viruses

Two methods are used to assay in vitro antiviral activity of IL-28 and IL-29 against a panel of pathogenic viruses including, among others, adenovirus, parainfluenza virus, respiratory syncytial virus, rhino virus, coxsackie virus, influenza virus, vaccinia virus, west nile virus, dengue virus, venezuelan equine encephalitis virus, pichinde virus and polio virus. These two methods are inhibition of virus-induced cytopathic effect (CPE) determined by visual (microscopic) examination of the cells and increase in neutral red (NR) dye uptake into cells. In the CPE inhibition method, seven concentrations of test drug (log10 dilutions, such as 1000, 100, 10, 1, 0.1, 0.01, 0.001 ng/ml) are evaluated against each virus in 96-well flat-bottomed microplates containing host cells. The compounds are added 24 hours prior to virus, which is used at a concentration of approximately 5 to 100 cell culture infectious doses per well, depending upon the virus, which equates to a multiplicity of infection (MOI) of 0.01 to 0.0001 infectious particles per cell. The tests are read after incubation at 37° C. for a specified time sufficient to allow adequate viral cytopathic effect to develop. In the NR uptake assay, dye (0.34% concentration in medium) is added to the same set of plates used to obtain the visual scores. After 2 h, the color intensity of the dye absorbed by and subsequently eluted from the cells is determined using a microplate autoreader. Antiviral activity is expressed as the 50% effective (virus-inhibitory) concentration (EC50) determined by plotting compound concentration versus percent inhibition on semilogarithmic graph paper. The EC50/IC50 data in some cases may be determined by appropriate regression analysis software. In general, the EC50s determined by NR assay are two- to fourfold higher than those obtained by the CPE method.

TABLE 29

| | | | | | |
|---|---|---|---|---|---|
| | | | Visual Assay | | |
| Virus | Cell line | Drug | EC50 Visual | IC50 Visual | SI Visual (IC50/EC50) |
| Adenovirus | A549 | IL-28A | >10 μg/ml | >10 μg/ml | 0 |
| Adenovirus | A549 | IL-29 | >10 μg/ml | >10 μg/ml | 0 |
| Adenovirus | A549 | MetIL-29C172S-PEG | >10 μg/ml | >10 μg/ml | 0 |
| Parainfluenza virus | MA-104 | IL-28A | >10 μg/ml | >10 μg/ml | 0 |
| Parainfluenza virus | MA-104 | IL-29 | >10 μg/ml | >10 μg/ml | 0 |
| Parainfluenza virus | MA-104 | MetIL-29C172S-PEG | >10 μg/ml | >10 μg/ml | 0 |
| Respiratory syncytial virus | MA-104 | IL-28A | >10 μg/ml | >10 μg/ml | 0 |
| Respiratory syncytial virus | MA-104 | IL-29 | >10 μg/ml | >10 μg/ml | 0 |
| Respiratory syncytial virus | MA-104 | MetIL-29C172S-PEG | >10 μg/ml | >10 μg/ml | 0 |
| Rhino 2 | KB | IL-28A | >10 μg/ml | >10 μg/ml | 0 |
| Rhino 2 | KB | IL-29 | >10 μg/ml | >10 μg/ml | 0 |
| Rhino 2 | KB | MetIL-29C172S-PEG | >10 μg/ml | >10 μg/ml | 0 |

TABLE 29-continued

Visual Assay

| Virus | Cell line | Drug | EC50 Visual | IC50 Visual | SI Visual (IC50/EC50) |
|---|---|---|---|---|---|
| Rhino 9 | HeLa | IL-28A | >10 μg/ml | >10 μg/ml | 0 |
| Rhino 9 | HeLa | IL-29 | >10 μg/ml | >10 μg/ml | 0 |
| Rhino 9 | HeLa | MetIL-29C172S-PEG | >10 μg/ml | >10 μg/ml | 0 |
| Coxsackie B4 virus | KB | IL-28A | >10 μg/ml | >10 μg/ml | 0 |
| Coxsackie B4 virus | KB | IL-29 | >10 μg/ml | >10 μg/ml | 0 |
| Coxsackie B4 virus | KB | MetIL-29C172S-PEG | >10 μg/ml | >10 μg/ml | 0 |
| Influenza (type A [H3N2]) | Maden-Darby Canine Kidney | IL-28A | >10 μg/ml | >10 μg/ml | 0 |
| Influenza (type A [H3N2]) | Maden-Darby Canine Kidney | IL-29 | >10 μg/ml | >10 μg/ml | 0 |
| Influenza (type A [H3N2]) | Maden-Darby Canine Kidney | MetIL-29C172S-PEG | >10 μg/ml | >10 μg/ml | 0 |
| Influenza (type A [H3N2]) | Vero | IL-28A | 0.1 μg/ml | >10 μg/ml | >100 |
| Influenza (type A [H3N2]) | Vero | IL-29 | >10 μg/ml | >10 μg/ml | 0 |
| Influenza (type A [H3N2]) | Vero | MetIL-29C172S-PEG | 0.045 μg/ml | >10 μg/ml | >222 |
| Vaccinia virus | Vero | IL-28A | >10 μg/ml | >10 μg/ml | 0 |
| Vaccinia virus | Vero | IL-29 | >10 μg/ml | >10 μg/ml | 0 |
| Vaccinia virus | Vero | MetIL-29C172S-PEG | >10 μg/ml | >10 μg/ml | 0 |
| West Nile virus | Vero | IL-28A | 0.00001 μg/ml | >10 μg/ml | >1,000,000 |
| West Nile virus | Vero | IL-29 | 0.000032 μg/ml | >10 μg/ml | >300,000 |
| West Nile virus | Vero | MetIL-29C172S-PEG | 0.001 μg/ml | >10 μg/ml | >10,000 |
| Dengue virus | Vero | IL-28A | 0.01 μg/ml | >10 μg/ml | >1000 |
| Dengue virus | Vero | IL-29 | 0.032 μg/ml | >10 μg/ml | >312 |
| Dengue virus | Vero | MetIL-29C172S-PEG | 0.0075 μg/ml | >10 μg/ml | >1330 |
| Venezuelan equine encephalitis virus | Vero | IL-28A | 0.01 μg/ml | >10 μg/ml | >1000 |
| Venezuelan equine encephalitis virus | Vero | IL-29 | 0.012 μg/ml | >10 μg/ml | >833 |
| Venezuelan equine encephalitis virus | Vero | MetIL-29C172S-PEG | 0.0065 μg/ml | >10 μg/ml | >1538 |
| Pichinde virus | BSC-1 | IL-28A | >10 μg/ml | >10 μg/ml | 0 |
| Pichinde virus | BSC-1 | IL-29 | >10 μg/ml | >10 μg/ml | 0 |
| Pichinde virus | BSC-1 | MetIL-29C172S-PEG | >10 μg/ml | >10 μg/ml | 0 |
| Polio virus | Vero | IL-28A | >10 μg/ml | >10 μg/ml | 0 |
| Polio virus | Vero | IL-29 | >10 μg/ml | >10 μg/ml | 0 |
| Polio virus | Vero | MetIL-29C172S-PEG | >10 μg/ml | >10 μg/ml | 0 |

TABLE 30

Neutral Red Assay

| Virus | Cell line | Drug | EC50 NR | IC50 NR | SI NR (IC50/EC50) |
|---|---|---|---|---|---|
| Adenovirus | A549 | IL-28A | >10 µg/ml | >10 µg/ml | 0 |
| Adenovirus | A549 | IL-29 | >10 µg/ml | >10 µg/ml | 0 |
| Adenovirus | A549 | MetIL-29C172S-PEG | >10 µg/ml | >10 µg/ml | 0 |
| Parainfluenza virus | MA-104 | IL-28A | >10 µg/ml | >10 µg/ml | 0 |
| Parainfluenza virus | MA-104 | IL-29 | >10 µg/ml | >10 µg/ml | 0 |
| Parainfluenza virus | MA-104 | MetIL-29C172S-PEG | >10 µg/ml | >10 µg/ml | 0 |
| Respiratory syncytial virus | MA-104 | IL-28A | >10 µg/ml | >10 µg/ml | 0 |
| Respiratory syncytial virus | MA-104 | IL-29 | >10 µg/ml | >10 µg/ml | 0 |
| Respiratory syncytial virus | MA-104 | MetIL-29C172S-PEG | 5.47 µg/ml | >10 µg/ml | >2 |
| Rhino 2 | KB | IL-28A | >10 µg/ml | >10 µg/ml | 0 |
| Rhino 2 | KB | IL-29 | >10 µg/ml | >10 µg/ml | 0 |
| Rhino 2 | KB | MetIL-29C172S-PEG | >10 µg/ml | >10 µg/ml | 0 |
| Rhino 9 | HeLa | IL-28A | 1.726 µg/ml | >10 µg/ml | >6 |
| Rhino 9 | HeLa | IL-29 | 0.982 µg/ml | >10 µg/ml | >10 |
| Rhino 9 | HeLa | MetIL-29C172S-PEG | 2.051 µg/ml | >10 µg/ml | >5 |
| Coxsackie B4 virus | KB | IL-28A | >10 µg/ml | >10 µg/ml | 0 |
| Coxsackie B4 virus | KB | IL-29 | >10 µg/ml | >10 µg/ml | 0 |
| Coxsackie B4 virus | KB | MetIL-29C172S-PEG | >10 µg/ml | >10 µg/ml | 0 |
| Influenza (type A [H3N2]) | Maden-Darby Canine Kidney | IL-28A | >10 µg/ml | >10 µg/ml | 0 |
| Influenza (type A [H3N2]) | Maden-Darby Canine Kidney | IL-29 | >10 µg/ml | >10 µg/ml | 0 |
| Influenza (type A [H3N2]) | Maden-Darby Canine Kidney | MetIL-29C172S-PEG | >10 µg/ml | >10 µg/ml | 0 |
| Influenza (type A [H3N2]) | Vero | IL-28A | 0.25 µg/ml | >10 µg/ml | >40 |
| Influenza (type A [H3N2]) | Vero | IL-29 | 2 µg/ml | >10 µg/ml | >5 |
| Influenza (type A [H3N2]) | Vero | MetIL-29C172S-PEG | 1.4 µg/ml | >10 µg/ml | >7 |
| Vaccinia virus | Vero | IL-28A | >10 µg/ml | >10 µg/ml | 0 |
| Vaccinia virus | Vero | IL-29 | >10 µg/ml | >10 µg/ml | 0 |
| Vaccinia virus | Vero | MetIL-29C172S-PEG | >10 µg/ml | >10 µg/ml | 0 |
| West Nile virus | Vero | IL-28A | 0.0001 µg/ml | >10 µg/ml | >100,000 |
| West Nile virus | Vero | IL-29 | 0.00025 µg/ml | >10 µg/ml | >40,000 |
| West Nile virus | Vero | MetIL-29C172S-PEG | 0.00037 µg/ml | >10 µg/ml | >27,000 |
| Dengue virus | Vero | IL-28A | 0.1 µg/ml | >10 µg/ml | >100 |
| Dengue virus | Vero | IL-29 | 0.05 µg/ml | >10 µg/ml | >200 |
| Dengue virus | Vero | MetIL-29C172S-PEG | 0.06 µg/ml | >10 µg/ml | >166 |
| Venezuelan equine encephalitis virus | Vero | IL-28A | 0.035 µg/ml | >10 µg/ml | >286 |
| Venezuelan equine encephalitis virus | Vero | IL-29 | 0.05 µg/ml | >10 µg/ml | >200 |
| Venezuelan equine encephalitis virus | Vero | MetIL-29C172S-PEG | 0.02 µg/ml | >10 µg/ml | >500 |
| Pichinde virus | BSC-1 | IL-28A | >10 µg/ml | >10 µg/ml | 0 |
| Pichinde virus | BSC-1 | IL-29 | >10 µg/ml | >10 µg/ml | 0 |
| Pichinde virus | BSC-1 | MetIL-29C172S-PEG | >10 µg/ml | >10 µg/ml | 0 |

TABLE 30-continued

Neutral Red Assay

| Virus | Cell line | Drug | EC50 NR | IC50 NR | SI NR (IC50/ EC50) |
|---|---|---|---|---|---|
| Polio virus | Vero | IL-28A | >1.672 µg/ml | >10 µg/ml | >6 |
| Polio virus | Vero | IL-29 | >10 µg/ml | >10 µg/ml | 0 |
| Polio virus | Vero | MetIL-29C172S-PEG | >10 µg/ml | >10 µg/ml | 0 |

Example 35

IL-28, IL-29, metIL-29-PEG and metIL-29C172S-PEG Stimulate ISG Induction in the Mouse Liver Cell Line AML-12

Interferon stimulated genes (ISGs) are genes that are induced by type I interferons (IFNs) and also by the IL-28 and IL-29 family molecules, suggesting that IFN and IL-28 and IL-29 induce similar pathways leading to antiviral activity. Human type I IFNs (IFNα1-4 and IFNβ) have little or no activity on mouse cells, which is thought to be caused by lack of species cross-reactivity. To test if human IL-28 and IL-29 have effects on mouse cells, ISG induction by human IL-28 and IL-29 was evaluated by real-time PCR on the mouse liver derived cell line AML-12.

AML-12 cells were plated in 6-well plates in complete DMEM media at a concentration of $2 \times 10^6$ cells/well. Twenty-four hours after plating cells, human IL-28 and IL-29 were added to the culture at a concentration of 20 ng/ml. As a control, cells were either stimulated with mouse IFNα (positive control) or unstimulated (negative). Cells were harvested at 8, 24, 48 and 72 hours after addition of CHO-derived human IL-28A (SEQ ID NO:2) or IL-29 (SEQ ID NO:4). RNA was isolated from cell pellets using RNAEasy-kit® (Qiagen, Valencia, Calif.). RNA was treated with DNase (Millipore, Billerica, Mass.) to clean RNA of any contaminating DNA. cDNA was generated using Perkin-Elmer RT mix. ISG gene induction was evaluated by real-time PCR using primers and probes specific for mouse OAS, Pkr and Mxl. To obtain quantitative data, HPRT real-time PCR was duplexed with ISG PCR. A standard curve was obtained using known amounts of RNA from IFN-stimulated mouse PBLs. All data are shown as expression relative to internal HPRT expression.

Human IL-28A and IL-29 stimulated ISG induction in the mouse hepatocyte cell line AML-12 and demonstrated that unlike type I IFNs, the IL-28/29 family proteins showed cross-species reactivity.

TABLE 31

| Stimulation | OAS | PkR | Mx1 |
|---|---|---|---|
| None | 0.001 | 0.001 | 0.001 |
| Human IL-28 | 0.04 | 0.02 | 0.06 |
| Human IL-29 | 0.04 | 0.02 | 0.07 |
| Mouse IL-28 | 0.04 | 0.02 | 0.08 |
| Mouse IFNα | 0.02 | 0.02 | 0.01 |

All data shown were expressed as fold relative to HPRT gene expression ng of OAS mRNA=normalized value of OAS mRNA amount relative to internal ng of HPRT mRNA housekeeping gene, HPRT As an example, the data for the 48 hour time point is shown.

TABLE 32

| | AML12's | | |
|---|---|---|---|
| | Mx1 Fold Induction | OAS Fold Induction | Pkr Fold Induction |
| MetIL-29-PEG | 728 | 614 | 8 |
| MetIL-29C172S-PEG | 761 | 657 | 8 |

Cells were stimulated with 20 ng/ml metIL-29-PEG or metIL-29C172S-PEG for 24 hours.

Data shown is normalized to HPRT and shown as fold induction over unstimulated cells.

Example 36

ISGs are Efficiently Induced in Spleens of Transzenic Mice Expressing Human IL-29

Transgenic (Tg) mice were generated expressing human IL-29 under the control of the Eu-lck promoter. To study if human IL-29 has biological activity in vivo in mice, expression of ISGs was analyzed by real-time PCR in the spleens of Eu-lck IL-29 transgenic mice.

Transgenic mice (C3H/C57BL/6) were generated using a construct that expressed the human IL-29 gene under the control of the Eu-lck promoter. This promoter is active in T cells and B cells. Transgenic mice and their non-transgenic littermates (n=2/gp) were sacrificed at about 10 weeks of age. Spleens of mice were isolated. RNA was isolated from cell pellets using RNAEasy-kit® (Qiagen). RNA was treated with DNase to clean RNA of any contaminating DNA. cDNA was generated using Perkin-Elmer RT® mix. ISG gene induction was evaluated by real-time PCR using primers and probes (5' FAM, 3' NFQ) specific for mouse OAS, Pkr and Mx1. To obtain quantitative data, HPRT real-time PCR was duplexed with ISG PCR. Furthermore, a standard curve was obtained using known amounts of IFN stimulated mouse PBLs. All data are shown as expression relative to internal HPRT expression.

Spleens isolated from IL-29 Tg mice showed high induction of ISGs OAS, Pkr and Mx1 compared to their non-Tg littermate controls suggesting that human IL-29 is biologically active in vivo in mice.

TABLE 33

| Mice | OAS | PkR | Mx1 |
|---|---|---|---|
| Non-Tg | 4.5 | 4.5 | 3.5 |
| IL-29 Tg | 12 | 8 | 21 |

All data shown are fold expression relative to HPRT gene expression. The average expression in two mice is shown Example 37

Human IL-28 and IL-29 Protein Induce ISG Gene Expression In Liver, Spleen and Blood of Mice To determine whether human IL-28 and IL-29 induce interferon stimulated genes in vivo, CHO-derived human IL-28A and IL-29 protein were injected into mice. In addition, *E. coli* derived IL-29 was also tested in in vivo assays as described above using MetIL-29C172S-PEG and MetIL-29-PEG. At various time points and at different doses, ISG gene induction was measured in the blood, spleen and livers of the mice.

C57BL/6 mice were injected i.p or i.v with a range of doses (10 µg-250 µg) of CHO-derived human IL-28A and IL-29 or MetIL-29C172S-PEG and MetIL-29C16-C113-PEG. Mice were sacrificed at various time points (1 hr-48 hr). Spleens and livers were isolated from mice, and RNA was isolated. RNA was also isolated from the blood cells. The cells were pelleted and RNA isolated from pellets using RNAEasy®-kit (Qiagen). RNA was treated with DNase (Amicon) to rid RNA of any contaminating DNA. cDNA was generated using Perkin-Elmer RT mix (Perkin-Elmer). ISG gene induction was measured by real-time PCR using primers and probes specific for mouse OAS, Pkr and Mx1. To obtain quantitative data, HPRT real-time PCR was duplexed with ISG PCR. A standard curve was calculated using known amounts of IFN-stimulated mouse PBLs. All data are shown as expression relative to internal HPRT expression.

Human IL-29 induced ISG gene expression (OAS, Pkr, Mx1) in the livers, spleen and blood of mice in a dose dependent manner. Expression of ISGs peaked between 1-6 hours after injection and showed sustained expression above control mice up to 48 hours. In this experiment, human IL-28A did not induce ISG gene expression.

TABLE 34

| Injection | OAS-1 hr | OAS-6 hr | OAS-24 hr | OAS-48 hr |
|---|---|---|---|---|
| None - liver | 1.6 | 1.6 | 1.6 | 1.6 |
| IL-29 liver | 2.5 | 4 | 2.5 | 2.8 |
| None - spleen | 1.8 | 1.8 | 1.8 | 1.8 |
| IL-29 - spleen | 4 | 6 | 3.2 | 3.2 |
| None - blood | 5 | 5 | 5 | 5 |
| IL-29 blood | 12 | 18 | 11 | 10 |

Results shown are fold expression relative to HPRT gene expression. A sample data set for IL-29 induced OAS in liver at a single injection of 250 µg i.v. is shown. The data shown is the average expression from 5 different animals/group.

TABLE 35

| Injection | OAS (24 hr) |
|---|---|
| None | 1.8 |
| IL-29 10 µg | 3.7 |
| IL-29 50 µg | 4.2 |
| IL-29 250 µg | 6 |

TABLE 36

| | MetIL-29-PEG | | | | MetIL-29C172S-PEG | | | | |
|---|---|---|---|---|---|---|---|---|---|
| | 3 hr | 6 hr | 12 hr | 24 hr | 3 hr | 6 hr | 12 hr | 24 hr | Naive 24 hr |
| PKR | 18.24 | 13.93 | 4.99 | 3.77 | 5.29 | 5.65 | 3.79 | 3.55 | 3.70 |
| OAS | 91.29 | 65.93 | 54.04 | 20.81 | 13.42 | 13.02 | 10.54 | 8.72 | 6.60 |
| Mx1 | 537.51 | 124.99 | 33.58 | 35.82 | 27.89 | 29.34 | 16.61 | 0.00 | 10.98 |

Mice were injected with 100 µg of proteins i.v. Data shown is fold expression over HPRT expression from livers of mice. Similar data was obtained from blood and spleens of mice.

Example 38

IL-28 and IL-29 Induce ISG Protein in Mice

To analyze of the effect of human IL-28 and IL-29 on induction of ISG protein (OAS), serum and plasma from IL-28 and IL-29 treated mice were tested for OAS activity.

C57BL/6 mice were injected i.v with PBS or a range of concentrations (10 µg-250 µg) of human IL-28 or IL-29. Serum and plasma were isolated from mice at varying time points, and OAS activity was measured using the OAS radio-immunoassay (RIA) kit from Eiken Chemicals (Tokyo, Japan).

IL-28 and IL-29 induced OAS activity in the serum and plasma of mice showing that these proteins are biologically active in vivo.

TABLE 37

| Injection | OAS-1 hr | OAS-6 hr | OAS-24 hr | OAS-48 hr |
|---|---|---|---|---|
| None | 80 | 80 | 80 | 80 |
| IL-29 | 80 | 80 | 180 | 200 |

OAS activity is shown at pmol/dL of plasma for a single concentration (250 µg) of human IL-29.

Example 39

IL-28 and IL-29 Inhibit Adenoviral Pathology in Mice

To test the antiviral activities of IL-28 and IL-29 against viruses that infect the liver, the test samples were tested in mice against infectious adenoviral vectors expressing an internal green fluorescent protein (GFP) gene. When injected intravenously, these viruses primarily target the liver for gene expression. The adenoviruses are replication deficient, but cause liver damage due to inflammatory cell infiltrate that can be monitored by measurement of serum levels of liver enzymes like AST and ALT, or by direct examination of liver pathology.

C57B1/6 mice were given once daily intraperitoneal injections of 50 µg mouse IL-28 (zcyto24 as shown in SEQ ID NO:8) or metIL-29C172S-PEG for 3 days. Control animals were injected with PBS. One hour following the $3^{rd}$ dose, mice were given a single bolus intravenous tail vein injection of the adenoviral vector, AdGFP ($1\times10^9$ plaque-forming units (pfu)). Following this, every other day mice were given an additional dose of PBS, mouse IL-28 or metIL-29C172S-PEG for 4 more doses (total of 7 doses). One hour following the final dose of PBS, mouse IL-28 or metIL-29C172S-PEG mice were terminally bleed and sacrificed. The serum and liver tissue were analyzed. Serum was analyzed for AST and ALT liver enzymes. Liver was isolated and analyzed for GFP expression and histology. For histology, liver specimens were fixed in formalin and then embedded in paraffin followed by H&E staining. Sections of liver that had been blinded to treat were examined with a light microscope. Changes were noted and scored on a scale designed to measure liver pathology and inflammation.

Mouse IL-28 and IL-29 inhibited adenoviral infection and gene expression as measured by liver fluorescence. PBS-treated mice (n=8) had an average relative liver fluorescence of 52.4 (arbitrary units). In contrast, IL-28-treated mice (n=8) had a relative liver fluorescence of 34.5, and IL-29-treated mice (n=8) had a relative liver fluorescence of 38.9. A reduction in adenoviral infection and gene expression led to a reduced liver pathology as measured by serum ALT and AST levels and histology. PBS-treated mice (n=8) had an average serum AST of 234 U/L (units/liter) and serum ALT of 250 U/L. In contrast, IL-28-treated mice (n=8) had an average serum AST of 193 U/L and serum ALT of 216 U/L, and IL-29-treated mice (n=8) had an average serum AST of 162 U/L and serum ALT of 184 U/L. In addition, the liver histology indicated that mice given either mouse IL-28 or IL-29 had lower liver and inflammation scores than the PBS-treated group. The livers from the IL-29 group also had less proliferation of sinusoidal cells, fewer mitotic figures and fewer changes in the hepatocytes (e.g. vacuolation, presence of multiple nuclei, hepatocyte enlargement) than in the PBS treatment group. These data demonstrate that mouse IL-28 and IL-29 have antiviral properties against a liver-trophic virus.

Example 40

LCMV Models

Lymphocytic choriomeningitis virus (LCMV) infections in mice mice are an excellent model of acute and chronic infection. These models are used to evaluate the effect of cytokines on the antiviral immune response and the effects IL-28 and IL-29 have viral load and the antiviral immune response. The two models used are: LCMV Armstrong (acute) infection and LCMV Clone 13 (chronic) infection. (See, e.g., Wherry et al., *J. Virol.* 77:4911-4927, 2003; Blattman et al., *Nature Med.* 9(5):540-547, 2003; Hoffman et al., *J. Immunol.* 170:1339-1353, 2003.) There are three stages of CD8 T cell development in response to virus: 1) expansion, 2) contraction, and 3) memory (acute model). IL-28 or IL-29 is injected during each stage for both acute and chronic models. In the chronic model, IL-28 or IL-29 is injected 60 days after infection to assess the effect of IL-28 or IL-29 on persistent viral load. For both acute and chronic models, IL-28 or IL-29 is injected, and the viral load in blood, spleen and liver is examined. Other parameter that can be examined include: tetramer staining by flow to count the number of LCMV-specific CD8+T cells; the ability of tetramer+cells to produce cytokines when stimulated with their cognate LCMV antigen; and the ability of LCMV-specific CD8+T cells to proliferate in response to their cognate LCMV antigen. LCMV-specific T cells are phenotyped by flow cytometry to assess the cells activation and differentiation state. Also, the ability of LCMV-specific CTL to lyse target cells bearing their cognate LCMV antigen is examined. The number and function of LCMV-specific CD4+T cells is also assessed.

A reduction in viral load after treatment with IL-28 or IL-29 is determined. A 50% reduction in viral load in any organ, especially liver, would be significant. For IL-28 or IL-29 treated mice, a 20% increase in the percentage of tetramer positive T cells that proliferate, make cytokine, or display a mature phenotype relative to untreated mice would also be considered significant.

IL-28 or IL-29 injection leading to a reduction in viral load is due to more effective control of viral infection especially in the chronic model where untreated the viral titers remain elevated for an extended period of time. A two fold reduction in viral titer relative to untreated mice is considered significant.

Example 41

Influenza Model of Acute Viral Infection

A. Preliminary Experiment to Test Antiviral Activity

To determine the antiviral activity of IL-28 or IL-29 on acute infection by Influenza virus, an in vivo study using influenza infected c57BI/6 mice is performed using the following protocol:

Animals: 6 weeks-old female BALB/c mice (Charles River) with 148 mice, 30 per group.

Groups:

Absolute control (not infected) to run in parallel for antibody titre and histopathology (2 animals per group)

Vehicle (i.p.) saline

Amantadine (positive control) 10 mg/day during 5 days (per os) starting 2 hours before infection IL-28 or IL-29 treated (5 µg, i.p. starting 2 hours after infection)

IL-28 or IL-29 (25 µg, i.p. starting 2 hours after infection)

IL-28 or IL-29 (125 µg, i.p. starting 2 hours after infection)

Day 0—Except for the absolute controls, all animals infected with Influenza virus For viral load (10 at LD50)

For immunology workout (LD30)

Day 0-9—daily injections of IL-28 or IL-29 (i.p.)

Body weight and general appearance recorded (3 times/week)

Day 3—sacrifice of 8 animals per group
Viral load in right lung (TCID50)
Histopathology in left lung
Blood sample for antibody titration
Day 10—sacrifice of all surviving animals collecting blood samples for antibody titration, isolating lung lymphocytes (4 pools of 3) for direct CTL assay (in all 5 groups), and quantitative immunophenotyping for the following markers: CD3/CD4, CD3/CD8, CD3/CD8/CD11b, CD8/CD44/CD62L, CD3/DX5, GR-1/F480, and CD19.

Study No.2

Efficacy study of IL-28 or IL-29 in C57B1/6 mice infected with mouse-adapted virus is done using 8 weeks-old female C57B1/6 mice (Charles River).

Group 1: Vehicle (i.p.)
Group 2: Positive control: Anti-influenza neutralizing antibody (goat anti-influenza A/USSR (H1N1) (Chemicon International, Temecula, Calif.); 40 ag/mouse at 2 h and 4 h post infection (10 µl intranasal)
Group 3: IL-28 or IL-29 (5 µg, i.p.)
Group 4: IL-28 or IL-29 (25 µg, i.p.)
Group 5: IL-28 or IL-29 (125 µg, i.p.)

Following-life observations and immunological workouts are prepared:

Day 0—all animals infected with Influenza virus (dose determined in experiment 2)
Day 0-9—daily injections of IL-28 or IL-29 (i.p.)
Body weight and general appearance recorded every other day
Day 10—sacrifice of surviving animals and perform viral assay to determine viral load in lung.
Isolation of lung lymphocytes (for direct CTL assay in the lungs using EL-4 as targets and different E:T ratio (based on best results from experiments 1 and 2).

Tetramer staining: The number of CD8+T cells binding MHC Class I tetramers containing influenza A nucleoprotein (NP) epitope are assessed using complexes of MHC class I with viral peptides: FLU-NP$_{366-374}$/D$^b$ (ASNENMETM), (LMCV peptide/D$^b$).

Quantitative immunophenotyping of the following: CD8, tetramer, intracellular IFNγ, NK1.1, CD8, tetramer, CD62L, CD44, CD3(+or –), NK1.1(+), intracellular IFNγ, CD4, CD8, NK1.1, DX5, CD3 (+or –), NK1.1, DX5, tetramer, Single colour samples for cytometer adjustment.

Survival Re-Challenze Study

Day 30: Survival study with mice are treated for 9 days with different doses of IL-28 or IL-29 or with positive anti-influenza antibody control. Body weight and antibody production in individual serum samples (Total, IgG1, IgG2a, IgG2b) are measured.

Re-Challenge Study:

Day 0: Both groups will be infected with A/PR virus (1LD30).
Group 6 will not be treated.
Group 7 will be treated for 9 days with 125 µg of IL-28 or IL-29.
Day 30: Survival study
Body weight and antibody production in individual serum samples (Total, IgG1, IgG2a, IgG2b) are measured.
Day 60: Re-challenge study
Survivors in each group will be divided into 2 subgroups
Group 6A and 7A will be re-challenge with A/PR virus (1 LD30)
Group 6B and 7B will be re-challenge with A/PR virus (1 LD30).

Both groups will be followed up and day of sacrifice will be determined. Body weight and antibody production in individual serum samples (Total, IgG1, IgG2a, IgG2b) are measured.

Example 42

IL-28 and IL-29 have Antiviral Activity Against Hepatitis B Virus (HBV) In Vivo

A transgenic mouse model (Guidotti et al., *J. Virology* 69:6158-6169, 1995) supports the replication of high levels of infectious HBV and has been used as a chemotherapeutic model for HBV infection. Transgenic mice are treated with antiviral drugs and the levels of HBV DNA and RNA are measured in the transgenic mouse liver and serum following treatment. HBV protein levels can also be measured in the transgenic mouse serum following treatment. This model has been used to evaluate the effectiveness of lamivudine and IFN-α in reducing HBV viral titers.

HBV TG mice (male) are given intraperitoneal injections of 2.5, 25 or 250 micrograms IL-28 or IL-29 every other day for 14 days (total of 8 doses). Mice are bled for serum collection on day of treatment (day 0) and day 7. One hour following the final dose of IL-29 mice undergo a terminal bleed and are sacrificed. Serum and liver are analyzed for liver HBV DNA, liver HBV RNA, serum HBV DNA, liver HBc, serum Hbe and serum HBs.

Reduction in liver HBV DNA, liver HBV RNA, serum HBV DNA, liver HBc, serum Hbe or serum HBs in response to IL-28 or IL-29 reflects antiviral activity of these compounds against HBV.

Example 43

IL-28 and IL-29 Inhibit Human Hemesvirus-8 (HHV-8) Replication in BCBL-1 Cells

The antiviral activities of IL-28 and IL-29 were tested against HHV-8 in an in vitro infection system using a B-lymphoid cell line, BCBL-1.

In the HHV-8 assay the test compound and a ganciclovir control were assayed at five concentrations each, diluted in a half-log series. The endpoints were TaqMan PCR for extracellular HHV-8 DNA (IC50) and cell numbers using CellTiter96® reagent (TC50; Promega, Madison, Wis.). Briefly, BCBL-1 cells were plated in 96-well microtiter plates. After 16-24 hours the cells were washed and the medium was replaced with complete medium containing various concentrations of the test compound in triplicate. Ganciclovir was the positive control, while media alone was a negative control (virus control, VC). Three days later the culture medium was replaced with fresh medium containing the appropriately diluted test compound. Six days following the initial administration of the test compound, the cell culture supernatant was collected, treated with pronase and DNAse and then used in a real-time quantitative TaqMan PCR assay. The PCR-amplified HHV-8 DNA was detected in real-time by monitoring increases in fluorescence signals that result from the exonucleolytic degradation of a quenched fluorescent probe molecule that hybridizes to the amplified HHV-8 DNA. For each PCR amplification, a standard curve was simultaneously generated using dilutions of purified HHV-8 DNA. Antiviral activity was calculated from the reduction in HHV-8 DNA levels (IC$_{50}$). A novel dye uptake assay was then employed to measure cell viability which was used to calculate toxicity (TC$_{50}$). The therapeutic index (TI) is calculated as TC$_{50}$/IC$_{50}$.

IL-28 and IL-29 inhibit HHV-8 viral replication in BCBL-1 cells. IL-28A had an IC$_{50}$ of 1 µg/ml and a TC$_{50}$ of >10 µg/ml (TI>10). IL-29 had an IC$_{50}$ of 6.5 µg/ml and a TC$_{50}$ of >10 µg/ml (TI>1.85). MetIL-29C172S-PEG had an IC$_{50}$ of 0.14 µg/ml and a TC$_{50}$ of >10 µg/ml (TI>100).

Example 44

IL-28 and IL-29 Antiviral Activity Against Epstein Barr Virus (EBV)

The antiviral activities of IL-28 and IL-29 are tested against EBV in an in vitro infection system in a B-lymphoid cell line, P3HR-1. In the EBV assay the test compound and a control are assayed at five concentrations each, diluted in a half-log series. The endpoints are TaqMan PCR for extracellular EBV DNA (IC50) and cell numbers using CellTiter96® reagent (TC50; Promega). Briefly, P3HR-1 cells are plated in 96-well microtiter plates. After 16-24 hours the cells are washed and the medium is replaced with complete medium containing various concentrations of the test compound in triplicate. In addition to a positive control, media alone is added to cells as a negative control (virus control, VC). Three days later the culture medium is replaced with fresh medium containing the appropriately diluted test compound. Six days following the initial administration of the test compound, the cell culture supernatant is collected, treated with pronase and DNAse and then used in a real-time quantitative TaqMan PCR assay. The PCR-amplified EBV DNA is detected in real-time by monitoring increases in fluorescence signals that result from the exonucleolytic degradation of a quenched fluorescent probe molecule that hybridizes to the amplified EBV DNA. For each PCR amplification, a standard curve was simultaneously generated using dilutions of purified EBV DNA. Antiviral activity is calculated from the reduction in EBV DNA levels (IC$_{50}$). A novel dye uptake assay was then employed to measure cell viability which was used to calculate toxicity (TC$_{50}$). The therapeutic index (T1) is calculated as TC$_{50}$/IC$_{50}$.

Example 45

IL-28 and IL-29 Antiviral Activity Against Herpes Simplex Virus-2 (HSV-2)

The antiviral activities of IL-28 and IL-29 were tested against HSV-2 in an in vitro infection system in Vero cells. The antiviral effects of IL-28 and IL-29 were assessed in inhibition of cytopathic effect assays (CPE). The assay involves the killing of Vero cells by the cytopathic HSV-2 virus and the inhibition of cell killing by IL-28 and IL-29. The Vero cells are propagated in Dulbecco's modified essential medium (DMEM) containing phenol red with 10% horse serum, 1% glutamine and 1% penicillin-streptomycin, while the CPE inhibition assays are performed in DMEM without phenol red with 2% FBS, 1% glutamine and 1% Pen-Strep. On the day preceding the assays, cells were trypsinized (1% trypsin-EDTA), washed, counted and plated out at $10^4$ cells/well in a 96-well flat-bottom BioCoat® plates (Fisher Scientific, Pittsburgh, Pa.) in a volume of 100 µl/well. The next morning, the medium was removed and a pre-titered aliquot of virus was added to the cells. The amount of virus used is the maximum dilution that would yield complete cell killing (>80%) at the time of maximal CPE development. Cell viability is determined using a CellTiter 96® reagent (Promega) according to the manufacturer's protocol, using a Vmax plate reader (Molecular Devices, Sunnyvale, Calif.). Compounds are tested at six concentrations each, diluted in assay medium in a half-log series. Acyclovir was used as a positive control. Compounds are added at the time of viral infection. The average background and drug color-corrected data for percent CPE reduction and percent cell viability at each concentration are determined relative to controls and the IC$_{50}$ calculated relative to the TC$_{50}$.

IL-28A, IL-29 and MetIL-29C172S-PEG did not inhibit cell death (IC$_{50}$ of >10 ug/ml) in this assay. There was also no antiviral activity of IFN⌐ in the assay.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An isolated polypeptide comprising amino acid residues 1-176 of SEQ ID NO:125.

2. The polypeptide of claim 1 wherein the polypeptide has anti-hepatitis C activity.

3. The polypeptide of claim 1 wherein the polypeptide further comprises a polyethylene glycol moiety covalently attached N-terminally to the polypeptide.

4. The polypeptide of claim 3 wherein the polyethylene glycol moiety is mPEG propionaldehyde.

5. The polypeptide of claim 4 wherein the mPEG propionaldehyde has a molecular weight of about 20 kD.

6. The polypeptide of claim 4 wherein the mPEG propionaldehyde is linear.

7. A fusion protein comprising a polypeptide that comprises amino acid residues 1-176 of SEQ ID NO:125 and a polyalkyl oxide moiety.

8. The fusion protein of claim 7 wherein the polyalkyl oxide moiety is polyethylene glycol.

9. The fusion protein of claim 8 wherein the polyethylene glycol is N-terminally or C-terminally attached to the polypeptide.

10. The fusion protein of claim 8 wherein the polyethylene glycol is mPEG propionaldehyde.

11. The fusion protein of claim 8 wherein the polyethylene glycol is branched or linear.

12. The fusion protein of claim 8 wherein the polyethylene glycol has a molecular weight of about 20 kD.

13. A formulation comprising:
    an isolated polypeptide comprising amino acid residues 1-176 of SEQ ID NO:125; and
    a pharmaceutically acceptable vehicle.

14. A kit comprising the formulation of claim 13.

* * * * *